United States Patent
Eden et al.

(10) Patent No.: US 12,338,497 B2
(45) Date of Patent: *Jun. 24, 2025

(54) ANALYZING RNA FOR DIAGNOSING INFECTION TYPE

(71) Applicant: MeMed Diagnostics Ltd., Tirat HaCarmel (IL)

(72) Inventors: Eran Eden, Haifa (IL); Kfir Oved, Hof HaCarmel (IL); Assaf Cohen-Dotan, Natania (IL); Roy Navon, Tel-Aviv (IL); Olga Boico, Haifa (IL); Gali Kronenfeld, Haifa (IL); Einav Simon, Atlit (IL)

(73) Assignee: MeMed Diagnostics Ltd., Tirat HaCarmel (IL)

( * ) Notice: Subject to any disclaimer, the term of this patent is extended or adjusted under 35 U.S.C. 154(b) by 0 days.

This patent is subject to a terminal disclaimer.

(21) Appl. No.: 16/081,069

(22) PCT Filed: Mar. 2, 2017

(86) PCT No.: PCT/IL2017/050270
§ 371 (c)(1),
(2) Date: Aug. 30, 2018

(87) PCT Pub. No.: WO2017/149547
PCT Pub. Date: Sep. 8, 2017

(65) Prior Publication Data
US 2019/0085378 A1    Mar. 21, 2019

Related U.S. Application Data

(60) Provisional application No. 62/302,994, filed on Mar. 3, 2016.

(51) Int. Cl.
C12Q 1/68       (2018.01)
C12Q 1/00       (2006.01)
C12Q 1/689      (2018.01)
C12Q 1/70       (2006.01)

(52) U.S. Cl.
CPC .............. *C12Q 1/689* (2013.01); *C12Q 1/00* (2013.01); *C12Q 1/70* (2013.01); *C12Q 1/701* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 5,639,617 A | 6/1997 | Bohuon | |
| 5,910,421 A | 6/1999 | Small, Jr. et al. | |
| 6,077,665 A | 6/2000 | Welrich et al. | |
| 6,136,526 A | 10/2000 | Venge | |
| 6,210,661 B1 | 4/2001 | Enssle et al. | |
| 6,709,855 B1 | 3/2004 | Stanton et al. | |
| 6,756,483 B1 | 6/2004 | Bergmann et al. | |
| 6,953,435 B2 | 10/2005 | Kondo et al. | |
| 7,115,717 B2 | 10/2006 | Mori et al. | |
| 7,132,246 B2 | 11/2006 | Bergmann et al. | |
| 7,153,662 B2 | 12/2006 | Bergmann et al. | |
| 7,157,081 B2 | 1/2007 | Bergmann et al. | |
| 7,598,031 B2 | 10/2009 | Lew | |
| 7,629,116 B2 | 12/2009 | Ott | |
| 7,892,539 B2 | 2/2011 | Winoto et al. | |
| 8,021,836 B2 | 9/2011 | Kolopp-Sarda et al. | |
| 8,155,993 B2 | 4/2012 | de Nijs et al. | |
| 8,465,951 B2 | 6/2013 | Rao et al. | |
| 8,507,210 B2 | 8/2013 | Bergmann et al. | |
| 8,563,476 B2 | 10/2013 | Lillard, Jr. | |
| 8,697,370 B2 | 4/2014 | Kas et al. | |
| 8,821,876 B2 | 9/2014 | Ginsburg et al. | |
| 9,034,328 B2 | 5/2015 | Takahashi | |
| 9,709,565 B2 | 7/2017 | Eden et al. | |
| 9,726,668 B2 | 8/2017 | Oved et al. | |
| 9,850,539 B2 | 12/2017 | Tsalik et al. | |
| 10,010,252 B2 | 7/2018 | Ide et al. | |
| 10,209,260 B2 | 2/2019 | Oved et al. | |
| 10,303,846 B2 | 5/2019 | Eden et al. | |
| 10,502,739 B2 | 12/2019 | Oved et al. | |
| 10,859,574 B2 | 12/2020 | Oved et al. | |

(Continued)

FOREIGN PATENT DOCUMENTS

| | | |
|---|---|---|
| AU | 2012244350 | 11/2012 |
| CN | 1656378 | 8/2005 |
| CN | 1751128 | 3/2006 |
| CN | 101208602 | 6/2008 |
| CN | 101479389 | 7/2009 |
| CN | 101541976 | 9/2009 |
| CN | 101611314 | 12/2009 |
| CN | 101617056 | 12/2009 |
| CN | 101617230 | 12/2009 |
| CN | 101622364 | 1/2010 |
| CN | 101790687 | 7/2010 |
| CN | 102301002 | 12/2011 |
| CN | 103119444 | 5/2013 |
| CN | 104159616 | 11/2014 |
| CN | 104204803 | 12/2014 |

(Continued)

OTHER PUBLICATIONS

Zaas et al. Sci Transl Med 5, 203ra126203ra126, 10 pages (Year: 2013).*

(Continued)

*Primary Examiner* — Juliet C Switzer

(57) ABSTRACT

A method of selecting an exon of an RNA whose expression level is informative with respect to infection type of a subject is disclosed. The method comprises comparing the expression level of the RNA in a sample derived from a bacterially-infected subject and a sample derived from a virally-infected subject at a plurality of exons, wherein the exon that provides a differential expression between the bacterially-infected subject and the virally-infected subject above a predetermined level is selected as the exon of the RNA whose expression is informative with respect to infection type.

6 Claims, 16 Drawing Sheets

(15 of 16 Drawing Sheet(s) Filed in Color)

(56) References Cited

U.S. PATENT DOCUMENTS

| | | |
|---|---|---|
| 11,385,241 B2 | 7/2022 | Eden et al. |
| 11,466,331 B2 | 10/2022 | Oved et al. |
| 11,776,658 B2 | 10/2023 | Eden et al. |
| 2002/0001402 A1 | 1/2002 | Berliner |
| 2002/0055176 A1 | 5/2002 | Ray |
| 2002/0059030 A1 | 5/2002 | Otworth et al. |
| 2004/0038201 A1 | 2/2004 | Nau et al. |
| 2004/0043379 A1 | 3/2004 | Hashimoto et al. |
| 2004/0171013 A1 | 9/2004 | Lilius et al. |
| 2004/0197769 A1 | 10/2004 | Wong et al. |
| 2004/0209307 A1 | 10/2004 | Valkirs et al. |
| 2005/0164238 A1 | 7/2005 | Valkirs et al. |
| 2005/0227223 A1 | 10/2005 | Miyawaki |
| 2005/0233395 A1 | 10/2005 | Weiser et al. |
| 2006/0040301 A1 | 2/2006 | Deirmengian |
| 2006/0052278 A1 | 3/2006 | Powell |
| 2006/0078998 A1 | 4/2006 | Puskas et al. |
| 2006/0099628 A1 | 5/2006 | Ching et al. |
| 2006/0246495 A1 | 11/2006 | Garrett et al. |
| 2007/0015172 A1 | 1/2007 | Zhang et al. |
| 2007/0184460 A1 | 8/2007 | Ching et al. |
| 2007/0231816 A1 | 10/2007 | Chaussabel et al. |
| 2007/0281319 A1 | 12/2007 | Kolopp-Sarda et al. |
| 2008/0020379 A1 | 1/2008 | Agan et al. |
| 2008/0064113 A1 | 3/2008 | Goix et al. |
| 2008/0171323 A1 | 7/2008 | Banchereau et al. |
| 2008/0261258 A1 | 10/2008 | Smith et al. |
| 2009/0155180 A1 | 6/2009 | Jump et al. |
| 2009/0203534 A1* | 8/2009 | Hossain ............... C12Q 1/6883 |
| | | 506/9 |
| 2009/0246790 A1 | 10/2009 | Cote et al. |
| 2010/0028874 A1 | 2/2010 | Ramachandran et al. |
| 2010/0068147 A1 | 3/2010 | Hibberd et al. |
| 2010/0143372 A1 | 6/2010 | Yao et al. |
| 2010/0267569 A1 | 10/2010 | Salmon et al. |
| 2010/0297611 A1 | 11/2010 | Sambursky et al. |
| 2011/0059858 A1 | 3/2011 | Kas et al. |
| 2011/0117563 A1 | 5/2011 | Filipowicz et al. |
| 2011/0144914 A1 | 6/2011 | Harrington et al. |
| 2011/0166166 A1 | 7/2011 | Henkin |
| 2011/0183856 A1 | 7/2011 | Agan et al. |
| 2011/0225114 A1 | 9/2011 | Gotthardt |
| 2011/0275542 A1 | 11/2011 | Eden et al. |
| 2011/0312534 A1 | 12/2011 | Kayser et al. |
| 2012/0114661 A1 | 5/2012 | Ginsburg et al. |
| 2013/0166219 A1 | 6/2013 | Shaw |
| 2013/0309168 A1 | 11/2013 | Ho |
| 2014/0127827 A1 | 5/2014 | Kim et al. |
| 2014/0206016 A1 | 7/2014 | Lozano Sanchez et al. |
| 2014/0227324 A1 | 8/2014 | Robinson et al. |
| 2014/0277284 A1 | 9/2014 | Chen et al. |
| 2014/0349326 A1 | 11/2014 | Ingber |
| 2015/0017630 A1 | 1/2015 | Oved et al. |
| 2016/0041153 A1 | 2/2016 | Brown et al. |
| 2016/0153993 A1 | 6/2016 | Eden et al. |
| 2017/0030909 A1 | 2/2017 | Oved et al. |
| 2017/0234873 A1 | 8/2017 | Oved et al. |
| 2017/0235871 A1 | 8/2017 | Eden et al. |
| 2017/0269081 A1 | 9/2017 | Oved et al. |
| 2018/0074057 A1 | 3/2018 | Eden et al. |
| 2018/0310854 A1 | 11/2018 | Geva et al. |
| 2019/0011456 A1 | 1/2019 | Oved et al. |
| 2019/0041388 A1 | 2/2019 | Oved et al. |
| 2019/0120837 A1 | 4/2019 | Eden et al. |
| 2019/0161813 A1 | 5/2019 | Oved et al. |
| 2019/0237156 A1 | 8/2019 | Eden et al. |
| 2019/0242894 A1 | 8/2019 | Oved et al. |
| 2019/0242895 A1 | 8/2019 | Eden et al. |
| 2019/0271709 A1 | 9/2019 | Eden et al. |
| 2019/0339189 A1 | 11/2019 | Takeda et al. |
| 2020/0088728 A1 | 3/2020 | Oved et al. |
| 2020/0124593 A1 | 4/2020 | Oved et al. |
| 2020/0388347 A1 | 12/2020 | Eden et al. |
| 2020/0393463 A1 | 12/2020 | Oved et al. |
| 2020/0400668 A1 | 12/2020 | Eden et al. |
| 2022/0011320 A1 | 1/2022 | Eden et al. |
| 2022/0042994 A1 | 2/2022 | Oved et al. |
| 2022/0236269 A1 | 7/2022 | Eden et al. |
| 2022/0326256 A1 | 10/2022 | Eden et al. |
| 2022/0329345 A1 | 10/2022 | Kaplan |
| 2022/0399074 A1 | 12/2022 | Eden et al. |
| 2023/0045305 A1 | 2/2023 | Oved et al. |
| 2023/0184760 A1 | 6/2023 | Oved et al. |
| 2024/0369552 A1 | 11/2024 | Eden et al. |

FOREIGN PATENT DOCUMENTS

| | | |
|---|---|---|
| CN | 105556308 | 5/2016 |
| EP | 1489416 | 12/2004 |
| JP | 2005-106694 | 4/2005 |
| JP | 2007-518062 | 7/2007 |
| JP | 2008-502908 | 1/2008 |
| JP | 2011-069696 | 4/2011 |
| KR | 10-2016-0072626 | 6/2016 |
| WO | WO 95/29404 | 11/1995 |
| WO | WO 99/33965 | 7/1999 |
| WO | WO 99/60171 | 11/1999 |
| WO | WO 01/14535 | 3/2001 |
| WO | WO 2004/108899 | 12/2004 |
| WO | WO2005/033327 | 4/2005 |
| WO | WO 2006/009702 | 1/2006 |
| WO | WO 2007/011412 | 1/2007 |
| WO | WO 2007/088355 | 8/2007 |
| WO | WO 2007/127801 | 11/2007 |
| WO | WO 2008/024642 | 2/2008 |
| WO | WO 2008/028489 | 3/2008 |
| WO | WO 2009/015821 | 2/2009 |
| WO | WO 2009/021521 | 2/2009 |
| WO | WO 2009/025743 | 2/2009 |
| WO | WO 2009/077864 | 6/2009 |
| WO | WO 2009/100907 | 8/2009 |
| WO | WO 2009/130176 | 10/2009 |
| WO | WO 2009/158521 | 12/2009 |
| WO | WO 2010/056637 | 5/2010 |
| WO | WO 2011/008349 | 1/2011 |
| WO | WO 2011/017682 | 2/2011 |
| WO | WO 2011/132086 | 10/2011 |
| WO | WO 2013/040062 | 3/2013 |
| WO | WO 2013/117746 | 8/2013 |
| WO | WO 2014/006408 | 1/2014 |
| WO | WO 2014/008545 | 1/2014 |
| WO | WO 2014049255 | 4/2014 |
| WO | WO 2014/117873 | 8/2014 |
| WO | WO 2015/048098 | 4/2015 |
| WO | WO-2015048098 A1 * | 4/2015 ............... C12Q 1/04 |
| WO | WO 2016/024278 | 2/2016 |
| WO | WO 2016/059636 | 4/2016 |
| WO | WO 2016/079219 | 5/2016 |
| WO | WO 2016/092554 | 6/2016 |
| WO | WO 2017/149547 | 9/2017 |
| WO | WO 2017/149548 | 9/2017 |
| WO | WO 2017/221255 | 12/2017 |
| WO | WO 2018/011795 | 1/2018 |
| WO | WO 2018/011796 | 1/2018 |
| WO | WO 2018/060998 | 4/2018 |
| WO | WO 2018/060999 | 4/2018 |

OTHER PUBLICATIONS

Supplementary Materials for Zaas et al. Published Sep. 18, 2013, Sci. Transl. Med. 5, 203ra126 (2013), 21 pages. (Year: 2013).*

Applied Biosystems. TaqMan Gene Expression Assay solutions, 18 pages (Year: 2015).*

ThermoFisher Scientific. IFI27 Product details. Obtained from www.thermofisher.com on Oct. 7, 2020; 2 pages (Year: 2020).*

ThermoFisher Scientific. IFI44LProduct details. Obtained from www.thermofisher.com on Oct. 7, 2020; 2 pages (Year: 2020).*

Affymetrix (Application Focus: Whole-transcript Expression Analysis Gene Expression, 8 pages, 2007, obtained from http://www.affymetrix.com/support/technical/byproduct.affx?product=huexonst on Sep. 2, 2021) (Year: 2007).*

(56) References Cited

OTHER PUBLICATIONS

New England Biolabs catalog (1996/1997), pp. 111. (Year: 1997).*
Rothstein et al. (1994) PNAS USA 91: 4155-4159 (Year: 1994).*
IFI27 UCSC genome browser. Obtained from https://genome.ucsc.edu/cgi-bin/hgTracks?db=hg38&lastVirtModeType=default&lastVirtModeExtraState=&virtModeType=default&virtMode=0&nonVirtPosition=&position=chr14%3A94110732%2D94116695&hgsid=1508725053_XhWKwP7iHICyHYwxll2DEZWzOSEL on Dec. 1, 2022. 7 pages. (Year: 2022).*
JUP UCSC genome browser graphics. https://genome.ucsc.edu/cgi-bin/hgTracks?db=hg38&lastVirtModeType=default&lastVirtModeExtraState=&virtModeType=default&virtMode=0&nonVirtPosition=&position=chr17%3A41754609%2D41786711&hgsid=1508725053_XhWKwP7iHICyHYwxll2DEZWzOSEL. 3 pages. (Year: 2022).*
Office Action dated Nov. 28, 2019 From the Israel Patent Office Re. Application No. 254095 and Its Translation Into English. (7 Pages).
Restriction Official Action dated Nov. 29, 2019 From the US Patent and Trademark Office Re. U.S. Appl. No. 16/238,582. (7 pages).
Translation of Reason for Rejection dated Nov. 21, 2019 of OA of Nov. 12, 2019 From the Japanese Patent Office Re. Application No. 2017-126712. (2 Pages).
Notification of Office Action and Search Report dated Jan. 11, 2019 From the State Intellectual Property Office of the People's Republic of China Re. Application No. 201580055946.0. (5 Pages).
Office Action dated Jul. 30, 2020 From the Israel Patent Office Re. Application No. 261529 and Its Translation Into English. (5 Pages).
Office Action dated Jul. 30, 2020 From the Israel Patent Office Re. Application No. 261530 and Its Translation Into English. (5 Pages).
Restriction Official Action dated Jul. 30, 2020 from the US Patent and Trademark Office Re. U.S. Appl. No. 16/081,906. (7 pages).
Notification of Office Action dated Aug. 22, 2019 From the State Intellectual Property Office of the People's Republic of China Re. Application No. 201580055946.0. (3 Pages).
International Preliminary Report on Patentability dated Apr. 11, 2019 From the International Bureau of WIPO Re. Application No. PCT/IL2017/051088. (6 Pages).
International Preliminary Report on Patentability dated Apr. 11, 2019 From the International Bureau of WIPO Re. Application No. PCT/IL2017/051089. (7 Pages).
Notice of Reasons for Rejection dated Apr. 2, 2019 From the Japan Patent Office Re. Application No. 2017-126712 and Its Translation Into English. (8 Pages).
Official Action dated Apr. 15, 2019 From the US Patent and Trademark Office Re. U.S. Appl. No. 15/237,728. (16 Pages).
Official Action dated Dec. 17, 2018 From the US Patent and Trademark Office Re. U.S. Appl. No. 15/237,728. (39 pages).
Eberl et al. "A Rapid Crosstalk of Human γδ T Cells and Monocytes Drives the Acute Inflammation in Bacterial Infections", PLOS Pathogens 5(2): 1-16, 2009.
Tisato et al. "Low Circulating TRAIL Levels Are Associated with Increase of Resistin and Lipocalin-2/ngal Adipokines in Postmenopausal Women", Mediators of Inflammation, Article ID 5356020, 8 Pages, 2017.
Official Action dated Mar. 5, 2020 From the US Patent and Trademark Office Re. U.S. Appl. No. 15/713,722. (24 pages).
Partial European Search Report and Provisional Opinion dated Jun. 25, 2020 From the European Search Report Re. Application No. 20164056.2. (11 Pages).
Pepe et al. "Combining Diagnostic Test Results to Increase Accuracy", Biostatistics, XP055033234, 1(2): 123-140, Jun. 2000.
Hearing Notice dated Jul. 16, 2019 From the Government of India, Patent Office, Intellectual Property Building Re. Application No. 1780/MUMNP/2014. (3 Pages).
Notice of Allowance dated Jul. 29, 2019 From the US Patent and Trademark Office Re. U.S. Appl. No. 15/237,728. (21 pages).
Communication Pursuant to Article 94(3) EPC dated May 25, 2020 From the European Patent Office Re. Application No. 11748712.4. (7 Pages).

Official Action dated May 15, 2020 from the US Patent and Trademark Office Re. U.S. Appl. No. 16/238,582. (92 pages).
Official Action dated May 7, 2020 from the US Patent and Trademark Office Re. U.S. Appl. No. 16/157,193. (23 pages).
Supplementary European Search Report and the European Search Opinion dated May 4, 2020 From the European Patent Office Re. Application No. 17855163.6. (9 Pages).
Ali et al. "Reliability of Serum Procalcitonin Concentrations for the Diagnosis of Sepsis in Neonates", Egypt Journal of Immunology, 15(1): 75-84, 2008. Abstract only.
Becker et al. "Procalcitonin in Sepsis and Systemic Inflammation: a Harmful Biomarker and a Therapeutic Target", British Journal of Pharmacology, 159: 253-264, 2010.
Forde et al. "The Beneficial Pleiotropic Effects of Tumour Necrosis Factor-Related Apoptosis-Inducing Ligand (TRAIL) Within the Vasculature: A Review of the Evidence", Atherosclerosis, XP029468976, 247: 87-96, Available Online Feb. 9, 2016.
Herzig et al. "The Role of CXCL10 in the Pathogenesis of Experimental Septic Shock", Critical Care, 18(3): 1-18, 2014.
Ng et al. "IP-10 Is an Early Diagnostic Marker for Identification of Late-Onset Bacterial Infection in Preterm Infants", Pediatric Research, 61(1): 93-98, 2007.
Povoa et al. "C-Reactive Protein, an Early Marker of Community-Acquired Sepsis Resolution: a Multi-Center Prospective Observational Study", Critical Care, 15(4): 1-10, 2011.
Sasaki et al. "Differentiating Between Bacterial and Viral Infection by Measuring Both C-Reactive Protein and 2'-5'-Oligoadenylate Synthetase as Inflammatory Markers", Journal of Infection and Chemotherapy, XP055696216, 8(1): 76-80, Mar. 2002.
Notification of Office Action and Search Report dated Jul. 28, 2020 From the State Intellectual Property Office of the People's Republic of China Re. Application No. 201810781584.9 and Its Translation of Office Action Into English.
Bai et al. "A New Early Diagnostic Marker for Inflammatory Diseases—sTREM-1", International Journal of Pathology and Clinical Medicine, 27(1): 73-76, Feb. 2007.
Cai et al. "The Study on the Relationship Between PCT and CRP in Infective Diseases", Journal of Qiqihar University of Medicine, 32(5): 696-697, 2011.
Ju et al. "Research Progress of Some Inflammatory Markers in Infectious Diseases", Chinese Journal of Practical Internal Medicine, 30(Suppl.1): 80-81, Jun. 2010.
Notification of Office Action dated Jul. 2, 2019 From the State Intellectual Property Office of the People's Republic of China Re. Application No. 201580075265.0. (3 Pages).
Request for Examination dated Jun. 18, 2019 From the Federal Government Institution, Federal Institute of Industrial Property of the Federal Service for Intellectual Property, Patents and Trade Marks of the Russian Federation Re. Application No. 2017107750 and Its Translation of Office Action Into English. (11 Pages).
Translation dated Jul. 10, 2019 of Notification of Office Action dated Jul. 2, 2019 From the State Intellectual Property Office of the People's Republic of China Re. Application No. 201580075265.0. (1 Page).
Examination Report Under Sections 12 & 13 of the Patents Act, 1970 and the Patents Rules, 2003 dated Oct. 21, 2019 From the Government of India, Intellectual Property India, Patents, Designs, Trade Marks, Geographical Indications Re. Application No. 9122/DELNP/2012 (5 Pages).
Notice of Reason for Rejection dated Nov. 12, 2019 From the Japan Patent Office Re. Application No. 2017-126712 and an English Summary. (3 Pages).
Communication Pursuant to Article 94(3) EPC dated Jun. 4, 2020 From the European Patent Office Re. Application No. 17759388.6. (3 Pages).
Supplementary European Search Report and the European Search Opinion dated May 18, 2020 From the European Patent Office Re. Application No. 17855164.4. (13 Pages).
Shommu et al. "Metabolomic and Inflammatory Mediator Based Biomarker Profiling as a Potential Novel Method to Aid Pediatric Appendicitis Identification", Plos One, XP055692841, 13(3): e0193563-1-e0193563-13, Mar. 12, 2018.

(56) References Cited

OTHER PUBLICATIONS

Official Action dated Jan. 4, 2019 From the US Patent and Trademark Office Re. Application No. 151713,722. (72 pages).
Corada et al. "Monoclonal Antibodies Directed to Different Regions of Vascular Endothelial Cadherin Extracellular Domain Affect Adhesion and Clustering of the Protein and Modulate Endothelial Permeability", Blood, 97(6): 1679-1684, Mar. 15, 2001.
Hinson et al. "Viperin Is Highly Induced in Neutrophils and Macrophages during Acute and Chronic Lymphocytic Choriomeningitis Virus Infection", The Journal of Immunology, 184:5723-5731, 2010.
Padlan "X-Ray Crystallography of Antibodies", Advances in Protein Chemistry, 49: 57-133; 1996.
Notice of Reason for Rejection dated Aug. 20, 2019 From the Japan Patent Office Re. Application No. 2017-507867 and Its Translation Into English. (5 Pages).
Final Official Action dated Sep. 8, 2020 from the US Patent and Trademark Office Re. U.S. Appl. No. 16/687,726. (28 pages).
Restriction Official Action dated Sep. 10, 2020 from the US Patent and Trademark Office Re. U.S. Appl. No. 16/316,631. (6 pages).
Communication Pursuant to Article 94(3) EPC dated Jul. 31, 2019 From the European Patent Office Re. Application No. 18162713.4. (4 Pages).
Ludwig et al. "Tumor Necrosis Factor Related Apoptosis Inducing Ligand: A Novell Mechanism for Bacillus Calmette Guerin Induced Antitumor Activity" Cancer Research 64: 3386-3390, May 15, 2004.
Restriction Official Action dated Dec. 5, 2019 From the US Patent and Trademark Office Re. U.S. Appl. No. 16/081,906. (9 pages).
Official Action dated Feb. 3, 2020 From the US Patent and Trademark Office Re. U.S. Appl. No. 16/355,984. (24 pages).
Search Report and Opinion dated Dec. 10, 2019 From the Servico Publico Federal, Ministerio da Economia, Instituto Nacional da Propriedade Industrial do Brasil Re. Application No. BR112017002884-0 and Its Translation Into English. (7 Pages).
Supplementary European Search Report and the European Search Opinion dated Jan. 21, 2020 From the European Patent Office Re. Application No. 17827122.7.
Official Action dated Oct. 15, 2019 From the US Patent and Trademark Office Re. Application No. 151713,722. (57 Pages).
Official Action dated Sep. 16, 2019 From the US Patent and Trademark Office Re. U.S. Appl. No. 16/355,984. (44 pages).
Official Action dated Sep. 18, 2019 From the US Patent and Trademark Office Re. U.S. Appl. No. 16/157,193. (30 pages).
Official Action dated Oct. 24, 2019 From the US Patent and Trademark Office Re. U.S. Appl. No. 15/531,747. (37 Pages).
Requisition by the Examiner dated Oct. 4, 2019 From the Innovation, Science and Economic Development Canada, Canadian Intellectual Property Office Re. Application No. 2,863,819. (3 Pages).
Supplementary European Search Report and the European Search Opinion dated Sep. 30, 2019 From the European Patent Office Re. Application No. 17759388.6. (11 Pages).
Supplementary Partial European Search Report and the European Provisional Opinion dated Oct. 24, 2019 From the European Patent Office Re. Application No. 17759389.4. (15 Pages).
Translation dated Sep. 22, 2019 of Search Report and Opinion dated Aug. 20, 2019 From the Servi?o Publico Federal, Ministerio da Economia, Instituto Nacional da Propriedade Industrial do Brasil Re. Application No. BR112014019733-4 and Its Summary in English. (4 Pages).
Barnhart et al. "Changes in Cellular mRNA Stability, Splicing, and Polyadenylation Through HuR Protein Sequestration by a Cytoplasmic RNA Virus", Cell Reports, XP055621573, 5(4): 909-917, Nov. 27, 2013.
Consiglio et al. "BEAT: Bioinformatics Exon Array Tool to Store, Analyze and Visualize Affymetrix GeneChip Human Exon Array Data From Disease Experiments", BMC Bioinformatics, XP021117755, 13(Suppl.4): S21-1-S21-14, Mar. 28, 2012.
UCSC "UCSC Browser on Human Feb. 2009 (GRCh37/hg19) Assembly: Showing Location of Probes on the Affymetrix ExonChip Binding to Exons of ANKRD22", UCSC Browser, XP055621243, Retrieved From the Internet, 7 P., Jan. 2009.
UCSC "UCSC Genome Browser on Human Feb. 2009 (GRCh37/hg19) Assembly: Showing Location of Probes on the Affymetrix ExonChip Binding to Exons of AIM2", UCSC Browser, XP055621240, Retrieved From the Internet, 8 P., Jan. 2009.
Zaas et al. "The Current Epidemiology and Clinical Decisions Surrounding Acute Respiratory Infections", Trends in Molecular Medicine, XP055522333, 20(10): 579-588, Published Online Sep. 5, 2014.
Noticification of Office Action and Search Report dated Feb. 19, 2019 From the State Intellectual Property Office of the People's Republic of China Re. Application No. 201580075265.0 and a Summary of the Notification of Office Action Into English. (7 Pages).
Search Report and Opinion dated Aug. 20, 2019 From the Serviço Publico Federal, Ministerio da Economia, Instituto Nacional da Propriedade Industrial do Brasil Re. Application No. BR112014 019733-4 and Its Summary in English. (4 Pages).
Translation dated Sep. 11, 2019 of Notification of Office Action dated Aug. 22, 2019 From the State Intellectual Property Office of the People's Republic of China Re. Application No. 201580055946.0. (1 Page).
Supplementary European Search Report and the European Search Opinion dated Jan. 28, 2020 From the European Patent Office Re. Application No. 17759389.4. (11 Pages).
Communication Pursuant to Article 94(3) EPC dated Aug. 18, 2020 From the European Patent Office Re. Application No. 11748712.4. (3 Pages).
Translation dated Mar. 20, 2019 of Notification of Office Action dated Feb. 19, 2019 From the State Intellectual Property Office of the People's Republic of China Re. Application No. 201580075265.0. (5 Pages).
Advisory Action Before the Filing of an Appeal Brief dated Dec. 23, 2019 From the US Patent and Trademark Office Re. U.S. Appl. No. 16/157,193. (3 pages).
Communication Pursuant to Article 94(3) EPC dated Mar. 25, 2020 From the European Patent Office Re. Application No. 18162713.4. (5 Pages).
Communication Pursuant to Article 94(3) EPC dated Mar. 27, 2020 From the European Patent Office Re. Application No. 15868614.7. (6 Pages).
Official Action dated Mar. 26, 2020 from the US Patent and Trademark Office Re. U.S. Appl. No. 16/687,726. (47 pages).
Official Action dated Mar. 31, 2020 from the US Patent and Trademark Office Re. U.S. Appl. No. 15/531,747. (21 pages).
Greenspan et al. "Defining Epitopes: It's Not as Easy as It Seems", Nature Biotechnology, 17: 936-937, Oct. 1999.
Lloyd et al. "Modelling The Human Immune Response: Performance of a 1011 Human Antibody Repertoire Against a Broad Panel of Therapeutically Relevant Antigens", Protein Engineering, Design & Selection 22(3): 159-168, Oct. 29, 2008.
Rudikoff et al. "Single Amino Acid Substitution Altering Antigen-Binding Specificity", PNAS, 79(6): 1979-1983, Mar. 1982.
Communication Pursuant to Article 94(3) EPC dated May 7, 2019 From the European Patent Office Re. Application No. 15831781.8. (3 Pages).
Examination Report dated May 29, 2019 From the Australian Government, IP Australia Re. Application No. 2018202302. (5 Pages).
Notification of Office Action dated Jun. 3, 2019 From the China National Intellectual Property Administration Re. Application No. 201610817276.8 and Its Translation Into English. (10 Pages).
International Preliminary Report on Patentability dated Jan. 24, 2019 From the International Bureau of WIPO Re. Application No. PCT/IL2017/050780. (9 Pages).
International Preliminary Report on Patentability dated Jan. 24, 2019 From the International Bureau of WIPO Re. Application No. PCT/IL2017/050781. (7 Pages).
Translation of Notification dated Jan. 30, 2019 From OA dated Jan. 11, 2019 From the State Intellectual Property Office of the People's Republic of China Re. Application No. 201580055946.0.(1 Page).

(56) References Cited

OTHER PUBLICATIONS

Applicant-Initiated Interview Summary dated Jul. 6, 2016 From the US Patent and Trademark Office Re. U.S. Appl. No. 14/377,887.
Applicant-Initiated Interview Summary dated Jul. 17, 2015 From the US Patent and Trademark Office Re. U.S. Appl. No. 13/090,893.
Applicant-Initiated Interview Summary dated Feb. 22, 2017 From the US Patent and Trademark Office Re. U.S. Appl. No. 14/377,887. (3 Pages).
Applicant-Initiated Interview Summary dated Oct. 26, 2017 From the US Patent and Trademark Office Re. U.S. Appl. No. 15/237,728. (3 pages).
Applicant-Initiated Interview Summary dated Jul. 30, 2018 From the US Patent and Trademark Office Re. U.S. Appl. No. 15/641,400. (3 pages).
Communication Pursuant to Article 94(3) EPC dated Dec. 9, 2016 From the European Patent Office Re. Application No. 13703112.6. (4 Pages).
Communication Pursuant to Article 94(3) EPC dated Oct. 9, 2018 From the European Patent Office Re. Application No. 11748712.4. (8 Pages).
Communication Pursuant to Article 94(3) EPC dated Jun. 17, 2016 From the European Patent Office Re. Application No. 11748712.4.
European Search Report and the European Search Opinion dated May 16, 2018 From the European Patent Office Re. Application No. 18162713.4. (7 Pages).
Examination Report dated Oct. 6, 2017 From the Australian Government, IP Australia Re. Application No. 2013217935. (2 Pages).
Examination Report Under Sections 12 & 13 of the Patents Act, 1970 and the Patents Rules, 2003 dated Mar. 26, 2018 From the Government of India, Intellectual Property India, Patents, Designs, Trade Marks, Geographical Indications Re. Application No. 9122/DELNP/2012. (7 Pages).
Examination Report Under Sections 12 & 13 of the Patents Act, 1970 and the Patents Rules, 2003 dated Nov. 30, 2018 From the Government of India, Intellectual Property India, Patents, Designs, Trade Marks, Geographical Indications Re. Application No. 1780/MUMNP/2014. (7 Pages).
Examiner-Initiated Interview Summary dated Nov. 27, 2017 From the US Patent and Trademark Office Re. U.S. Appl. No. 15/518,491. (2 pages).
International Preliminary Report on Patentability dated Sep. 13, 2018 From the International Bureau of WIPO Re. Application No. PCT/IL2017/050270. (7 Pages).
International Preliminary Report on Patentability dated Sep. 13, 2018 From the International Bureau of WIPO Re. Application No. PCT/IL2017/050271. (9 Pages).
International Preliminary Report on Patentability dated Jun. 22, 2017 From the International Bureau of WIPO Re. Application No. PCT/IL2015/051201. (7 Pages).
International Preliminary Report on Patentability dated Feb. 23, 2017 From the International Bureau of WIPO Re. Application No. PCT/IL2015/050823. (7 Pages).
International Preliminary Report on Patentability dated Apr. 27, 2017 From the International Bureau of WIPO Re. Application No. PCT/IL2015/051024. (7 Pages).
International Search Report and the Written Opinion dated Mar. 12, 2012 From the International Searching Authority Re. Application No. PCT/IB2011/001299.
International Search Report and the Written Opinion dated Sep. 14, 2017 From the International Searching Authority Re. Application No. PCT/IL2017/050781. (12 Pages).
International Search Report and the Written Opinion dated Jun. 15, 2017 From the International Searching Authority Re. Application No. PCT/IL2017/050270. (13 Pages).
International Search Report and the Written Opinion dated Jun. 15, 2017 From the International Searching Authority Re. Application No. PCT/IL2017/050271. (16 Pages).
International Search Report and the Written Opinion dated Sep. 18, 2017 From the International Searching Authority Re. Application No. PCT/IL2017/050780. (15 Pages).
International Search Report and the Written Opinion dated Jan. 20, 2016 From the International Searching Authority Re. Application No. PCT/IL2015/051024.
International Search Report and the Written Opinion dated Feb. 22, 2016 From the International Searching Authority Re. Application No. PCT/IL2015/051201.
International Search Report and the Written Opinion dated Dec. 25, 2017 From the International Searching Authority Re. Application No. PCT/IL2017/051088. (9 Pages).
International Search Report and the Written Opinion dated Dec. 28, 2017 From the International Searching Authority Re. Application No. PCT/IL2017/051089. (10 Pages).
International Search Report and the Written Opinion dated Nov. 29, 2015 From the International Searching Authority Re. Application No. PCT/IL2015/050823.
International Search Report dated Apr. 5, 2013 From the International Searching Authority Re. Application No. PCT/EP2013/052619.
Notice of Non-Compliant Amendment dated Aug. 4, 2015 From the US Patent and Trademark Office Re. U.S. Appl. No. 13/090,893.
Notice of Reasons for Rejection dated Nov. 1, 2016 From the Japan Patent Office Re. Application No. 2014-556086 and Its Translation Into English. (12 Pages).
Notice of Reasons for Rejection dated Jun. 19, 2018 From the Japan Patent Office Re. Application No. 2017-126712 and Its Translation Into English. (9 Pages).
Notice on Office Action and the Search Report dated Feb. 25, 2015 From the State Intellectual Property Office of the People's Republic of China Re. Application No. 201180030792.1 and Its Translation Into English.
Notification of Office Action and Search Report dated Mar. 4, 2016 From the State Intellectual Property Office of the People's Republic of China Re. Application No. 201380019055.0.
Notification of Office Action and Search Report dated Jun. 19, 2018 From the State Intellectual Property Office of the People's Republic of China Re. Application No. 201580075265.0 and its English Summary. (14 Pages).
Notification of Office Action and Search Report dated Oct. 30, 2017 From the State Intellectual Property Office of the People's Republic of China Re. Application No. 201610817276.8. (10 Pages).
Notification of Office Action dated Jul. 3, 2015 From the State Intellectual Property Office of the People's Republic of China Re. Application No. 201380019055.0.
Notification of Office Action dated Aug. 4, 2016 From the State Intellectual Property Office of the People's Republic of China Re. Application No. 201380019055.0 and Its Translation Into English.
Notification of Office Action dated May 6, 2014 From the State Intellectual Property Office of the People's Republic of China Re. Application No. 201180030792.1 and Its Translation Into English.
Notification of Office Action dated Jan. 21, 2016 From the State Intellectual Property Office of the People's Republic of China Re. Application No. 201180030792.1 and its Translation into English.
Notification of Office Action dated Aug. 25, 2017 From the State Intellectual Property Office of the People's Republic of China Re. Application No. 201380019055.0. (6 Pages).
Notification of Office Action dated Aug. 28, 2015 From the State Intellectual Property Office of the People's Republic of China Re. Application No. 201180030792.1 and Its Translation Into English.
Notification of Office Action dated Aug. 30, 2018 From the State Intellectual Property Office of the People's Republic of China Re. Application No. 201610817276.8 and Its Translation Into English. (22 Pages).
Notification of Reexamination dated Jan. 12, 2018 From the State Intellectual Property Office of the People's Republic of China Re. Application No. 2013800190and Its Machine Translation into English.
Office Action dated Jun. 20, 2018 From the State Intellectual Property Office of the People's Republic of China Re. Application No. 201580055946.0 and Its Summary of the Notification of Office Action Into English.).(5 Pages).
Office Action dated Feb. 29, 2016 From the Israel Patent Office Re. Application No. 233998 and Its Translation Into English.

(56) References Cited

OTHER PUBLICATIONS

Official Action dated Sep. 1, 2015 From the US Patent and Trademark Office Re. U.S. Appl. No. 13/090,893.
Official Action dated Apr. 4, 2016 From the US Patent and Trademark Office Re. U.S. Appl. No. 13/090,893.
Official Action dated Feb. 6, 2018 From the US Patent and Trademark Office Re. U.S. Appl. No. 15/503,439. (63 pages).
Official Action dated Nov. 7, 2016 From the US Patent and Trademark Office Re. U.S. Appl. No. 13/090,893. (26 pages).
Official Action dated Jun. 10, 2013 From the US Patent and Trademark Office Re. U.S. Appl. No. 13/090,893.
Official Action dated Apr. 12, 2018 From the US Patent and Trademark Office Re. U.S. Appl. No. 15/518,491. (59 pages).
Official Action dated Aug. 12, 2015 From the US Patent and Trademark Office Re. U.S. Appl. No. 14/377,887.
Official Action dated May 12, 2017 From the US Patent and Trademark Office Re. U.S. Appl. No. 15/237,728. (27 pages).
Official Action dated Apr. 13, 2016 From the US Patent and Trademark Office Re. U.S. Appl. No. 14/377,887.
Official Action dated Mar. 13, 2014 From the US Patent and Trademark Office Re. U.S. Appl. No. 13/090,893.
Official Action dated Dec. 15, 2016 From the US Patent and Trademark Office Re. U.S. Appl. No. 14/377,887. (22 pages).
Official Action dated May 15, 2018 From the US Patent and Trademark Office Re. U.S. Appl. No. 15/237,728. (55 pages).
Official Action dated Nov. 16, 2018 From the US Patent and Trademark Office Re. U.S. Appl. No. 15/503,439. (41 pages).
Official Action dated Nov. 18, 2016 From the US Patent and Trademark Office Re. U.S. Appl. No. 15/237,728. (33 pages).
Official Action dated Jan. 26, 2017 From the US Patent and Trademark Office Re. U.S. Appl. No. 15/015,309. (45 pages).
Official Action dated Mar. 26, 2015 From the US Patent and Trademark Office Re. U.S. Appl. No. 13/090,893.
Official Action dated Apr. 30, 2018 From the US Patent and Trademark Office Re. U.S. Appl. No. 15/641,400. (62 pages).
Official Action dated Mar. 30, 2018 From the US Patent and Trademark Office Re. U.S. Appl. No. 15/531,747. (67 pages).
Requisition by the Examiner dated Nov. 9, 2018 From the Innovation, Science and Economic Development Canada, Canadian Intellectual Property Office Re. Application No. 2,796,666. (3 Pages).
Requisition by the Examiner dated Jan. 18, 2018 From the Innovation, Science and Economic Development Canada, Canadian Intellectual Property Office Re. Application No. 2,796,666. (5 Pages).
Restriction Official Action dated Nov. 2, 2017 From the US Patent and Trademark Office Re. U.S. Appl. No. 15/531,747. (9 pages).
Restriction Official Action dated Nov. 8, 2018 From the US Patent and Trademark Office Re. U.S. Appl. No. 16/157,193. (5 pages).
Restriction Official Action dated May 10, 2018 From the US Patent and Trademark Office Re. U.S. Appl. No. 15/713,722. (6 Pages).
Restriction Official Action dated Feb. 13, 2013 From the US Patent and Trademark Office Re. U.S. Appl. No. 13/090,893.
Restriction Official Action dated May 15, 2015 From the US Patent and Trademark Office Re. U.S. Appl. No. 14/377,887.
Restriction Official Action dated Aug. 31, 2017 From the US Patent and Trademark Office Re. U.S. Appl. No. 15/518,491. (6 pages).
Search Report dated May 6, 2014 From the State Intellectual Property Office of the People's Republic of China Re. Application No. 201180030792.1 and Its Translation Into English.
Second Notice of Allowance dated Dec. 12, 2018 From the US Patent and Trademark Office Re. U.S. Appl. No. 15/641,400. (7 pages).
Supplementary European Search Report and the European Search Opinion dated Mar. 15, 2018 From the European Patent Office Re. Application No. 15831781.8. (11 Pages).
Supplementary European Search Report and the European Search Opinion dated Sep. 17, 2018 From the European Patent Office Re. Application No. 15868614.7. (18 Pages).
Supplementary Partial European Search Report and the European Provisional Opinion dated Jun. 1, 2018 From the European Patent Office Re. Application No. 15868614.7. (23 Pages).
Translation dated Sep. 4, 2017 of Notification of Office Action dated Aug. 25, 2017 From the State Intellectual Property Office of the People's Republic of China Re. Application No. 201380019055.0.
Translation dated Apr. 5, 2016 of Notification of Office Action dated Mar. 4, 2016 From the State Intellectual Property Office of the People's Republic of China Re. Application No. 201380019055.0.
Translation dated Sep. 21, 2015 of Office Action dated Jul. 3, 2015 From the State Intellectual Property Office of the People's Republic of China Re. Application No. 201380019055.0.
Translation of Notification of Office Action and Search Report dated Oct. 30, 2017 From the State Intellectual Property Office of the People's Republic of China Re. Application No. 201610817276.8. (16 Pages).
Alexander et al. "*Staphylococcus aureus* and *Salmonella* enterica Serovar Dublin Induce Tumor Necrosis Factor-Related Apoptosis-Inducing Ligand Expression by Normal 1/1ouse and Human Osteoblasts", Infection and Immunity, 69(3): 1581-1586, Mar. 2001.
Biezeveld et al. "Sustained Activation of Neutrophils in the Course of Kawasaki Disease: An Association with Matrix Metalloproteinases", Clinical & Experimental Immunology 141(1): 183-188, Jul. 2005.
Boldrick et al. "Stereotyped and Specific Gene Expression Programs in Human Innate Immune Responses to Bacteria", Proc. Natl. Acad. Sci. USA, PNAS, 99(2): 972-977, Jan. 22, 2002.
Borjesson et al. "Insights Into Pathogen Immune Evasion Mechanisms: Anaplasma Phagocytophilum Fails to Induce an Apoptosis Differentiation Program in Human Neutrophils", The Jurnal of Immunology, 174: 6364-6372, 2005.
Boser et al. "A Training Algorithm for Optimal Margin Classifiers", Proceedings of the 5th Annual ACM Workshop on Computational Learning Theory, COLT'92, Pittsburgh, PA, USA, Jul. 27-29, 1992, p. 144-152, Jul. 27, 1992.
Calvano et al. "A Network-Based Analysis of Systemic Inflammation in Humans", Nature, 437: 1032-1037, Oct. 13, 2005.
Carrol et al. "The Diagnostic and Prognostic Accuracy of Five Markers of Serious Bacterial Infection in Malawian Children With Sign of Severe Infection", PLoS ONE, 4(8): e6621-1-e6621-8, Aug. 2009.
Chagan-Yasutan et al. "Persistent Elevation of Plasma Osteopontin Levels in HIV Patients Despite Highly Active Antiretroviral Therapy", The Tohoku Journal of Experimental Medicine, 218(4): 285-292, Aug. 2009.
Chaussabel et al. "Analysis of Significance Patterns Identifies Ubiquitous and Disease-Specific Gene-Expression Signatures in Patient Peripheral Blood Leukocytes", Annals of the New York Academy of Sciences, 1062: 146-154, 2005.
Chen et al. "Discordant Protein and mRNA Expression in Lung Adenocarcinomas", Molecular & Cellular Proteomics: MCP, 1(4): 304-313, Apr. 2002.
Chieux et al. "MxA Protein in Capillary Blood of Children With Viral Infections", Journal of Medical Virology, 59: 547-551, 1999.
Chieux et al. "The MxA Protein Levels in Whole Blood Lysates of Patients With Various Viral Infections", Journal of Virological Methods, 70: 183-191, 1998.
Cowland et al. "Molerular Charaderization and Pattern of Tissue Expression of the Gene for Neutrophil Gelatinase-Associated Upocalin from Humans", Genomics, 45:17-23,1997.
Cristianini et al. "An Introduction to Support Vector Machines and Other Kernel-Based Learning Methods: Contents", Cambridge University Press, 4 P., 2000.
Crowe et al. "Quantitative Immunocytofluorographic Analysis of CD4 Surface Antigen Expression and HIV Infection of Human Peripheral Blood Monocyte/Macrophages", Aids Research and Human Retroviruses, 3(2): 135-145, 1987.
Cummins et al. "The TRAIL to Viral Pathogenesis: The Good, the Bad and the Ugly", Current Molecular Medicine, XP055056835, 9(4): 495-505, May 1, 2009.
Duda et al. "Contents". Pattern Classification, 2nd Ed., 11 P., 2001.

(56) References Cited

OTHER PUBLICATIONS

Falschlehner et al. "Following TRAIL'S Path in the Immune System", Immunology, XP055056763, 127(2): 145-154, Jun. 1, 2009. Chapter 'TRAIL in Viral and Bacterial Infections'.

Feezor et al. "Molecular Characterization of the Acute Inflammatory Response to Infections With Gram-Negaitve Versus Gram-Positive Bacteria", Infection and Immunity, 71(10): 5803-5813, Oct. 2003.

Furey et al. "Support Vector Machine Classification and Validation of Cancer Tissue Samples Using Microarray Expression Data", Bioinformatics, 16(10): 906-914, Oct. 2000.

Halminen et al. "Expression of MxA Protein in Blood Lymphocytes Discriminates Between Viral and Bacterial Infections in Febrile Children", Pediatric Research, 41(5): 647-650, May 1997.

Hanley et al. "A Method of Comparing the Areas Under Receiver Operating Characteristics Curves Derived From the Same Cases", Radiology, 148(3): 839-843, Sep. 1983.

Hastie et al. "The Elements of Statistical Learning: Data Mining, Inference, and Prediction", Springer Series in Statistics, 2nd Ed., p. 1-745, 2001.

Hoffmann et al. "TRAIL Limits Excessive Host Immune Responses in Bacterial Meningitis", JCI the Journal of Clinical Investigation. 117(7): 2004-2013, Jul. 2, 2007.

Holland et al. "STAT3 Mutations in the Hyper-IgE Syndrome", The New England Journal of Medicine, 357(16): 1608-1619, Oct. 18, 2007.

Janols et al. "Lymphocyte and Monocyte Flow Cytometry Immunophenotyping as a Diagnostic Tool in Uncharacteristic Inflammatory Disorders", BMC Infectious Diseases, XP002663504, 10(205): 1-9, 2010. Abstract.

Jenner et al. "Insights Into Host Responses Against Pathogens From Transcriptional Profiling", Nature Review Microbiology, 3: 281-294, Apr. 2005.

Kaizer et al. "Gene Expression in Peripheral Blood Mononuclear Cells From Children With Diabetes", The Journal of Clinical Endocrinology & Metabolism, 92(9): 3705-3711, 2007.

Kawada et al. "Analysis of Gene-Expression Profiles by Oligonucleotide Microarray in Children With Influenza", Journal of General Virology, 87: 1677-1683, 2006.

Kohavi et al. "Wrappers for Feature Subset Selection", Artifical Intelligence, 97: 273-324, 1997.

Kotelkin et al. "Respiratory Syncytial Virus Infections Sensitizes Cells to Apoptosis Mediated by Tumor Necrosis Factor-Related Apoptosis-Inducing Ligand", Journal of Virology, XP055056816, 77(17): 9156-9172, Aug. 12, 2003. Fig.5B.

Lampe et al. "Expression of the Interferon-Induced MxA Protein in Viral Encephalitis", Neuropathology and Applied Neurobiology, 29(3): 273-279, May 27, 2003.

Le Roux "Les Examens a Visee Etiologique Dans les Pneumopathies Communautaires de l'Enfant (Hors Imagerie) [Laboratory Investigations in Acute Lower Respiratory Tract Infections in Children]", Archives de Pediatrie, XP002663501, 5(Suppl.1): 28S-32S, 1998. Abstract.

Leibovici et al. "The Benefit of Appropriate Empirical Antibiotic Treatment in Patients with Bloodstream Infection", Journal of Internal Medicine, 244(5): 379-386, Nov. 1, 1998.

Liabeuf et al. "The Circulating Soluble TRAIL Is a Negative Marker for Inflammation Inversely Associated With the Mortality Risk in Chronic Kidney Disease Patients", Nephrology Dialysis Transplantation, 25(8): 2596-2602, Advance Access Publication Feb. 26, 2010. Abstract, p. 2597, Right Col. 2nd Para, Figs.2, 3.

Liu et al. "Early Days: Genomics and Human Responses to Infection", Current Opinion in Microbiology, 9: 312-319, Available Online May 6, 2006.

Malcolm et al. "Microarrays Analysis of Lipopolysaccharide-Treated Human Neutrophils", American Journal of Physiology, Lung Cellular & Molecular Physiology, 284(4): L663-L670, First Published Dec. 20, 2002.

Mount "Bioinformatics: Sequence and Genome Analysis", Chaps. 1-10: 1-564, 2001.

Nakabayashi et al. "MxA-Based Recognition of Viral Illness in Febrile Children by a Whole Blood Assay", Pediatric Research, 60(6): 770-774, 2006.

Neu et al. "Expression of Tumor Necrosis Factor-?-Related Apoptosis-Inducing Ligand and Its Proapoptotic Receptors Is Down-Regulated during Gastric Infection with Virulent cagA+/vacAsl+ Helicobacter pylori Strains", The Journal of Infectious Diseases 191(4): 571-578, Feb. 15, 2005.

Niederman "Biological Markers to Determine Eligibility in Trials for Community-Acquired Pneumonia: A Focus on Procalcitonin", Clinical Infectious Diseases, XP002670357, 47(Suppl.3): S127-S132, Dec. 2008.

Niessner et al. "Prognostic Value of Apoptosis Markers in Advanced Heart Failure Patients", European Heart Journal, 30(7): 789-796, Published Online Feb. 4, 2009. Abstract, Table 2, Fig.2.

Oda et al. "A Comprehensive Map of the Toll-Like Receptor Signaling Network", Molecular Systems Biology, 2(2006.0015): 1-20, Apr. 18, 2006.

Oved et al. "A Novel Host-Proteome Signature for Distinguishing Between Acute Bacterial and Viral Infections", Plos One, 10(3): e0120012-1-e120012-18, Mar. 18, 2015. Figs.3C, 4.

Paul et al. "Systematic Review and Meta-Analysis of the Efficacy of Appropriate Empiric Antibiotic Therapy for Sepsis", Antimicrobial Agents and Chemotherapy, 54(11): 4851-4863, Nov. 2010.

Radom-Aizik et al. "Effects of 30 Min. of Aerobic Exercise on Gene Expression in Human Neutrophils", Journal of Applied Physiology, 104: 236-243, 2008.

Ramilo et al. "Gene Expression Patterns in Blood Leukocytes Discriminate Patients With Acute Infections", Blood, 109(5): 2066-2077, Mar. 1, 2007.

RayBiotech "Mouse L308 Array, Membrane [AAM-BLM-1]1-Series-308-Label-Based-Mouse-Cytok", RayBiotech, XP055473187, Retrieved From the Internet, 7 P., May 7, 2018.

Rosseau et al. "Comparative Transcriptional Profiling of the Lung Reveals Shared and Distinct Features of *Streptococcus* Pneumoniae and Influenza A Virus Infection", Immunology, 120: 380-391, 2006.

Secchiero et al. "Potential Prognostic Significance of Decreased Serum Levels of TRAIL After Acute Myocardial Infarction", PLoS One, XP055056988, 4(2): e4442-1-e4442-6, Feb. 16, 2009. Fig.1.

Shimetani et al. "Levels of Three Inflammation Markers, C-Reactive Protein, Serum Amyloid a Protein and Procalcitonin, in the Serum and Cerebrospinal Fluid of Patients With Meningitis", Scandinavian Journal of Clinical and Laboratory Investigation, XP008113027, 61(7): 567-574, 2001. Abstract.

Singer et al. "The Third International Consensus Definitions for Sepsis and Septic Shock (Sepsis-3)", Journal of the American Medical Association, JAMA, 315(8): 801-810, Feb. 23, 2016. Box 3, Fig.

Smith et al. "Quantitative Assessment of Human Whole Blood RNA as a Potential Biomarker for Infectious Disease", Analyst, 132: 1200-1209, First Published Oct. 31, 2007.

Sukumaran et al. "Early Transcriptional Response of Human Neutrophils to Anaplasma Phagocytophilum Infection", Infection and Immunity, 73(12): 8089-8099, Dec. 1, 2005.

Sullivan Pepe et al. "Combining Diagnostic Test Results to Increase Accuracy", Biostatistics, XP055033234, 1(2): 123-140, Jun. 1, 2000. Abstract, Section 2.4.

Tang et al. "Gene-Expression Profiling of Gram-Positive and Gram-Negative Sepsis in Critically Ill Patients", Critical Care Medicine, 36(4): 1125-1128, 2008.

Tang et al. "Hvpoxic Preconditioning Enhances the Benefit of Cardiac Progenitor Cell Therapy for Treatment of Myocardial Infarction bv Inducing CXCR4 Expression", Circulation Research, XP055473182, 104(10): 1209-1216, May 22, 2009. Online Table 1.

Tang et al. "The Use of Gene-Expression Profiling to Identify Candidate Genes in Human Sepsis", American Journal of Respiratory and Critical Care Medicine, 176: 676-684, Originally Published Jun. 15, 2007.

Thivierge et al. "Eukaryotic Elongation Factor 1A Interacts With Turnip Mosaic Virus RNA-Dependent RNA Polymerase and VPg-Pro in Virus-Induced Vesicles", Virology, XP002663503, 377(1): 216-225, Jul. 2008. Abstract, p. 220, r-h Col., Para 3—p. 222, r-h Col., Para 1.

(56) References Cited

OTHER PUBLICATIONS

Tian et al. "Soluble Tumor Necrosis Factor Related Apoptosis Inducing Ligand Level as a Predictor of Severity of Sepsis and the Risk of Mortality in Septic Patients", PLOS One, 8(12): e82204-1-e82204-5, Dec. 12, 2013. 'Study Design' Para, 'Inclusion Criteria' Para, Table 1, Figs.1, 3, Abstract, Table 1.
Torkkola "Feature Extraction by Non-Parametric Mutual Information Maximization", Journal of Machine Learning Research, 3: 1415-1438, Mar. 2003.
Tsuji "TRAILing Gastrointestinal Pathogenesis", Journal of Gastroenterology and Hepatology, 18(7): 753-755, Published Online Jun. 10, 2003.
Tworoger et al. "Collection, Processing, and Storage of Biological Samples in Epidemiologic Studies: Sex Hormones, Carotenoids, Inflammatory Markers, and Proteomics as Examples", Cancer Epidemiol Biomarkers and Prevention,15(9): 1578-1581, Sep. 2006.
Vapnik "Statistical Learning Theory", Adaptive and Learning Systems for Signal Processing, Communications, and Control, p. 1-732, 1998.—Part I.
Vapnik "Statistical Learning Theory", Adaptive and Learning Systems for Signal Processing, Communications, and Control, p. 1-732, 1998.—Part II.
Vapnik "Statistical Learning Theory", Adaptive and Learning Systems for Signal Processing, Communications, and Control, p. 1-732, 1998.—Part III.
Vapnik "Statistical Learning Theory", Adaptive and Learning Systems for Signal Processing, Communications, and Control, p. 1-732, 1998.—Part IV.
Vogel et al. "Sequence Signatures and mRNA Concentration Can Explain Two-Thirds of Protein Abundance Variation in a Human Cell Line", Molecular Systems Biology, 6(Art.400): 1-9, Published Online Aug. 24, 2010.
Wang et al. "Rotavirus Infection Alters Peripheral T-Cell Homeostasis in Children With Acute Diarrhea", Journal of Virology, 81(8): 3904-3912, Apr. 2007.
Whiteside et al. "Role of Human Natural Killer Cells in Health and Disease", Clinical and Diagnostic Laboratory Immunology, 1(2): 125-133, Mar. 31, 1994.
Xu et al. "Lipocalins as Biochemical Markers of Disease", Biochimica et Biophysica Acta, XP002376345, 1482(1): 298-307, Oct. 18, 2000. Abstract, Sections 3, 5, p. 303, col. 2—p. 304, col. 1, Bridging Para, p. 304, cols. 1-2, Bidging Para, Fig.1, Table 1.
Yamaji et al. "Significance of Eukaryotic Translation Elongation Factor 1A in Tobacco Mosaic Virus Infection", Archives of Virology. XP002663502, 155(2): 263-268, Feb. 2010. Abstract.
Yeung et al. "Serum Cytokines in Differentiating Between Viral and Bacterial Enterocolitis", Annals of Tropical Paediatrics, 24(4): 337-343, Published Online Jul. 18, 2013.
Zaas et al. "A Host-Based RT-PCR Gene Expression Signature to Identify Acute Respiratory Viral Infection", Science Translational Medicine, 5(203): 203ra126-1-203ra126-19, Sep. 18, 2013.
Zaas et al. "Gene Expression Signatures Diagnose Influenza and Other Symptomatic Respiratory Viral Infections in Humans", Cell Host & Microbe, XP002670360, 6(3): 207-217, Sep. 17, 2009. Abstract, p. 212, 1-h Col., p. 213, 1-h Col., Fig.4.
Zhu et al. "Use of Differential Display Analysis to Assess the Effect of Human Cytomegalovirus Infection on the Accumulation of Cellular RNAs: Induction of Interferon-Responsive RNAs", Proc. Natl. Acad. Sci. USA, XP002088235, 94(25): 13985-13990, Dec. 9, 1997. Abstract, Fig.2.
Zilliox et al. "Gene Expression Changes in Peripheral Blood Mononuclear Cells During Measles Virus Infection", Clinical and Vaccine Immunology, 14(7): 918-923, Jul. 2007.
Applicant-Initiated Interview Summary dated Feb. 10, 2020 From the US Patent and Trademark Office Re. U.S. Appl. No. 16/157,193. (3 pages).
Supplementary European Search Report and the European Search Opinion dated Feb. 18, 2020 From the European Patent Office Re. Application No. 17827121.9. (5 Pages).

Official Action dated Apr. 23, 2019 From the US Patent and Trademark Office Re. U.S. Appl. No. 16/157,193. (47 pages).
Dirke et al. "TRATL and DcR1 Expressions Are Differentially Regulated in the Pancreatic Islets of STZ-Versus CY-AppHed NOD Mice", Experimental Diabetes Research, Article ID 625813, pp. 1-11, 2011.
Kichev et al. "Tumor Necrosis Factor-Related Apoptosis-Inducing Ligand (TRAiL) Signaling and Cell Death in the Immature Central Nervous System after Hypoxia-Ischemia and Inflammation", Journal of Biological Chemistry 289(13): 9430-9439, 2014.
Notification of Lack of Unity and Search Report dated Jan. 21, 2019 From the Federal Government Institution, Federal Institute of Industrial Property of the Federal Service for Intellectual Property, Patents and Trade Marks of the Russian Federation Re. Application No. 2017107750 and Its Translation of Office Action Into English. (12 Pages).
Office Action dated Feb. 18, 2019 From the Israel Patent Office Re. Application No. 250585 and Its Translation Into English. (6 Pages).
Requisition by the Examiner dated Feb. 21, 2019 From the Innovation, Science and Economic Development Canada, Canadian Intellectual Property Office Re. Application No. 2,863,819. (8 Pages).
Official Action dated Dec. 30, 2020 from the US Patent and Trademark Office Re. U.S. Appl. No. 16/334,033. (112 pages).
Bone et al. "Definitions for Sepsis and Organ Failure and Guidelines for the Use of Innovative Therapies in Sepsis", Chest, 101(6): 1644-1655, 1992.
Kang et al. "Low serum TNF-Related Apoptosis-Inducing Ligand (TRAIL) Levels Are Associated with Acute Ischemic Stroke Severity", Atherosclerosis, 240: 228-233, 2015.
Michowitz et al. "The Involvement of Tumor Necrosis Factor-Related Apoptosis-Inducing Lisand(TRAIL) in Atherosclerosis.", Journal of the American College of Cardiology, 45(7): 1018-1024, 2005.
Osmancik et al. "Prognostic Value of TNF-Related Apoptosis Inducing Ligand (TRAIL) in Acute Coronary Syndrome Patients", PLoS One, 8(2): e53860, 2013.
Volpato et al. "Association of Tumor Necrosis Factor-Related Apoptosis-Inducing Ligand with Total and Cardiovascular Mortality in Older Adults", Atherosclerosis, 215: 452-458, 2011.
Notification of Office Action and Search Report dated Jun. 3, 2021 From the State Intellectual Property Office of the People's Republic of China Re. Application No. 20180014541.1 and Its Translation Into English. (17 Pages).
Requisition by the Examiner dated Jul. 30, 2021 From the Innovation, Science and Economic Development Canada, Canadian Intellectual Property Office Re. Application No. 2,954,601. (4 Pages).
Requisition by the Examiner dated Dec. 7, 2020 From the Innovation, Science and Economic Development Canada, Canadian Intellectual Property Office Re. Application No. 2,863,819. (4 Pages).
Examination Report Under Sections 12 & 13 of the Patents Act, 1970 and the Patents Rules, 2003 dated Mar. 31, 2021 From the Government of India, Intellectual Property India, Patents, Designs, Trade Marks, Geographical Indications, The Patent Office Re. Application No. 201727005513. (7 Pages).
Notice of Allowance dated Apr. 19, 2021 from the US Patent and Trademark Office Re. U.S. Appl. No. 16/238,582. (22 pages).
Bloos et al. "Rapid Diagnosis of Sepsis"; Virulence, 5(1): 154-160, 2014.
Henriquez-Camacho et al. "Biomarkers for Sepsis"; BioMed Research International, 547818: 6 pages, 2014.
Communication Pursuant to Article 94(3) EPC dated Nov. 12, 2020 From the European Patent Office Re. Application No. 17759389.4. (6 Page).
Official Action dated Nov. 23, 2020 From the US Patent and Trademark Office Re. U.S. Appl. No. 16/355,984. (9 pages).
Communication Pursuant to Article 94(3) EPC dated Jun. 2, 2021 From the European Patent Office Re. Application No. 17827121.9. (5 Pages).
Official Action dated Mar. 9, 2021 From the US Patent and Trademark Office Re. U.S. Appl. No. 16/316,631. (121 Pages).
Restriction Official Action dated Dec. 9, 2020 from the US Patent and Trademark Office Re. U.S. Appl. No. 16/336,528. (7 pages).

(56) References Cited

OTHER PUBLICATIONS

Notice of Reasons for Rejection dated Apr. 20, 2021 From the Japan Patent Office Re. Application No. 2020-021606 and Its Translation Into English. (9 Pages).
Official Action dated May 5, 2021 From the US Patent and Trademark Office Re. U.S. Appl. No. 16/336,528. (108 Pages).
Brost et al. "Differential Expression of the TRAIL/TRAIL-receptor System in Patients with Inflammatory Bowel Disease", Pathology—Research and Practice, 206(1):43-50, Jan. 15, 2010.
Communication Pursuant to Article 94(3) EPC dated Sep. 25, 2020 From the European Patent Office Re. Application No. 17827122.7. (5 Pages).
European Search Report and the European Search Opinion dated Sep. 28, 2020 From the European Patent Office Re. Application No. 20164056.2. (10 Pages).
Interview Summary dated Oct. 14, 2020 from the US Patent and Trademark Office Re. U.S. Appl. No. 16/081,906. (3 pages).
Notification of Office Action dated Mar. 5, 2021 From the State Intellectual Property Office of the People's Republic of China Re. Application No. 201810781584.9 and Its Translation of Office Action Into English. (13 Pages).
Official Action dated Mar. 10, 2021 From the US Patent and Trademark Office Re. U.S. Appl. No. 16/081,906. (127 Pages).
Shair et al. "Epstein-Barr Virus Latent Membrane Protein-1 Effects on Junctional Plakoglobin and Induction of a Cadherin Switch", Cancer Research, Cell, Tumor, and Stem Cell Biology, 69(14): 5734-5742, Jul. 15, 2009.
Interview Summary dated Feb. 1, 2021 From the US Patent and Trademark Office Re. U.S. Appl. No. 16/687,726. (2 Pages).
Notification of Office Action and Search Report dated Feb. 20, 2021 From the State Intellectual Property Office of the People's Republic of China Re. Application No. 201780014568.0. (9 Pages).
Notification of Office Action and Search Report dated Jul. 2, 2021 From the State Intellectual Property Office of the People's Republic of China Re. Application No. 201780055014.5. (23 Pages).
Notification of Office Action and Search Report dated Jul. 13, 2021 From the State Intellectual Property Office of the People's Republic of China Re. Application No. 20180781584.9 and an English Summary. (4 Pages).
Official Action dated Nov. 4, 2020 From the US Patent and Trademark Office Re. U.S. Appl. No. 16/238,582. (37 Pages).
Final Official Action dated Jun. 15, 2021 From the US Patent and Trademark Office Re. U.S. Appl. No. 16/334,033. (36 Pages).
Notice of Reason(s) for Rejection dated Jun. 15, 2021 From the Japan Patent Office Re. Application No. 2020-109710 and Its Translation Into English. (12 Pages).
European Search Report and the European Search Opinion dated Jul. 14, 2021 From the European Patent Office Re. Application No. 21170448.1. (6 Pages).
Notice of Allowance dated and Interview Summary Jul. 19, 2021 from the US Patent and Trademark Office Re. U.S. Appl. No. 16/687,726. (24 pages).
Translation dated Jul. 22, 2021 of Notification of Office Action dated Jul. 13, 2021 From the State Intellectual Property Office of the People's Republic of China Re. Application No. 20180781584.9. (2 Pages).
Translation dated Jul. 27, 2021 of Notification of Office Action dated Jul. 2, 2021 From the State Intellectual Property Office of the People's Republic of China Re. Application No. 201780055014.5. (12 Pages).
Patent Examination Report dated Feb. 8, 2021 From the Australian Government, IP Australia Re. Application No. 2015302870. (4 Pages).
Final Official Action dated Nov. 29 together with Interview Summary dated Nov. 14, 2021 from US Patent and Trademark Office Re. U.S. Appl. No. 16/081,906. (45 pages).
Notification of Office Action and Search Report dated Sep. 30, 2021 From the State Intellectual Property Office of the People's Republic of China Re. Application No. 201780073531.5 and Its Translation of Office Action Into English. (14 Pages).

Official Action dated Nov. 22, 2021 from the US Patent and Trademark Office Re. U.S. Appl. No. 16/998,006. (116 pages).
Requisition by the Examiner dated Nov. 5, 2021 From the Innovation, Science and Economic Development Canada, Canadian Intellectual Property Office Re. Application No. 2,968,650. (7 Pages).
Ioannidis et al. "Plasticity and Virus Specifity of the Airway Epithelial Cell Immune Response During Respiratory Virus Infection", Journal of Virology, 86(10): 5422-36, Mar. 7, 2012.
Zhang "Research Progress of Interferon-Inducible Protein 10 and Its Effect in Newborn Infection Diagnosis", Chinese Journal of Neonatology, 4: 60-62, Jul. 15, 2013.
Notification of Office Action and Search Report dated Dec. 23, 2021 From the State Intellectual Property Office of the People's Republic of China Re. Application No. 201780014541.1 and Its Translation of Office Action Into English. (14 Pages).
Notice of Allowance dated Jan. 5, 2022 from US Patent and Trademark Office Re. U.S. Appl. No. 16/316,631. (9 pages).
Notice of Reason(s) for Rejection dated Dec. 7, 2021 From the Japan Patent Office Re. Application No. 2020-021606 and Its Translation Into English. (11 Pages).
Notice of Reason(s) for Rejection dated Dec. 14, 2021 From the Japan Patent Office Re. Application No. 2020-109710 and Its Translation Into English. (7 Pages).
Notification of Office Action dated Dec. 3, 2021 From the State Intellectual Property Office of the People's Republic of China Re. Application No. 201780055014.5 and Its Translation Into English. (5 Pages).
English Translation Dated Feb. 16, 2022 of Grounds of Reason of Rejection dated Jan. 27, 2022 From the Korean Intellectual Property Office Re. Application No. 10-2017-7007002. (6 Pages).
Interview Summary dated Feb. 22, 2022 from US Patent and Trademark Office Re. U.S. Appl. No. 16/081,906 (2 pages).
Notification of Office Action dated Jan. 24, 2022 From the State Intellectual Property Office of the People's Republic of China Re. Application No. 201780014568.0 and its Translation into English, (9 Pages).
Notice of Allowance dated Feb. 7, 2022 from US Patent and Trademark Office Re. U.S. Appl. No. 16/336,528. (46 pages).
Requisition by the Examiner dated Feb. 9, 2022 From the Innovation, Science and Economic Development Canada, Canadian Intellectual Property Office Re. Application No. 2,954,601. (3 Pages).
Restriction Official Action dated Feb. 4, 2022 from US Patent and Trademark Office Re. U.S. Appl. No. 17/007,095. (6 pages).
Opposition to European Patent No. 3423589 Memed Diagnostics Ltd. on Behalf of J.A. Kemp LLP Dated Apr. 21, 2022 From the European Patent Office Re. Application No. 17759388.6. (31 Pages).
Chaussabel et al. "Assessing the Human Immune System Through Blood Transcriptomics", BMC Biology, 8: 84-1-84-14, Jul. 1, 2010.
De la Grange et al. "A New Advance in Alternative Splicing Databases: From Catalogue to Detailed Analysis of Regulation of Expression and Function of Human Alternative Splicing Variants", BMC Bioinformatics, 8: 180-1-180-14, Jun. 4, 2007.
Hu et al. "Gene Expression Profiles in Febrile Children With Defined Viral and Bacterial Infection", Proc. Natl. Acad. Sci. USA, PNAS, 110(31): 12792-12797, Published Online Jul. 15, 2013.
Qian et al. "Identification of Genes Critical for Resistance to Infection by West Nile Virus Using RNA-Seq Analysis", Viruses, 5(7): 1664-1681, Jul. 8, 2013.
UCSC "Human Gene IFI27 (ENST00000621160.5) From Gencode V39", UCSC Browser, Retrieved From the Interent, 3 Pages, Last Updated Jan. 17, 2022.
UCSC "Human Gene IFIT1 (ENST00000371804.4) From Gencode V39", UCSC Browser, Retrieved From the Internet, 4 Pages, Last Updated Jan. 17, 2022.
UCSC "UCSC Genome Browser on Human (GRCh38/hg38)", UCSC Browser, Retrieved From the Internet, 1 Page, Apr. 14, 2022.
Decision on Rejection Dated Aug. 30, 2022 From the National Intellectual Property Adminstration of the People's Republic of China Re. Application No. 201780073531.5 and Its Translation Into English. (13 Pages).
Technical Examination Report Dated Aug. 11, 2022 from the National Institute of Industrial Property of Brazil Re. Application No. BR 11 2017 002884 0 with an English Translation. (8 pages).

(56) References Cited

OTHER PUBLICATIONS

Notification of Office Action Dated May 11, 2022 From the State Intellectual Property Office of the People's Republic of China Re. Application No. 201780014541.1 and Its Translation Into English. (11 Pages).
Official Action Dated Jun. 9, 2022 from US Patent and Trademark Office Re. Application No. 17/007,095. (118 pages).
Requisition by the Examiner Dated Jun. 7, 2022 From the Innovation, Science and Economic Development Canada, Canadian Intellectual Property Office Re. Application No. 2,968,650. (3 Pages).
Summons to attend Oral Proceedings Pursuant to Rule 115(1) EPC Dated Jun. 10, 2022 From the European Patent Office Re. Application No. 17759389.4, (5 Pages).
Communication Pursuant to Article 94(3) EPC Dated Sep. 23, 2022 From the European Patent Office Re. Application No. 17855163.6. (7 Pages).
Requisition by the Examiner Dated Jul. 15, 2022 From the Innovation, Science and Economic Development Canada, Canadian Intellectual Property Office Re. Application No. 3,133,249. (4 Pages).
English Summary Dated Dec. 29, 2022 of Notification of Office Action Dated Dec. 2, 2022 From the State Intellectual Property Office of the People's Republic of China Re. Application No. 202010370187.X. (1 Page).
CNKI "Clinical Study on the Level of Plasma Tumor Necrosis Factor-Related Apoptosis-Inducing Ligang (TRAIL) in Evaluating the Prognosis of Patients With Sepsis", CNKI Master's E-Journals, 5: 4-26, Apr. 16, 2014.
Partial European Search Report and the European Search Opinion Dated Jan. 31, 2023 From the European Patent Office Re. Application No. 22169859.0. (13 Pages).
Decision to Refuse A European Patent Application Dated Mar. 15, 2023 From the European Patent Office Re. Application No. 17759389. 4. (4 Pages).
CNKI English Translation of "Clinical Study on the Level of Plasma Tumor Necrosis Factor-Related Apoptosis-Inducing Ligang (TRAIL) in Evaluating the Prognosis of Patients With Sepsis", CNKI Master's E-Journals, 5: 4-26, Apr. 16, 2014.
Requisition by the Examiner Dated Mar. 2, 2023 From the Innovation, Science and Economic Development Canada, Canadian Intellectual Property Office Re. Application No. 3,015,043. (5 Pages).
Requisition by the Examiner Dated Mar. 21, 2023 From the Innovation, Science and Economic Development Canada, Canadian Intellectual Property Office Re. Application No. 3,015,046. (6 pages).
Wang et al. "The significance of MMP-8, MMP-9 and FFN levels in pregnant women with bacterial vaginosis", Maternal and CHild Health Care of China, vol. 28, No. 28, 2013, pp. 4615-4617.
Notification of Office Action and Search Report Dated Dec. 9, 2022 From the State Intellectual Propertt Office of the People's Republic of China Re. Application No. 202010215941.2. (11 Pages).
Summary Dated Dec. 22, 2022 of Notification of Office Action and Search Report Dated Dec. 9, 2022 From the State Intellectual Property Office of the People's Republic of China Re. Application No. 202010215941.2. (4 Pages).
Ip et al. "Value of serum Procalcitonin, neopterin, and C-reactice protein in differentiating bacterial from viral etiologies in patients presenting with lower respiratory tract infections", Diagnostic Microbiology and Infectious Disease, 59(2):131-136, Oct. 2007.
Pauksen et al. "Serum Mesurements of Human Neutrophil Lipocalin (HNL) Discriminate Between Acute Bacterial and Viral Infections", Scandinavian Journal of Clinical and Laboratory Investigation, 55(2):125-131, 1995.
Notice of Allowance Dated May 10, 2023 from the U.S. Appl. No. 17/875,467. (122 pages).
Official Action Dated Apr. 19, 2023 from the U.S. Appl. No. 17/507,994. (189 pages).

Kramer et al. "Development and Characerization of New Rat Monoclonal Antibodies for Procalcitonin", Analytical and Bionalytical Chemistry, 392: 727-736, Aug. 19, 2008.
Vermot-Desroches et al. "Characterization of Monoclonal Antibodies Directed Against Trail or Trail Receptors", Cellular Immunology, 236(1-2): 86-91, Jul.-Aug. 2005.
Supplementary European Search Report and the European Search Opinion Dated Mar. 28, 2023 From the European Patent Office Re. Application No. 22204952.0. (12 Pages).
Abdel-Razik et al. "Diagnostic Utility of Interferon Gamma-induced Protein 10 kDa in Spontaneous Bacterial Peritonitis: Single-Center Study", European Journal of Gastroenterology & Hepatology, 27(9): 1087-1093, Sep. 2015.
Lighter et al. "Chemokine IP-10: an Adjunct Marker for Latent Tuberculosis Infection in Children", The International Journal of Tuberculosis and Lung Disease, 13(6): 731-736, Jun. 2009.
Punyadeera et al. "A Biomarker Panel to Discriminate Between Systemic Inflammatory Response Syndrome and Sepsis and Sepsis Severity", Journal of Emergencies, Trauma and Shock, 3(1): 26-35, Jan.-Mar. 2010.
Quint et al. "Serum IP-10 as a Biomarker of Human Rhinovirus Infection at Exacerbation of COPD", Science Direct, Chest, 137(4): 812-822, Apr. 2010.
Ruhwald et al. "IP-10 Can be Measured in Dried Plasma Spots in Patients with Chronic Hepatitis C Infection", PLoS One 7(9): e45181, 1-4, Sep. 14, 2012.
"C-Reactive Protein", Australian Prescriber, 20(3): 74-76, Jun. 2007.
Official Action Dated Apr. 3, 2024 from the U.S. Appl. No. 17/507,994. (50 pages).
Official Action Dated Apr. 8, 2024 from the U.S. Appl. No. 17/010,912. (233 pages).
Requisition by the Examiner Dated Apr. 5, 2024 From the Innovation, Science and Economic Development Canada, Canadian Intellectual Property Office Re. Application No. 3,190,715. (3 Pages).
Haider et al. "C-Reactive Protein is Expressed and Secreted by Peripheral Blood Mononuclear Cells", Clinical and Experimental Immunology, 146: 533-539, 2006.
Striver "The Treatment of Influenza With Antiviral Drugs", CMAJ, Canadian Medical Association, 168(1): 49-57, Jan. 7, 2003.
Suarez et al. "Superiority of Transcriptional Profiling Over Procalcitonin for Distinguishing Bacterial From Viral Lower Respiratory Tract Infections in Hospitalized Adults", The Journal of Infectious Diseases, 212:213-222, Jul. 15, 2015.
Communication Pursuant to Article 94(3) EPC Dated Apr. 8, 2024 From the European Patent Office Re. Application No. 22169859.0. (6 Pages).
Communication Pursuant to Article 94(3) EPC Dated Jul. 21, 2023 From the European Patent Office Re. Application No. 21178885.6 (6 Pages).
English Summary and Translation Dated Sep. 13, 2023 of Notification of Office Action Dated Aug. 29, 2023 From the State Intellectual Property Office of the People's Republic of China Re. Application No. 202010370187.X. (3 pages).
Hearing Notice Dated Sep. 9, 2023 From the Government of India, Intellectual Property India, The Patent Office Re. Application No. 201727005513. (3 Pages).
Notification of Office Action Dated Aug. 29, 2023 From the State Intellectual Property Office of the People's Republic of China Re. Application No. 202010370187.X. (3 Pages).
Official Action Dated Aug. 29, 2023 from the U.S. Appl. No. 17/372,575. (144 pages).
Fosgerau et al. "Interleukin-6 Autoantibodies are Involved in the Pathogenesis of a Subset of Type 2 Diabetes", Journal of Endocrinology,204: 265-273, 2010.
Gupta et al. "Distinct Functions of Autoantibodies Against Interferon in Systemic Lupus Erythematosus", Arthritis & Rheumatology, 68(7): 1677-1687, Jul. 2016.
Meyer "Anti-CRP antibodies in Systemic Lupus Erythematosus", Joint Bone Spine, 77"384-389, Jun. 2, 2010.
Thermo Scientific "ELISA Technical Guide and Protocols", Thermo Scientific, TR0065.0, 2010 (14 Pages).

(56) References Cited

OTHER PUBLICATIONS

Decision on Rejection Dated Jan. 4, 2024 From the State Intellectual Property Office of the People's Republic of China Re. Application No. 202010370187.X and Its Machine Translation Into English. (9 Pages).
English Summary Dated Jan. 25, 2024 of Decision on Rejection Dated Jan. 4, 2024 From the State Intellectual Property Office of the People's Republic of China Re. Application No. 202010370187.X (1 Page).
Official Action Dated May 8, 2024 from the U.S. Appl. No. 18/077,277. (63 pages).
Official Action Dated May 8, 2024 from the U.S. Appl. No. 17/841,704. (166 pages).
Landro et al. "Decreased Serum Lipocalin-2 Levels in Human Immunodeficiency Virus-infected Patients: Increase During Highly Active Anti-retroviral Therapy", Clinical and Experimantal Immunology, 152: 57-53. 2008.
Nicholson et al. "Late-Breaking Abstract: Plasma Level of TRAIL is Associated with Severity of Sepsis and Predicts Survival After Critical Illness", European Respiratory Journal, 48:OA3021, pp. 1-5, Nov. 2016.
Notice of Allowance Dated Mar. 13, 2024 from the U.S. Appl. No. 17/372,575. (28 pages).
Official Action Dated Jul. 17, 2023 from U.S. Appl. No. 17/717,200. (133 pages).
Liu et al. "CXCL10/IP-10 in Infectious Diseases Pathogenesis and Potential Therapeutic Implications", Cytokine & Growth Factor Reviews, 22(3): 121-130, Jun. 2011.
Communication Pursuant to Article 94(3) EPC Dated Jan. 31, 2024 From the European Patent Office Re. Application No. 17855163.6 (4 Pages).
Restriction Official Action Dated Feb. 1, 2024 from the U.S. Appl. No. 17/841,704. (6 pages).
Notice of Allowance Dated Mar. 27, 2024 from the U.S. Appl. No. 17/717,200. (34 pages).
Official Action Dated Mar. 26, 2024 from the U.S. Appl. No. 18/230,718. (67 pages).
Askarieh et al. "Systemic and Intrahepatic Interferon-Gamma-Inducible Protein 10 kDa Predicts the First-Phase Decline in Hepatitis C Virus RNA and Overall Viral Response to Therapy in Chronic Hepatitis C", Hepatology, 51: 1523:1530, 2010.
Bartolome et al. "Interleukin-28B Polymorphisms and Interferon Gamma Inducible Protein-10 Serum Levels in Seronegative Occult Hepatitis C Virus Infection", Journal of Medical Virology, 88(2):268-274, Feb. 2016.
Feld et al. "Plasma Interferon-Gamma Inducible Protein-10 Levels Are Associated with Early, but Not Sustained Virological Response during Treatment of Acute or Early Chronic HCV Infection", PLoS One 8(11): e80003, 1-11, Nov. 20, 2013.
Grebely et al. "Plasma Interferon-gamma-Inducible Protein-10 (IP-10) Levels During Acute Hepatitis C Virus Infection", Hepatology 57(6): 2124-2134, Jun. 2013.
Lagging et al. "IP-10 Predicts Viral Response and Therapeutic Outcome in Difficult-to-treat Patients with HCV Genotype 1 Infection", Hepatology 44(6): 1617-1625, Dec. 2006.
Sonneveld et al. "Pre-treatment Levels of IP-10 Predict Response to Peginterferon in HBeAg-positive Chronic Hepatitis B Patients 396", Hepatology 56(4): 386A-387A, Oct. 2012.
Communication Pursuant to Article 94(3) EPC Dated Oct. 30, 2023 From the European Patent Office Re. Application No. 17855164.4 (7 Pages).
Examination Report Dated Nov. 1, 2023 From the Australian Government, IP Australia Re. Application No. 2022200802. (6 Pages).
Official Action Dated Oct. 26, 2023 from the U.S. Appl. No. 18/077,277. (252 pages).
Requisition by the Examiner Dated Oct. 10, 2023 From the Innovation, Science and Economic Development Canada, Canadian Intellectual Property Office Re. Application No. 3,027,341. (5 Pages).
Restriction Official Action Dated Nov. 27, 2023 from the U.S. Appl. No. 17/010,912. (8 pages).
Van Deursen et al. "Prognostic Value of Plasma Neutrophil Gelatinase-Associated Lipocalin for Mortality in Patients with Heart Failure", Circulation: Heart Failure, 7: 35-42, Jan. 2014.
Communication Pursuant to Article 94(3) EPC Dated Jul. 9, 2024 From the European Patent Office Re. Application No. 15868614.7. (5 Pages).
Notification of Office Action and Search Report Dated Sep. 10, 2024 From the State Intellectual Property Office of the People's Republic of China Re. Application No. 202210796759.X and Its Translation into English. (26 Pages).
Consiglio et al. "BEAT: Bioinformatics Exon Array Tool to Store, Analyze and Visualize Affymetrix GeneChip Human Exon Array data from Disease Experiments", BMC Bioinformatics, 13 (Suppl 4): S21: 1-14, Mar. 28, 2012.
Interview Summary Dated Jul. 26, 2024 from the U.S. Appl. No. 17/507,994. (2 pages).
Notice of Allowance Dated Oct. 10, 2024 from the U.S. Appl. No. 17/841,704. (20 pages).
Notice of Allowance Dated Aug. 28, 2024 from U.S. Appl. No. 17/507,994. (10 pages).
Notice of Allowance Dated Jun. 18, 2024 from the U.S. Appl. No. 18/230,718. (17 pages).
Communication Pursuant to Article 94(3) EPC Dated Oct. 11, 2024 From the European Patent Office Re. Application No. 21170448.1 (5 Pages).
Herbeuval et al. "CD4+ T-cell Death Induced by Infectious and Noninfectious HIV-1: Role of Type 1 Interferon-dependent, TRAIL/DR5-mediated apoptosis", Blood, Immunobiology, 106(10): 3524-3531, Nov. 15, 2005.
Official Action Dated Nov. 7, 2024 from the U.S. Appl. No. 18/077,277. (162 pages).

* cited by examiner

ANALYZING RNA FOR DIAGNOSING INFECTION TYPE

RELATED APPLICATIONS

This application is a National Phase of PCT Patent Application No. PCT/IL2017/050270 having International filing date of Mar. 2, 2017, which claims the benefit of priority under 35 USC § 119(e) of U.S. Provisional Patent Application No. 62/302,994, filed on Mar. 3, 2016. The contents of the above applications are all incorporated by reference as if fully set forth herein in their entirety.

FIELD AND BACKGROUND OF THE INVENTION

The present invention, in some embodiments thereof, relates to the identification of signatures and determinants associated with bacterial and viral infections. More specifically, the present invention relates to RNA determinants that are differentially expressed in a statistically significant manner in subjects with bacterial and viral infections.

Antibiotics (Abx) are the world's most prescribed class of drugs with a 25-30 billion $US global market. Abx are also the world's most misused drug with a significant fraction of all drugs (40-70%) being wrongly prescribed (Linder and Stafford 2001; Scott and Cohen 2001; Davey, P. and E. Brown, et al 2006; Cadieux, G. and R. Tamblyn, et al. 2007; Pulcini, C. and E. Cua, et al. 2007)'("CDC—Get Smart: Fast Facts About Antibiotic Resistance" 2011).

One type of Abx misuse is when the drug is administered in case of a non-bacterial disease, such as a viral infection, for which Abx is ineffective. For example, according to the USA center for disease control and prevention CDC, over 60 Million wrong Abx prescriptions are given annually to treat flu in the US. The health-care and economic consequences of the Abx over-prescription include: (i) the cost of antibiotics that are unnecessarily prescribed globally, estimated at >$10 billion annually; (ii) side effects resulting from unnecessary Abx treatment are reducing quality of healthcare, causing complications and prolonged hospitalization (e.g. allergic reactions, Abx associated diarrhea, intestinal yeast etc.) and (iii) the emergence of resistant strains of bacteria as a result of the overuse.

Resistance of microbial pathogens to antibiotics is increasing world-wide at an accelerating rate ("CDC—Get Smart: Fast Facts About Antibiotic Resistance" 2013; "European Surveillance of Antimicrobial Consumption Network (ESAC-Net)" 2014; "CDC—About Antimicrobial Resistance" 2013; "Threat Report 2013 | Antimicrobial Resistance | CDC" 2013), with a concomitant increase in morbidity and mortality associated with infections caused by antibiotic resistant pathogens ("Threat Report 2013 | Antimicrobial Resistance | CDC" 2013). At least 2 million people are infected with antibiotic resistant bacteria each year in the US alone, and at least 23,000 people die as a direct result of these infections ("Threat Report 2013 | Antimicrobial Resistance | CDC" 2013). In the European Union, an estimated 400,000 patients present with resistant bacterial strains each year, of which 25,000 patients die ("WHO Europe-Data and Statistics" 2014). Consequently, the World Health Organization has warned that therapeutic coverage will be insufficient within 10 years, putting the world at risk of entering a "post-antibiotic era", in which antibiotics will no longer be effective against infectious diseases ("WHO | Antimicrobial Resistance" 2013). The CDC considers this phenomenon "one of the world's most pressing health problems in the $21^{st}$ century" ("CDC—About Antimicrobial Resistance" 2013; Arias and Murray 2009).

Antibiotics under-prescription is not uncommon either. For example up to 15% of adult bacterial pneumonia hospitalized patients in the US receive delayed or no Abx treatment, even though in these instances early treatment can save lives and reduce complications (Houck, P. M. and D. W. Bratzler, et al 2002).

Technologies for infectious disease diagnostics have the potential to reduce the associated health and financial burden associated with Abx misuse. Ideally, such a technology should: (i) accurately differentiate between a bacterial and viral infections; (ii) be rapid (within minutes); (iii) be able to differentiate between pathogenic and non-pathogenic bacteria that are part of the body's natural flora; (iv) differentiate between mixed co-infections and pure viral infections and (v) be applicable in cases where the pathogen is inaccessible (e.g. sinusitis, pneumonia, otitis-media, bronchitis, etc).

Current solutions (such as culture, PCR and immunoassays) do not fulfill all these requirements: (i) Some of the assays yield poor diagnostic accuracy (e.g. low sensitivity or specificity) (Uyeki et al. 2009), and are restricted to a limited set of bacterial or viral strains; (ii) they often require hours to days; (iii) they do not distinguish between pathogenic and non-pathogenic bacteria (Del Mar, C 1992), thus leading to false positives; (iv) they often fail to distinguish between a mixed and a pure viral infections and (v) they require direct sampling of the infection site in which traces of the disease causing agent are searched for, thus prohibiting the diagnosis in cases where the pathogen resides in an inaccessible tissue, which is often the case. Moreover, currently available diagnostic approaches often suffer from reduced clinical utility because they do not distinguish between pathogenic strains of microorganisms and potential colonizers, which can be present as part of the natural microbiota without causing an infection (Kim, Shin, and Kim 2009; Shin, Han, and Kim 2009; Jung, Lee, and Chung 2010; Rhedin et al. 2014). For example, Rhedin and colleagues recently tested the clinical utility of qPCR for common viruses in acute respiratory illness (Rhedin et al. 2014). The authors concluded that qPCR detection of several respiratory viruses including rhinovirus, enterovirus and coronavirus should be interpreted with caution due to high detection rates in asymptomatic children. Other studies reached similar conclusions after analyzing the detection rates of different bacterial strains in asymptomatic patients (Bogaert, De Groot, and Hermans 2004; Spuesens et al. 2013).

Consequentially, there is still a diagnostic gap, which in turn often leads physicians to either over-prescribe Abx (the "Just-in-case-approach"), or under-prescribe Abx (the "Wait-and-see-approach") (Little, P. S. and I. Williamson 1994; Little, P. 2005; Spiro, D. M. and K. Y. Tay, et al 2006), both of which have far reaching health and financial consequences.

Accordingly, a need exists for a rapid method that accurately differentiates between bacterial, viral, mixed and non-infectious disease patients that addresses these challenges. An approach that has the potential to address these challenges relies on monitoring the host's immune-response to infection, rather than direct pathogen detection (Cohen et al. 2015). Bacterial-induced host proteins such as procalcitonin, C-reactive protein (CRP), and Interleukin-6, are routinely used to support diagnosis of infection. However, their performance is negatively affected by inter-patient variability, including time from symptom onset, clinical syndrome, and pathogen species (Tang et al. 2007; Limper et al. 2010;

Engel et al. 2012; Quenot et al. 2013; van der Meer et al. 2005; Falk and Fahey 2009). Oved et al. 2015 has developed an immune signature, combining both bacterial- and viral-induced circulating host-proteins, which can aid in the correct diagnosis of patients with acute infections.

Additional background art includes Ramilo et al., Blood, Mar. 1, 2007, Vol 109, No. 5, pages 2066-2077, Zaas et al., *Sci Transl Med.* 2013 Sep. 18; 5(203) 203ra126. doi: 10.1126/scitranslmed.3006280; US Patent Application No. 20080171323, WO2011/132086, WO2013/117746, WO2007011412 and WO2004108899 A2.

SUMMARY OF THE INVENTION

According to an aspect of the present invention there is provided a method of determining an infection type in a subject comprising measuring the expression of at least one RNA determinant in a sample of the subject, wherein the measuring is effected at an exon or plurality of exons whose expression level distinguishes between a bacterial and viral infection with a degree of accuracy above a predetermined level, thereby determining the infection type of the subject.

According to an aspect of the present invention there is provided a method of selecting an exon of an RNA whose expression level is informative with respect to infection type of a subject comprising comparing the expression level of the RNA in a sample derived from a bacterially-infected subject and a sample derived from a virally-infected subject at a plurality of exons, wherein the exon that provides a differential expression between the bacterially-infected subject and the virally-infected subject above a predetermined level is selected as the exon of the RNA whose expression is informative with respect to infection type.

According to an aspect of the present invention there is provided a kit comprising at least two oligonucleotides, wherein the first of the at least two oligonucleotides specifically hybridizes to a first RNA at a first exon, and a second of the at least two oligonucleotides specifically hybridizes to the first RNA at a second exon, the first and the second exon being selected such that the expression level from the first exon distinguishes between a bacterial and viral infection with a degree of accuracy above a predetermined level and the expression level from the second exon distinguishes between a bacterial and viral infection with a degree of accuracy above the predetermined level.

According to an aspect of the present invention there is provided a kit comprising at least two oligonucleotides, wherein the first of the at least two oligonucleotides specifically hybridizes to a first RNA at a first exon, and a second of the at least two oligonucleotides specifically hybridizes to a second RNA at a second exon, the first and the second exon being selected such that the expression level from the first exon distinguishes between a bacterial and viral infection with a degree of accuracy above a predetermined level and the expression level from the second exon distinguishes between a bacterial and viral infection with a degree of accuracy above the predetermined level.

According to an aspect of the present invention there is provided a primer pair which hybridize to an RNA at an exon whose expression level distinguishes between a bacterial and viral infection with a degree of accuracy above a predetermined level.

According to an aspect of the present invention there is provided an array comprising a solid support and a polynucleotide that specifically hybridizes to a first RNA at a predetermined exon, the polynucleotide being attached to the solid support, the predetermined exon being selected such that the expression level therefrom distinguishes between a bacterial and viral infection with a degree of accuracy above a predetermined level, wherein the array comprises oligonucleotides that hybridize to no more than 3 exons of the first RNA.

According to an aspect of the present invention there is provided a array comprising a solid support, a first polynucleotide that specifically hybridizes to a first RNA at a first exon and a second polynucleotide that specifically hybridizes to a second exon of a second RNA, the first and second polynucleotide being attached to the solid support, the first exon being selected such that the expression level therefrom distinguishes between a bacterial and viral infection with a degree of accuracy above a predetermined level and the second exon being selected such that the expression level therefrom distinguishes between a bacterial and viral infection with a degree of accuracy above a predetermined level, wherein the array comprises oligonucleotides that hybridize to no more than 20 non-identical RNAs.

According to embodiments of the present invention, the exon provides a differential expression between a bacterially-infected subject and a virally-infected subject above a predetermined level.

According to embodiments of the present invention, the exon provides the highest degree of differential expression in a sample derived from a bacterially infected subject compared with a virally infected subject, compared to all the exons of the RNA.

According to embodiments of the present invention, the RNA is set forth in Tables 10A or 10B.

According to embodiments of the present invention, the exon of the RNA is selected as set forth in Table 10A or 10B.

According to embodiments of the present invention, the sample comprises RNA.

According to embodiments of the present invention, the sample comprises cDNA.

According to embodiments of the present invention, the comparing is effected using a plurality of oligonucleotides.

According to embodiments of the present invention, the method comprises: (a) analyzing the expression level of the RNA in a sample derived from the bacterially-infected subject using a plurality of oligonucleotides which hybridize to non-identical exons of the RNA or cDNA generated therefrom;

(b) analyzing the expression level of the RNA in a sample derived from the virally-infected subject using a plurality of oligonucleotides which hybridize to the non-identical exons, wherein the plurality of oligonucleotides of step (a) have the same binding stringency to the exons as the plurality of oligonucleotides of step (b) to the exons.

According to embodiments of the present invention, the nucleic acid sequence of the oligonucleotides of step (a) is identical to the nucleic acid sequence of the oligonucleotides of step (b).

According to embodiments of the present invention, the method further comprises comparing the expression level of the RNA across each exon of the RNA.

According to embodiments of the present invention, the exon that provides the highest degree of differential expression is selected as the exon of the RNA whose expression is informative with respect to infection type.

According to embodiments of the present invention, the comparing is performed under identical experimental conditions.

According to embodiments of the present invention, the sample is whole blood or a fraction thereof.

According to embodiments of the present invention, the blood fraction sample comprises cells selected from the group consisting of lymphocytes, monocytes and granulocytes.

According to embodiments of the present invention, the blood fraction sample comprises serum or plasma.

According to embodiments of the present invention, the plurality of exons comprise no more than 2 exons.

According to embodiments of the present invention, the plurality of exons comprise no more than 5 exons.

According to embodiments of the present invention, the oligonucleotides are attached to a detectable moiety.

According to embodiments of the present invention, the kit comprises oligonucleotides that hybridize to no more than 3 exons of the first RNA.

According to embodiments of the present invention, the kit comprises oligonucleotides that hybridize to no more than 20 RNAs.

According to embodiments of the present invention, the kit comprises oligonucleotides that hybridize to no more than 10 RNAs.

According to embodiments of the present invention, the kit comprises oligonucleotides that hybridize to no more than 3 RNAs.

According to embodiments of the present invention, the array comprises oligonucleotides that hybridize to no more than 20 non-identical RNAs.

According to embodiments of the present invention, the array comprises oligonucleotides that hybridize to no more than 3 exons of the first RNA and/or the second RNA.

According to embodiments of the present invention, the RNA is set forth in Table 10A or 10B.

According to embodiments of the present invention, at least one of the oligonucleotides hybridize to the exon of the RNA set forth in Table 10A or 10B.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 is a flow-chart of the clinical study design.

Figure 2A:
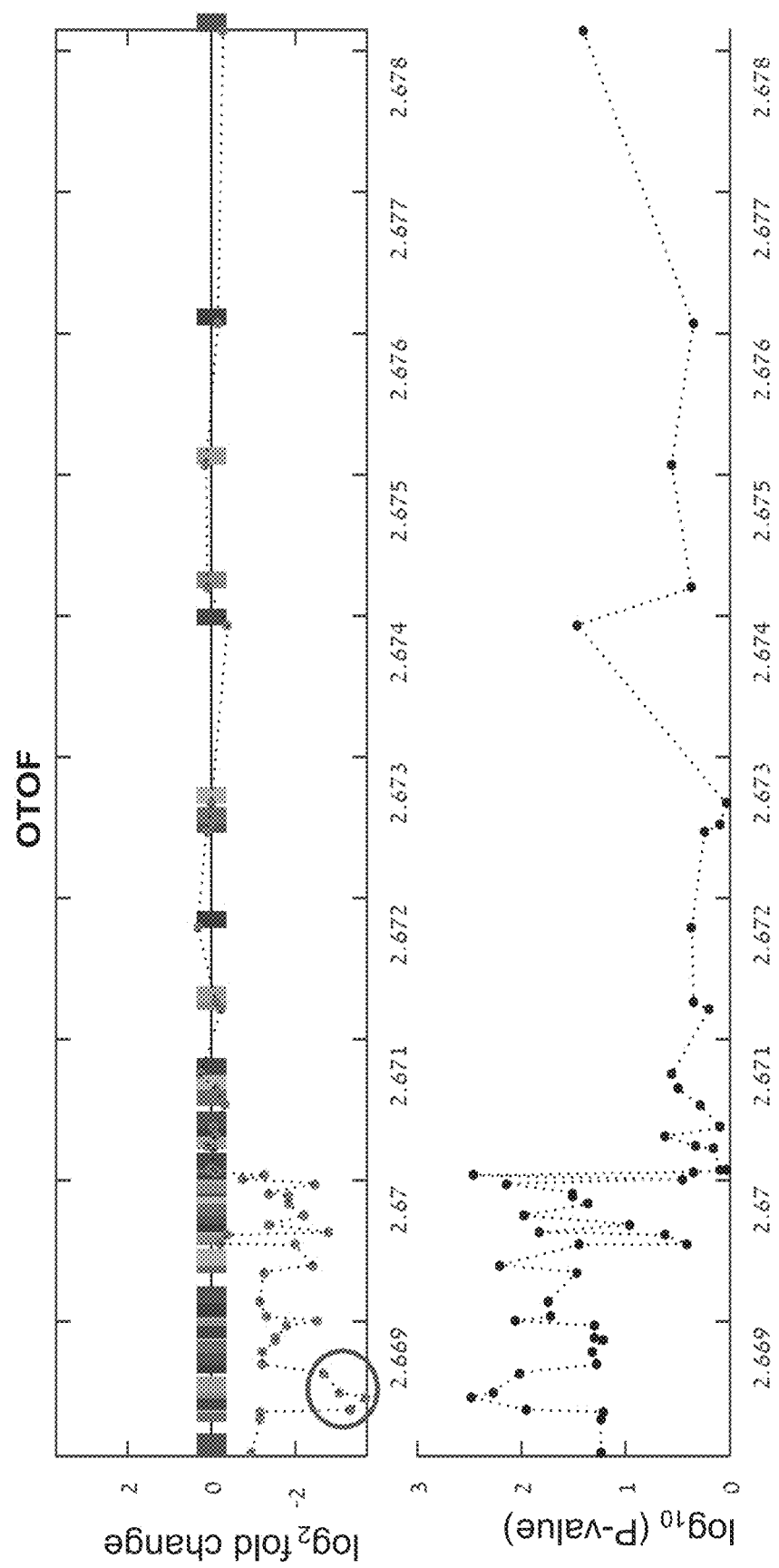
Figure 2B:
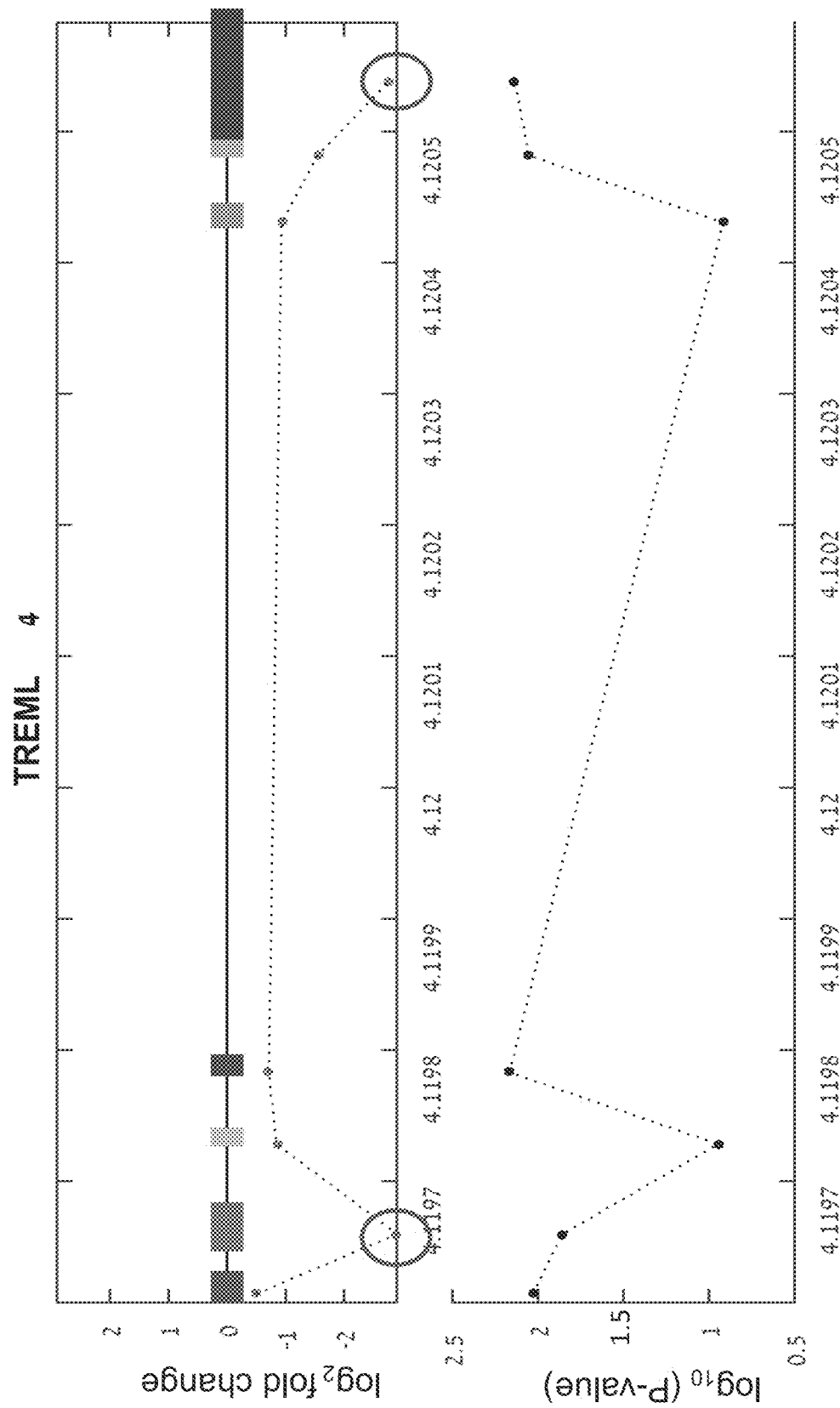
Figure 2C:
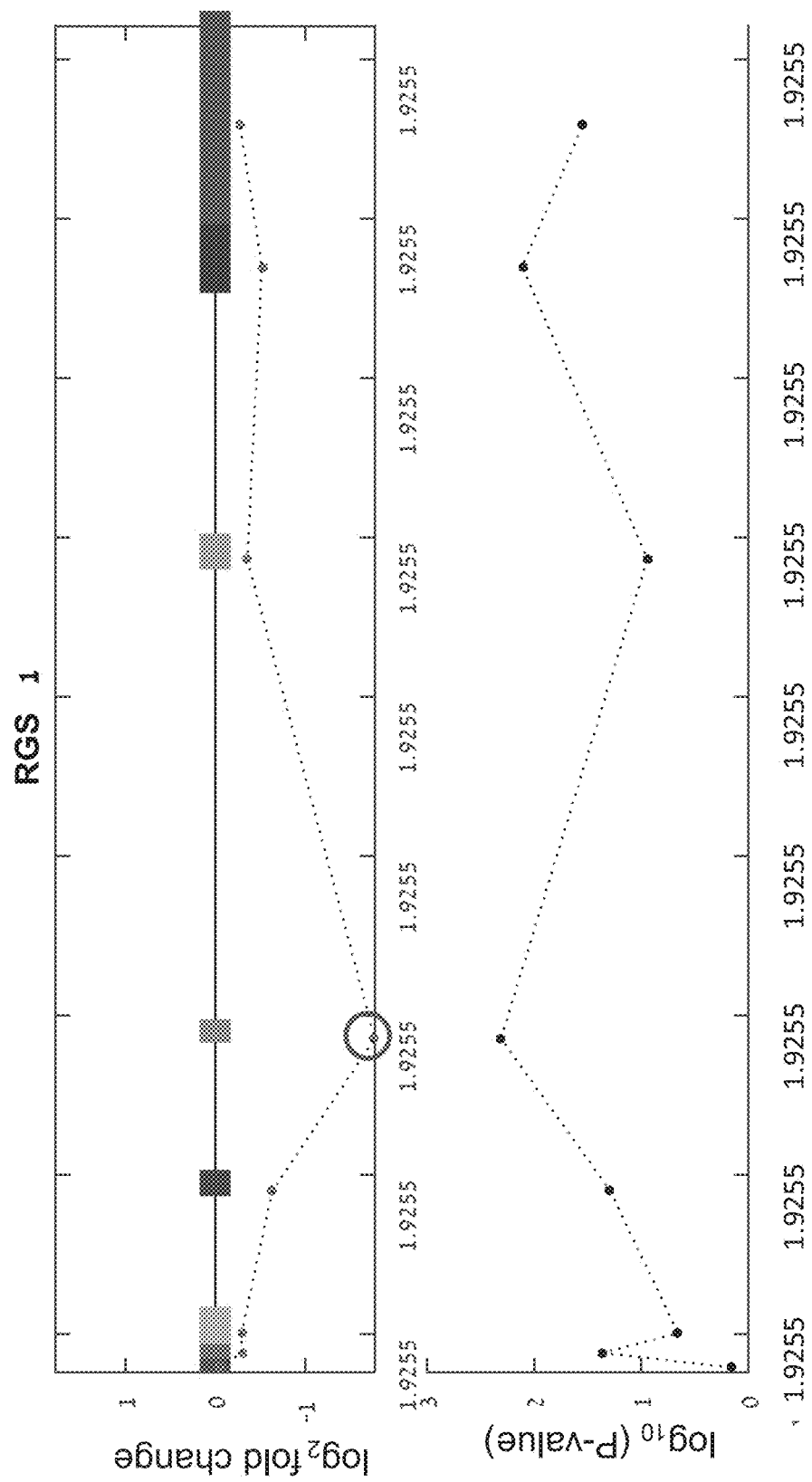
Figure 3A:
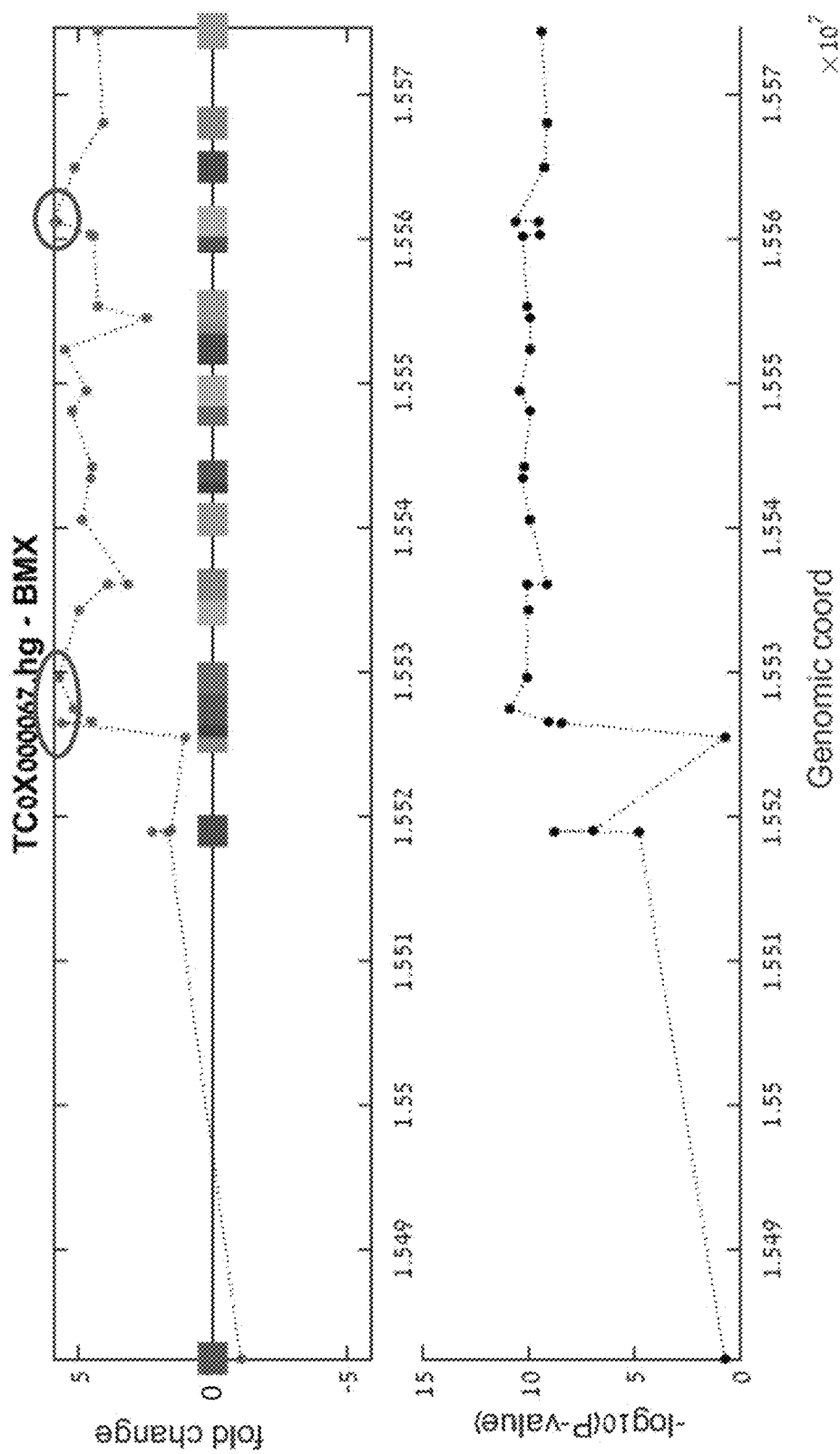
Figure 3B:
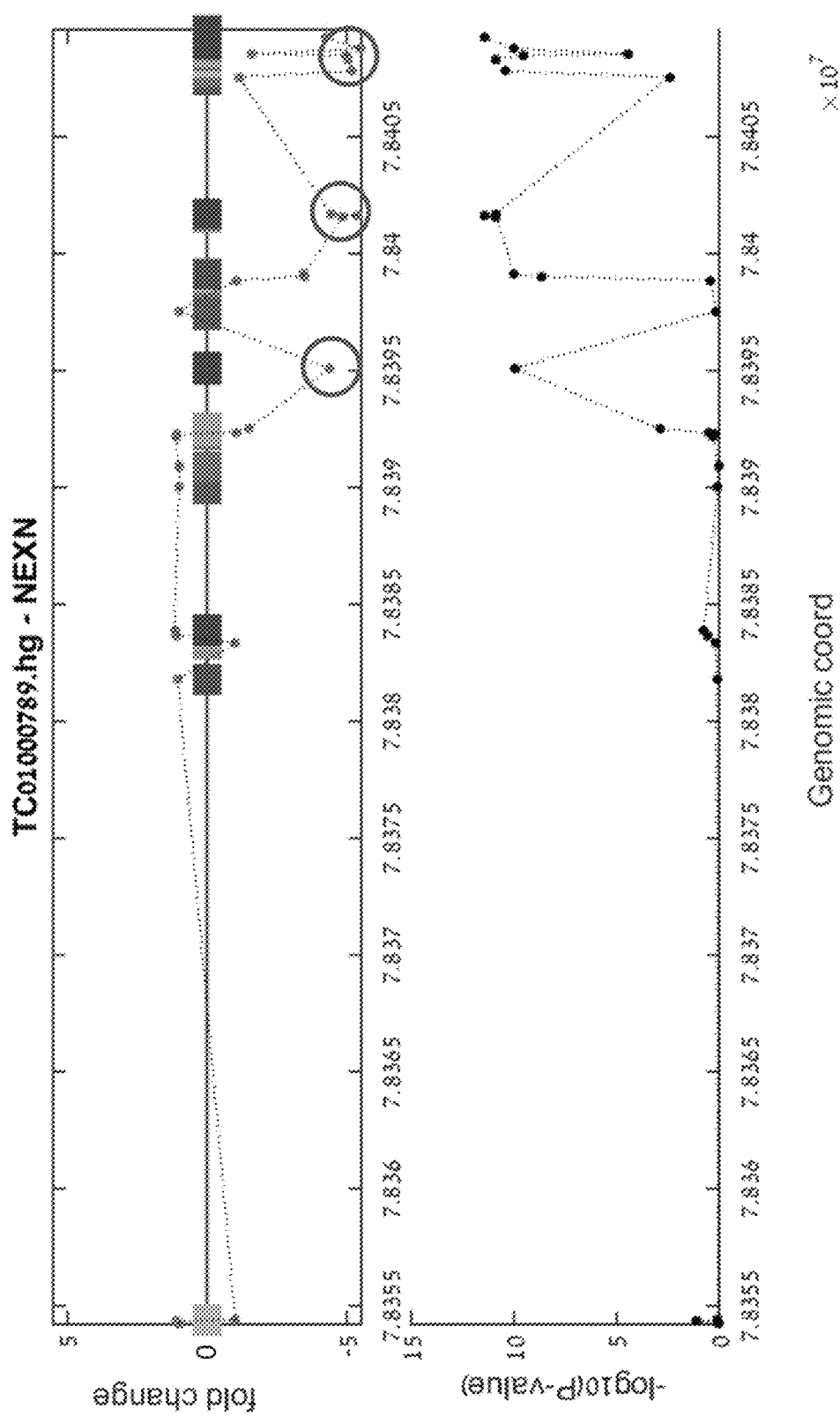
Figure 3C:
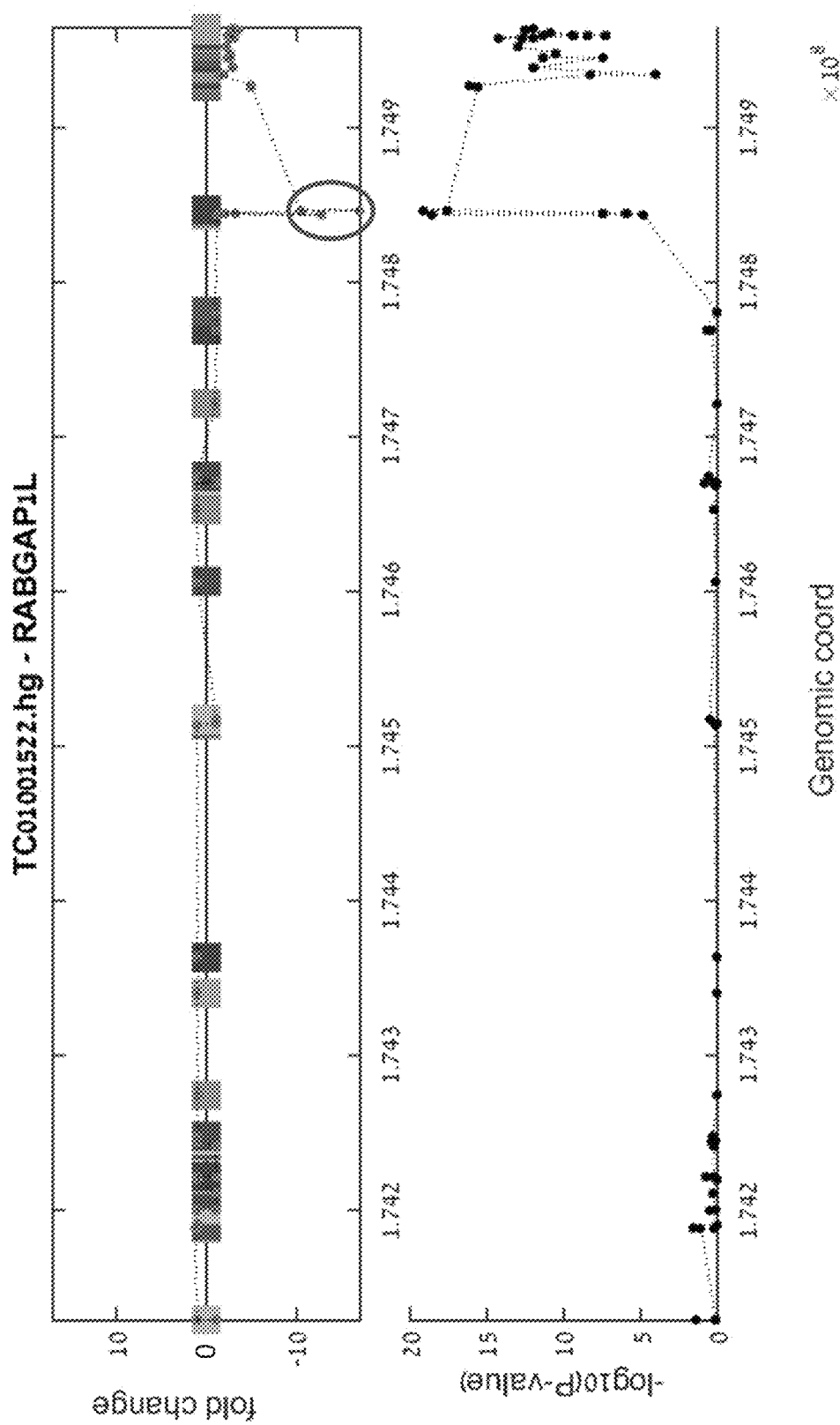
Figure 3D:
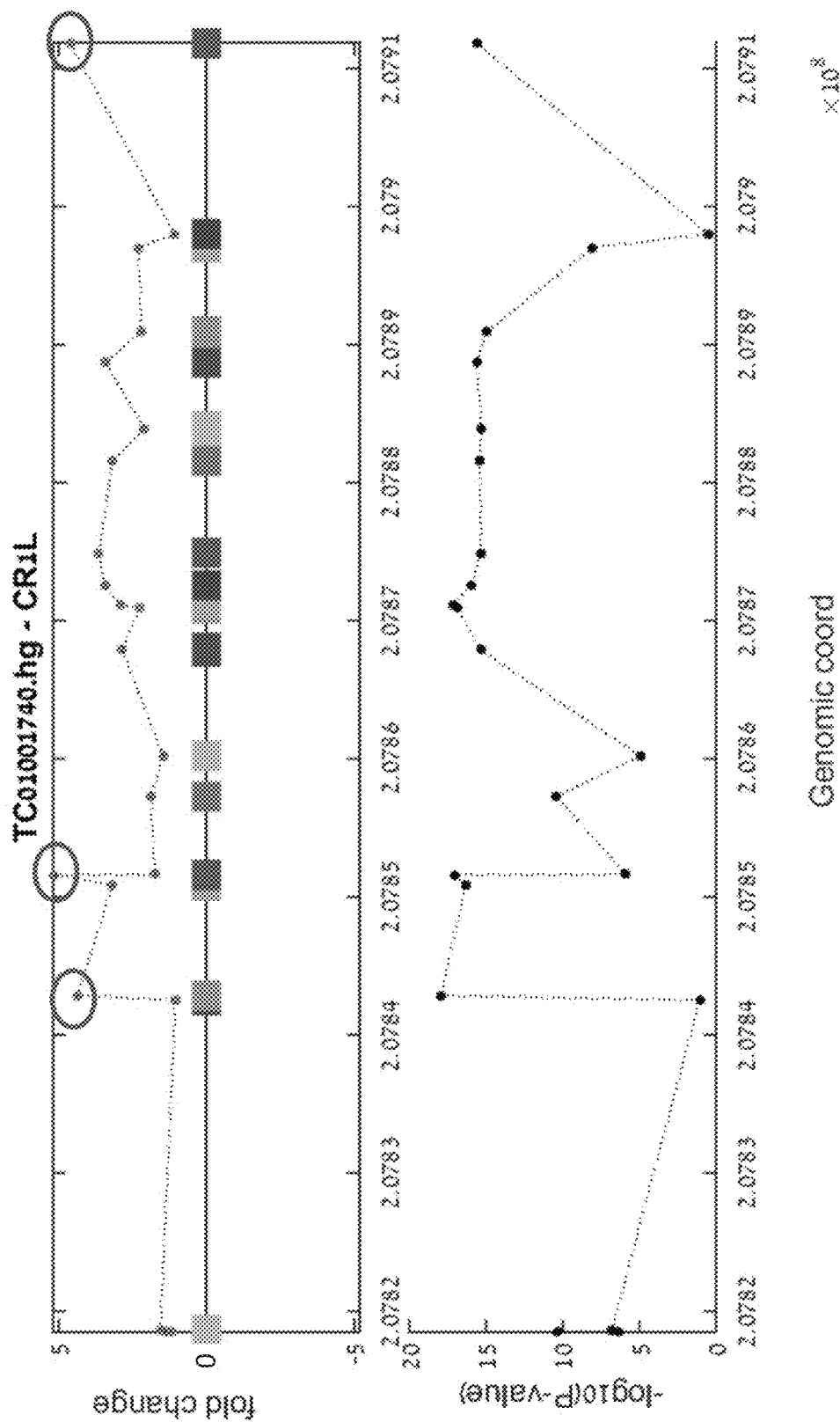
Figure 3E:
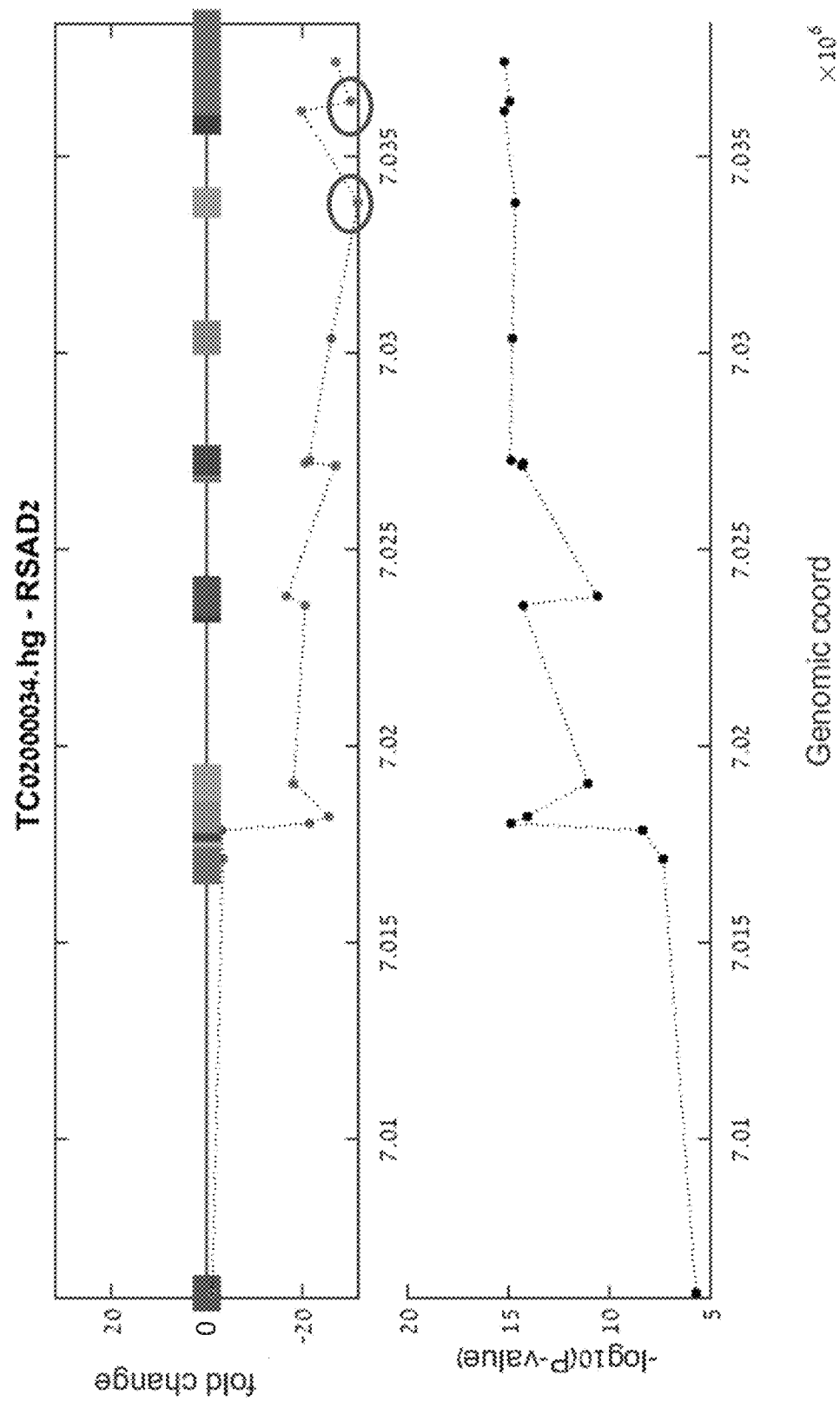
Figure 3F:
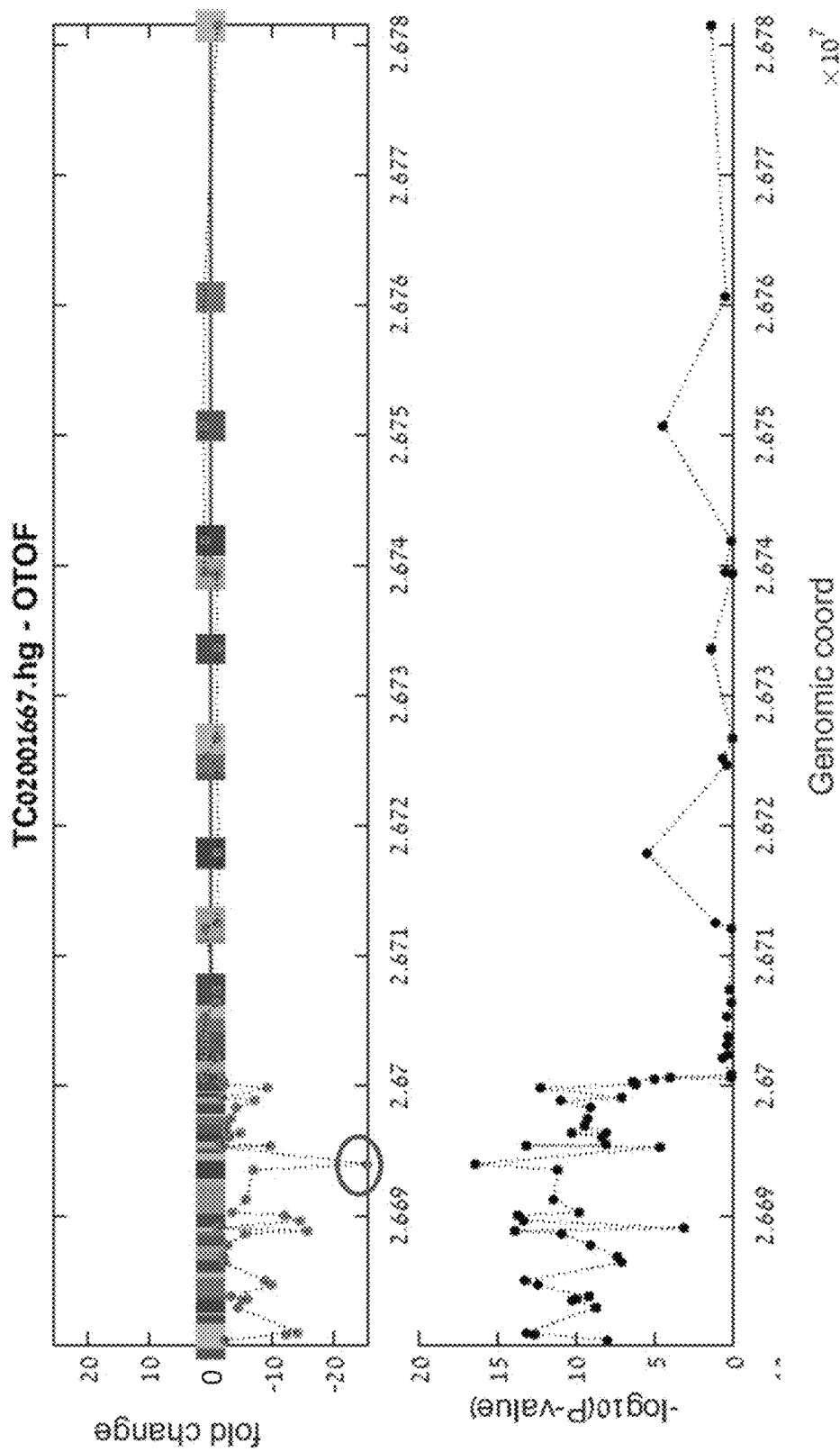
Figure 3G:
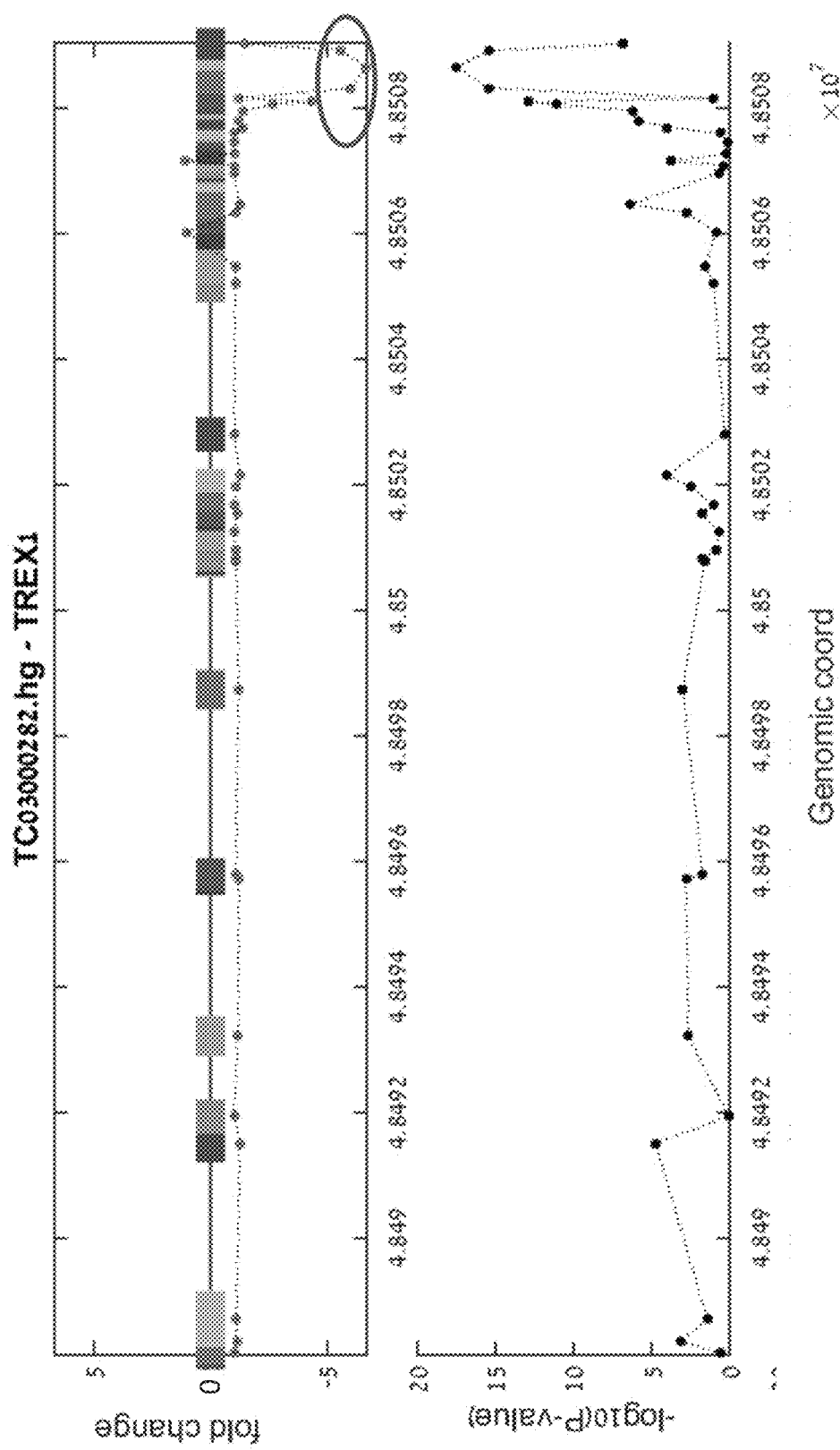
Figure 3H:
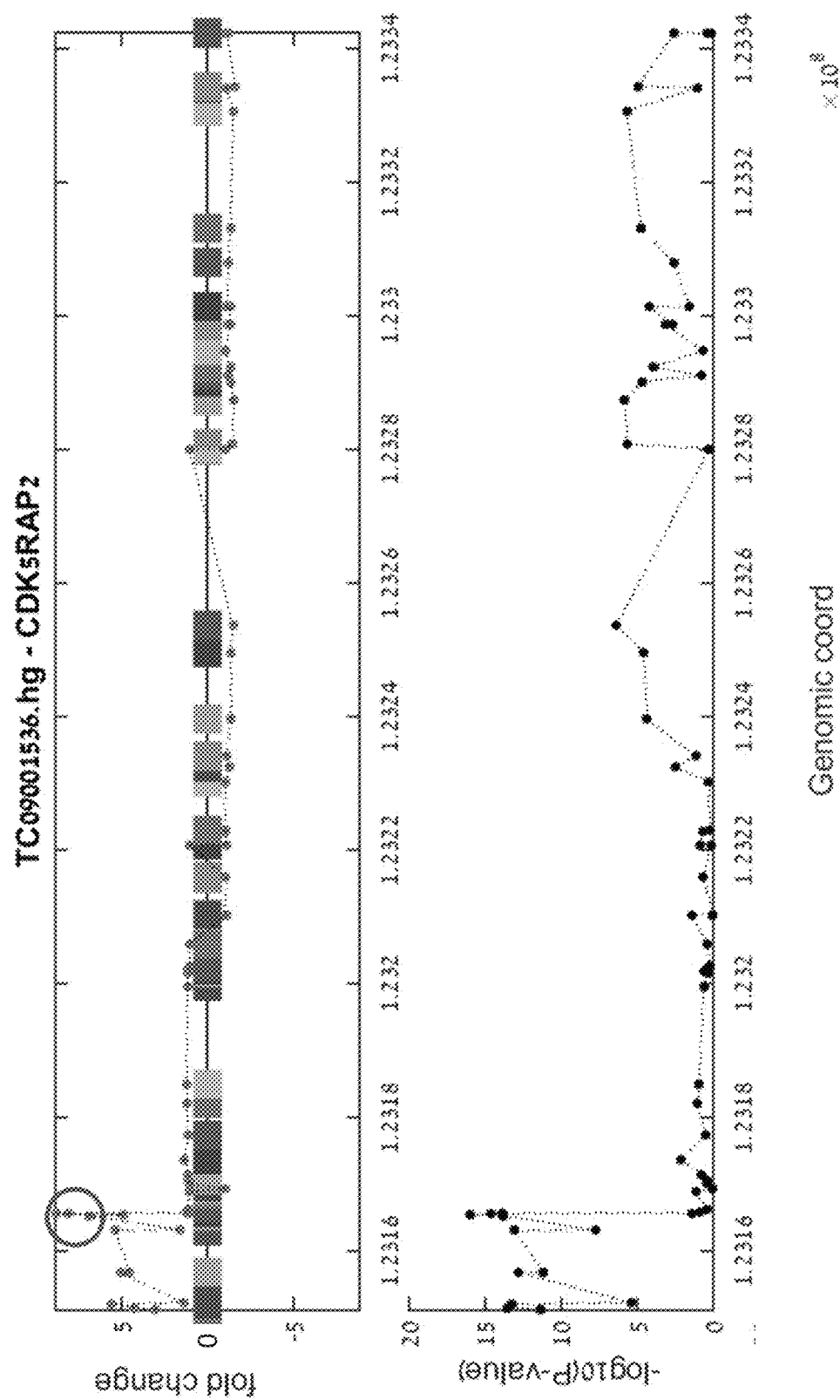
Figure 3I:
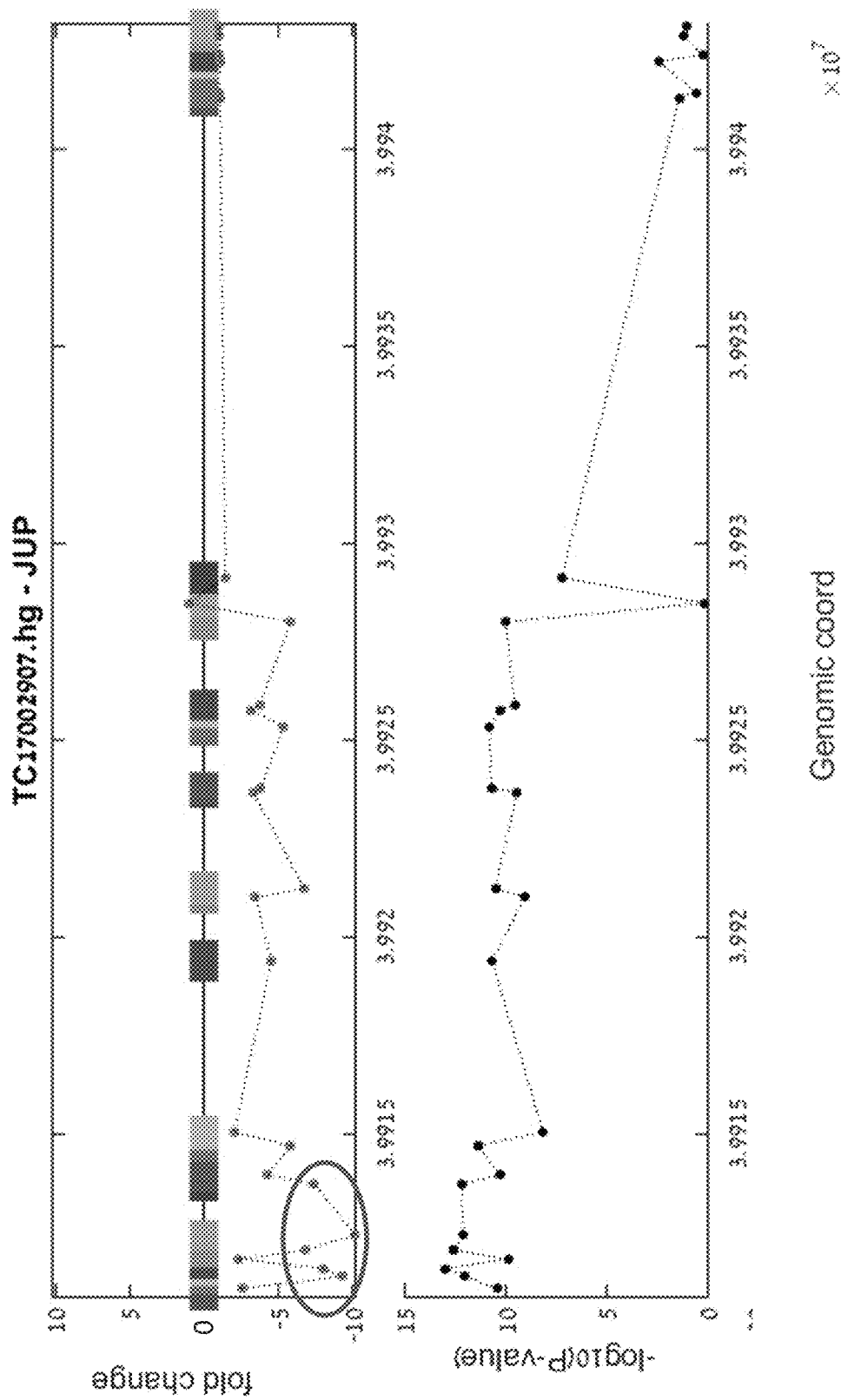
Figure 3J:
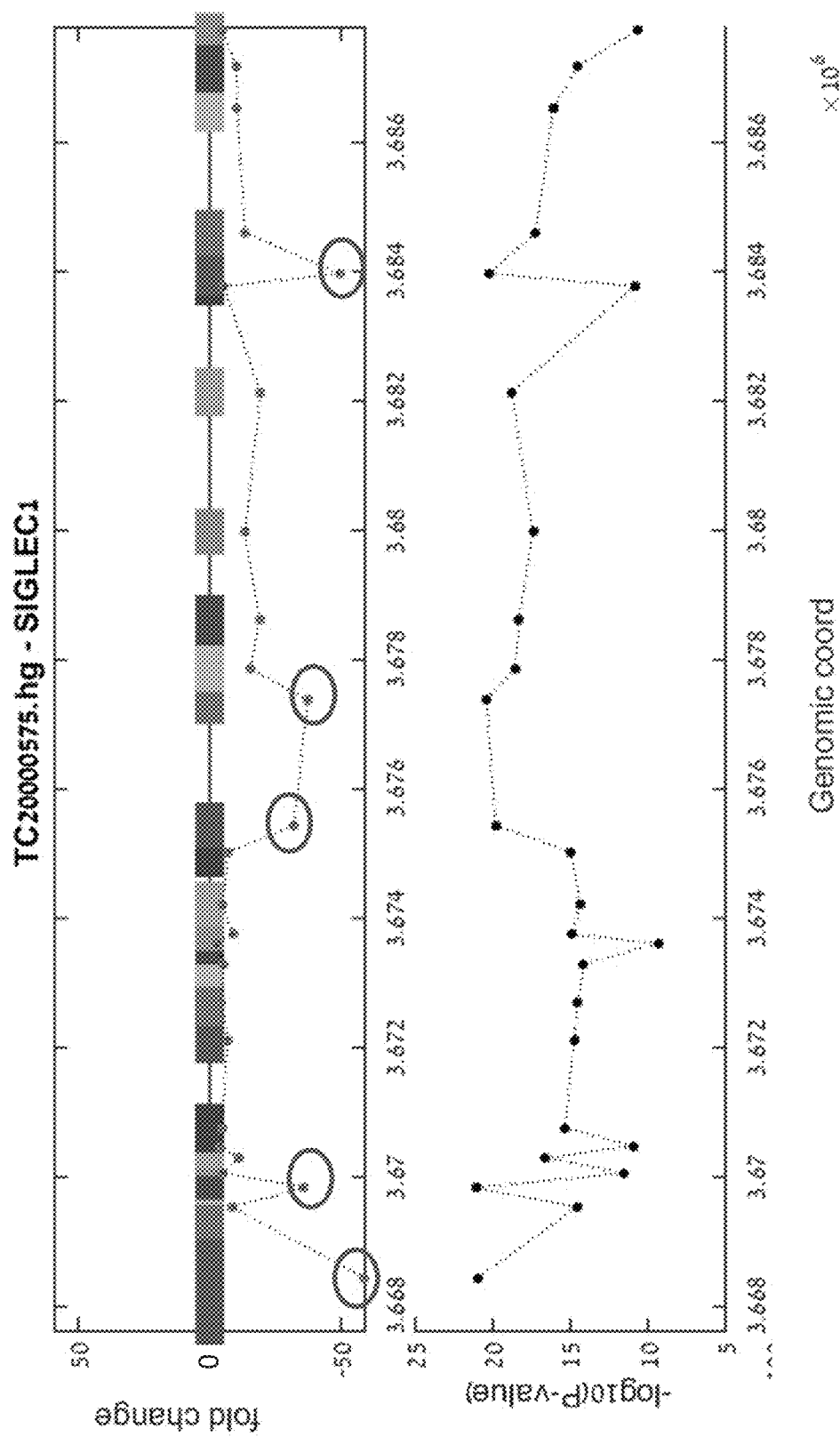
Figure 3K:
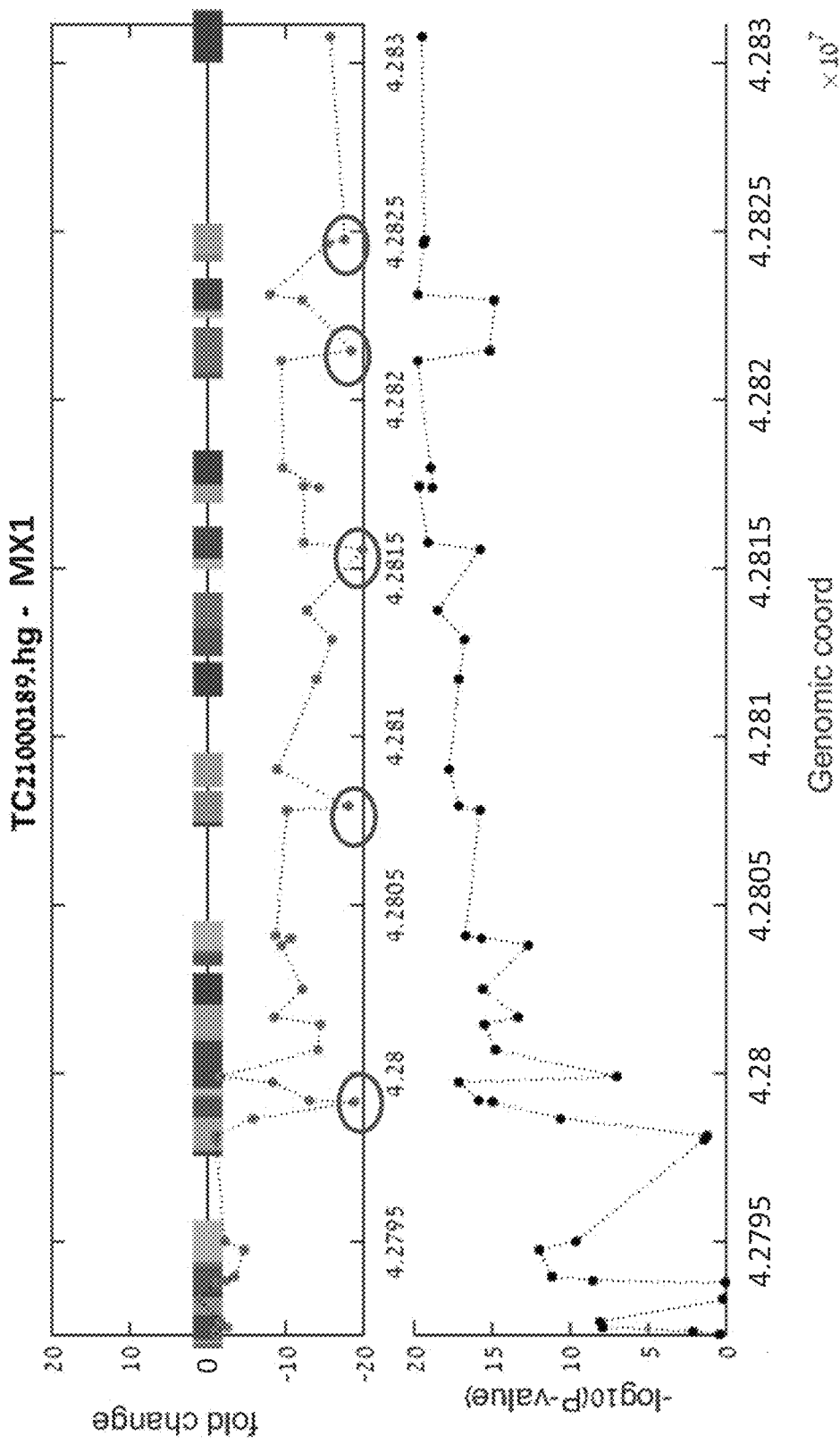
Figure 3L:
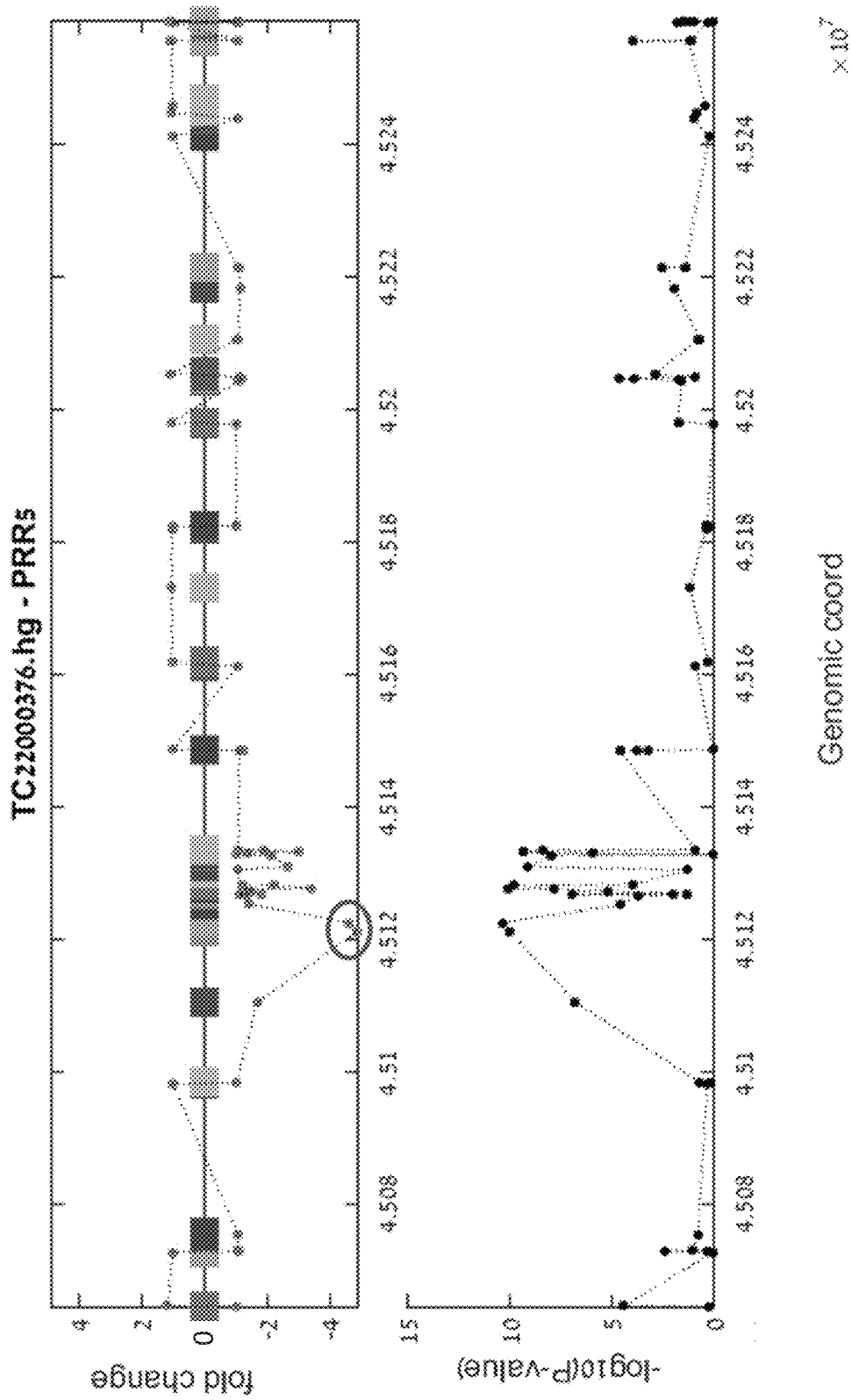

FIGS. 2A-C illustrate that single exons are differentially expressed between bacterial and viral patients (A. OTOF gene; B. TREML4 gene; C. RGS1 gene). The x-axis represents genomic coordinates; exons are indicated in colored rectangles; broken line depict the log 2 fold change between bacterial and viral infections (with positive and negative numbers indicating over-expression of bacterial and viral infections respectively). In the bottom part of the image the Wilcoxon rank sum log 10 (P-value) of the differential expression is depicted. Highly discriminative exons are marked by red circle.

FIGS. 3A-L illustrate that specific single exons are differentially expressed between bacterial and viral patients. The x-axis represents genomic coordinates; exons are indicated in colored rectangles; broken line depict the fold change between bacterial and viral infections (with positive and negative numbers indicating over-expression of bacterial and viral infections respectively). In the bottom part of the image the −log 10 (t-test P-value) of the differential expression is depicted. Data is based on experiments described in Example 2. Exemplary highly discriminative exons are marked by red circles.

DESCRIPTION OF SPECIFIC EMBODIMENTS OF THE INVENTION

The present invention, in some embodiments thereof, relates to the identification of signatures and determinants associated with bacterial and viral infections. More specifically, the present invention relates to RNA determinants that are differentially expressed in a statistically significant manner in subjects with bacterial and viral infections.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Methods of distinguishing between bacterial and viral infections by analyzing protein determinants have been disclosed in International Patent Application WO2013/117746, to the present inventors. Seeking to expand the number and type of determinants that can aid in accurate diagnosis, the present inventors have now carried out additional clinical experiments and have identified other determinants that can be used for this aim.

The present inventors studied the gene expression profiles of blood leukocytes obtained from patients with acute infections. The results indicate there is a differential response of the immune system to bacterial and viral infections, which can potentially be used to classify acute infection patients. Initially, the present inventors identified 62 RNA determinants that were differentially expressed in the bacterial and viral patients tested (Table 11).

Whilst reducing the present invention to practice, the present inventors computed the exon-level differential expression of the 62 genes described in Table 11 and compared the median log fold change of each individual exon to its full length gene (Table 12). Unexpectedly, the present inventors found that particular exons of the determinants showed a higher differential expression in samples derived from bacterial and virally infected subjects than the corresponding full length RNA.

Using a larger cohort of patients, the present inventors found additional RNA determinants of which particular exons could be used to accurately distinguish between bacterial and viral infections. These are described in Tables 13 and 14 of the Examples section herein below.

All these exons have the potential to serve as diagnostic biomarkers or to enhance the performance of transcriptomic signatures composed of several full or partial RNA determinants. For example, the present inventors found the full length OTOF gene to be a poor-moderate discriminator between bacterial and viral patients (log 2-fold change of −0.83; Table 11), while a subset of its exons was highly discriminative (log 2-fold change between −2.3 and −3.9; FIG. 2A) and could potentially serve as useful biomarkers.

Consequently, the present teachings suggest that in order to distinguish between bacterial and viral infections using RNA determinants it is important to select the location on the RNA which provides the most discriminative results.

Thus, according to a first aspect of the present invention, there is provided a method of selecting an exon of an RNA whose expression level is informative with respect to infection type of a subject comprising comparing the expression level of the RNA in a sample derived from a bacterially-infected subject and a sample derived from a virally-infected subject at a plurality of exons, wherein the exon that provides a differential expression between the bacterially-infected subject and the virally-infected subject above a predetermined level is selected as the exon of the RNA whose expression is informative with respect to infection type.

The term "RNA determinant" refers to an RNA whose expression level is informative with respect to infection type of a subject. The RNA may code for a polypeptide. In another embodiment, the RNA is a non-coding RNA.

The numbering of the exons of an RNA (i.e. gene annotation) may be found using the Affymetrix database and other public domains such as the UCSC genome browser. For each of the RNAs in the application, the position of the exon is annotated in the Tables of the Examples section herein below.

The term "sample" as used herein refers to a biological sample isolated from a subject and can include, by way of example and not limitation, whole blood, serum, plasma, saliva, mucus, breath, urine, CSF, sputum, sweat, stool, hair, seminal fluid, biopsy, rhinorrhea, tissue biopsy, cytological sample, platelets, reticulocytes, leukocytes, epithelial cells, or whole blood cells.

For measuring RNA determinants, preferably the sample is a blood sample comprising white blood cells such as lymphocytes, monocytes and granulocytes (which is depleted of red blood cells). In one embodiment, the sample is not a serum sample.

Methods of depleting red blood cells are known in the art and include for example hemolysis, centrifugation, sedimentation, filtration or combinations thereof.

In one embodiment, the sample of this aspect of the present invention comprises RNA.

The RNA sample of this aspect of the present invention may comprise RNA from a heterogeneous population of cells or from a single population of cells. The RNA may comprise total RNA, mRNA, mitochondrial RNA, chloroplast RNA, DNA-RNA hybrids, viral RNA, cell free RNA, and mixtures thereof. In one embodiment, the RNA sample is devoid of DNA.

The sample may be fresh or frozen.

Isolation, extraction or derivation of RNA may be carried out by any suitable method. Isolating RNA from a biological sample generally includes treating a biological sample in such a manner that the RNA present in the sample is extracted and made available for analysis. Any isolation method that results in extracted RNA may be used in the practice of the present invention. It will be understood that the particular method used to extract RNA will depend on the nature of the source.

Methods of RNA extraction are well-known in the art and further described herein under.

Phenol Based Extraction Methods:

These single-step RNA isolation methods based on Guanidine isothiocyanate (GITC)/phenol/chloroform extraction require much less time than traditional methods (e.g. $CsCl_2$ ultracentrifugation). Many commercial reagents (e.g. Trizol, RNAzol, RNAWIZ) are based on this principle. The entire procedure can be completed within an hour to produce high yields of total RNA.

Silica Gel—Based Purification Methods:

RNeasy is a purification kit marketed by Qiagen. It uses a silica gel-based membrane in a spin-column to selectively bind RNA larger than 200 bases. The method is quick and does not involve the use of phenol.

Oligo-dT Based Affinity Purification of mRNA:

Due to the low abundance of mRNA in the total pool of cellular RNA, reducing the amount of rRNA and tRNA in a total RNA preparation greatly increases the relative amount of mRNA. The use of oligo-dT affinity chromatography to selectively enrich poly (A)+RNA has been practiced for over 20 years. The result of the preparation is an enriched mRNA population that has minimal rRNA or other small RNA contamination. mRNA enrichment is essential for construction of cDNA libraries and other applications where intact mRNA is highly desirable. The original method utilized oligo-dT conjugated resin column chromatography and can be time consuming. Recently more convenient formats such as spin-column and magnetic bead based reagent kits have become available.

The sample may also be processed prior to carrying out the diagnostic methods of the present invention. Processing of the sample may involve one or more of: filtration, distillation, centrifugation, extraction, concentration, dilution, purification, inactivation of interfering components, addition of reagents, and the like.

In another embodiment, the sample of this aspect of the present invention comprises cDNA.

For synthesis of cDNA, template mRNA may be obtained directly from lysed cells or may be purified from a total RNA or mRNA sample. The total RNA sample may be subjected to a force to encourage shearing of the RNA molecules such that the average size of each of the RNA molecules is between 100-300 nucleotides, e.g. about 200 nucleotides. To separate the heterogeneous population of mRNA from the majority of the RNA found in the cell, various technologies may be used which are based on the use of oligo(dT) oligonucleotides attached to a solid support. Examples of such oligo(dT) oligonucleotides include: oligo (dT) cellulose/spin columns, oligo(dT)/magnetic beads, and oligo(dT) oligonucleotide coated plates.

Generation of cDNA from RNA requires synthesis of an intermediate RNA-DNA hybrid. For this, a primer is required that hybridizes to the 3' end of the RNA. Annealing temperature and timing are determined both by the efficiency with which the primer is expected to anneal to a template and the degree of mismatch that is to be tolerated.

The annealing temperature is usually chosen to provide optimal efficiency and specificity, and generally ranges from about 50° C. to about 80° C., usually from about 55° C. to about 70° C., and more usually from about 60° C. to about 68° C. Annealing conditions are generally maintained for a period of time ranging from about 15 seconds to about 30 minutes, usually from about 30 seconds to about 5 minutes.

According to a specific embodiment, the primer comprises a polydT oligonucleotide sequence.

Preferably the polydT sequence comprises at least 5 nucleotides. According to another is between about 5 to 50 nucleotides, more preferably between about 5-25 nucleotides, and even more preferably between about 12 to 14 nucleotides.

Following annealing of the primer (e.g. polydT primer) to the RNA sample, an RNA-DNA hybrid is synthesized by reverse transcription using an RNA-dependent DNA polymerase. Suitable RNA-dependent DNA polymerases for use in the methods and compositions of the invention include reverse transcriptases (RTs). Examples of RTs include, but are not limited to, Moloney murine leukemia virus (M-MLV) reverse transcriptase, human immunodeficiency virus (HIV) reverse transcriptase, rous sarcoma virus (RSV) reverse transcriptase, avian myeloblastosis virus (AMV) reverse transcriptase, rous associated virus (RAV) reverse transcriptase, and myeloblastosis associated virus (MAV) reverse transcriptase or other avian sarcoma-leukosis virus (ASLV) reverse transcriptases, and modified RTs derived therefrom. See e.g. U.S. Pat. No. 7,056,716. Many reverse transcriptases, such as those from avian myeloblastosis virus (AMV-RT), and Moloney murine leukemia virus (MMLV-RT) comprise more than one activity (for example, polymerase activity and ribonuclease activity) and can function in the formation of the double stranded cDNA molecules.

Additional components required in a reverse transcription reaction include dNTPS (dATP, dCTP, dGTP and dTTP) and optionally a reducing agent such as Dithiothreitol (DTT) and $MnCl_2$.

A "subject" in the context of the present invention may be a mammal (e.g. human dog, cat, horse, cow, sheep, pig, goat). According to another embodiment, the subject is a bird (e.g. chicken, turkey, duck or goose). According to a particular embodiment, the subject is a human. The subject can be male or female.

A "virally-infected subject", as used herein, refers to a subject who has been infected with a virus, preferably a pathogenic virus.

Exemplary pathogenic viruses may belong to the following families: Adenoviridae, Picornaviridae, Herpesviridae, Hepadnaviridae, Flaviviridae, Retroviridae, Orthomyxoviridae, Paramyxoviridae, Papovaviridae, Polyomavirus, Rhabdoviridae, Togaviridae. Particular pathogenic viruses contemplated by the present invention are those that cause smallpox, influenza, mumps, measles, chickenpox, ebola, or rubella.

According to a particular embodiment, the virus is one which brings about a respiratory infection (e.g. an upper respiratory tract infection and/or a lower respiratory tract infection).

Thus, according to a particular embodiment, the pathogenic virus is an influenza virus (e.g. influenza virus A—(e.g. H1N1, H2N2, H3N2, H5N1, H7N7, H1N2, H9N2, H7N2, H7N3, H10N7 and H7N9), influenza virus B or influenza virus C).

In another embodiment, the pathogenic virus is a parainfluenza virus (hPIV) including the human parainfluenza virus type 1 (hPIV-1) (causes croup); the human parainfluenza virus type 2 (hPIV-2) (causes croup and other upper and lower respiratory tract illnesses), the human parainfluenza virus type 3 (hPIV-3) (associated with bronchiolitis and pneumonia) and the human parainfluenza virus type 4 (hPIV-4).

In yet another embodiment, the pathogenic virus is a respiratory syncytial virus (RSV).

A "bacterially-infected subject", as used herein, refers to a subject who has been infected with a bacteria, preferably a pathogenic bacteria.

Exemplary pathogenic bacteria include *Mycobacterium tuberculosis* which causes tuberculosis, *Streptococcus* and *Pseudomonas* which cause pneumonia, and *Shigella*, *Campylobacter* and *Salmonella* which cause foodborne illnesses. Other exemplary pathogenic bacteria contemplated by the present invention are those that cause infections such as tetanus, typhoid fever, diphtheria, syphilis and Hansen's disease.

As mentioned, this aspect of the present invention comprises comparing the expression level of an RNA in a sample derived from a bacterially infected subject at a plurality of exons with the expression level of the same RNA in a sample derived from a virally infected subject at the same plurality of exon.

For the comparison to be accurate, it is preferable that the sample type from the bacterially infected subject is the same as the sample type from the virally infected subject. Thus, for example, if the bacterial sample type is a blood sample, the viral sample type should also be a blood sample. As another example, if the bacterial sample comprises cDNA, then the viral sample should also comprise cDNA.

Preferably, the sample of the bacterial subject is prepared in the same way as the sample of the viral subject. In some embodiments, identical protocols are used for preparing the sample.

As mentioned, the expression level of the RNA is analyzed at a plurality of exons. According to this aspect of the present invention, the expression level of at least two exons of a particular RNA are analyzed per sample, the expression level of at least three exons of a particular RNA are analyzed per sample, the expression level of at least four exons of a particular RNA are analyzed per sample, the expression level of at least five exons of a particular RNA are analyzed per sample. According to other embodiments at least 10% of the exons of a particular RNA are analyzed per sample, at least 20% of the exons of a particular RNA are analyzed per sample, at least 30% of the exons of a particular RNA are analyzed per sample, at least 40% of the exons of a particular RNA are analyzed per sample, at least 50% of the exons of a particular RNA are analyzed per sample, at least 60% of the exons of a particular RNA are analyzed per sample, at least 70% of the exons of a particular RNA are analyzed per sample, at least 80% of the exons of a particular RNA are analyzed per sample, at least 90% of the exons of a particular RNA are analyzed per sample, 100% of the exons of a particular RNA are analyzed per sample.

In one embodiment, at least one of the exons which is analyzed is the 3' exon. In another embodiment, at least one of the exons which is analyzed is the 5' exon.

In some embodiments, an oligonucleotide is used to analyze the expression level of an RNA at a particular exon. The oligonucleotide preferably hybridizes discriminately to the target exon over the other exons of the RNA.

Oligonucleotides (e.g. DNA or RNA oligonucleotides) typically comprises a region of complementary nucleotide sequence that hybridizes under stringent conditions to at least about 8, 10, 13, 16, 18, 20, 22, 25, 30, 40, 50, 55, 60, 65, 70, 80, 90, 100, 120 (or any other number in-between) or more consecutive nucleotides in a target nucleic acid molecule.

In order to identify an oligonucleotide specific for any of the determinant sequences, the gene/transcript of interest is typically examined using a computer algorithm which starts at the 5' or at the 3' end of the nucleotide sequence. Typical algorithms will then identify oligonucleotides of defined length that are unique to the gene, have a GC content within a range suitable for hybridization, lack predicted secondary structure that may interfere with hybridization, and/or possess other desired characteristics or that lack other undesired characteristics.

Following identification of the oligonucleotide it may be tested for specificity towards the determinant under wet or dry conditions. Thus, for example, in the case where the oligonucleotide is a primer, the primer may be tested for its ability to amplify a sequence of the determinant using PCR to generate a detectable product and for its non ability to amplify other determinants in the sample. The products of the PCR reaction may be analyzed on a gel and verified according to presence and/or size.

Additionally, or alternatively, the sequence of the oligonucleotide may be analyzed by computer analysis to see if it is homologous (or is capable of hybridizing to) other known sequences. A BLAST 2.2.10 (Basic Local Alignment Search Tool) analysis may be performed on the chosen oligonucleotide (worldwideweb(dot)ncbi(dot)nlm(dot)nih(dot)gov/blast/). The BLAST program finds regions of local similarity between sequences. It compares nucleotide or protein sequences to sequence databases and calculates the statistical significance of matches thereby providing valuable information about the possible identity and integrity of the 'query' sequences.

According to additional embodiments, the oligonucleotide is about 8, 9, 10, 11, 12, 13, 14, 15, 16, 17, 18, 19, 20, 21, 22, 23, 24 or 25 nucleotides in length. While the maximal length of a probe can be as long as the target sequence to be detected, depending on the type of assay in which it is employed, it is typically less than about 50, 60, 65, or 70 nucleotides in length. In the case of a primer, it is typically less than about 30 nucleotides in length. In a specific preferred embodiment of the invention, a primer or a probe is within the length of about 18 and about 28 nucleotides. It will be appreciated that when attached to a solid support, the probe may be of about 30-70, 75, 80, 90, 100, or more nucleotides in length.

The oligonucleotide of this aspect of the present invention need not reflect the exact sequence of the determinant exon nucleic acid sequence (i.e. need not be fully complementary), but must be sufficiently complementary to hybridize with the determinant exon nucleic acid sequence under the particular experimental conditions. Accordingly, the sequence of the oligonucleotide typically has at least 70% homology, preferably at least 80%, 90%, 95%, 97%, 99% or 100% homology, for example over a region of at least 13 or more contiguous nucleotides with the target determinant exon nucleic acid sequence. The conditions are selected such that hybridization of the oligonucleotide to the determinant exon nucleic acid sequence is favored and hybridization to other determinant exon nucleic acid sequences is minimized.

By way of example, hybridization of short nucleic acids (below 200 bp in length, e.g. 13-50 bp in length) can be effected by the following hybridization protocols depending on the desired stringency; (i) hybridization solution of 6×SSC and 1% SDS or 3 M TMAC1, 0.01 M sodium phosphate (pH 6.8), 1 mM EDTA (pH 7.6), 0.5% SDS, 100 µg/ml denatured salmon sperm DNA and 0.1% nonfat dried milk, hybridization temperature of 1-1.5° C. below the Tm, final wash solution of 3 M TMAC1, 0.01 M sodium phosphate (pH 6.8), 1 mM EDTA (pH 7.6), 0.5% SDS at 1-1.5° C. below the Tm (stringent hybridization conditions) (ii) hybridization solution of 6×SSC and 0.1% SDS or 3 M TMACI, 0.01 M sodium phosphate (pH 6.8), 1 mM EDTA (pH 7.6), 0.5% SDS, 100 µg/ml denatured salmon sperm DNA and 0.1% nonfat dried milk, hybridization temperature of 2-2.5° C. below the Tm, final wash solution of 3 M TMAC1, 0.01 M sodium phosphate (pH 6.8), 1 mM EDTA (pH 7.6), 0.5% SDS at 1-1.5° C. below the Tm, final wash solution of 6×SSC, and final wash at 22° C. (stringent to moderate hybridization conditions); and (iii) hybridization solution of 6×SSC and 1% SDS or 3 M TMACI, 0.01 M sodium phosphate (pH 6.8), 1 mM EDTA (pH 7.6), 0.5% SDS, 100 µg/ml denatured salmon sperm DNA and 0.1% nonfat dried milk, hybridization temperature at 2.5-3° C. below the Tm and final wash solution of 6×SSC at 22° C. (moderate hybridization solution).

It will be appreciated that the oligonucleotide which is used to analyze expression of a particular exon in the sample derived from the bacterially infected subject should have the same binding stringency as the oligonucleotide which is used to analyze the expression of that same exon in the sample derived from the virally infected subject.

In a particular embodiment, the oligonucleotide which is used to analyze expression of a particular exon in the sample derived from the bacterially infected subject is identical (i.e. has an identical sequence) to the oligonucleotide which is used to analyze the expression of that same exon in the sample derived from the virally infected subject.

According to one embodiment, the oligonucleotide is a probe.

As used herein, the term "probe" refers to an oligonucleotide which hybridizes to a particular exon of the determinant specific nucleic acid sequence to provide a detectable signal under experimental conditions and which does not hybridize to additional exons of the RNA to provide a detectable signal under identical experimental conditions.

The probes of this embodiment of this aspect of the present invention may be, for example, affixed to a solid support (e.g., arrays or beads).

Solid supports are solid-state substrates or supports onto which the nucleic acid molecules of the present invention may be associated. The nucleic acids may be associated directly or indirectly. Solid-state substrates for use in solid supports can include any solid material with which components can be associated, directly or indirectly. This includes materials such as acrylamide, agarose, cellulose, nitrocellulose, glass, gold, polystyrene, polyethylene vinyl acetate, polypropylene, polymethacrylate, polyethylene, polyethylene oxide, polysilicates, polycarbonates, teflon, fluorocarbons, nylon, silicon rubber, polyanhydrides, polyglycolic acid, polylactic acid, polyorthoesters, functionalized silane, polypropylfumerate, collagen, glycosaminoglycans, and polyamino acids. Solid-state substrates can have any useful form including thin film, membrane, bottles, dishes, fibers, woven fibers, shaped polymers, particles, beads, microparticles, or a combination. Solid-state substrates and solid supports can be porous or non-porous. A chip is a rectangular or square small piece of material. Preferred forms for solid-state substrates are thin films, beads, or chips. A useful form for a solid-state substrate is a microtiter dish. In some embodiments, a multiwell glass slide can be employed.

In one embodiment, the solid support is an array which comprises a plurality of nucleic acids of the present invention immobilized at identified or predefined locations on the solid support. Each predefined location on the solid support generally has one type of component (that is, all the components at that location are the same). Alternatively, multiple types of components can be immobilized in the same predefined location on a solid support. Each location will have multiple copies of the given components. The spatial separation of different components on the solid support allows separate detection and identification.

According to particular embodiments, the array comprises nucleic acids that specifically bind to no more than 10% of the exons of one particular RNA determinant, no more than 20% of the exons of one particular RNA determinant, no more than 30% of the exons of one particular RNA determinant, no more than 40% of the exons of one particular RNA determinant, no more than 50% of the exons of one particular RNA determinant. In some embodiments the array comprises a nucleic acid that specifically binds to only one exon of a particular RNA determinant, 2 exons of a particular RNA determinant, 3 exons of a particular RNA determinant, 4 exons of a particular RNA determinant, or 5 or more exons of a particular RNA determinant. It will be appreciated that the array may comprise more than one nucleic acid that specifically binds to the same exon—for example, two nucleic acids per exon or even three nucleic acids per exon.

Methods for immobilization of oligonucleotides to solid-state substrates are well established. Oligonucleotides, including address probes and detection probes, can be coupled to substrates using established coupling methods. For example, suitable attachment methods are described by Pease et al., Proc. Natl. Acad. Sci. USA 91(11):5022-5026 (1994), and Khrapko et al., Mol Biol (Mosk) (USSR) 25:718-730 (1991). A method for immobilization of 3'-amine oligonucleotides on casein-coated slides is described by Stimpson et al., Proc. Natl. Acad. Sci. USA 92:6379-6383 (1995). A useful method of attaching oligonucleotides to solid-state substrates is described by Guo et al., Nucleic Acids Res. 22:5456-5465 (1994).

According to another embodiment, the oligonucleotide is a primer of a primer pair. As used herein, the term "primer" refers to an oligonucleotide which acts as a point of initiation of a template-directed synthesis using methods such as PCR (polymerase chain reaction) or LCR (ligase chain reaction) under appropriate conditions (e.g., in the presence of four different nucleotide triphosphates and a polymerization agent, such as DNA polymerase, RNA polymerase or reverse-transcriptase, DNA ligase, etc, in an appropriate buffer solution containing any necessary co-factors and at suitable temperature(s)). Such a template directed synthesis is also called "primer extension". For example, a primer pair may be designed to amplify a region of DNA using PCR. Such a pair will include a "forward primer" and a "reverse primer" that hybridize to complementary strands of a DNA molecule and that delimit a region to be synthesized/amplified. A primer of this aspect of the present invention is capable of amplifying, together with its pair (e.g. by PCR) an exon-specific nucleic acid sequence to provide a detectable signal under experimental conditions and which does not amplify other exons of the determinant nucleic acid sequence to provide a detectable signal under identical experimental conditions.

Oligonucleotides of the invention may be prepared by any of a variety of methods (see, for example, J. Sambrook et al., "Molecular Cloning: A Laboratory Manual", 1989, 2.sup.nd Ed., Cold Spring Harbour Laboratory Press: New York, N.Y.; "PCR Protocols: A Guide to Methods and Applications", 1990, M. A. Innis (Ed.), Academic Press: New York, N.Y.; P. Tijssen "Hybridization with Nucleic Acid Probes—Laboratory Techniques in Biochemistry and Molecular Biology (Parts I and II)", 1993, Elsevier Science; "PCR Strategies", 1995, M. A. Innis (Ed.), Academic Press: New York, N.Y.; and "Short Protocols in Molecular Biology", 2002, F. M. Ausubel (Ed.), 5.sup.th Ed., John Wiley & Sons: Secaucus, N.J.). For example, oligonucleotides may be prepared using any of a variety of chemical techniques well-known in the art, including, for example, chemical synthesis and polymerization based on a template as described, for example, in S. A. Narang et al., Meth. Enzymol. 1979, 68: 90-98; E. L. Brown et al., Meth. Enzymol. 1979, 68: 109-151; E. S. Belousov et al., Nucleic Acids Res. 1997, 25: 3440-3444; D. Guschin et al., Anal. Biochem. 1997, 250: 203-211; M. J. Blommers et al., Biochemistry, 1994, 33: 7886-7896; and K. Frenkel et al., Free Radic. Biol. Med. 1995, 19: 373-380; and U.S. Pat. No. 4,458,066.

For example, oligonucleotides may be prepared using an automated, solid-phase procedure based on the phosphoramidite approach. In such a method, each nucleotide is individually added to the 5'-end of the growing oligonucleotide chain, which is attached at the 3'-end to a solid support. The added nucleotides are in the form of trivalent 3'-phosphoramidites that are protected from polymerization by a dimethoxytriyl (or DMT) group at the 5'-position. After base-induced phosphoramidite coupling, mild oxidation to give a pentavalent phosphotriester intermediate and DMT removal provides a new site for oligonucleotide elongation. The oligonucleotides are then cleaved off the solid support, and the phosphodiester and exocyclic amino groups are deprotected with ammonium hydroxide. These syntheses may be performed on oligo synthesizers such as those commercially available from Perkin Elmer/Applied Biosystems, Inc. (Foster City, Calif.), DuPont (Wilmington, Del.) or Milligen (Bedford, Mass.). Alternatively, oligonucleotides can be custom made and ordered from a variety of commercial sources well-known in the art, including, for example, the Midland Certified Reagent Company (Midland, Tex.), ExpressGen, Inc. (Chicago, Ill.), Operon Technologies, Inc. (Huntsville, Ala.), and many others.

Purification of the oligonucleotides of the invention, where necessary or desirable, may be carried out by any of a variety of methods well-known in the art. Purification of oligonucleotides is typically performed either by native acrylamide gel electrophoresis, by anion-exchange HPLC as described, for example, by J. D. Pearson and F. E. Regnier (J. Chrom., 1983, 255: 137-149) or by reverse phase HPLC (G. D. McFarland and P. N. Borer, Nucleic Acids Res., 1979, 7: 1067-1080).

The sequence of oligonucleotides can be verified using any suitable sequencing method including, but not limited to, chemical degradation (A. M. Maxam and W. Gilbert, Methods of Enzymology, 1980, 65: 499-560), matrix-assisted laser desorption ionization time-of-flight (MALDI-TOF) mass spectrometry (U. Pieles et al., Nucleic Acids Res., 1993, 21: 3191-3196), mass spectrometry following a combination of alkaline phosphatase and exonuclease digestions (H. Wu and H. Aboleneen, Anal. Biochem., 2001, 290: 347-352), and the like.

As already mentioned above, modified oligonucleotides may be prepared using any of several means known in the art. Non-limiting examples of such modifications include methylation, "caps", substitution of one or more of the naturally occurring nucleotides with an analog, and internucleotide modifications such as, for example, those with uncharged linkages (e.g., methyl phosphonates, phosphotriesters, phosphoroamidates, carbamates, etc), or charged linkages (e.g., phosphorothioates, phosphorodithioates, etc). Oligonucleotides may contain one or more additional covalently linked moieties, such as, for example, proteins (e.g., nucleases, toxins, antibodies, signal peptides, poly-L-lysine, etc), intercalators (e.g., acridine, psoralen, etc), chelators (e.g., metals, radioactive metals, iron, oxidative metals, etc), and alkylators. The oligonucleotide may also be derivatized by formation of a methyl or ethyl phosphotriester or an alkyl phosphoramidate linkage. Furthermore, the oligonucleotide sequences of the present invention may also be modified with a label.

In certain embodiments, the detection probes or amplification primers or both probes and primers are labeled with a detectable agent or moiety before being used in amplification/detection assays. In certain embodiments, the detection probes are labeled with a detectable agent. Preferably, a detectable agent is selected such that it generates a signal which can be measured and whose intensity is related (e.g., proportional) to the amount of amplification products in the sample being analyzed.

The association between the oligonucleotide and detectable agent can be covalent or non-covalent. Labeled detection probes can be prepared by incorporation of or conjugation to a detectable moiety. Labels can be attached directly to the nucleic acid sequence or indirectly (e.g., through a linker). Linkers or spacer arms of various lengths are known in the art and are commercially available, and can be selected to reduce steric hindrance, or to confer other useful or desired properties to the resulting labeled molecules (see, for example, E. S. Mansfield et al., Mol. Cell. Probes, 1995, 9: 145-156).

Methods for labeling nucleic acid molecules are well-known in the art. For a review of labeling protocols, label detection techniques, and recent developments in the field, see, for example, L. J. Kricka, Ann. Clin. Biochem. 2002, 39: 114-129; R. P. van Gijlswijk et al., Expert Rev. Mol. Diagn. 2001, 1: 81-91; and S. Joos et al., J. Biotechnol. 1994, 35: 135-153. Standard nucleic acid labeling methods include: incorporation of radioactive agents, direct attachments of fluorescent dyes (L. M. Smith et al., Nucl. Acids Res., 1985, 13: 2399-2412) or of enzymes (B. A. Connoly and O. Rider, Nucl. Acids. Res., 1985, 13: 4485-4502); chemical modifications of nucleic acid molecules making them detectable immunochemically or by other affinity reactions (T. R. Broker et al., Nucl. Acids Res. 1978, 5: 363-384; E. A. Bayer et al., Methods of Biochem. Analysis, 1980, 26: 1-45; R. Langer et al., Proc. Natl. Acad. Sci. USA, 1981, 78: 6633-6637; R. W. Richardson et al., Nucl. Acids Res. 1983, 11: 6167-6184; D. J. Brigati et al., Virol. 1983, 126: 32-50; P. Tchen et al., Proc. Natl. Acad. Sci. USA, 1984, 81: 3466-3470; J. E. Landegent et al., Exp. Cell Res. 1984, 15: 61-72; and A. H. Hopman et al., Exp. Cell Res. 1987, 169: 357-368); and enzyme-mediated labeling methods, such as random priming, nick translation, PCR and tailing with terminal transferase (for a review on enzymatic labeling, see, for example, J. Temsamani and S. Agrawal, Mol. Biotechnol. 1996, 5: 223-232). More recently developed nucleic acid labeling systems include, but are not limited to: ULS (Universal Linkage System), which is based on the reaction of mono-reactive cisplatin derivatives with the N7 position of guanine moieties in DNA (R. J. Heetebrij et al., Cytogenet. Cell. Genet. 1999, 87: 47-52), psoralen-biotin, which intercalates into nucleic acids and upon UV irradiation becomes covalently bonded to the nucleotide bases (C. Levenson et al., Methods Enzymol. 1990, 184: 577-583; and C. Pfannschmidt et al., Nucleic Acids Res. 1996, 24: 1702-1709), photoreactive azido derivatives (C. Neves et al., Bioconjugate Chem. 2000, 11: 51-55), and DNA alkylating agents (M. G. Sebestyen et al., Nat. Biotechnol. 1998, 16: 568-576).

Any of a wide variety of detectable agents can be used in the practice of the present invention. Suitable detectable agents include, but are not limited to, various ligands, radionuclides (such as, for example, $^{32}P$, $^{35}S$, $^{3}H$, $^{14}C$, $^{125}I$, $^{131}I$, and the like); fluorescent dyes (for specific exemplary fluorescent dyes, see below); chemiluminescent agents (such as, for example, acridinium esters, stabilized dioxetanes, and the like); spectrally resolvable inorganic fluorescent semiconductor nanocrystals (i.e., quantum dots), metal nanoparticles (e.g., gold, silver, copper and platinum) or nanoclusters; enzymes (such as, for example, those used in an ELISA, i.e., horseradish peroxidase, beta-galactosidase, luciferase, alkaline phosphatase); colorimetric labels (such as, for example, dyes, colloidal gold, and the like); magnetic labels (such as, for example, Dynabeads™); and biotin, dioxigenin or other haptens and proteins for which antisera or monoclonal antibodies are available.

In certain embodiments, the inventive detection probes are fluorescently labeled. Numerous known fluorescent labeling moieties of a wide variety of chemical structures and physical characteristics are suitable for use in the practice of this invention. Suitable fluorescent dyes include, but are not limited to, fluorescein and fluorescein dyes (e.g., fluorescein isothiocyanine or FITC, naphthofluorescein, 4',5'-dichloro-2',7'-dimethoxy-fluorescein, 6 carboxyfluorescein or FAM), carbocyanine, merocyanine, styryl dyes, oxonol dyes, phycoerythrin, erythrosin, eosin, rhodamine dyes (e.g., carboxytetramethylrhodamine or TAMRA, carboxyrhodamine 6G, carboxy-X-rhodamine (ROX), lissamine rhodamine B, rhodamine 6G, rhodamine Green, rhodamine Red, tetramethylrhodamine or TMR), coumarin and coumarin dyes (e.g., methoxycoumarin, dialkylaminocoumarin, hydroxycoumarin and aminomethylcoumarin or AMCA), Oregon Green Dyes (e.g., Oregon Green 488, Oregon Green 500, Oregon Green 514), Texas Red, Texas Red-X, Spectrum Red™, Spectrum Green™, cyanine dyes (e.g., Cy-3™, Cy-5™, Cy-3.5™, Cy-5.5™), Alexa Fluor dyes (e.g., Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), BODIPY dyes (e.g., BODIPY FL, BODIPY R6G, BODIPY TMR, BODIPY TR, BODIPY 530/550, BODIPY 558/568, BODIPY 564/570, BODIPY 576/589, BODIPY 581/591, BODIPY 630/650, BODIPY 650/665), IRDyes (e.g., IRD40, IRD 700, IRD 800), and the like. For more examples of suitable fluorescent dyes and methods for linking or incorporating fluorescent dyes to nucleic acid molecules see, for example, "The Handbook of Fluorescent Probes and Research Products", 9th Ed., Molecular Probes, Inc., Eugene, Oreg. Fluorescent dyes as well as labeling kits are commercially available from, for example, Amersham Biosciences, Inc. (Piscataway, N.J.), Molecular Probes Inc. (Eugene, Oreg.), and New England Biolabs Inc. (Berverly, Mass.).

Methods of analyzing the amount of RNA using oligonucleotides are known in the art and are summarized infra:

Northern Blot Analysis:

This method involves the detection of a particular RNA in a mixture of RNAs. An RNA sample is denatured by treatment with an agent (e.g., formaldehyde) that prevents hydrogen bonding between base pairs, ensuring that all the RNA molecules have an unfolded, linear conformation. The individual RNA molecules are then separated according to size by gel electrophoresis and transferred to a nitrocellulose or a nylon-based membrane to which the denatured RNAs adhere. The membrane is then exposed to labeled DNA probes. Probes may be labeled using radio-isotopes or enzyme linked nucleotides. Detection may be using autoradiography, colorimetric reaction or chemiluminescence. This method allows both quantitation of an amount of particular RNA molecules and determination of its identity by a relative position on the membrane which is indicative of a migration distance in the gel during electrophoresis.

Amplification Reactions:

Identification of the exon on the determinant may be carried out using an amplification reaction.

As used herein, the term "amplification" refers to a process that increases the representation of a population of specific nucleic acid sequences in a sample by producing multiple (i.e., at least 2) copies of the desired sequences. Methods for nucleic acid amplification are known in the art and include, but are not limited to, polymerase chain reaction (PCR) and ligase chain reaction (LCR). In a typical PCR amplification reaction, a nucleic acid sequence of interest is often amplified at least fifty thousand fold in amount over its amount in the starting sample. A "copy" or "amplicon" does not necessarily mean perfect sequence complementarity or identity to the template sequence. For example, copies can include nucleotide analogs such as deoxyinosine, intentional sequence alterations (such as sequence alterations introduced through a primer comprising a sequence that is hybridizable but not complementary to the template), and/or sequence errors that occur during amplification.

A typical amplification reaction is carried out by contacting a forward and reverse primer (a primer pair) to the sample DNA together with any additional amplification reaction reagents under conditions which allow amplification of the target sequence.

The terms "forward primer" and "forward amplification primer" are used herein interchangeably, and refer to a primer that hybridizes (or anneals) to the target (template strand). The terms "reverse primer" and "reverse amplification primer" are used herein interchangeably, and refer to a primer that hybridizes (or anneals) to the complementary target strand. The forward primer hybridizes with the target sequence 5' with respect to the reverse primer.

The term "amplification conditions", as used herein, refers to conditions that promote annealing and/or extension of primer sequences. Such conditions are well-known in the art and depend on the amplification method selected. Thus, for example, in a PCR reaction, amplification conditions generally comprise thermal cycling, i.e., cycling of the reaction mixture between two or more temperatures. In isothermal amplification reactions, amplification occurs without thermal cycling although an initial temperature increase may be required to initiate the reaction. Amplification conditions encompass all reaction conditions including, but not limited to, temperature and temperature cycling, buffer, salt, ionic strength, and pH, and the like.

As used herein, the term "amplification reaction reagents", refers to reagents used in nucleic acid amplification reactions and may include, but are not limited to, buffers, reagents, enzymes having reverse transcriptase and/or polymerase activity or exonuclease activity, enzyme cofactors such as magnesium or manganese, salts, nicotinamide adenine dinuclease (NAD) and deoxynucleoside triphosphates (dNTPs), such as deoxyadenosine triphospate, deoxyguanosine triphosphate, deoxycytidine triphosphate and thymidine triphosphate. Amplification reaction reagents may readily be selected by one skilled in the art depending on the amplification method used.

According to this aspect of the present invention, the amplifying may be effected using techniques such as polymerase chain reaction (PCR), which includes, but is not limited to Allele-specific PCR, Assembly PCR or Polymerase Cycling Assembly (PCA), Asymmetric PCR, Helicase-dependent amplification, Hot-start PCR, Intersequence-specific PCR (ISSR), Inverse PCR, Ligation-mediated PCR, Methylation-specific PCR (MSP), Miniprimer PCR, Multiplex Ligation-dependent Probe Amplification, Multiplex-PCR, Nested PCR, Overlap-extension PCR, Quantitative PCR (Q-PCR), Reverse Transcription PCR (RT-PCR), Solid Phase PCR: encompasses multiple meanings, including Polony Amplification (where PCR colonies are derived in a gel matrix, for example), Bridge PCR (primers are covalently linked to a solid-support surface), conventional Solid Phase PCR (where Asymmetric PCR is applied in the presence of solid support bearing primer with sequence matching one of the aqueous primers) and Enhanced Solid Phase PCR (where conventional Solid Phase PCR can be improved by employing high Tm and nested solid support primer with optional application of a thermal 'step' to favour solid support priming), Thermal asymmetric interlaced PCR (TAIL-PCR), Touchdown PCR (Step-down PCR), PAN-AC and Universal Fast Walking.

The PCR (or polymerase chain reaction) technique is well-known in the art and has been disclosed, for example, in K. B. Mullis and F. A. Faloona, Methods Enzymol., 1987, 155: 350-355 and U.S. Pat. Nos. 4,683,202; 4,683,195; and 4,800,159 (each of which is incorporated herein by reference in its entirety). In its simplest form, PCR is an in vitro method for the enzymatic synthesis of specific DNA sequences, using two oligonucleotide primers that hybridize to opposite strands and flank the region of interest in the target DNA. A plurality of reaction cycles, each cycle comprising: a denaturation step, an annealing step, and a polymerization step, results in the exponential accumulation of a specific DNA fragment ("PCR Protocols: A Guide to Methods and Applications", M. A. Innis (Ed.), 1990, Academic Press: New York; "PCR Strategies", M. A. Innis (Ed.), 1995, Academic Press: New York; "Polymerase chain reaction: basic principles and automation in PCR: A Practical Approach", McPherson et al. (Eds.), 1991, IRL Press: Oxford; R. K. Saiki et al., Nature, 1986, 324: 163-166). The termini of the amplified fragments are defined as the 5' ends of the primers. Examples of DNA polymerases capable of producing amplification products in PCR reactions include, but are not limited to: *E. coli* DNA polymerase I, Klenow fragment of DNA polymerase I, T4 DNA polymerase, thermostable DNA polymerases isolated from *Thermus aquaticus* (Taq), available from a variety of sources (for example, Perkin Elmer), *Thermus thermophilus* (United States Biochemicals), *Bacillus stereothermophilus* (Bio-Rad), or *Thermococcus litoralis* ("Vent" polymerase, New England Biolabs). RNA target sequences may be amplified by reverse transcribing the mRNA into cDNA, and then performing PCR (RT-PCR), as described above. Alternatively, a single enzyme may be used for both steps as described in U.S. Pat. No. 5,322,770.

The duration and temperature of each step of a PCR cycle, as well as the number of cycles, are generally adjusted according to the stringency requirements in effect. Annealing temperature and timing are determined both by the efficiency with which a primer is expected to anneal to a template and the degree of mismatch that is to be tolerated. The ability to optimize the reaction cycle conditions is well within the knowledge of one of ordinary skill in the art. Although the number of reaction cycles may vary depending on the detection analysis being performed, it usually is at least 15, more usually at least 20, and may be as high as 60 or higher. However, in many situations, the number of reaction cycles typically ranges from about 20 to about 40.

The denaturation step of a PCR cycle generally comprises heating the reaction mixture to an elevated temperature and maintaining the mixture at the elevated temperature for a period of time sufficient for any double-stranded or hybridized nucleic acid present in the reaction mixture to dissociate. For denaturation, the temperature of the reaction mixture is usually raised to, and maintained at, a temperature ranging from about 85° C. to about 100° C., usually from about 90° C. to about 98° C., and more usually from about 93° C. to about 96° C. for a period of time ranging from about 3 to about 120 seconds, usually from about 5 to about 30 seconds.

Following denaturation, the reaction mixture is subjected to conditions sufficient for primer annealing to template DNA present in the mixture. The temperature to which the reaction mixture is lowered to achieve these conditions is usually chosen to provide optimal efficiency and specificity, and generally ranges from about 50° C. to about 70° C., usually from about 55° C. to about 70° C., and more usually from about 60° C. to about 68° C. Annealing conditions are generally maintained for a period of time ranging from about 15 seconds to about 30 minutes, usually from about 30 seconds to about 5 minutes.

Following annealing of primer to template DNA or during annealing of primer to template DNA, the reaction mixture is subjected to conditions sufficient to provide for polymerization of nucleotides to the primer's end in a such manner that the primer is extended in a 5' to 3' direction using the DNA to which it is hybridized as a template, (i.e., conditions sufficient for enzymatic production of primer extension product). To achieve primer extension conditions, the temperature of the reaction mixture is typically raised to a temperature ranging from about 65° C. to about 75° C., usually from about 67° C. to about 73° C., and maintained at that temperature for a period of time ranging from about 15 seconds to about 20 minutes, usually from about 30 seconds to about 5 minutes.

The above cycles of denaturation, annealing, and polymerization may be performed using an automated device typically known as a thermal cycler or thermocycler. Thermal cyclers that may be employed are described in U.S. Pat. Nos. 5,612,473; 5,602,756; 5,538,871; and 5,475,610 (each of which is incorporated herein by reference in its entirety). Thermal cyclers are commercially available, for example, from Perkin Elmer-Applied Biosystems (Norwalk, Conn.), BioRad (Hercules, Calif.), Roche Applied Science (Indianapolis, Ind.), and Stratagene (La Jolla, Calif.).

Amplification products obtained using primers of the present invention may be detected using agarose gel electrophoresis and visualization by ethidium bromide staining and exposure to ultraviolet (UV) light or by sequence analysis of the amplification product.

According to one embodiment, the amplification and quantification of the amplification product may be effected in real-time (qRT-PCR). Typically, QRT-PCR methods use double stranded DNA detecting molecules to measure the amount of amplified product in real time.

As used herein the phrase "double stranded DNA detecting molecule" refers to a double stranded DNA interacting molecule that produces a quantifiable signal (e.g., fluorescent signal). For example such a double stranded DNA detecting molecule can be a fluorescent dye that (1) interacts with a fragment of DNA or an amplicon and (2) emits at a different wavelength in the presence of an amplicon in duplex formation than in the presence of the amplicon in separation. A double stranded DNA detecting molecule can be a double stranded DNA intercalating detecting molecule or a primer-based double stranded DNA detecting molecule.

A double stranded DNA intercalating detecting molecule is not covalently linked to a primer, an amplicon or a nucleic acid template. The detecting molecule increases its emission in the presence of double stranded DNA and decreases its emission when duplex DNA unwinds. Examples include, but are not limited to, ethidium bromide, YO-PRO-1, Hoechst 33258, SYBR Gold, and SYBR Green I. Ethidium bromide is a fluorescent chemical that intercalates between base pairs in a double stranded DNA fragment and is commonly used to detect DNA following gel electrophoresis. When excited by ultraviolet light between 254 nm and 366 nm, it emits fluorescent light at 590 nm. The DNA-ethidium bromide complex produces about 50 times more fluorescence than ethidium bromide in the presence of single stranded DNA. SYBR Green I is excited at 497 nm and emits at 520 nm. The fluorescence intensity of SYBR Green I increases over 100 fold upon binding to double stranded DNA against single stranded DNA. An alternative to SYBR Green I is SYBR Gold introduced by Molecular Probes Inc. Similar to SYBR Green I, the fluorescence emission of SYBR Gold enhances in the presence of DNA in duplex and decreases when double stranded DNA unwinds. However, SYBR Gold's excitation peak is at 495 nm and the emission peak is at 537 nm. SYBR Gold reportedly appears more stable than SYBR Green I. Hoechst 33258 is a known bisbenzimide double stranded DNA detecting molecule that binds to the AT rich regions of DNA in duplex. Hoechst 33258 excites at 350 nm and emits at 450 nm. YO-PRO-1, exciting at 450 nm and emitting at 550 nm, has been reported to be a double stranded DNA specific detecting molecule. In a particular embodiment of the present invention, the double stranded DNA detecting molecule is SYBR Green I.

A primer-based double stranded DNA detecting molecule is covalently linked to a primer and either increases or decreases fluorescence emission when amplicons form a duplex structure. Increased fluorescence emission is observed when a primer-based double stranded DNA detecting molecule is attached close to the 3' end of a primer and the primer terminal base is either dG or dC. The detecting molecule is quenched in the proximity of terminal dC-dG and dG-dC base pairs and dequenched as a result of duplex formation of the amplicon when the detecting molecule is located internally at least 6 nucleotides away from the ends of the primer. The dequenching results in a substantial increase in fluorescence emission. Examples of these type of detecting molecules include but are not limited to fluorescein (exciting at 488 nm and emitting at 530 nm), FAM (exciting at 494 nm and emitting at 518 nm), JOE (exciting at 527 and emitting at 548), HEX (exciting at 535 nm and emitting at 556 nm), TET (exciting at 521 nm and emitting at 536 nm), Alexa Fluor 594 (exciting at 590 nm and emitting at 615 nm), ROX (exciting at 575 nm and emitting at 602 nm), and TAMRA (exciting at 555 nm and emitting at 580 nm). In contrast, some primer-based double stranded DNA detecting molecules decrease their emission in the presence of double stranded DNA against single stranded DNA. Examples include, but are not limited to, rhodamine, and BODIPY-FI (exciting at 504 nm and emitting at 513 nm). These detecting molecules are usually covalently conjugated to a primer at the 5' terminal dC or dG and emit less fluorescence when amplicons are in duplex. It is believed that the decrease of fluorescence upon the formation of duplex is due to the quenching of guanosine in the complementary strand in close proximity to the detecting molecule or the quenching of the terminal dC-dG base pairs.

According to one embodiment, the primer-based double stranded DNA detecting molecule is a 5' nuclease probe.

Such probes incorporate a fluorescent reporter molecule at either the 5' or 3' end of an oligonucleotide and a quencher at the opposite end. The first step of the amplification process involves heating to denature the double stranded DNA target molecule into a single stranded DNA. During the second step, a forward primer anneals to the target strand of the DNA and is extended by Taq polymerase. A reverse primer and a 5' nuclease probe then anneal to this newly replicated strand.

In this embodiment, at least one of the primer pairs or 5' nuclease probe should hybridize with a unique determinant sequence. The polymerase extends and cleaves the probe from the target strand. Upon cleavage, the reporter is no longer quenched by its proximity to the quencher and fluorescence is released. Each replication will result in the cleavage of a probe. As a result, the fluorescent signal will increase proportionally to the amount of amplification product.

RNA In Situ Hybridization Stain:

In this method DNA or RNA probes are attached to the RNA molecules present in the cells. Generally, the cells are first fixed to microscopic slides to preserve the cellular structure and to prevent the RNA molecules from being degraded and then are subjected to hybridization buffer containing the labeled probe. The hybridization buffer includes reagents such as formamide and salts (e.g., sodium chloride and sodium citrate) which enable specific hybridization of the DNA or RNA probes with their target mRNA molecules in situ while avoiding non-specific binding of probe. Those of skills in the art are capable of adjusting the hybridization conditions (i.e., temperature, concentration of salts and formamide and the like) to specific probes and types of cells. Following hybridization, any unbound probe is washed off and the bound probe is detected using known methods. For example, if a radio-labeled probe is used, then the slide is subjected to a photographic emulsion which reveals signals generated using radio-labeled probes; if the probe was labeled with an enzyme then the enzyme-specific substrate is added for the formation of a colorimetric reaction; if the probe is labeled using a fluorescent label, then the bound probe is revealed using a fluorescent microscope; if the probe is labeled using a tag (e.g., digoxigenin, biotin, and the like) then the bound probe can be detected following interaction with a tag-specific antibody which can be detected using known methods.

In Situ RT-PCR Stain:

This method is described in Nuovo G J, et al. [Intracellular localization of polymerase chain reaction (PCR)-amplified hepatitis C cDNA. Am J Surg Pathol. 1993, 17: 683-90] and Komminoth P, et al. [Evaluation of methods for hepatitis C virus detection in archival liver biopsies. Comparison of histology, immunohistochemistry, in situ hybridization, reverse transcriptase polymerase chain reaction (RT-PCR) and in situ RT-PCR. Pathol Res Pract. 1994, 190: 1017-25]. Briefly, the RT-PCR reaction is performed on fixed cells by incorporating labeled nucleotides to the PCR reaction. The reaction is carried on using a specific in situ RT-PCR apparatus such as the laser-capture microdissection PixCell I LCM system available from Arcturus Engineering (Mountainview, Calif.).

DNA Microarrays/DNA Chips:

The expression of thousands of genes may be analyzed simultaneously using DNA microarrays, allowing analysis of the complete transcriptional program of an organism during specific developmental processes or physiological responses. DNA microarrays consist of thousands of individual gene sequences attached to closely packed areas on the surface of a support such as a glass microscope slide. Various methods have been developed for preparing DNA microarrays. In one method, an approximately 1 kilobase segment of the coding region of each gene for analysis is individually PCR amplified. A robotic apparatus is employed to apply each amplified DNA sample to closely spaced zones on the surface of a glass microscope slide, which is subsequently processed by thermal and chemical treatment to bind the DNA sequences to the surface of the support and denature them. Typically, such arrays are about 2×2 cm and contain about individual nucleic acids 6000 spots. In a variant of the technique, multiple DNA oligonucleotides, usually 20 nucleotides in length, are synthesized from an initial nucleotide that is covalently bound to the surface of a support, such that tens of thousands of identical oligonucleotides are synthesized in a small square zone on the surface of the support. Multiple oligonucleotide sequences from a single gene are synthesized in neighboring regions of the slide for analysis of expression of that gene. Hence, thousands of genes can be represented on one glass slide. Such arrays of synthetic oligonucleotides may be referred to in the art as "DNA chips", as opposed to "DNA microarrays", as described above [Lodish et al. (eds.). Chapter 7.8: DNA Microarrays: Analyzing Genome-Wide Expression. In: Molecular Cell Biology, 4th ed., W. H. Freeman, New York. (2000)].

Oligonucleotide Microarray—

In this method oligonucleotide probes capable of specifically hybridizing with the polynucleotides of some embodiments of the invention are attached to a solid surface (e.g., a glass wafer). Each oligonucleotide probe is of approximately 20-25 nucleic acids in length. To detect the expression pattern of the polynucleotides of some embodiments of the invention in a specific cell sample (e.g., blood cells), RNA is extracted from the cell sample using methods known in the art (using e.g., a TRIZOL solution, Gibco BRL, USA). Hybridization can take place using either labeled oligonucleotide probes (e.g., 5'-biotinylated probes) or labeled fragments of complementary DNA (cDNA) or RNA (cRNA). Briefly, double stranded cDNA is prepared from the RNA using reverse transcriptase (RT) (e.g., Superscript II RT), DNA ligase and DNA polymerase I, all according to manufacturer's instructions (Invitrogen Life Technologies, Frederick, Md., USA). To prepare labeled cRNA, the double stranded cDNA is subjected to an in vitro transcription reaction in the presence of biotinylated nucleotides using e.g., the BioArray High Yield RNA Transcript Labeling Kit (Enzo, Diagnostics, Affymetix Santa Clara Calif.). For efficient hybridization the labeled cRNA can be fragmented by incubating the RNA in 40 mM Tris Acetate (pH 8.1), 100 mM potassium acetate and 30 mM magnesium acetate for 35 minutes at 94° C. Following hybridization, the microarray is washed and the hybridization signal is scanned using a confocal laser fluorescence scanner which measures fluorescence intensity emitted by the labeled cRNA bound to the probe arrays.

For example, in the Affymetrix microarray (Affymetrix™, Santa Clara, Calif.) each gene on the array is represented by a series of different oligonucleotide probes, of which, each probe pair consists of a perfect match oligonucleotide and a mismatch oligonucleotide. While the perfect match probe has a sequence exactly complimentary to the particular gene, thus enabling the measurement of the level of expression of the particular gene, the mismatch probe differs from the perfect match probe by a single base substitution at the center base position. The hybridization signal is scanned using the Agilent scanner, and the Microarray Suite software subtracts the non-specific signal resulting from the mismatch probe from the signal resulting from the perfect match probe.

It will be appreciated that the expression of an RNA from a particular exon can be analyzed without the use of exon-specific oligonucleotides—e.g. by RNA sequencing, as further described herein below.

RNA Sequencing:

Methods for RNA sequence determination are generally known to the person skilled in the art. Preferred sequencing methods are next generation sequencing methods or parallel high throughput sequencing methods. An example of an envisaged sequence method is pyrosequencing, in particular 454 pyrosequencing, e.g. based on the Roche 454 Genome Sequencer. This method amplifies DNA inside water droplets in an oil solution with each droplet containing a single DNA template attached to a single primer-coated bead that then forms a clonal colony. Pyrosequencing uses luciferase to generate light for detection of the individual nucleotides added to the nascent DNA, and the combined data are used to generate sequence read-outs. Yet another envisaged example is Illumina or Solexa sequencing, e.g. by using the Illumina Genome Analyzer technology, which is based on reversible dye-terminators. DNA molecules are typically attached to primers on a slide and amplified so that local clonal colonies are formed. Subsequently one type of nucleotide at a time may be added, and non-incorporated nucleotides are washed away. Subsequently, images of the fluorescently labeled nucleotides may be taken and the dye is chemically removed from the DNA, allowing a next cycle. Yet another example is the use of Applied Biosystems' SOLiD technology, which employs sequencing by ligation. This method is based on the use of a pool of all possible oligonucleotides of a fixed length, which are labeled according to the sequenced position. Such oligonucleotides are annealed and ligated. Subsequently, the preferential ligation by DNA ligase for matching sequences typically results in a signal informative of the nucleotide at that position. Since the DNA is typically amplified by emulsion PCR, the resulting bead, each containing only copies of the same DNA molecule, can be deposited on a glass slide resulting in sequences of quantities and lengths comparable to Illumina sequencing. A further method is based on Helicos' Heliscope technology, wherein fragments are captured by polyT oligomers tethered to an array. At each sequencing cycle, polymerase and single fluorescently labeled nucleotides are added and the array is imaged. The fluorescent tag is subsequently removed and the cycle is repeated. Further examples of sequencing techniques encompassed within the methods of the present invention are sequencing by hybridization, sequencing by use of nanopores, microscopy-based sequencing techniques, microfluidic Sanger sequencing, or microchip-based sequencing methods. The present invention also envisages further developments of these techniques, e.g. further improvements of the accuracy of the sequence determination, or the time needed for the determination of the genomic sequence of an organism etc.

According to one embodiment, the sequencing method comprises deep sequencing.

As used herein, the term "deep sequencing" refers to a sequencing method wherein the target sequence is read multiple times in the single test. A single deep sequencing run is composed of a multitude of sequencing reactions run on the same target sequence and each, generating independent sequence readout.

Selection of the optimal exon or exons may be based fully or partially on the differential expression level between the bacterial and viral samples. In one embodiment, the exon which provides the highest differential expression is selected as the optimal exon. It will be appreciated that secondary considerations such as the GC content of the probe, the length of the probe, the two or three dimensional structure of the probe, the specificity of the probe etc. may also be taken into account when selecting the optimal exon/exons. Thus, it is envisaged that due to these secondary considerations, the exon with the second or even third highest differential expression is selected as the optimal exon. So long as the differential expression is above a predetermined level, the secondary considerations may be deemed relevant and taken into account.

Once the optimal exon has been selected, determining the expression therefrom in a sample of an infectious subject may enable diagnosis of infection type.

Thus, according to another aspect of the present invention there is provided a method of determining an infection type in a subject comprising measuring the expression of at least one RNA determinant in a sample of the subject, wherein the measuring is effected at an exon or plurality of exons whose expression level distinguishes between a bacterial and viral infection with a degree of accuracy above a predetermined level, thereby determining the infection type of the subject.

As used herein, the term "analyzing" or "analysis", "measuring" or "measurement," or alternatively "detecting" or "detection," means assessing the presence, absence, quantity or amount (which can be an effective amount) of the determinant within a clinical or subject-derived sample, including the derivation of qualitative or quantitative concentration levels of such determinants.

It will be appreciated that the exon whose expression level distinguishes between a bacterial and viral infection with a degree of accuracy above a predetermined level is based on differential expression analysis and may be selected according to the method described herein above.

In one embodiment, expression level of the exon which provides the highest differential expression between bacterial and viral samples out of all the exons of the RNA is measured. In another embodiment, the expression level of the exon which provides a higher accuracy (based on differential expression analysis) than that provided when measuring expression of the full length RNA determinant is measured. As mentioned herein above, secondary considerations such as the GC content of the probe, the length of the probe, the two or three dimensional structure of the probe, the specificity of the probe, identity of other probes in the assay etc. may also be taken into account when selecting the exon/exons from which to analyze expression. Thus, it is envisaged that due to these secondary considerations, expression level from the exon with the second or even third highest differential expression (between bacterial and viral samples) is measured. So long as the differential expression is above a predetermined level, the secondary considerations may be deemed relevant and taken into account.

According to a particular embodiment, the exon is not the 3' exon.

The expression levels of full length RNA determinant can be differently calculated depending on the type of array used to measure it. Some arrays rely on averaging areas at the 3' end of the gene, for example 3'-based expression array that have probes localized to the extreme 3' end of the gene (such as Affymetrix U133A and B series), or classical 3' assays that typically rely on priming from a transcript's poly-A tail.

Other arrays (including the Human Gene 1.0 ST Array (Affymetrix) described in the examples section) use probes that are distributed across the full length of the gene, providing a more complete and accurate picture of overall gene expression. In these arrays, the gene-level analysis of multiple probes on different exons is summarized into an expression value representing all transcripts from the same gene.

The term "accuracy" refers to the degree of conformity of a measured or calculated quantity (a test reported value) to its actual (or true) value. Clinical accuracy relates to the proportion of true outcomes (true positives (TP) or true negatives (TN) versus misclassified outcomes (false positives (FP) or false negatives (FN)), and may be stated as a sensitivity, specificity, positive predictive values (PPV) or negative predictive values (NPV), Matthews correlation coefficient (MCC), or as a likelihood, odds ratio, Receiver Operating Characteristic (ROC) curve, Area Under the Curve (AUC) among other measures.

In one embodiment, the expression level is measured at an exon which presents the highest degree of differential expression as measured in a bacterial and viral sample as compared to all the other exons of the RNA determinant.

Exemplary RNA determinants that may be measured are set forth in Tables 1-4 herein below.

TABLE 1

| Gene symbol | REFSEQ NO. | Gene Name |
| --- | --- | --- |
| AIM2 | NC_000001.11<br>NT_004487.20,<br>NC_018912.2 | Absent In Melanoma 2 |
| ANKRD2 | NC_000010.11<br>NC_018921.2<br>NT_030059.14 | Ankyrin Repeat Domain 2 |
| BMX | NC_000023.11<br>NT_167197.2,<br>NC_018934.2 | BMX Non-Receptor Tyrosine Kinase |
| C19orf59 | NC_000019.10<br>NC_018930.2<br>NT_01129512 | Mast Cel4-Expressed Membrane Protein 1 |
| CD177 | NC_000019.10<br>NC_018930.2,<br>NT_011109.17 | CD177 Molecule |
| CEACAM1 | NC_000019.10<br>NT_011109.17,<br>NC_018930.2 | Carcinoembryonic Antigen-Related Cell Adhesion Molecule 1 |
| CLEC4D | NC_000012.12<br>NT_009714.18,<br>NC_018923.2 | C-Type Lectin Domain Family 4, Member D |
| CMPK2 | NC_000002.12<br>NT_005334.17,<br>NC_018913.2 | Cytidine/uridine monophosphate kinase 2 |
| EIF1AY | NC_000024.10<br>NT_011875.13 | Eukaryotic Translation Initiation Factor 1A, Y-Linked |
| EIF2AK2 | NC_000002.12<br>NT_022184.16<br>NC_018913.2 | Eukaryotic Translation Initiation Factor 2-Alpha Kinase 2 |
| EPSTI1 | NC_000013.11<br>NT_024524.15<br>NC_018924.2 | Epithelial Stromal Interaction 1 (breast) |
| FFAR3 | NC_000019.10<br>NT_011109.17<br>NC_018930.2 | Free Fatty Acid Receptor 3 |
| GALM | NC_000002.12<br>NT_022184.16<br>NC_018913.2 | galactose mutarotase (aldose 1-epimerase) |
| IFITM3 | NC_000011.10<br>NC_018922.2<br>NT_009237.19 | interferon induced transmembrane protein 3 |
| INCA | NC_000011.10<br>NT_033899.9<br>NC_018922.2 | caspase recruitment domain family member 17 |
| IRF7 | NC_000011.10<br>NT_009237.19<br>NT_187586.1<br>NC_018922.2 | interferon regulatory factor 7 |

TABLE 1-continued

| Gene symbol | REFSEQ NO. | Gene Name |
| --- | --- | --- |
| JARID1D | NC_000024.<br>NT_011875.13 | lysine (K)-specific demethylase 5D |
| JUP | NC_000017.11<br>NT_010783.16<br>NC_018928.2 | junction plakoglobin |
| MT2A | NC_000016.<br>NC_018927.2<br>NT_010498.16 | metallothionein 2A |
| OTOF | NC_000002.12<br>NT_022184.16<br>NC_018913.2 | otoferlin |
| PLSCR1 | NC_000003.12<br>NT_005612.17<br>NC_018914.2 | phospholipid scramblase 1 |
| PSTPIP2 | NC_000018.10<br>NT_010966.15<br>NC_018929.2 | proline-serine-threonine phosphatase interacting protein 2 |
| RGS1 | NC_000001.11<br>NC_018912.2<br>NT_004487.20 | regulator of G-protein signaling 1 |
| TREML4 | NC_000006.12<br>NC_018917.2<br>NT_007592.16 | triggering receptor expressed on myeloid cells like 4 |
| UTY | NC_000024.10<br>NT_011875.13 | ubiquitously transcribed tetratricopeptide repeat containing, Y-linked |
| PARP12 | NC_000007.14<br>NC_018918.2 | Poly(ADP-Ribose) Polymerase Family Member 12 |
| PNPT1 | NC_000002.12<br>NC_018913.2 | Polyribonucleotide Nucleotidyltransferase 1 |
| TRIB2 | NC_000002.12<br>NC_018913.2 | Tribbles Pseudokinase 2 |
| uc003hrl.1 | chr4: 89178768-89180508 | N/A |
| USP41 | NC_018933.2<br>NC_000022.11 | Ubiquitin Specific Peptidase 41 |
| ZCCHC2 | NC_000018.10<br>NC_018929.2 | Zinc Finger CCHC-Type Containing 2 |
| TCONS_00003184-XLOC_001966 | Affymetrix transcript ID: TC02004017.hg.1 chr2: 6968645-6973662 | linc-RNASEH1-12 |

TABLE 2

| Gene symbol | REFSEQ NO. | Gene Name |
| --- | --- | --- |
| CYBRD1 | NC_000002.12<br>NC_018913.2<br>NT_005403.18 | Cytochrome B Reductase 1 |
| CYP1B1 | NC_000002.12<br>NC_018913.2<br>NT_022184.16 | Cytochrome P450, Family 1, Subfamily B, Polypeptide 1 |
| F13A1 | NC_000006.12<br>NT_007592.16<br>NC_018917.2 | Coagulation factor XIII A chain |
| RASA4 | NC_000007.14<br>NT_007933.16<br>NC_018918.2 | RAS P21 Protein Activator 4 (clone name FLJ21767) |
| HLA-DQA1 | NT_167247.2<br>NT_167245.2<br>NT_167246.2<br>NT_167249.2<br>NC_000006.12<br>NT_007592.16<br>NT_113891.3<br>NT_167248.2<br>NC_018917.2 | major histocompatibility complex, class II, DQ alpha 1 |
| LOC100132244 | NC_000007.12 | uncharacterized LOC100132244 |

TABLE 2-continued

| Gene symbol | REFSEQ NO. | Gene Name |
|---|---|---|
| PHOSPHO1 | NC_000017.11<br>NT_010783.16<br>NC_018928.2 | phosphatase, orphan 1 |
| PPBP | NC_000004.12<br>NC_018915.2<br>NT_016354.20 | pro-platelet basic protein |
| SH3BGRL2 | NC_000006.12<br>NT_025741.16<br>NC_018917.2 | SH3 domain binding glutamate-rich protein like 2 |
| TMEM176A | NC_000007.14<br>NT_007933.16<br>NC_018918.2 | transmembrane protein 176A |
| CR1 | NC_000001.11<br>NC_018912.2 | Complement C3b/C4b Receptor 1 (Knops Blood Group) |
| DGAT2 | NC_000011.10;<br>NC_018922.2 | Diacylglycerol O-Acyltransferase 2 |
| PYGL | NC_000014.9<br>NC_018925.2 | Phosphorylase, Glycogen, Liver |
| SULT1B1 | NC_000004.12<br>NC_018915.2 | Sulfotransferase Family 1B Member 1 |

TABLE 3

| Gene symbol | | Gene name |
|---|---|---|
| CCL2 | NC_000017.11<br>NC_018928.2<br>NT_010783.16 | chemokine (C-C motif) ligand 2 |
| HERC5 | NC_000004.12)<br>NT_016354.20<br>NC_018915.2 | HECT and RLD domain containing E3 ubiquitin protein ligase 5 |
| IFI44L | NC_000001.11<br>NT_032977.10<br>NC_018912.2 | interferon induced protein 44 like |
| IFI6 | NC_000001.11<br>NC_018912.2<br>NT_032977.10 | interferon, alpha-inducible protein 6 |
| IFIT1 | NC_000010.11<br>NC_018921.2<br>NT_030059.14 | interferon induced protein with tetratricopeptide repeats 1 |
| ISG15 | NC_000001.11<br>NC_018912.2<br>NT_032977.10 | ISG15 ubiquitin-like modifier |
| LAMP3 | NC_000003.12<br>NT_005612.17<br>NC_018914.2 | lysosomal associated membrane protein 3 |
| LOC26010 (SPATS2L) | NC_000002.12<br>NT_005403.18<br>NC_018913.2 | spermatogenesis associated, serine rich 2 like |
| LY6E | NC_000008.11<br>NC_018919.2<br>NT_008046.17<br>NT_187573.1 | lymphocyte antigen 6 complex, locus E |
| MX1 | NC_000021.9<br>NT_011512.12<br>NC_018932.2 | MX dynamin-like GTPase 1 |
| OAS3 | NC_000012.12<br>NT_029419.13<br>NC_018923.2 | 2'-5'-oligoadenylate synthetase 3 |
| OAS1 | NC_000012.12<br>NT_029419.13<br>NC_018923.2 | 2'-5'-Oligoadenylate Synthetase 1, 40/46 kDa |
| RTP4 | NC_000003.12<br>NC_018914.2<br>NT_005612.17 | receptor (chemosensory) transporter protein 4 |
| SERPING1 | NC_000011.10<br>NC_018922.2<br>NT_167190.2 | serpin peptidase inhibitor, clade G (C1 inhibitor), member 1 |
| SIGLEC1 | NC_000020.11<br>NT_011387.9<br>NC_018931.2 | sialic acid binding Ig like lectin 1 |

TABLE 3-continued

| Gene symbol | | Gene name |
|---|---|---|
| TNFAIP6 | NC_000002.12<br>NT_005403.18<br>NC_018913.2 | TNF alpha induced protein 6 |
| USP18 | NC_000022.11<br>NT_187355.1<br>NC_018933.2 | ubiquitin specific peptidase 18 |
| XAF1 | NC_000017.11<br>NT_010718.17<br>NC_018928.2 | XIAP associated factor 1 |
| CXCL10 | NC_000004.12<br>NC_018915.2<br>NT_016354.20 | chemokine (C-X-C motif) ligand 10 |
| DDX60 | NC_000004.12<br>NT_016354.20<br>NC_018915.2 | DEXD/H-box helicase 60 |
| HERC6 | NC_000004.12<br>NT_016354.20<br>NC_018915.2 | HECT and RLD domain containing E3 ubiquitin protein ligase family member 6 |
| PPM1K | NC_000004.12,<br>NC_018915.2 | Protein Phosphatase, Mg2+/Mn2+ Dependent 1K |
| RSAD2 | NC_000002.12<br>NT_005334.17<br>NC_018913.2 | radical S-adenosyl methionine domain containing 2 |
| OAS2 | NC_000012.12<br>NT_029419.13<br>NC_018923.2 | 2'-5'-oligoadenylate synthetase 2 |
| OASL | NC_000012.12<br>NC_018923.2<br>NT_029419.13 | 2'-5'-oligoadenylate synthetase-like |
| IFI27 | NC_018925.2<br>NT_187601.1<br>NC_000014.9<br>NT_026437.13 | interferon, alpha-inducible protein 27 |
| IFI44 | NC_000001.11<br>NT_032977.10<br>NC_018912.2 | interferon induced protein 44 |
| IFIT2 | NC_000010.11<br>NC_018921.2<br>NT_030059.14 | interferon induced protein with tetratricopeptide repeats 2 |
| IFIT3 | NC_000010.11<br>NC_018921.2<br>NT_030059.14 | interferon induced protein with tetratricopeptide repeats 3 |

TABLE 4

| Probe ID | Gene Name/mRNA accession number |
|---|---|
| TC01004260.hg | n363820 or TCONS_00000869-XLOC_000105 |
| TC02002080.hg | ENST00000443397 |
| TC02004398.hg | n336681 |
| TC16001577.hg | n375375 or TCONS_00024856-XLOC_011736 |
| TC16001578.hg | n406211 |
| TC22000951.hg | n384079 |
| TC22001004.hg | n387236 or n386315 |
| TC22001243.hg | n332472 |
| TC22001248.hg | n346241 |
| TC17000386.hg | CCL8 |
| TC09001536.hg | CDK5RAP2 |
| TC04002928.hg | FAM200B |
| TC09000608.hg | GSN |
| TC02004983.hg | IGKV3D-15 |
| TC02000720.hg | IL1RN |
| TC17002906.hg | KRT19 |
| TC07000704.hg | LRRN3 |
| TC22001450.hg | MIR650 |
| TC16002035.hg | MT1A |
| TC16000470.hg | MT1DP |
| TC16000468.hg | MT1E |

TABLE 4-continued

| Probe ID | Gene Name/mRNA accession number |
|---|---|
| TC16000475.hg | MT1IP |
| TC16002074.hg | MT1M |
| TC06000961.hg | NCOA7 |
| TC01000789.hg | NEXN |
| TC22000376.hg | PRR5 |
| TC01001522.hg | RABGAP1L |
| TC09001730.hg | SDCCAG3 |
| TC03000198.hg | TTC21A |

Exemplary genomic sequences are provided in each of Tables 1-3 for particular determinants.

The present invention contemplates analyzing any number of exons per RNA determinant, wherein each of the exons selected show a degree of accuracy (based on differential expression analysis) above a predetermined level. Thus for example, in some embodiments expression level from only 1 exon is measured, from no more than 2 exons are measured, from no more than 3 exons are measured, from no more than four exons are measured or from no more than five exons are measured pre RNA determinant. In some embodiments, no more than 75% of the exons of a determinant are measured, no more than 50% of the exons of a determinant are measured, no more than 40% of the exons of a determinant are measured, no more than 30% of the exons of a determinant are measured, no more than 20% of the exons of a determinant are measured, no more than 10% of the exons of a determinant are measured per RNA determinant.

In one embodiment, one exon per RNA determinant is analyzed, wherein the exon shows a degree of accuracy (based on differential expression analysis) above a predetermined level.

In another embodiment, two exons per RNA determinant are analyzed wherein at least one of the exons show a degree of accuracy (based on differential expression analysis) above a predetermined level. It is further considered that two exons per RNA determinant are analyzed wherein each of the exons show a degree of accuracy (based on differential expression analysis) above a predetermined level. Preferably, one of the exons of the two exons analysed presents the highest degree of differential expression in a bacterial and viral sample as compared to all the other exons of the RNA determinant.

In another embodiment, three exons per RNA determinant are analyzed wherein at least one of the exons show a degree of accuracy above a predetermined level. It is further considered that three exons per RNA determinant are analyzed wherein each of the exons show a degree of accuracy (based on differential expression analysis) above a predetermined level. Preferably, one of the exons of the three exons analyzed presents the highest degree of differential expression in a bacterial and viral sample as compared to all the other exons of the RNA determinant.

In another embodiment, four exons per RNA determinant are analyzed wherein at least one of the exons show a degree of accuracy above a predetermined level. It is further considered that four exons per RNA determinant are analyzed wherein each of the exons show a degree of accuracy (based on differential expression analysis) above a predetermined level. Preferably, one of the exons of the four exons analyzed presents the highest degree of differential expression in a bacterial and viral sample as compared to all the other exons of the RNA determinant.

In another embodiment, five exons per RNA determinant are analyzed wherein at least one of the exons show a degree of accuracy above a predetermined level. It is further considered that four exons per RNA determinant are analyzed wherein each of the exons show a degree of accuracy (based on differential expression analysis) above a predetermined level. Preferably, one of the exons of the five exons analyzed presents the highest degree of differential expression in a bacterial and viral sample as compared to all the other exons of the RNA determinant.

It will be appreciated that in order to enhance the accuracy of the diagnosis, more than 1 RNA determinant may be analyzed, wherein each RNA determinant may be measured at one or more exons as specified herein above. Thus, information regarding two or more RNA determinants can be combined and made clinically useful through the use of various formulae, including statistical classification algorithms and others, combining and in many cases extending the performance characteristics of the combination beyond that of the individual RNA determinants. These specific combinations may show an acceptable level of diagnostic accuracy, and, when sufficient information from multiple RNA determinants is combined in a trained formula, often reliably achieve a high level of diagnostic accuracy transportable from one population to another.

The general concept of how two less specific or lower performing RNA determinants are combined into novel and more useful combinations for the intended indications, is a key aspect of the invention. Multiple biomarkers can often yield better performance than the individual components when proper mathematical and clinical algorithms are used; this is often evident in both sensitivity and specificity, and results in a greater AUC. Secondly, there is often novel unperceived information in the existing biomarkers, as such was necessary in order to achieve through the new formula an improved level of sensitivity or specificity. This hidden information may hold true even for biomarkers which are generally regarded to have suboptimal clinical performance on their own. In fact, the suboptimal performance in terms of high false positive rates on a single biomarker measured alone may very well be an indicator that some important additional information is contained within the biomarker results—information which would not be elucidated absent the combination with a second biomarker and a mathematical formula.

Several statistical and modeling algorithms known in the art can be used to both assist in RNA determinant selection choices and optimize the algorithms combining these choices. Statistical tools such as factor and cross-biomarker correlation/covariance analyses allow more rationale approaches to panel construction. Mathematical clustering and classification tree showing the Euclidean standardized distance between the RNA determinants can be advantageously used. Pathway informed seeding of such statistical classification techniques also may be employed, as may rational approaches based on the selection of individual RNA determinants based on their participation across in particular pathways or physiological functions.

Ultimately, formula such as statistical classification algorithms can be directly used to both select RNA determinants and to generate and train the optimal formula necessary to combine the results from multiple determinants into a single index. Often, techniques such as forward (from zero potential explanatory parameters) and backwards selection (from all available potential explanatory parameters) are used, and information criteria, such as AIC or BIC, are used to quantify the tradeoff between the performance and diagnostic accuracy of the panel and the number of RNA determinants used. The position of the individual RNA determinant on a forward or backwards selected panel can be closely related to its provision of incremental information content for the algorithm, so the order of contribution is highly dependent on the other constituent RNA determinants in the panel. Additional examples of statistical classification algorithms that could be used include Support Vector Machine (SVM), Logistic Regression (Log Reg), Neural Network, Bayesian Network, and a Hidden Markov Model.

Exemplary pairs of RNA determinants that may be measured according to aspects of the present invention are set forth in Tables 5-7.

TABLE 5

| RNA #1 | RNA #2 |
|---|---|
| BMX | CYP1B1 |
| C19orf59 | CYP1B1 |
| CLEC4D | CYP1B1 |
| CYP1B1 | PLSCR1 |
| CYP1B1 | FFAR3 |
| CYP1B1 | PSTPIP2 |
| FFAR3 | LOC100132244 |
| PLSCR1 | TMEM176A |
| ANKRD22 | CYP1B1 |
| BMX | TMEM176A |
| CD177 | CYP1B1 |
| CD177 | FFAR3 |
| AIM2 | CYP1B1 |
| CLEC4D | TMEM176A |
| CYP1B1 | TNFAIP6 |
| CYP1B1 | INCA |
| LOC100132244 | PLSCR1 |
| BMX | LOC100132244 |
| CEACAM1 | CYP1B1 |
| CLEC4D | LOC100132244 |
| PSTPIP2 | TMEM176A |
| AIM2 | CYBRD1 |
| BMX | CYBRD1 |
| C19orf59 | FFAR3 |
| CEACAM1 | CYBRD1 |
| CYBRD1 | EIF2AK2 |
| CYBRD1 | EPSTI1 |
| CYBRD1 | HERC5 |
| CYBRD1 | IFI44 |
| CYBRD1 | IFI6 |
| CYBRD1 | IFIT2 |
| CYBRD1 | IFIT3 |
| CYBRD1 | IFITM3 |
| CYBRD1 | INCA |
| CYBRD1 | OAS1 |
| CYBRD1 | PLSCR1 |
| CYBRD1 | PSTPIP2 |
| CYBRD1 | SERPING1 |
| CYBRD1 | TNFAIP6 |
| CYP1B1 | RASA4 |
| CYP1B1 | IRF7 |
| FFAR3 | TMEM176A |
| CEACAM1 | TMEM176A |
| LOC100132244 | PPBP |
| CCL2 | CYBRD1 |
| CD177 | LOC26010 (SPATS2L) |
| CMPK2 | CYBRD1 |
| CYBRD1 | LOC26010 (SPATS2L) |
| CYBRD1 | MX1 |

TABLE 6

| RNA #1 | RNA #2 |
|---|---|
| EIF1AY | OTOF |
| HLA-DQA1 | OTOF |

TABLE 6-continued

| RNA #1 | RNA #2 |
|---|---|
| LAMP3 | OTOF |
| OTOF | UTY |
| IFI6 | OTOF |
| CXCL10 | OTOF |
| JARID1D | OTOF |
| OTOF | RGS1 |
| CCL2 | OTOF |
| CEACAM1 | OTOF |
| IFI44L | OTOF |
| CYP1B1 | OTOF |
| F13A1 | OTOF |
| IFI27 | OTOF |
| IFI44 | OTOF |
| IRF7 | OTOF |
| ISG15 | OTOF |
| OAS3 | OTOF |
| OASL | OTOF |
| OTOF | PLSCR1 |
| OTOF | PPBP |
| OTOF | PSTPIP2 |
| OTOF | SIGLEC1 |
| OTOF | TMEM176A |
| AIM2 | OTOF |
| BMX | OTOF |
| CYBRD1 | OTOF |
| EIF2AK2 | OTOF |
| IFIT1 | OTOF |
| IFIT2 | OTOF |
| IFIT3 | OTOF |
| JUP | OTOF |
| LY6E | OTOF |
| OAS1 | OTOF |
| OTOF | RSAD2 |
| OTOF | RTP4 |
| OTOF | TNFAIP6 |
| OTOF | USP18 |
| HERC5 | OTOF |
| OAS2 | OTOF |
| OTOF | SERPING1 |
| MX1 | OTOF |
| HLA-DQA1 | USP18 |

TABLE 7

| RNA 1 | RNA 2 |
|---|---|
| LAMP3 | USP18 |
| CXCL10 | USP18 |
| IFI6 | LY6E |
| CCL2 | IF127 |
| IFI6 | USP18 |

Other exemplary pairs are provided herein below:
CMPK2+CR1, CMPK2+CYP1B1, CMPK2+DDX60, CMPK2+DGAT2, CMPK2+PARP12, CMPK2+PNPT1, CMPK2+PYGL, CMPK2+SULT1B1, CMPK2+TRIB2, CMPK2+uc003hrl.1, CMPK2+USP41, CMPK2+ZCCHC2, CMPK2+n332762, CMPK2+n407780, CMPK2+n332510, CMPK2+n334829, CMPK2+n332456, CMPK2+n333319, CMPK2+TCONS_00003184-XLOC_001966, CMPK2+TCONS_00013664-XLOC_006324, CMPK2+TCONS_12_00028242-XLOC_12_014551, CMPK2+TCONS_12_00001926-XLOC_12_000004, CMPK2+TCONS_12_00002386-XLOC_12_000726, CMPK2+TCONS_12_00002811-XLOC_12_001398, CMPK2+TCONS_12_00003949-XLOC_12_001561, CMPK2+TCONS_00019559-XLOC_009354, CMPK2+TCONS_12_00010440-XLOC_12_005352, CMPK2+TCONS_12_00016828-XLOC_12_008724, CMPK2+TCONS_12_00021682-XLOC_12_010810, CMPK2+TCONS_12_00002367-XLOC_12_000720, CMPK2+

FAM89A, CMPK2+MX1, CMPK2+RSAD2, CMPK2+IFI44L, CMPK2+USP18, CMPK2+IFI27, CR1+CYP1B1, CR1+DDX60, CR1+DGAT2, CR1+PARP12, CR1+PNPT1, CR1+PYGL, CR1+SULT1B1, CR1+TRIB2, CR1+uc003hrl.1, CR1+USP41, CR1+ZCCHC2, CR1+n332762, CR1+n407780, CR1+n332510, CR1+n334829, CR1+n332456, CR1+n333319, CR1+TCONS_00003184-XLOC_001966, CR1+TCONS_00013664-XLOC_006324, CR1+TCONS_12_00028242-XLOC_12_014551, CR1+TCONS_12_000001926-XLOC_12_000004, CR1+TCONS_12_00002386-XLOC_12_000726, CR1+TCONS_12_00002811-XLOC_12_001398, CR1+TCONS_12_00003949-XLOC_12_001561, CR1+TCONS_00019559-XLOC_009354, CR1+TCONS_12_00010440-XLOC_12_005352, CR1+TCONS_12_00016828-XLOC_12_008724, CR1+TCONS_12_00021682-XLOC_12_010810, CR1+TCONS_12_00002367-XLOC_12_000720, CR1+FAM89A, CR1+MX1, CR1+RSAD2, CR1+IFI44L, CR1+USP18, CR1+IFI27, CYP1B1+DDX60, CYP1B1+DGAT2, CYP1B1+PARP12, CYP1B1+PNPT1, CYP1B1+PYGL, CYP1B1+SULT1B1, CYP1B1+TRIB2, CYP1B1+uc003hrl.1, CYP1B1+USP41, CYP1B1+ZCCHC2, CYP1B1+n332762, CYP1B1+n407780, CYP1B1+n332510, CYP1B1+n334829, CYP1B1+n332456, CYP1B1+n333319, CYP1B1+TCONS_00003184-XLOC_001966, CYP1B1+TCONS_00013664-XLOC_006324, CYP1B1+TCONS_12_00028242-XLOC_12_014551, CYP1B1+TCONS_12_00001926-XLOC_12_000004, CYP1B1+TCONS_12_00002386-XLOC_12_000726, CYP1B1+TCONS_12_00002811-XLOC_12_001398, CYP1B1+TCONS_12_00003949-XLOC_12_001561, CYP1B1+TCONS_00019559-XLOC_009354, CYP1B1+TCONS_12_00010440-XLOC_12_005352, CYP1B1+TCONS_12_00016828-XLOC_12_008724, CYP1B1+TCONS_12_00021682-XLOC_12_010810, CYP1B1+TCONS_12_00002367-XLOC_12_000720, CYP1B1+FAM89A, CYP1B1+MX1, CYP1B1+RSAD2, CYP1B1+IFI44L, CYP1B1+USP18, CYP1B+IFI27, DDX60+DGAT2, DDX60+PARP12, DDX60+PNPT1, DDX60+PYGL, DDX60+SULT1B1, DDX60+TRIB2, DDX60+uc003hrl.1, DDX60+USP41, DDX60+ZCCHC2, DDX60+n332762, DDX60+n407780, DDX60+n334829, DDX60+n332456, DDX60+n333319, DDX60+TCONS_00003184-XLOC_001966, DDX60+TCONS_00013664-XLOC_006324, DDX60+TCONS_12_00028242-XLOC_12_014551, DDX60+TCONS_12_00001926-XLOC_12_000004, DDX60+TCONS_12_00002386-XLOC_12_000726, DDX60+TCONS_12_00002811-XLOC_12_001398, DDX60+TCONS_12_00003949-XLOC_12_001561, DDX60+TCONS_00019559-XLOC_009354, DDX60+TCONS_12_00010440-XLOC_12_005352, DDX60+TCONS_12_00016828-XLOC_12_008724, DDX60+TCONS_12_00021682-XLOC_12_010810, DDX60+TCONS_12_00002367-XLOC_12_000720, DDX60+FAM89A, DDX60+MX1, DDX60+RSAD2, DDX60+IFI44L, DDX60+USP18, DDX60+IFI27, DGAT2+PARP12, DGAT2+PNPT1, DGAT2+PYGL, DGAT2+SULT1B1, DGAT2+TRIB2, DGAT2+uc003hrl.1, DGAT2+USP41, DGAT2+ZCCHC2, DGAT2+n332762, DGAT2+n407780, DGAT2+n332510, DGAT2+n334829, DGAT2+n332456, DGAT2+n333319, DGAT2+TCONS_00003184-XLOC_001966, DGAT2+TCONS_00013664-XLOC_006324, DGAT2+TCONS_12_00028242-XLOC_12_014551, DGAT2+TCONS_12_00001926-XLOC_12_000004, DGAT2+TCONS_12_00002386-XLOC_12_000726, DGAT2+TCONS_12_00002811-XLOC_12_001398, DGAT2+TCONS_12_00003949-XLOC_12_001561, DGAT2+TCONS_00019559-XLOC_009354, DGAT2+TCONS_12_00010440-XLOC_12_005352, DGAT2+TCONS_12_00016828-XLOC_12_008724, DGAT2+TCONS_12_00021682-XLOC_12_010810, DGAT2+TCONS_12_00002367-XLOC_12_000720, DGAT2+FAM89A, DGAT2+MX1, DGAT2+RSAD2, DGAT2+IFI44L, DGAT2+USP18, DGAT2+IFI27, PARP12+PNPT1, PARP12+PYGL, PARP12+SULT1B1, PARP12+TRIB2, PARP12+uc003hrl.1, PARP12+USP41, PARP12+ZCCHC2, PARP2+n332762, PARP12+n407780, PARP2+n332510, PARP12+n334829, PARP12+n332456, PARP12+n333319, PARP12+TCONS_00003184-XLOC_001966, PARP12+TCONS_00013664-XLOC_006324, PARP12+TCONS_12_00028242-XLOC_12_014551, PARP12+TCONS_12_00001926-XLOC_12_000004, PARP12+TCONS_12_00002386-XLOC_12_000726, PARP12+TCONS_12_00002811-XLOC_12_001398, PARP12+TCONS_12_00003949-XLOC_12_001561, PARP12+TCONS_00019559-XLOC_009354, PARP12+TCONS_12_00010440-XLOC_12_005352, PARP12+TCONS_12_00016828-XLOC_12_008724, PARP12+TCONS_12_00021682-XLOC_12_010810, PARP12+TCONS_12_00002367-XLOC_12_000720, PARP12+FAM89A, PARP12+MX1, PARP12+RSAD2, PARP12+IFI44L, PARP12+USP18, PARP12+IFI27, PNPT1+PYGL, PNPT1+SULT1B1, PNPT1+TRIB2, PNPT1+uc003hrl.1, PNPT1+USP41, PNPT1+ZCCHC2, PNPT1+n332762, PNPT1+n407780, PNPT1+n332510, PNPT1+n334829, PNPT1+n332456, PNPT1+n333319, PNPT1+TCONS_00003184-XLOC_001966, PNPT1+TCONS_00013664-XLOC_006324, PNPT1+TCONS_12_00028242-XLOC_12_014551, PNPT1+TCONS_12_00001926-XLOC_12_000004, PNPT1+TCONS_12_00002386-XLOC_12_000726, PNPT1+TCONS_12_00002811-XLOC_12_001398, PNPT1+TCONS_12_00003949-XLOC_12_001561, PNPT1+TCONS_00019559-XLOC_009354, PNPT1+TCONS_12_00010440-XLOC_12_005352, PNPT1+TCONS_12_00016828-XLOC_12_008724, PNPT1+TCONS_12_00021682-XLOC_12_010810, PNPT1+TCONS_12_00002367-XLOC_12_000720, PNPT1+FAM89A, PNPT1+MX1, PNPT1+RSAD2, PNPT1+IFI44L, PNPT1+USP18, PNPT1+IFI27, PYGL+SULT1B1, PYGL+TRIB2, PYGL+uc003hrl.1, PYGL+USP41, PYGL+ZCCHC2, PYGL+n332762, PYGL+n407780, PYGL+n332510, PYGL+n334829, PYGL+n332456, PYGL+n333319, PYGL+TCONS_00003184-XLOC_001966, PYGL+TCONS_00013664-XLOC_006324, PYGL+TCONS_12_00028242-XLOC_12_014551, PYGL+TCONS_12_00001926-XLOC_12_000004, PYGL+TCONS_12_00002386-XLOC_12_000726, PYGL+TCONS_12_00002811-XLOC_12_001398, PYGL+TCONS_12_00003949-XLOC_12_001561, PYGL+TCONS_00019559-XLOC_009354, PYGL+TCONS_12_00010440-XLOC_12_005352, PYGL+TCONS_12_00016828-XLOC_12_008724, PYGL+TCONS_12_00021682-XLOC_12_010810, PYGL+TCONS_12_00002367-XLOC_12_000720, PYGL+FAM89A, PYGL+MX1, PYGL+RSAD2, PYGL+IFI44L, PYGL+USP18, PYGL+IFI27, SULT1B1+TRIB2, SULT1B1+uc003hrl.1, SULT1B1+USP41, SULT1B1+ZCCHC2, SULT1B1+n332762, SULT1B1+n407780, SULT1B1+n332510, SULT1B1+n334829, SULT1B1+n332456, SULT1B1+n333319, SULT1B1+

TCONS_00003184-XLOC_001966, TCONS_00013664-XLOC_006324, TCONS_12_00028242-XLOC_12_014551, TCONS_12_00001926-XLOC_12_000004, TCONS_12_00002386-XLOC_12_000726, TCONS_12_00002811-XLOC_12_001398, TCONS_12_00003949-XLOC_12_001561, TCONS_00019559-XLOC_009354, TCONS_12_00010440-XLOC_12_005352, TCONS_12_00016828-XLOC_12_008724, TCONS_12_00021682-XLOC_12_010810, TCONS_12_00002367-XLOC_12_000720, SULT1B1+FAM89A, SULT1B1+MX1, SULT1B1+RSAD2, SULT1B1+IFI44L, SULT1B1+USP18, SULT1B1+IFI27, TRIB2+uc003hrl.1, TRIB2+USP41, TRIB2+ZCCHC2, TRIB2+n332762, TRIB2+n407780, TRIB2+n332510, TRIB2+n334829, TRIB2+n332456, TRIB2+n333319, TRIB2+TCONS_00003184-XLOC_001966, TRIB2+TCONS_00013664-XLOC_006324, TRIB2+TCONS_12_00028242-XLOC_12_014551, TRIB2+TCONS_12_00001926-XLOC_12_000004, TRIB2+TCONS_12_00002386-XLOC_12_000726, TRIB2+TCONS_12_00002811-XLOC_12_001398, TRIB2+TCONS_12_00003949-XLOC_12_001561, TRIB2+TCONS_00019559-XLOC_009354, TRIB2+TCONS_12_00010440-XLOC_12_005352, TRIB2+TCONS_12_00016828-XLOC_12_008724, TRIB2+TCONS_12_00021682-XLOC_12_010810, TRIB2+TCONS_12_00002367-XLOC_12_000720, TRIB2+FAM89A, TRIB2+MX1, TRIB2+RSAD2, TRIB2+IFI44L, TRIB2+USP18, TRIB2+IFI27, uc003hrl.1+USP41, uc003hrl.1+ZCCHC2, uc003hrl.1+n332762, uc003hrl.1+n407780, uc003hrl.1+n332510, uc003hrl.1+n334829, uc003hrl.1+n332456, uc003hrl.1+n333319, uc003hrl.1+TCONS_00003184-XLOC_001966, uc003hrl.1+TCONS_00013664-XLOC_006324, uc003hrl.1+TCONS_12_00028242-XLOC_12_014551, uc003hrl.1+TCONS_12_00001926-XLOC_12_000004, uc003hrl.1+TCONS_12_00002386-XLOC_12_000726, uc003hrl.1+TCONS_12_00002811-XLOC_12_001398, uc003hrl.1+TCONS_12_00003949-XLOC_12_001561, uc003hrl.1+TCONS_00019559-XLOC_009354, uc003hrl.1+TCONS_12_00010440-XLOC_12_005352, uc003hrl.1+TCONS_12_00016828-XLOC_12_008724, uc003hrl.1+TCONS_12_00021682-XLOC_12_010810, uc003hrl.1+TCONS_12_00002367-XLOC_12_000720, uc003hrl.1+FAM89A, uc003hrl.1+MX1, uc003hrl.1+RSAD2, uc003hrl.1+IFI44L, uc003hrl.1+US P18, uc003hrl.1+IFI27, USP41+ZCCHC2, USP41+n332762, USP41+n407780, USP41+n332510, USP41+n334829, USP41+n332456, USP41+n333319, USP41+TCONS_00003184-XLOC_001966, USP41+TCONS_00013664-XLOC_006324, USP41+TCONS_12_00028242-XLOC_12_014551, USP41+TCONS_12_00001926-XLOC_12_000004, USP41+TCONS_12_00002386-XLOC_12_000726, USP41+TCONS_12_0002811-XLOC_12_001398, USP41+TCONS_12_00003949-XLOC_12_001561, USP41+TCONS_00019559-XLOC_009354, USP41+TCONS_12_00010440-XLOC_12_005352, USP41+TCONS_12_00016828-XLOC_12_008724, USP41+TCONS_12_00021682-XLOC_12_010810, USP41+TCONS_12_00002367-XLOC_12_000720, USP41+FAM89A, USP41+MX1, USP41+RSAD2, USP41+IFI44L, USP41+USP18, USP41+IFI27, ZCCHC2+n332762, ZCCHC2+n407780, ZCCHC2+n332510, ZCCHC2+n334829, ZCCHC2+n332456, ZCCHC2+n333319, ZCCHC2+TCONS_00003184-XLOC_001966, ZCCHC2+TCONS_00013664-XLOC_006324, ZCCHC2+TCONS_12_00028242-XLOC_12_014551, ZCCHC2+TCONS_12_00001926-XLOC_12_000004, ZCCHC2+TCONS_12_00002386-XLOC_12_000726, ZCCHC2+TCONS_12_00002811-XLOC_12_001398, ZCCHC2+TCONS_12_00003949-XLOC_12_001561, ZCCHC2+TCONS_00019559-XLOC_009354, ZCCHC2+TCONS_12_00010440-XLOC_12_005352, ZCCHC2+TCONS_12_00016828-XLOC_12_008724, ZCCHC2+TCONS_12_00021682-XLOC_12_010810, ZCCHC2+TCONS_12_00002367-XLOC_12_000720, ZCCHC2+FAM89A, ZCCHC2+MX1, ZCCHC2+RSAD2, ZCCHC2+IFI44L, ZCCHC2+USP18, ZCCHC2+IFI27, n332762+n407780, n332762+n332510, n332762+n334829, n332762+n332456, n332762+n333319, n332762+TCONS_00003184-XLOC_001966, n332762+TCONS_00013664-XLOC_006324, n332762+TCONS_12_00028242-XLOC_12_014551, n332762+TCONS_12_00001926-XLOC_12_000004, n332762+TCONS_12_00002386-XLOC_12_000726, n332762+TCONS_12_00002811-XLOC_12_001398, n332762+TCONS_12_00003949-XLOC_12_001561, n332762+TCONS_00019559-XLOC_009354, n332762+TCONS_12_00010440-XLOC_12_005352, n332762+TCONS_12_00016828-XLOC_12_008724, n332762+TCONS_12_00021682-XLOC_12_010810, n332762+TCONS_12_00002367-XLOC_12_000720, n332762+FAM89A, n332762+MX1, n332762+RSAD2, n332762+IFI44L, n332762+USP18, n332762+IFI27, n407780+n332510, n407780+n334829, n407780+n332456, n407780+n333319, n407780+TCONS_00003184-XLOC_001966, n407780+TCONS_00013664-XLOC_006324, n407780+TCONS_12_00028242-XLOC_12_014551, n407780+TCONS_12_00001926-XLOC_12_000004, n407780+TCONS_12_00002386-XLOC_12_000726, n407780+TCONS_12_00002811-XLOC_12_001398, n407780+TCONS_12_00003949-XLOC_12_001561, n407780+TCONS_00019559-XLOC_009354, n407780+TCONS_12_00010440-XLOC_12_005352, n407780+TCONS_12_00016828-XLOC_12_008724, n407780+TCONS_12_00021682-XLOC_12_010810, n407780+TCONS_12_00002367-XLOC_12_000720, n407780+FAM89A, n407780+MX1, n407780+RSAD2, n407780+IFI44L, n407780+USP18, n407780+IFI27, n332510+n334829, n332510+n332456, n332510+n333319, n332510+TCONS_00003184-XLOC_001966, n332510+TCONS_00013664-XLOC_006324, n332510+TCONS_12_00028242-XLOC_12_014551, n332510+TCONS_12_00001926-XLOC_12_000004, n332510+TCONS_12_00002386-XLOC_12_000726, n332510+TCONS_12_00002811-XLOC_12_001398, n332510+TCONS_12_00003949-XLOC_12_001561, n332510+TCONS_00019559-XLOC_009354, n332510+TCONS_12_00010440-XLOC_12_005352, n332510+TCONS_12_00016828-XLOC_12_008724, n332510+TCONS_12_00021682-XLOC_12_010810, n332510+TCONS_12_00002367-XLOC_12_000720, n332510+FAM89A, n332510+MX1, n332510+RSAD2, n332510+IFI44L, n332510+USP18, n332510+IFI27, n334829+n332456, n334829+n333319, n334829+TCONS_00003184-XLOC_001966, n334829+TCONS_00013664-XLOC_006324, n334829+TCONS_12_00028242-XLOC_12_014551, n334829+TCONS_12_00001926-XLOC_12_000004, n334829+TCONS_12_00002386-XLOC_12_000726, n334829+TCONS_12_00002811-XLOC_12_001398, n334829+TCONS_12_00003949-XLOC_12_001561, n334829+

TCONS_00019559-XLOC_009354,
TCONS_12_00010440-XLOC_12_005352,
TCONS_12_00016828-XLOC_12_008724,
TCONS_12_00021682-XLOC_12_010810,
TCONS_12_00002367-XLOC_12_000720,
FAM89A, n334829+MX1, n334829+RSAD2, n334829+IFI44L, n334829+USP18, n334829+IFI27, n332456+n333319, n332456+TCONS_00003184-XLOC_001966, n332456+TCONS_00013664-XLOC_006324, n332456+TCONS_12_00028242-XLOC_12_014551, n332456+TCONS_12_00001926-XLOC_12_000004, n332456+TCONS_12_00002386-XLOC_12_000726, n332456+TCONS_12_00002811-XLOC_12_001398, n332456+TCONS_12_00003949-XLOC_12_001561, n332456+TCONS_00019559-XLOC_009354, n332456+TCONS_12_00010440-XLOC_12_005352, n332456+TCONS_12_00016828-XLOC_12_008724, n332456+TCONS_12_00021682-XLOC_12_010810, n332456+TCONS_12_00002367-XLOC_12_000720, n332456+FAM89A, n332456+MX1, n332456+RSAD2, n332456+IFI44L, n332456+USP18, n332456+IFI27, n333319+TCONS_00003184-XLOC_001966, n333319+TCONS_00013664-XLOC_006324, n333319+TCONS_12_00028242-XLOC_12_014551, n333319+TCONS_1200001926-XLOC_12000004, n333319+TCONS_12_00002386-XLOC_12_000726, n333319+TCONS_12_00002811-XLOC_12_001398, n333319+TCONS_12_00003949-XLOC_12_001561, n333319+TCONS_00019559-XLOC_009354, n333319+TCONS_12_00010440-XLOC_12_005352, n333319+TCONS_12_00016828-XLOC_12_008724, n333319+TCONS_12_00021682-XLOC_12_010810, n333319+TCONS_12_00002367-XLOC_12_000720, n333319+FAM89A, n333319+MX1, n333319+RSAD2, n333319+IFI44L, n333319+USP18, n333319+IFI27,
TCONS_00003184-XLOC_001966+TCONS_00013664-XLOC_006324, TCONS_00003184-XLOC_001966+TCONS_12_00028242-XLOC_12_014551, TCONS_00003184-XLOC_001966+TCONS_12_00001926-XLOC_12_000004, TCONS_00003184-XLOC_001966+TCONS_12_00002386-XLOC_12_000726, TCONS_00003184-XLOC_001966+TCONS_12_00002811-XLOC_12_001398, TCONS_00003184-XLOC_001966+TCONS_12_00003949-XLOC_12_001561, TCONS_00003184-XLOC_001966+TCONS_00019559-XLOC_009354, TCONS_00003184-XLOC_001966+TCONS_12_00010440-XLOC_12_005352, TCONS_00003184-XLOC_001966+TCONS_12_00016828-XLOC_12_008724, TCONS_00003184-XLOC_001966+TCONS_12_00021682-XLOC_12_010810, TCONS_00003184-XLOC_001966+TCONS_12_00002367-XLOC_12_000720, TCONS_00003184-XLOC_001966+FAM89A, TCONS_00003184-XLOC_001966+MX1, TCONS_00003184-XLOC_001966+RSAD2, TCONS_00003184-XLOC_001966+IFI44L, TCONS_00003184-XLOC_001966+USP18, TCONS_00003184-XLOC_001966+IFI27, TCONS_00013664-XLOC_006324+TCONS_12_00028242-XLOC_12_014551, TCONS_00013664-XLOC_006324+TCONS_12_00001926-XLOC_12_000004, TCONS_00013664-XLOC_006324+TCONS_12_00002386-XLOC_12_000726, TCONS_00013664-XLOC_006324+TCONS_12_0002811-XLOC_12_001398, TCONS_00013664-XLOC_006324+TCONS_12_00003949-XLOC_12_001561, TCONS_00013664-XLOC_006324+TCONS_00019559-XLOC_009354, TCONS_00013664-XLOC_006324+TCONS_12_00010440-XLOC_12_005352, TCONS_00013664-XLOC_006324+TCONS_12_00016828-XLOC_12_008724, TCONS_00013664-XLOC_006324+TCONS_12_00021682-XLOC_12_010810, TCONS_00013664-XLOC_006324+TCONS_12_00002367-XLOC_12_000720, TCONS_00013664-XLOC_006324+FAM89A, TCONS_00013664-XLOC_006324+MX1, TCONS_00013664-XLOC_006324+RSAD2, TCONS_00013664-XLOC_006324+IFI44L, TCONS_00013664-XLOC_006324+USP18, TCONS_00013664-XLOC_006324+IFI27, TCONS_12_00028242-XLOC_12_014551+TCONS_12_00001926-XLOC_12_000004, TCONS_12_00028242-XLOC_12_014551+TCONS_12_00002386-XLOC_12_000726, TCONS_12_00028242-XLOC_12_014551+TCONS_12_00002811-XLOC_12_001398, TCONS_12_00028242-XLOC_12_014551+TCONS_12_00003949-XLOC_12_001561, TCONS_12_00028242-XLOC_12_014551+TCONS_00019559-XLOC_009354, TCONS_12_00028242-XLOC_12_014551+TCONS_12_00010440-XLOC_12_005352, TCONS_12_00028242-XLOC_12_014551+TCONS_12_00016828-XLOC_12_008724, TCONS_12_00028242-XLOC_12_014551+TCONS_12_00021682-XLOC_12_010810, TCONS_12_00028242-XLOC_12_014551+TCONS_12_00002367-XLOC_12_000720, TCONS_12_00028242-XLOC_12_014551+FAM89A, TCONS_12_00028242-XLOC_12_014551+MX1, TCONS_12_00028242-XLOC_12_014551+RSAD2, TCONS_12_00028242-XLOC_12_014551+IFI44L, TCONS_12_00028242-XLOC_12_014551+USP18, TCONS_12_00028242-XLOC_12_014551+IFI27, TCONS_12_00001926-XLOC_12_000004+TCONS_12_00002386-XLOC_12_000726, TCONS_12_00001926-XLOC_12_000004+TCONS_12_00002811-XLOC_12_001398, TCONS_12_00001926-XLOC_12_000004+TCONS_12_00003949-XLOC_12_001561, TCONS_12_00001926-XLOC_12_000004+TCONS_00019559-XLOC_009354, TCONS_12_00001926-XLOC_12_000004+TCONS_12_00010440-XLOC_12_005352, TCONS_12_00001926-XLOC_12_000004+TCONS_12_00016828-XLOC_12_008724, TCONS_12_00001926-XLOC_12_000004+TCONS_12_00021682-XLOC_12_010810, TCONS_12_00001926-XLOC_12_000004+TCONS_12_00002367-XLOC_12_000720, TCONS_12_00001926-XLOC_12_000004+FAM89A, TCONS_12_00001926-XLOC_12_000004+MX1, TCONS_12_00001926-XLOC_12_000004+RSAD2, TCONS_12_00001926-XLOC_12_000004+IFI44L, TCONS_12_00001926-XLOC_12_000004+USP18, TCONS_12_00001926-XLOC_12_000004+IFI27, TCONS_12_00002386-XLOC_12_000726+TCONS_12_00002811-XLOC_12_001398, TCONS_12_00002386-XLOC_12_000726+

TCONS_12_00003949-XLOC_12_001561,
TCONS_12_00002386-XLOC_12_000726+
TCONS_00019559-XLOC_009354,
TCONS_12_00002386-XLOC_12_000726+
TCONS_12_00010440-XLOC_12_005352,
TCONS_12_00002386-XLOC_12_000726+
TCONS_12_00016828-XLOC_12_008724,
TCONS_12_00002386-XLOC_12_000726+
TCONS_12_00021682-XLOC_12_010810,
TCONS_12_00002386-XLOC_12_000726+
TCONS_12_00002367-XLOC_12_000720,
TCONS_12_00002386-XLOC_12_000726+FAM89A,
TCONS_12_00002386-XLOC_12_000726+MX1,
TCONS_12_00002386-XLOC_12_000726+RSAD2,
TCONS_12_00002386-XLOC_12_000726+IFI44L,
TCONS_12_00002386-XLOC_12_000726+USP18,
TCONS_12_00002386-XLOC_12_000726+IFI27,
TCONS_12_00002811-XLOC_12_001398+
TCONS_12_00003949-XLOC_12_001561,
TCONS_12_00002811-XLOC_12_001398+
TCONS_00019559-XLOC_009354,
TCONS_12_00002811-XLOC_12_001398+
TCONS_12_00010440-XLOC_12_005352,
TCONS_12_00002811-XLOC_12_001398+
TCONS_12_00016828-XLOC_12_008724,
TCONS_12_00002811-XLOC_12_001398+
TCONS_12_00021682-XLOC_12_010810,
TCONS_12_00002811-XLOC_12_001398+
TCONS_12_00002367-XLOC_12_000720,
TCONS_12_00002811-XLOC_12_001398+FAM89A,
TCONS_12_00002811-XLOC_12_001398+MX1,
TCONS_12_00002811-XLOC_12_001398+RSAD2,
TCONS_12_00002811-XLOC_12_001398+IFI44L,
TCONS_12_00002811-XLOC_12_001398+USP18,
TCONS_12_00002811-XLOC_12_001398+IFI27,
TCONS_12_00003949-XLOC_12_001561+
TCONS_00019559-XLOC_009354,
TCONS_12_00003949-XLOC_12_001561+
TCONS_12_00010440-XLOC_12_005352,
TCONS_12_00003949-XLOC_12001561+
TCONS_1200016828-XLOC_12008724,
TCONS_12_00003949-XLOC_12_001561+
TCONS_12_00021682-XLOC_12_010810,
TCONS_12_00003949-XLOC_12_001561+
TCONS_12_00002367-XLOC_12_000720,
TCONS_12_00003949-XLOC_12_001561+FAM89A,
TCONS_12_00003949-XLOC_12_001561+MX1,
TCONS_12_00003949-XLOC_12_001561+RSAD2,
TCONS_12_00003949-XLOC_12_001561+IFI44L,
TCONS_12_00003949-XLOC_12_001561+USP18,
TCONS_12_00003949-XLOC_12_001561+IFI27,
TCONS_00019559-XLOC_009354+
TCONS_12_00010440-XLOC_12_005352,
TCONS_00019559-XLOC_009354+
TCONS_12_00016828-XLOC_12_008724,
TCONS_00019559-XLOC_009354+
TCONS_12_00021682-XLOC_12_010810,
TCONS_00019559-XLOC_009354+
TCONS_12_00002367-XLOC_12_000720,
TCONS_00019559-XLOC_009354+FAM89A,
TCONS_00019559-XLOC_009354+MX1,
TCONS_00019559-XLOC_009354+RSAD2,
TCONS_00019559-XLOC_009354+IFI44L,
TCONS_00019559-XLOC_009354+USP18,
TCONS_00019559-XLOC_009354+IFI27,
TCONS_12_00010440-XLOC_12_005352+
TCONS_12_00016828-XLOC_12_008724,
TCONS_12_00010440-XLOC_12_005352+
TCONS_12_00021682-XLOC_12_010810,
TCONS_12_00010440-XLOC_12_005352+
TCONS_12_00002367-XLOC_12_000720,
TCONS_12_00010440-XLOC_12_005352+FAM89A,
TCONS_12_00010440-XLOC_12_005352+MX1,
TCONS_12_00010440-XLOC_12_005352+RSAD2,
TCONS_12_00010440-XLOC_12_005352+IFI44L,
TCONS_12_00010440-XLOC_12_005352+USP18,
TCONS_12_00010440-XLOC_12_005352+IFI27,
TCONS_12_00016828-XLOC_12_008724+
TCONS_12_00021682-XLOC_12_010810,
TCONS_12_00016828-XLOC_12_008724+
TCONS_12_00002367-XLOC_12_000720,
TCONS_12_00016828-XLOC_12_008724+FAM89A,
TCONS_12_00016828-XLOC_12_008724+MX1,
TCONS_12_00016828-XLOC_12_008724+RSAD2,
TCONS_12_00016828-XLOC_12_008724+IFI44L,
TCONS_12_00016828-XLOC_12_008724+USP18,
TCONS_12_00016828-XLOC_12_008724+IFI27,
TCONS_12_00021682-XLOC_12_010810+
TCONS_12_00002367-XLOC_12_000720,
TCONS_12_00021682-XLOC_12_010810+FAM89A,
TCONS_12_00021682-XLOC_12_010810+MX1,
TCONS_12_00021682-XLOC_12_010810+RSAD2,
TCONS_12_00021682-XLOC_12_010810+IFI44L,
TCONS_12_00021682-XLOC_12_010810+USP18,
TCONS_12_00021682-XLOC_12_010810+IFI27,
TCONS_12_00002367-XLOC_12_000720+FAM89A,
TCONS_12_00002367-XLOC_12_000720+MX1,
TCONS_12_00002367-XLOC_12_000720+RSAD2,
TCONS_12_00002367-XLOC_12_000720+IFI44L,
TCONS_12_00002367-XLOC_12_000720+USP18,
TCONS_12_00002367-XLOC_12_000720+IFI27,
FAM89A+MX1, FAM89A+RSAD2, FAM89A+IFI44L, FAM89A+USP18, FAM89A+IFI27, MX1+RSAD2, MX1+IFI44L, MX1+USP18, MX1+IFI27, RSAD2+IFI44L, RSAD2+USP18, RSAD2+IFI27, IFI44L+USP18, IFI44L+IFI27, USP18+IFI27.

Exemplary triplets of RNA determinants that may be measured according to aspects of the present invention are set forth in Tables 8-9,

TABLE 8

| RNA #1 | RNA #2 | RNA #3 |
|---|---|---|
| EIF1AY | F13A1 | OTOF |
| EIF1AY | HERC5 | OTOF |
| EIF1AY | HLA-DQA1 | OTOF |
| EIF1AY | OTOF | RGS1 |
| EIF2AK2 | LAMP3 | USP18 |
| HLA-DQA1 | LAMP3 | USP18 |
| HLA-DQA1 | OTOF | UTY |
| IFI44L | OTOF | UTY |
| IFI6 | JARID1D | OTOF |
| IFI6 | OTOF | UTY |
| LAMP3 | OAS1 | USP18 |
| LAMP3 | OAS3 | USP18 |
| OTOF | PLSCR1 | UTY |
| OTOF | PSTPIP2 | UTY |
| CCL2 | EIF1AY | OTOF |
| EIF1AY | EIF2AK2 | OTOF |
| EIF1AY | IFI44 | OTOF |
| EIF1AY | IFI6 | OTOF |
| EIF1AY | ISG15 | OTOF |
| EIF1AY | LAMP3 | OTOF |
| EIF1AY | OASL | OTOF |
| LAMP3 | PSTPIP2 | USP18 |
| LAMP3 | TMEM176A | USP18 |
| AIM2 | EIF1AY | OTOF |

TABLE 8-continued

| RNA #1 | RNA #2 | RNA #3 |
| --- | --- | --- |
| AIM2 | LAMP3 | USP18 |
| CCL2 | OTOF | UTY |
| CXCL10 | EIF1AY | OTOF |
| CYBRD1 | LAMP3 | USP18 |
| CYP1B1 | EIF1AY | OTOF |
| EIF1AY | IFI44L | OTOF |
| EIF1AY | IFIT1 | OTOF |
| EIF1AY | IFIT2 | OTOF |
| EIF1AY | IFIT3 | OTOF |
| EIF1AY | IRF7 | OTOF |
| EIF1AY | JARID1D | OTOF |
| EIF1AY | JUP | OTOF |
| IFI44 | Mx1 | OTOF |
| IFI44 | OTOF | RSAD2 |
| IFI44L | Mx1 | OTOF |
| IFI44 | IFI44L | OTOF |
| IFI44L | OTOF | RSAD2 |
| Mx1 | OTOF | RSAD2 |

TABLE 9

| RNA #1 | RNA #2 | RNA #3 |
| --- | --- | --- |
| HERC5 | LAMP3 | USP18 |
| IFI44 | LAMP3 | USP18 |
| IFI6 | LAMP3 | USP18 |
| IFIT3 | LAMP3 | USP18 |
| ISG15 | LAMP3 | USP18 |
| LAMP3 | MX1 | USP18 |
| LAMP3 | PLSCR1 | USP18 |
| LAMP3 | RSAD2 | USP18 |
| LAMP3 | SERPING1 | USP18 |
| LAMP3 | SIGLEC1 | USP18 |
| IRF7 | LAMP3 | USP18 |
| LAMP3 | OAS2 | USP18 |
| IFI44 | IFI44L | RSAD2 |
| IFI44 | IFI44L | Mx1 |
| IFI44L | Mx1 | RSAD2 |
| IFI44 | Mx1 | RSAD2 |

Other exemplary triplets which may be measured according to this aspect of the present invention are provided herein below:

CMPK2+CR1+CYP1B1, CMPK2+CR1+DDX60, CMPK2+CR1+DGAT2, CMPK2+CR1+PARP12, CMPK2+CR1+PNPT1, CMPK2+CR1+PYGL, CMPK2+CR1+SULT1B1, CMPK2+CR1+TRIB2, CMPK2+CR1+uc003hrl.1, CMPK2+CR1+USP41, CMPK2+CR1+ZCCHC2, CMPK2+CYP1B1+DDX60, CMPK2+CYP1B1+DGAT2, CMPK2+CYP1B1+PARP12, CMPK2+CYP1B1+PNPT1, CMPK2+CYP1B1+PYGL, CMPK2+CYP1B1+SULT1B1, CMPK2+CYP1B1+TRIB2, CMPK2+CYP1B1+uc003hrl.1, CMPK2+CYP1B1+USP41, CMPK2+CYP1B1+ZCCHC2, CMPK2+DDX60+DGAT2, CMPK2+DDX60+PARP12, CMPK2+DDX60+PNPT1, CMPK2+DDX60+PYGL, CMPK2+DDX60+SULT1B1, CMPK2+DDX60+TRIB2, CMPK2+DDX60+uc003hrl.1, CMPK2+DDX60+USP41, CMPK2+DDX60+ZCCHC2, CMPK2+DGAT2+PARP12, CMPK2+DGAT2+PNPT1, CMPK2+DGAT2+PYGL, CMPK2+DGAT2+SULT1B1, CMPK2+DGAT2+TRIB2, CMPK2+DGAT2+uc003hrl.1, CMPK2+DGAT2+USP41, CMPK2+DGAT2+ZCCHC2, CMPK2+PARP12+PNPT1, CMPK2+PARP12+PYGL, CMPK2+PARP12+SULT1B1, CMPK2+PARP12+TRIB2, CMPK2+PARP12+uc003hrl.1, CMPK2+PARP12+USP41, CMPK2+PARP12+ZCCHC2, CMPK2+PNPT1+PYGL, CMPK2+PNPT1+SULT1B1, CMPK2+PNPT1+TRIB2, CMPK2+PNPT1+uc003hrl.1, CMPK2+PNPT1+USP41, CMPK2+PNPT1+ZCCHC2, CMPK2+PYGL+SULT1B1, CMPK2+PYGL+TRIB2, CMPK2+PYGL+uc003hrl.1, CMPK2+PYGL+USP41, CMPK2+PYGL+ZCCHC2, CMPK2+SULT1B1+TRIB2, CMPK2+SULT1B1+uc003hrl.1, CMPK2+SULT1B1+USP41, CMPK2+SULT1B1+ZCCHC2, CMPK2+TRIB2+uc003hrl.1, CMPK2+TRIB2+USP41, CMPK2+TRIB2+ZCCHC2, CMPK2+uc003hrl.1+USP41, CMPK2+uc003hrl.1+ZCCHC2, CMPK2+USP41+ZCCHC2, CR1+CYP1B1+DDX60, CR1+CYP1B1+DGAT2, CR1+CYP1B1+PARP12, CR1+CYP1B1+PNPT1, CR1+CYP1B1+PYGL, CR1+CYP1B1+SULT1B1, CR1+CYP1B1+TRIB2, CR1+CYP1B1+uc003hrl.1, CR1+CYP1B1+USP41, CR1+CYP1B1+ZCCHC2, CR1+DDX60+DGAT2, CR1+DDX60+PARP12, CR1+DDX60+PNPT1, CR1+DDX60+PYGL, CR1+DDX60+SULT1B1, CR1+DDX60+TRIB2, CR1+DDX60+uc003hrl.1, CR1+DDX60+USP41, CR1+DDX60+ZCCHC2, CR1+DGAT2+PARP12, CR1+DGAT2+PNPT1, CR1+DGAT2+PYGL, CR1+DGAT2+SULT1B1, CR1+DGAT2+TRIB2, CR1+DGAT2+uc003hrl.1, CR1+DGAT2+USP41, CR1+DGAT2+ZCCHC2, CR1+PARP12+PNPT1, CR1+PARP12+PYGL, CR1+PARP12+SULT1B1, CR1+PARP12+TRIB2, CR1+PARP12+uc003hrl.1, CR1+PARP12+USP41, CR1+PARP12+ZCCHC2, CR1+PNPT1+PYGL, CR1+PNPT1+SULT1B1, CR1+PNPT1+TRIB2, CR1+PNPT1+uc003hrl.1, CR1+PNPT1+USP41, CR1+PNPT1+ZCCHC2, CR1+PYGL+SULT1B1, CR1+PYGL+TRIB2, CR1+PYGL+uc003hrl.1, CR1+PYGL+USP41, CR1+PYGL+ZCCHC2, CR1+SULT1B1+TRIB2, CR1+SULT1B1+uc003hrl.1, CR1+SULT1B1+USP41, CR1+SULT1B1+ZCCHC2, CR1+TRIB2+uc003hrl.1, CR1+TRIB2+USP41, CR1+TRIB2+ZCCHC2, CR1+uc003hrl.1+USP41, CR1+uc003hrl.1+ZCCHC2, CR1+USP41+ZCCHC2, CYP1B1+DDX60+DGAT2, CYP1B1+DDX60+PARP12, CYP1B1+DDX60+PNPT1, CYP1B1+DDX60+PYGL, CYP1B1+DDX60+SULT1B1, CYP1B1+DDX60+TRIB2, CYP1B1+DDX60+uc003hrl.1, CYP1B1+DDX60+USP41, CYP1B1+DDX60+ZCCHC2, CYP1B1+DGAT2+PARP12, CYP1B1+DGAT2+PNPT1, CYP1B1+DGAT2+PYGL, CYP1B1+DGAT2+SULT1B1, CYP1B1+DGAT2+TRIB2, CYP1B1+DGAT2+uc003hrl.1, CYP1B1+DGAT2+USP41, CYP1B1+DGAT2+ZCCHC2, CYP1B1+PARP12+PNPT1, CYP1B1+PARP12+PYGL, CYP1B1+PARP12+SULT1B1, CYP1B1+PARP12+TRIB2, CYP1B1+PARP12+uc003hrl.1, CYP1B1+PARP12+USP41, CYP1B1+PARP12+ZCCHC2, CYP1B1+PNPT1+PYGL, CYP1B1+PNPT1+SULT1B1, CYP1B1+PNPT1+TRIB2, CYP1B1+PNPT1+uc003hrl.1, CYP1B1+PNPT1+USP41, CYP1B1+PNPT1+ZCCHC2, CYP1B1+PYGL+SULT1B1, CYP1B1+PYGL+TRIB2, CYP1B1+PYGL+uc003hrl.1, CYP1B1+PYGL+USP41, CYP1B1+PYGL+ZCCHC2, CYP1B1+SULT1B1+TRIB2, CYP1B1+SULT1B1+uc003hrl.1, CYP1B1+SULT1B1+USP41, CYP1B1+SULT1B1+ZCCHC2, CYP1B1+TRIB2+uc003hrl.1, CYP1B1+TRIB2+USP41, CYP1B1+TRIB2+ZCCHC2, CYP1B1+uc003hrl.1+USP41, CYP1B1+uc003hrl.1+ZCCHC2, CYP1B1+USP41+ZCCHC2, DDX60+DGAT2+PARP12, DDX60+DGAT2+PNPT1, DDX60+DGAT2+PYGL, DDX60+DGAT2+SULT1B1, DDX60+DGAT2+TRIB2, DDX60+DGAT2+uc003hrl.1, DDX60+DGAT2+USP41, DDX60+DGAT2+ZCCHC2, DDX60+PARP12+PNPT1, DDX60+PARP12+PYGL, DDX60+PARP12+SULT1B1, DDX60+PARP12+TRIB2, DDX60+PARP12+uc003hrl.1, DDX60+PARP12+USP41, DDX60+PARP12+ZCCHC2, DDX60+PNPT1+PYGL, DDX60+PNPT1+SULT1B1, DDX60+PNPT1+TRIB2, DDX60+PNPT1+uc003hrl.1, DDX60+PNPT1+USP41, DDX60+PNPT1+ZCCHC2, DDX60+PYGL+SULT1B1, DDX60+PYGL+TRIB2, DDX60+PYGL+uc003hrl.1, DDX60+PYGL+USP41, DDX60+PYGL+ZCCHC2, DDX60+SULT1B1+TRIB2, DDX60+SULT1B1+uc003hrl.1, DDX60+SULT1B1+USP41, DDX60+SULT1B1+ZCCHC2, DDX60+TRIB2+uc003hrl.1, DDX60+TRIB2+USP41, DDX60+TRIB2+ZCCHC2, DDX60+uc003hrl.1+USP41, DDX60+uc003hrl.1+ZCCHC2, DDX60+USP41+ZCCHC2, DGAT2+PARP12+PNPT1, DGAT2+PARP12+PYGL, DGAT2+PARP12+SULT1B1, DGAT2+PARP12+TRIB2, DGAT2+PARP12+uc003hrl.1, DGAT2+PARP12+USP41, DGAT2+PARP12+ZCCHC2, DGAT2+PNPT1+PYGL, DGAT2+PNPT1+SULT1B1, DGAT2+PNPT1+TRIB2, DGAT2+PNPT1+uc003hrl.1, DGAT2+PNPT1+USP41, DGAT2+PNPT1+ZCCHC2, DGAT2+PYGL+SULT1B1, DGAT2+PYGL+TRIB2, DGAT2+PYGL+uc003hrl.1, DGAT2+PYGL+USP41, DGAT2+PYGL+ZCCHC2, DGAT2+SULT1B1+TRIB2, DGAT2+SULT1B1+uc003hrl.1, DGAT2+SULT1B1+USP41, DGAT2+SULT1B1+ZCCHC2, DGAT2+TRIB2+uc003hrl.1, DGAT2+TRIB2+USP41, DGAT2+TRIB2+ZCCHC2, DGAT2+uc003hrl.1+USP41, DGAT2+uc003hrl.1+ZCCHC2, DGAT2+USP41+ZCCHC2, PARP12+PNPT1+PYGL, PARP12+PNPT1+SULT1B1, PARP12+PNPT1+TRIB2, PARP12+PNPT1+uc003hrl.1, PARP12+PNPT1+USP41, PARP12+PNPT1+ZCCHC2, PARP12+PYGL+SULT1B1, PARP12+PYGL+TRIB2, PARP12+PYGL+uc003hrl.1, PARP12+PYGL+USP41, PARP12+PYGL+ZCCHC2, PARP12+SULT1B1+TRIB2, PARP12+SULT1B1+uc003hrl.1, PARP12+SULT1B1+USP41, PARP12+SULT1B1+ZCCHC2, PARP12+TRIB2+uc003hrl.1, PARP12+TRIB2+USP41, PARP12+TRIB2+ZCCHC2, PARP12+uc003hrl.1+USP41, PARP12+uc003hrl.1+ZCCHC2, PARP12+USP41+ZCCHC2, PNPT1+PYGL+SULT1B1, PNPT1+PYGL+TRIB2, PNPT1+PYGL+uc003hrl.1, PNPT1+PYGL+USP41, PNPT1+PYGL+ZCCHC2, PNPT1+SULT1B1+TRIB2, PNPT1+SULT1B1+uc003hrl.1, PNPT1+SULT1B1+USP41, PNPT1+SULT1B1+ZCCHC2, PNPT1+TRIB2+uc003hrl.1, PNPT1+TRIB2+USP41, PNPT1+TRIB2+ZCCHC2, PNPT1+uc003hrl.1+USP41, PNPT1+uc003hrl.1+ZCCHC2, PNPT1+USP41+ZCCHC2, PYGL+SULT1B1+TRIB2, PYGL+SULT1B1+uc003hrl.1, PYGL+SULT1B1+USP41, PYGL+SULT1B1+ZCCHC2, PYGL+TRIB2+uc003hrl.1, PYGL+TRIB2+USP41, PYGL+TRIB2+ZCCHC2, PYGL+uc003hrl.1+USP41, PYGL+uc003hrl.1+ZCCHC2, PYGL+USP41+ZCCHC2, SULT1B1+TRIB2+uc003hrl.1, SULT1B1+TRIB2+USP41, SULT1B1+TRIB2+ZCCHC2, SULT1B1+uc003hrl.1+USP41, SULT1B1+uc003hrl.1+ZCCHC2, SULT1B1+USP41+ZCCHC2, TRIB2+uc003hrl.1+USP41, TRIB2+uc003hrl.1+ZCCHC2, TRIB2+USP41+ZCCHC2, uc003hrl.1+USP41+ZCCHC2

Additional determinants that may be measured according to aspects of the present invention include pathogen (bacterial or viral) specific RNA determinants. This may be carried out in order to aid in identification of a specific pathogen. The measurements may be effected simultaneously with the above described measurements or consecutively. The measurement may be performed on the biological sample used to determine the patient immune response (as described herein above) or on a different biological patient-derived sample (e.g., blood sample; serum sample; saliva; nasopharyngeal sample; etc.). In one embodiment, the host immune RNA determinants are measured in a patient derived serum sample and analysis of the pathogen specific RNA determinants is performed on a nasopharyngeal sample.

The infection type may be a bacterial infection, a viral infection or a mixed infection (a combination of bacterial and viral infection).

The infection may be an acute or chronic infection.

A chronic infection is an infection that develops slowly and lasts a long time. Viruses that may cause a chronic infection include Hepatitis C and HIV. One difference between acute and chronic infection is that during acute infection the immune system often produces IgM+ antibodies against the infectious agent, whereas the chronic phase of the infection is usually characteristic of IgM−/IgG+ antibodies. In addition, acute infections cause immune mediated necrotic processes while chronic infections often cause inflammatory mediated fibrotic processes and scarring (e.g. Hepatitis C in the liver). Thus, acute and chronic infections may elicit different underlying immunological mechanisms.

In one embodiment, the level of the determinant may be used to rule in an infection type. In another embodiment, the level of the determinant may be used to rule out an infection type.

By "ruling in" an infection it is meant that the subject has that type of infection.

By "ruling out" an infection it is meant that the subject does not have that type of infection.

For all determinants that have been classified as increasing during bacterial infection (as specified in Tables 11 or 13), when the level of that determinant is above a predetermined level, it is indicative that the subject has a bacterial infection (e.g. when measured by analyzing at the exon specified in Tables 10A or 10B; i.e. a bacterial infection is ruled in).

For all determinants that have been classified as increasing during a viral infection (as specified in Tables 11 or 13), when the level of that determinant is above a predetermined level, it is indicative that the subject has a virl infection (e.g. when measured by analyzing at the exon specified in Tables 10A or 10B; i.e. a viral infection is ruled in).

The preset/predetermined level of any of the aspects of the present invention may be a reference value derived from population studies, including without limitation, such subjects having a known infection, subject having the same or similar age range, subjects in the same or similar ethnic group, or relative to the starting sample of a subject undergoing treatment for an infection. Such reference values can be derived from statistical analyses and/or risk prediction data of populations obtained from mathematical algorithms and computed indices of infection. Reference determinant indices can also be constructed and used using algorithms and other methods of statistical and structural classification.

In one embodiment of the present invention, the preset level is the amount (i.e. level) of determinants in a control sample derived from one or more subjects who do not have an infection (i.e., healthy, and or non-infectious individuals). In a further embodiment, such subjects are monitored and/or periodically retested for a diagnostically relevant period of time ("longitudinal studies") following such test to verify continued absence of infection. Such period of time may be one day, two days, two to five days, five days, five to ten days, ten days, or ten or more days from the initial testing date for determination of the reference value. Furthermore, retrospective measurement of determinants in properly banked historical subject samples may be used in establishing these reference values, thus shortening the study time required.

A reference value can also comprise the amounts of determinants derived from subjects who show an improvement as a result of treatments and/or therapies for the infection. A reference value can also comprise the amounts of determinants derived from subjects who have confirmed infection by known techniques.

An example of a bacterially infected reference value is the mean or median concentrations of that determinant in a statistically significant number of subjects having been diagnosed as having a bacterial infection.

An example of a virally infected reference value is the mean or median concentrations of that determinant in a statistically significant number of subjects having been diagnosed as having a viral infection.

Tables 10A and 10B herein below provides a list of exons that present a higher degree of differential expression compared to its full length gene in exemplary RNA determinants. For Table 10A, the probe set ID and exon genomic coordinates are included in Table 12 in Example 1 herein below. For Table 10B, the probe set ID and exon genomic coordinates are included in Table 13 in Example 2, herein below.

TABLE 10A

| Gene Name/ RNA determinant | Exon # |
|---|---|
| AIM2 | 4, 5, 7 |
| ANKRD22 | 1, 3 |
| BMX | 5, 6, 7, 9, 12, 13, 14, 17, 18, 19, 21 |
| C19orf59 | 6, 9, 10 |
| CCL2 | 4, 5, 6 |
| CD177 | 7, 8, 2 |
| CEACAM1 | 1, 2, 6, 9, 13, 14, 16 |
| CLEC4D | 3, 4, 7, 8 |
| CMPK2 | 1, 2, 3, 4, 5, 6 |
| CXCL10 | 2, 3 |
| CYBRD1 | 2, 3, 4, 5, 6 |
| CYP1B1 | 4, 5 |
| DDX60 | 3, 4, 5, 6, 7, 8, 9, 10, 11, 12, 13, 17, 18, 19, 24, 25, 29, 30, 31, 32, 33, 35 |
| EIF1AY | 3, 4, 5, 6, 7 |
| EIF2AK2 | 1, 2, 3, 6, 8, 9, 14, 16, 17 |
| EPSTI1 | 2, 5, 6, 7, 11, 12, 13 |
| F13A1 | 1, 3, 8, 11, 12, 13 |
| FFAR3 | 2 |
| GALM | 4, 5, 6, 7, 8, 9 |
| HERC5 | 2, 3, 4, 5, 6, 8, 9, 10, 11, 13, 14, 16, 19, 21, 22 |
| HLA-DQA1 | 2, 5, 7, 1, 2, 7, 8 |
| IFI27 | 4, 6, 7 |
| IFI44 | 2, 4, 5, 6, 8 |
| IFI44L | 1, 3, 5 |
| IFI6 | 1, 4, 5 |
| IFIT1 | 3, 4 |
| IFIT2 | 4 |
| IFIT3 | 2, 3, 4, 8 |
| IFITM3 | 3, 4 |
| IRF7 | 1, 2, 3, 7, 9, 12 |
| ISG15 | 2, 3, 4 |
| JUP | 6, 7, 8, 9, 11, 15, 16 |
| LAMP3 | 1, 2, 3 |
| LY6E | 4, 7 |
| MT2A | 1, 2 |
| MX1 | 2, 4, 6, 8, 9, 10, 11, 12, 13, 14, 15, 16, 17 |
| OAS2 | 1, 3, 5, 9, 13, 17 |
| OAS3 | 3, 4, 5, 7, 9, 10, 12, 14, 15 |
| OASL | 1, 2, 4, 5, 6 |
| OTOF | 2, 4, 5, 6, 7, 10, 13, 14, 16, 17, 18, 21, 23, 25, 26, 27, 28, 29 |
| PHOSPHO1 | 2, 3 |
| PLSCR1 | 4, 6, 8, 9, 10, 11 |
| PPBP | 1, 3, 5 |
| PSTPIP2 | 7, 10, 12, 13 |
| RGS1 | 4, 5 |
| RSAD2 | 2, 3, 4, 5, 6, 8, 9 |
| RTP4 | 2, 3, 4 |
| SERPING1 | 4, 5, 6, 7, 9, 11, 12 |
| SH3BGRL2 | 2, 3, 4 |
| SIGLEC1 | 2, 3, 8, 10, 11, 14, 15, 16, 17, 18 |

TABLE 10A-continued

| Gene Name/ RNA determinant | Exon # |
|---|---|
| TMEM176A | 2, 3, 5 |
| TNFAIP6 | 1, 2, 3 |
| TREML4 | 2, 6, 7 |
| USP18 | 5, 6, 9, 10, 11 |
| UTY | 5, 8, 9, 14, 15, 16, 17, 18, 19, 20, 21, 22, 23, 24, 25 |
| XAF1 | 4, 5, 6, 7, 9, 10 |

Thus, for example when said RNA is ISG15, said exon corresponds to exon 2, 3 and/or 4;

when said RNA is IFI44L, said exon corresponds to exons 1, 3 and/or 5;

when said RNA is IFI44, said exon corresponds to exons 2, 4, 5, 6 and/or 8;

when said RNA is RGS1, said exon corresponds to exons 4 and/or 5;

when said RNA is IFI6, said exon corresponds to exons 1, 4 and/or 5;

when said RNA is AIM2, said exon corresponds to exons 4, 5 and/or 7;

when said RNA is IFIT2, said exon corresponds to exon 4;

when said RNA is IFIT3, said exon corresponds to exons 2, 3, 4 and/or 8;

when said RNA is IFIT1, said exon corresponds to exons 3 or 4;

when said RNA is ANKRD22, said exon corresponds to exons 1 or 3;

when said RNA is SERPING1, said exon corresponds to exons 4, 5, 6, 7, 9, 11 or 12;

when said RNA is IFITM3, said exon corresponds to exons 3 and/or 4;

when said RNA is IRF7, said exon corresponds to exons 1, 2, 3, 7, 9 and/or 12;

when said RNA is CLEC4D, said exon corresponds to exons 3, 4, 7 and/or 8;

when said RNA is OAS3, said exon corresponds to exons 3, 4, 5, 7, 9, 10, 12, 14 and/or 15;

when said RNA is OAS2, said exon corresponds to exons 1, 3, 5, 9, 13 and/or 17;

when said RNA is OASL, said exon corresponds to exons 1, 2, 4, 5 and/or 6;

when said RNA is EPSTI1, said exon corresponds to exons 2, 5, 6, 7, 11, 12 and/or 13;

when said RNA is IFI27, said exon corresponds to exons 4, 6, and/or 7;

when said RNA is MT2A, said exon corresponds to exons 1 and/or 2;

when said RNA is XAF1, said exon corresponds to exons 4, 5, 6, 7, 9 and/or 10;

when said RNA is CCL2, said exon corresponds to exons 4, 5 and/or 6;

when said RNA is JUP, said exon corresponds to exons 6, 7, 8, 9, 11, 15 and/or 16;

when said RNA is PHOSPHO1, said exon corresponds to exons 2 and/or 3;

when said RNA is PSTPIP2, said exon corresponds to exons 7, 10, 12 and/or 13;

when said RNA is C19orf59, said exon corresponds to exons 6, 9 and/or 10;

when said RNA is FFAR3, said exon corresponds to exon 2;

when said RNA is CD177, said exon corresponds to exons 7 and/or 8;

when said RNA is CEACAM1, said exon corresponds to exons 1, 2, 6, 9, 13, 14 and/or 16;

when said RNA is CD177, said exon corresponds to exon 2;

when said RNA is RSAD2, said exon corresponds to exons 2-6, 8 and/or 9;

when said RNA is GALM, said exon corresponds to exons 4-8 and/or 9;

when said RNA is TNFAIP6, said exon corresponds to exons 1, 2 and/or 3;

when said RNA is CYBRD1, said exon corresponds to exons 2-5 and/or 6;

when said RNA is CMPK2, said exon corresponds to exons 1-5 and/or 6;

when said RNA is OTOF, said exon corresponds to exons 2, 4, 5, 6, 7, 10, 13, 14, 16, 17, 18, 21, 23, 25-28 and/or 29;

when said RNA is EIF2AK2, said exon corresponds to exons 1, 2, 3, 6, 8, 9, 14, 16 and/or 17;

when said RNA is CYP1B1, said exon corresponds to exons 4 and/or 5;

when said RNA is SIGLEC1, said exon corresponds to exons 2, 3 8, 10, 11, 14-17 and/or 18;

when said RNA is MX1, said exon corresponds to exons 2, 4, 6, 8-16 and/or 17;

when said RNA is USP18, said exon corresponds to exons 5, 6, 9, 10 and/or 11;

when said RNA is RTP4, said exon corresponds to exons 2, 3 and/or 4;

when said RNA is PLSCR1, said exon corresponds to exons 4, 6, 8, 9, 10 and/or 11;

when said RNA is LAMP5, said exon corresponds to exons 1, 2 and/or 3;

when said RNA is HERC5, said exon corresponds to exons 2-6, 8-11, 13, 14, 16, 19, 21 and/or 22;

when said RNA is PPBP, said exon corresponds to exons 1, 3 and/or 5;

when said RNA is CXCL10, said exon corresponds to exons 2 and/or 3;

when said RNA is DX60, said exon corresponds to exons 3-13, 17-19, 24, 25, 29, 30, 31-33 and/or 35;

when said RNA is HLA-DQA1, said exon corresponds to exons 2, 5 and/or 7;

when said RNA is TREML4, said exon corresponds to exons 2, 6 and/or 7;

when said RNA is SH3BGRL2, said exon corresponds to exons 2, 3 and/or 4;

when said RNA is F13A1, said exon corresponds to exons 1, 3, 8, 11, 12 and/or 13;

when said RNA is TREM176A, said exon corresponds to exons 2, 3 and/or 5;

when said RNA is LY6E, said exon corresponds to exons 4 and/or 7;

when said RNA is BMX, said exon corresponds to exons 5-7, 9, 12, 13, 14, 17-19 and/or 21;

when said RNA is EIF1AY, said exon corresponds to exons 3-6 and/or 7;

when said RNA is UTY, said exon corresponds to exons 5, 8, 9, 14 24 and/or 25; or when said RNA is HLA-DQA1, said position corresponds to exons 1, 2, 7 and/or 8.

TABLE 10B

| Gene Symbol | mRNA Accession | Exon # |
|---|---|---|
| | RNA determinant | |
| PGD | NM_002631 | 2, 5, 7, 8, 9, 10, 11, 16, 17, 18, 26 |
| ALPL | NM_000478 | 2, 4, 5, 6, 7, 8, 9, 10, 12, 13, 15, 17, 19 |
| ZNF684 | NM_152373 | 4, 5, 7, 9, 10, 11, 12 |
| NEXN | NM_001172309 | 14, 17, 18, 19, 20, 21, 23, 24, 25, 27, 28 |
| MOV10 | NM_001130079 | 9, 11, 13, 15, 17, 18, 19, 20, 22, 25, 26, 28, 29, 30, 31, 33, 35, 36, 38, 39, 43, 46, 47, 49, 50, 52, 53, 54, 56, 58 |
| RABGAP1L | NM_001035230 | 38, 39, 40, 41, 42, 43, 44, 45, 46, 47, 48, 49, 50, 51, 52, 53, 54, 55, 56, 57, 58, 59, 60, 61, 62 |
| SRGAP2 | NM_001042758 | 1, 2, 3, 4, 5, 6, 8, 9, 10, 11, 12, 13, 14, 15, 16, 17, 18, 19, 20, 21, 22, 24, 25, 26, 27, 28, 30, 33, 34 |
| CR1 | NM_000573 | 2, 4, 5, 6, 8, 10, 19, 29, 38, 39, 44, 45, 46, 49, 50, 51, 54, 55, 56 |
| CR1L | NM_175710 | 5, 6, 7, 11, 13, 14, 15, 16, 18, 22 |
| chr1: 16542404-16543823 | ENST00000442385 | 3, 4 |
| PADI2 | NM_007365 | 7, 12, 13, 16, 17, 18, 19, 22, 23 |
| MIR1182 | NR_031593 | 1, 2, 3, 4, 5, 6 |
| chr1: 27364505-27391197 | TCONS_00000869-XLOC_000105 | 1, 2, 3, 4 |
| TRIB2 | NM_021643 | 5, 6, 7, 9, 10, 11 |
| PLB1 | NM_001170585 | 6, 10, 11, 28, 32, 33, 34, 35, 36, 38, 41, 42, 43, 44, 45, 46, 47, 48, 49, 50, 51, 52, 53, 54, 55, 57, 58, 60, 61, 62, 64, 65, 66, 67, 68, 69, 70, 71, 72, 73, 74, 75 |
| RASGRP3 | NM_001139488 | 8, 11, 16, 17, 19, 20, 21, 24, 25, 26, 27, 28, 29, 30, 31, 34, 35, 43, 44, 45, 47, 48, 49, 50 |
| IGKV3D-15 | ENST00000417279 | 3 |
| IL1RN | NM_173843 | 2, 3, 4, 5, 10, 11, 13, 16, 17, 18, 19, 20 |
| chr2: 179278390-179303866 | ENST00000436616 | 2, 5, 6, 7, 8, 9, 12, 13, 14, 15, 16 |
| SPATS2L | NM_001100422 | 14, 20, 22, 25, 26, 27, 28, 29, 30, 31, 32, 33, 34, 35, 36, 39, 41, 42, 43, 44, 45, 46, 47, 48, 49 |
| chr2: 6968645-6973662 | ENST00000366140 | 1, 3 |
| GALNT14 | NM_001253826 | 4, 5, 6, 7, 9, 10, 12, 13, 14, 15, 17, 21, 22, 23, 24, 25, 31, 37, 38 |
| NLRC4 | NM_001199138 | 6, 8, 11, 13 |

TABLE 10B-continued

RNA determinant

| Gene Symbol | mRNA Accession | Exon # |
|---|---|---|
| PNPT1 | NM_033109 | 9, 11, 14, 16, 17, 18, 19, 20, 21, 22, 23, 24, 25, 26, 27, 29, 30, 31, 34, 35, 37 |
| IGKC | ENST00000390237 | 5, 6, 7, 13, 16, 22, 28, 31, 32, 35 |
| IGKV1-9 | ENST00000493819 | 1 |
| chr2: 90537799-90538363 | ENST00000443397 | 2 |
| IFIH1 | NM_022168 | 1, 2, 3, 4, 5, 6, 7, 9, 10 |
| PGAP1 | NM_024989 | 4, 7, 9, 12, 15, 18, 21, 22, 26, 29, 33, 35, 36, 37, 40 |
| chr2: 12856998-12882860 | n407780 | 4, 5, 6, 7, 8 |
| chr2: 179278390-179303866 | n383778 | 2, 5, 6, 7, 8, 9, 12, 13, 14, 15, 16 |
| chr2: 243030784-243102469 | n346494 | 9, 10, 11, 12, 13, 14, 16, 17, 18, 19, 20, 21 |
| chr2: 6968645-6973662 | TCONS_00003184-XLOC_001966 | 3, 4 |
| chr2: 89109725-89619842 | n346551 | 32, 45, 52, 53 |
| chr2: 89475774-89476620 | n336681 | 2 |
| TTC21A | NM_001105513 | 4, 5, 8, 9, 10, 11, 12, 13, 14, 15, 16, 17, 18, 19, 20, 21, 22, 23, 25, 26, 27, 29, 31, 32, 33, 34, 35, 36, 37, 40, 42, 44, 45, 48, 50, 51 |
| TREX1 | NM_016381 | 4, 7, 17, 23, 30, 32, 33, 34, 36, 37, 38, 39 |
| PARP14 | NM_017554 | 5, 12, 18, 19, 20, 21, 23, 24, 25, 27, 28, 30, 31, 32, 33, 35 |
| HESX1 | NM_003865 | 2, 3, 4, 5, 6, 7 |
| ZDHHC19 | NM_001039617 | 1, 2, 3, 4, 5, 8, 9, 14 |
| FAM200B | NM_001145191 | 2, 9, 10, 11, 12, 13, 14, 15, 16, 17, 18, 19, 20, 21, 22, 23 |
| NSUN7 | NM_024677 | 4, 5, 6, 9, 10, 12, 14, 16, 17, 18, 19, 20, 21, 22, 23 |
| STAP1 | NM_012108 | 3, 4, 6, 7, 8, 9, 10 |
| ANXA3 | NM_005139 | 3, 4, 8, 10, 11, 12, 13, 14, 15, 16, 18, 20, 22, 23 |
| HERC6 | NM_001165136 | 11, 13, 15, 21, 22, 23, 24, 27, 28, 29, 30, 31, 34 |
| SULT1B1 | NM_014465 | 2, 3, 5, 6, 7 |
| IGJ | NM_144646 | 4 |
| PPM1K | NM_152542 | 1, 2, 3, 4, 5, 6, 7, 8, 13, 14, 16, 19, 22, 23 |
| HPGD | NM_000860 | 2, 3, 4, 5, 6, 7, 8, 9, 10, 13, 16, 17, 18 |
| ANKRD34B | NM_001004441 | 1, 2, 3, 4, 5, 6, 7, 8, 9 |
| MAPK14 | NM_001315 | 5, 6, 9, 10, 12, 13, 15, 17, 18, 20, 27, 28 |
| FTSJD2 | NM_015050 | 12, 13, 20, 22, 23, 24, 25, 26, 27, 28, 29, 31, 32, 33, 34, 35, 36, 38, 39 |
| CD2AP | NM_012120 | 3, 4, 5, 6, 8, 9, 10, 11, 12, 15, 17, 18, 19, 21, 22, 24, 25, 26 |
| NCOA7 | NM_001122842 | 3, 10, 14, 15, 16, 17, 19, 21, 23, 27, 28, 29, 30, 31, 32, 33, 34, 35, 36 |
| ARG1 | NM_000045 | 2, 6, 15, 17 |
| VNN1 | NM_004666 | 7 |
| LRRN3 | NM_001099658 | 4, 8, 9, 10, 12 |
| MGAM | NM_004668 | 7, 10, 11, 14, 15, 17, 19, 20, 23, 27, 36, 37, 40, 41, 42, 45, 46, 48, 51, 55, 60, 64, 65, 66, 70, 71, 72, 73, 83, 85 |
| PARP12 | NM_022750 | 3, 5, 8, 11, 14, 16, 18, 28 |
| AKAP2 | NM_001004065 | 27, 28, 29, 30, 31, 32, 33, 34, 35, 36, 37, 38, 39 |
| C9orf91 | NM_153045 | 7, 8, 9, 10, 11, 12, 13, 14, 15, 16, 17, 18 |
| GSN | NM_198252 | 3, 4, 5, 6, 8, 9, 10, 13, 14, 15, 16, 20, 21, 24, 26, 27, 28, 29, 30, 32, 35, 37, 38, 39, 41, 42, 43, 44, 45, 46, 47, 51, 53, 55, 56, 58, 59, 61 |
| CNTNAP3 | NM_033655 | 1, 3, 5, 9, 10, 11, 12, 13, 14, 15, 17, 18, 20, 22, 23, 24, 30, 31, 32, 33, 34, 35, 36, 37, 38 |
| chr9: 40498481-40633261 | uc004abr.1 | 2, 3, 4, 5, 6 |
| chr9: 47295855-47314322 | ENST00000438517 | 2, 3, 10, 11, 12, 13, 16, 17, 18, 19 |
| CDK5RAP2 | NM_001011649 | 1, 2, 3, 4, 5, 6, 7, 8, 9, 10, 11, 12, 13, 14, 15, 16, 18, 19, 20, 21, 22, 23, 24, 25, 26, 27, 28, 30, 31, 33, 35, 36, 39, 40, 41, 42, 43, 46, 47, 48, 49, 50, 51, 53, 54, 55, 56, 57, 58, 59, 60, 61, 62 |
| SDCCAG3 | NM_001039707 | 1, 2, 3, 4, 6, 8, 9, 10, 11, 12, 14, 16, 17, 18, 19, 20 |
| TMEM255A | NM_001104544 | 1, 2, 3, 4, 5, 8, 9, 10 |
| IFIT5 | NM_012420 | 5 |
| CD44 | NM_001001391 | 2, 3, 5, 10, 11, 13, 14, 15, 16, 17, 18, 19, 23, 24, 27, 28 |
| DGAT2 | NM_001253891 | 5, 6, 7, 8, 9, 10, 11 |
| TMEM123 | NM_052932 | 1, 3, 4, 8, 9, 10 |
| MMP8 | NM_002424 | 3, 4, 5, 7, 8, 9, 10, 11, 12, 13, 16 |
| chr11: 57373517-57381926 | n333961 | 1, 3, 4 |
| LTA4H | NM_000895 | 8, 9, 17, 18, 19, 21, 22, 23, 25 |
| chr12: 113345433-113455556 | ENST00000552784 | 1, 2 |
| TDRD9 | NM_153046 | 5, 6, 7, 9, 10, 11, 12, 14, 15, 16, 17, 18, 20, 22, 23, 25, 26, 29, 30, 35, 36, 37, 38 |

TABLE 10B-continued

| Gene Symbol | mRNA Accession | Exon # |
|---|---|---|
| | RNA determinant | |
| PYGL | NM_001163940 | 2, 6, 7, 8, 9, 10, 11, 12, 13, 14, 15, 17, 18, 23 |
| chr14: 94577084-94582176 | n334829 | 3 |
| ATP10A | NM_024490 | 3, 4, 6, 7, 8, 10, 11, 16, 17, 19, 20, 22 |
| chr15: 67457682-67473649 | n332456 | 1 |
| MT1A | NM_005946 | 2 |
| MT1M | NM_176870 | 3, 5 |
| MT1E | NM_175617 | 3, 4, 6, 7 |
| MT1JP | NR_036677 | 3, 4 |
| MT1DP | NR_003658 | 3, 4 |
| MT1B | NM_005947 | 2, 3 |
| MT1F | NM_005949 | 2 |
| MT1H | NM_005951 | 2, 3, 4 |
| MT1IP | NR_003669 | 4, 6 |
| MT1X | NM_005952 | 2, 3, 5, 6 |
| HP | NM_001126102 | 6, 7, 8 |
| HPR | NM_020995 | 1, 3, 4, 5 |
| MT1G | NM_005950 | 2 |
| chr16: 56669651-56670998 | n382996 | 3, 4 |
| chr16: 56677385-56678852 | TCONS_00024856-XLOC_011736 | 5, 6 |
| chr16: 56709649-56711789 | n406211 | 4, 6 |
| FBXO39 | NM_153230 | 3, 4, 5 |
| CCL8 | NM_005623 | 3, 4, 5 |
| CA4 | NM_000717 | 4, 5, 6, 7, 8, 10 |
| GAS7 | NM_201433 | 1, 8, 9, 10, 11, 12, 14, 16, 21, 22, 26 |
| KRT19 | NM_002276 | 1, 2, 3, 4, 5, 6, 7, 8, 9, 10, 11, 12, 13, 14, 15 |
| DHX58 | NM_024119 | 1, 2, 8, 10, 11, 13, 14, 15, 16 |
| LGALS3BP | NM_005567 | 1, 2, 3, 5, 7 |
| chr17: 66531257-66554568 | n407998 | 3, 5, 6, 7 |
| IMPA2 | NM_014214 | 4, 6, 7, 8, 10, 11, 12 |
| ZCCHC2 | NM_017742 | 12, 14, 15 |
| RFX2 | NM_000635 | 2, 3, 7, 9, 12, 13, 14, 16, 19 |
| RIN2 | NM_001242581 | 7, 8, 9, 10, 11, 12, 13, 14, 15, 16, 17, 18, 19, 20 |
| MMP9 | NM_004994 | 1, 2, 3, 4, 5, 6, 9, 13, 17, 18 |
| ATP9A | NM_006045 | 2, 4, 5, 6, 7, 8, 9, 13, 16, 19, 20, 21, 23, 25, 27, 28, 29, 30 |
| ZBP1 | NM_001160418 | 2, 3, 4, 5, 6, 8, 10, 12, 13, 14, 15, 17, 19 |
| chr20: 19867165-19981449 | n339591 | 4, 5, 6, 7, 8, 10, 11, 12, 13 |
| chr20: 24911303-24912191 | TCONS_00028139-XLOC_013499 | 2 |
| MIR650 | NR_030755 | 20, 21, 22, 26, 27, 28, 30, 32, 34, 35, 36, 37, 38, 39, 42, 43, 45, 46, 47, 50, 51, 52, 53, 54, 55, 56, 57, 59, 61, 62, 63, 69, 71, 73, 74, 75, 77, 79, 80, 81 |
| KREMEN1 | NM_001039570 | 2, 3, 4, 5, 7, 8, 9, 10, 12, 13, 14, 15, 16 |
| TSPO | NM_000714 | 5, 7, 8, 9 |
| PRR5 | NM_181333 | 2, 4, 11, 12, 13, 14, 15, 16, 17, 18, 19, 20, 21, 22, 23, 25, 26, 28, 29, 30, 32, 33, 34, 45, 47, 48, 49, 50, 53, 54, 61, 67, 68, 69 |
| USP41 | ENST00000454608 | 2, 3, 4, 5, 6, 7, 10 |
| chr22: 18840392-18851914 | n384079 | 6, 7, 10 |
| chr22: 22652463-22677324 | n386315 | 3, 4, 5, 6, 7, 8, 10, 13, 15, 16, 17, 20 |
| chr22: 22550382-23248828 | n332472 | 3 |
| chr22: 23242926-23265153 | n346241 | 5 |

Particular RNA determinants which may be used to distinguish between bacterial and viral infection include for example:
  Exons 38 and/or 42 of RABGAP1L;
  Exons 11 and/or 21 of PNPT1;
  Exons 34 and/or 30 of HERC6
  Exons 4 and/or 7 of IMPA2;
  Exon 1 of TMEM123;
  Exons 17 and/or 18 of LTA4H;
  Exons 13 and/or 14 of ENST00000436616;
  Exons 2 and/or 3 of USP41;
  Exons 13 and/or 15 of n383778;
  Exons 5 and/or 6 of MIR1182/FAM89A;
  Exons 14 and/or 16 of RSAD2;
  Exons 33 and/or 39 of MX1;
  Exons 26 and/or 27 of IFI44L;
  Exons 3 and/or 7 of IFI27.

According to this aspect of the present invention mRNA is the biological precursor of proteins and changes in its expression levels are expected to precede those of its protein counterparts. Consequently, protein and RNA biomarkers may differ in their temporal dynamics patterns and can complement each other to detect infection prior to symptom onset or following convalescence. Therefore, it will be appreciated that as well as determining the level of the RNA determinants described herein, the present inventors also contemplate combining these measurements with measurements of polypeptide determinants that are known to be indicative of infection type. Examples of polypeptide determinants that are contemplated by the present invention include those that are described in WO 2013/117746, WO 2011/132086, PCT Application IL 2015/051024 and PCT Application IL 2015/051201, the contents of each are incorporated herein by reference. Other polypeptide determinants contemplated by the present inventors are the polypeptide counterparts of the RNA determinants described herein.

Examples of polypeptides contemplated by the present inventors include, but are not limited to: TRAIL, CRP, IP-10, MX1, RSAD2, PCT, OTOF, CYBRD1, EIF2AK2, NGAL and CMPK2.

Kits

Some aspects of the invention also include a determinant-detection reagent such as an oligonucleotide packaged together in the form of a kit for diagnosing infection type. The kit may contain in separate containers oligonucleotides (either already bound to a solid matrix or packaged separately with reagents for binding them to the matrix), control formulations (positive and/or negative), and/or a detectable label such as fluorescein, green fluorescent protein, rhodamine, cyanine dyes, Alexa dyes, luciferase, radiolabels, among others. Instructions (e.g., written, tape, VCR, CD-ROM, etc.) for carrying out the assay may be included in the kit.

The kits of this aspect of the present invention may comprise additional components that aid in the detection of the determinants such as enzymes, salts, buffers etc. necessary to carry out the detection reactions.

Thus, according to another aspect of the present invention, there is provided a kit comprising at least two oligonucleotides, wherein the first of said at least two oligonucleotides specifically hybridizes to a first RNA at a first exon, and a second of said at least two oligonucleotides specifically hybridizes to the first RNA at a second exon, the first and said second exon being selected such that the expression level from the first exon distinguishes between a bacterial and viral infection with a degree of accuracy above a predetermined level (based on differential expression data, as described herein above) and the expression level from said second exon distinguishes between a bacterial and viral infection with a degree of accuracy above the predetermined level (based on differential expression data, as described herein above).

In another aspect of the present invention there is provided a primer pair which hybridizes to an RNA at an exon whose expression level distinguishes between a bacterial and viral infection with a degree of accuracy above a predetermined level (based on differential expression data as described herein above).

According to still another aspect, there is provided a kit comprising at least two oligonucleotides, wherein the first of the at least two oligonucleotides specifically hybridizes to a first RNA at a first exon, and a second of said at least two oligonucleotides specifically hybridizes to a second RNA at a second exon, the first exon being selected so as to distinguish between a bacterial and viral infection with a degree of accuracy above a predetermined level (based on differential expression data between bacterial and viral samples as described herein above), and the second exon being selected so as to distinguish between a bacterial and viral infection with a degree of accuracy above the predetermined level (based on differential expression data between bacterial and viral samples, as described herein above).

According to still another aspect of the present invention there is provided a kit comprising at least two oligonucleotides, wherein the at least two oligonucleotides hybridize to one of the specified exons of the RNA determinants set forth in Table 10A or Table 10B:

The oligonucleotides may be attached to detectable moieties as described herein above.

Preferably, the kit contains a number of oligonucleotides such that no more than 20 determinants (e.g. RNAs) can be detected.

Preferably, the kit contains a number of oligonucleotides such that no more than 10 determinants (e.g. RNAs) can be detected.

Preferably, the kit contains a number of oligonucleotides such that no more than 5 determinants (e.g. RNAs) can be detected.

Preferably, the kit contains a number of oligonucleotides such that no more than 3 determinants (e.g. RNAs) can be detected.

Preferably, the kit contains a number of oligonucleotides such that no more than 2 determinants (e.g. RNAs) can be detected.

In one embodiment, the detection reagents in the kit are only capable of detecting determinants which appear in Tables 1-2.

In other embodiments, the detection reagents in the kit are only capable of analyzing expression of determinants which appear in one of Tables 1-4.

In still other embodiments, at least one of the detection reagents in the kit is capable of analyzing expression of a determinant which appears in one of Tables 1-4. Additional RNA determinants which may be measured include for example pathogen specific RNA determinants.

According to further embodiments, the kits of the present invention comprise a number of oligonucleotides such that the expression level from no more than 1 exon per RNA determinant is measured.

According to further embodiments, the kits of the present invention comprise a number of oligonucleotides such that the expression level from no more than 2 exons per RNA determinant is measured. According to further embodiments, the kits of the present invention comprise a number of oligonucleotides such that the expression level from no more than 3 exons per RNA determinant is measured. According to further embodiments, the kits of the present invention comprise a number of oligonucleotides such that the expression level from no more than 4 exons per RNA determinant is measured. According to further embodiments, the kits of the present invention comprise a number of oligonucleotides such that the expression level from no more than 5 exons per RNA determinant is measured.

As mentioned, the present invention also contemplates use of arrays to determine the expression level from particular exons of RNA.

Thus, according to another aspect of the present invention there is provided an array comprising a solid support, and a polynucleotide that specifically hybridizes to a first RNA at a predetermined exon, the polynucleotide being attached to the solid support, the predetermined exon being selected such that the expression level therefrom distinguishes between a bacterial and viral infection with a degree of accuracy above a predetermined level, wherein the array comprises oligonucleotides that hybridize to no more than 3 exons of said first RNA.

According to still another aspect of the present invention there is provided an array comprising a solid support, a first polynucleotide that specifically hybridizes to a first RNA at a first exon and a second polynucleotide that specifically hybridizes to a second exon of a second RNA, said first and second polynucleotide being attached to the solid support, said first exon being selected such that the expression level therefrom distinguishes between a bacterial and viral infection with a degree of accuracy above a predetermined level and said second exon being selected such that the expression level therefrom distinguishes between a bacterial and viral infection with a degree of accuracy above a predetermined level, wherein said array comprises oligonucleotides that hybridize to no more than 20 non-identical RNAs.

Some aspects of the present invention can also be used to screen patients or subject populations in any number of settings. For example, a health maintenance organization, public health entity or school health program can screen a group of subjects to identify those requiring interventions, as described above, or for the collection of epidemiological data. Insurance companies (e.g., health, life or disability) may screen applicants in the process of determining coverage or pricing, or existing clients for possible intervention. Data collected in such population screens, particularly when tied to any clinical progression to conditions like infection, will be of value in the operations of, for example, health maintenance organizations, public health programs and insurance companies. Such data arrays or collections can be stored in machine-readable media and used in any number of health-related data management systems to provide improved healthcare services, cost effective healthcare, improved insurance operation, etc. See, for example, U.S. Patent Application No. 2002/0038227; U.S. Patent Application No. US 2004/0122296; U.S. Patent Application No. US 2004/0122297; and U.S. Pat. No. 5,018,067. Such systems can access the data directly from internal data storage or remotely from one or more data storage sites as further detailed herein.

A machine-readable storage medium can comprise a data storage material encoded with machine readable data or data arrays which, when using a machine programmed with instructions for using the data, is capable of use for a variety of purposes. Measurements of effective amounts of the biomarkers of the invention and/or the resulting evaluation of risk from those biomarkers can be implemented in computer programs executing on programmable computers, comprising, inter alia, a processor, a data storage system (including volatile and non-volatile memory and/or storage elements), at least one input device, and at least one output device. Program code can be applied to input data to perform the functions described above and generate output information. The output information can be applied to one or more output devices, according to methods known in the art. The computer may be, for example, a personal computer, microcomputer, or workstation of conventional design.

Each program can be implemented in a high level procedural or object oriented programming language to communicate with a computer system. However, the programs can be implemented in assembly or machine language, if desired. The language can be a compiled or interpreted language. Each such computer program can be stored on a storage media or device (e.g., ROM or magnetic diskette or others as defined elsewhere in this disclosure) readable by a general or special purpose programmable computer, for configuring and operating the computer when the storage media or device is read by the computer to perform the procedures described herein. The health-related data management system used in some aspects of the invention may also be considered to be implemented as a computer-readable storage medium, configured with a computer program, where the storage medium so configured causes a computer to operate in a specific and predefined manner to perform various functions described herein.

The determinants of the present invention, in some embodiments thereof, can be used to generate a "reference determinant profile" of those subjects who do not have an infection. The determinants disclosed herein can also be used to generate a "subject determinant profile" taken from subjects who have an infection. The subject determinant profiles can be compared to a reference determinant profile to diagnose or identify subjects with an infection. The subject determinant profile of different infection types can be compared to diagnose or identify the type of infection. The reference and subject determinant profiles of the present invention, in some embodiments thereof, can be contained in a machine-readable medium, such as but not limited to, analog tapes like those readable by a VCR, CD-ROM, DVD-ROM, USB flash media, among others. Such machine-readable media can also contain additional test results, such as, without limitation, measurements of clinical parameters and traditional laboratory risk factors. Alternatively or additionally, the machine-readable media can also comprise subject information such as medical history and any relevant family history. The machine-readable media can also contain information relating to other disease-risk algorithms and computed indices such as those described herein.

The effectiveness of a treatment regimen can be monitored by detecting a determinant in an effective amount (which may be one or more) of samples obtained from a subject over time and comparing the amount of determinants detected. For example, a first sample can be obtained prior to the subject receiving treatment and one or more subsequent samples are taken after or during treatment of the subject.

For example, the methods of the invention can be used to discriminate between bacterial and viral infections (i.e. bacterial and viral co-infections). This will allow patients to be stratified and treated accordingly.

In a specific embodiment of the invention a treatment recommendation (i.e., selecting a treatment regimen) for a subject is provided by identifying the type infection (i.e., bacterial or viral) in the subject according to the method of any of the disclosed methods and recommending that the subject receive an antibiotic treatment if the subject is identified as having bacterial infection; or an anti-viral treatment is if the subject is identified as having a viral infection.

In another embodiment, the methods of the invention can be used to prompt additional targeted diagnosis such as pathogen specific PCRs, chest-X-ray, cultures etc. For example, a diagnosis that indicates a viral infection according to embodiments of this invention, may prompt the usage of additional viral specific multiplex-PCRs, whereas a diagnosis that indicates a bacterial infection according to embodiments of this invention may prompt the usage of a bacterial specific multiplex-PCR. Thus, one can reduce the costs of unwarranted expensive diagnostics.

In a specific embodiment, a diagnostic test recommendation for a subject is provided by identifying the infection type (i.e., bacterial or viral infection) in the subject according to any of the disclosed methods and recommending a test to determine the source of the bacterial infection if the subject is identified as having a bacterial infection or a mixed infection; or a test to determine the source of the viral infection if the subject is identified as having a viral infection.

Performance and Accuracy Measures of the Invention.

The performance and thus absolute and relative clinical usefulness of the invention may be assessed in multiple ways as noted above. Amongst the various assessments of performance, some aspects of the invention are intended to provide accuracy in clinical diagnosis and prognosis. The accuracy of a diagnostic or prognostic test, assay, or method concerns the ability of the test, assay, or method to distinguish between subjects having an infection is based on whether the subjects have, a "significant alteration" (e.g., clinically significant and diagnostically significant) in the levels of a determinant. By "effective amount" it is meant that the measurement of an appropriate number of determinants (which may be one or more) to produce a "significant alteration" (e.g. level of expression or activity of a determinant) that is different than the predetermined cut-off point (or threshold value) for that determinant (s) and therefore indicates that the subject has an infection for which the determinant (s) is an indication. The difference in the level of determinant is preferably statistically significant. As noted below, and without any limitation of the invention, achieving statistical significance, and thus the preferred analytical, diagnostic, and clinical accuracy, may require that combinations of several determinants be used together in panels and combined with mathematical algorithms in order to achieve a statistically significant determinant index.

In the categorical diagnosis of a disease state, changing the cut-off point or threshold value of a test (or assay) usually changes the sensitivity and specificity, but in a qualitatively inverse relationship. Therefore, in assessing the accuracy and usefulness of a proposed medical test, assay, or method for assessing a subject's condition, one should always take both sensitivity and specificity into account and be mindful of what the cut point is at which the sensitivity and specificity are being reported because sensitivity and specificity may vary significantly over the range of cut points. One way to achieve this is by using the Matthews correlation coefficient (MCC) metric, which depends upon both sensitivity and specificity. Use of statistics such as area under the ROC curve (AUC), encompassing all potential cut point values, is preferred for most categorical risk measures when using some aspects of the invention, while for continuous risk measures, statistics of goodness-of-fit and calibration to observed results or other gold standards, are preferred.

By predetermined level of predictability it is meant that the method provides an acceptable level of clinical or diagnostic accuracy. Using such statistics, an "acceptable degree of diagnostic accuracy", is herein defined as a test or assay (such as the test used in some aspects of the invention for determining the clinically significant presence of determinants, which thereby indicates the presence an infection type) in which the AUC (area under the ROC curve for the test or assay) is at least 0.60, desirably at least 0.65, more desirably at least 0.70, preferably at least 0.75, more preferably at least 0.80, and most preferably at least 0.85.

By a "very high degree of diagnostic accuracy", it is meant a test or assay in which the AUC (area under the ROC curve for the test or assay) is at least 0.75, 0.80, desirably at least 0.85, more desirably at least 0.875, preferably at least 0.90, more preferably at least 0.925, and most preferably at least 0.95.

Alternatively, the methods predict the presence or absence of an infection or response to therapy with at least 75% total accuracy, more preferably 80%, 85%, 90%, 95%, 97%, 98%, 99% or greater total accuracy.

Alternatively, the methods predict the presence of a bacterial infection or response to therapy with at least 75% sensitivity, more preferably 80%, 85%, 90%, 95%, 97%, 98%, 99% or greater sensitivity.

Alternatively, the methods predict the presence of a viral infection or response to therapy with at least 75% specificity, more preferably 80%, 85%, 90%, 95%, 97%, 98%, 99% or greater specificity. Alternatively, the methods predict the presence or absence of an infection or response to therapy with an MCC larger than 0.2, 0.3, 0.4, 0.5, 0.6, 0.7, 0.8, 0.9 or 1.0.

In general, alternative methods of determining diagnostic accuracy are commonly used for continuous measures, when a disease category has not yet been clearly defined by the relevant medical societies and practice of medicine, where thresholds for therapeutic use are not yet established, or where there is no existing gold standard for diagnosis of the pre-disease. For continuous measures of risk, measures of diagnostic accuracy for a calculated index are typically based on curve fit and calibration between the predicted continuous value and the actual observed values (or a historical index calculated value) and utilize measures such as R squared, Hosmer-Lemeshow P-value statistics and confidence intervals. It is not unusual for predicted values using such algorithms to be reported including a confidence interval (usually 90% or 95% CI) based on a historical observed cohort's predictions, as in the test for risk of future breast cancer recurrence commercialized by Genomic Health, Inc. (Redwood City, Calif.).

In general, by defining the degree of diagnostic accuracy, i.e., cut points on a ROC curve, defining an acceptable AUC value, and determining the acceptable ranges in relative concentration of what constitutes an effective amount of the determinants of the invention allows for one of skill in the art to use the determinants to identify, diagnose, or prognose subjects with a pre-determined level of predictability and performance.

Furthermore, other unlisted biomarkers will be very highly correlated with the determinants (for the purpose of this application, any two variables will be considered to be "very highly correlated" when they have a Coefficient of Determination ($R^2$) of 0.5 or greater). Some aspects of the present invention encompass such functional and statistical equivalents to the aforementioned determinants. Furthermore, the statistical utility of such additional determinants is substantially dependent on the cross-correlation between multiple biomarkers and any new biomarkers will often be required to operate within a panel in order to elaborate the meaning of the underlying biology.

One or more of the listed determinants can be detected in the practice of the present invention, in some embodiments thereof. For example, two (2), three (3), four (4), five (5), ten (10), fifteen (15), twenty (20), forty (40), or more determinants can be detected.

In some aspects, all determinants listed herein can be detected. Preferred ranges from which the number of determinants can be detected include ranges bounded by any minimum selected from between one and, particularly two, three, four, five, six, seven, eight, nine ten, twenty, or forty.

Particularly preferred ranges include two to five (2-5), two to ten (2-10), two to twenty (2-20), or two to forty (2-40).

Construction of Clinical Algorithms

Any formula may be used to combine determinant results into indices useful in the practice of the invention. As indicated above, and without limitation, such indices may indicate, among the various other indications, the probability, likelihood, absolute or relative risk, time to or rate of conversion from one to another disease states, or make predictions of future biomarker measurements of infection. This may be for a specific time period or horizon, or for remaining lifetime risk, or simply be provided as an index relative to another reference subject population.

Although various preferred formula are described here, several other model and formula types beyond those mentioned herein and in the definitions above are well known to one skilled in the art. The actual model type or formula used may itself be selected from the field of potential models based on the performance and diagnostic accuracy characteristics of its results in a training population. The specifics of the formula itself may commonly be derived from determinant results in the relevant training population. Amongst other uses, such formula may be intended to map the feature space derived from one or more determinant inputs to a set of subject classes (e.g. useful in predicting class membership of subjects as normal, having an infection), to derive an estimation of a probability function of risk using a Bayesian approach, or to estimate the class-conditional probabilities, then use Bayes' rule to produce the class probability function as in the previous case.

Preferred formulas include the broad class of statistical classification algorithms, and in particular the use of discriminant analysis. The goal of discriminant analysis is to predict class membership from a previously identified set of features. In the case of linear discriminant analysis (LDA), the linear combination of features is identified that maximizes the separation among groups by some criteria. Features can be identified for LDA using an eigengene based approach with different thresholds (ELDA) or a stepping algorithm based on a multivariate analysis of variance (MANOVA). Forward, backward, and stepwise algorithms can be performed that minimize the probability of no separation based on the Hotelling-Lawley statistic.

Eigengene-based Linear Discriminant Analysis (ELDA) is a feature selection technique developed by Shen et al. (2006). The formula selects features (e.g. biomarkers) in a multivariate framework using a modified eigen analysis to identify features associated with the most important eigenvectors. "Important" is defined as those eigenvectors that explain the most variance in the differences among samples that are trying to be classified relative to some threshold.

A support vector machine (SVM) is a classification formula that attempts to find a hyperplane that separates two classes. This hyperplane contains support vectors, data points that are exactly the margin distance away from the hyperplane. In the likely event that no separating hyperplane exists in the current dimensions of the data, the dimensionality is expanded greatly by projecting the data into larger dimensions by taking non-linear functions of the original variables (Venables and Ripley, 2002). Although not required, filtering of features for SVM often improves prediction. Features (e.g., biomarkers) can be identified for a support vector machine using a non-parametric Kruskal-Wallis (KW) test to select the best univariate features. A random forest (RF, Breiman, 2001) or recursive partitioning (RPART, Breiman et al., 1984) can also be used separately or in combination to identify biomarker combinations that are most important. Both KW and RF require that a number of features be selected from the total. RPART creates a single classification tree using a subset of available biomarkers.

Other formula may be used in order to pre-process the results of individual determinant measurements into more valuable forms of information, prior to their presentation to the predictive formula. Most notably, normalization of biomarker results, using either common mathematical transformations such as logarithmic or logistic functions, as normal or other distribution positions, in reference to a population's mean values, etc. are all well known to those skilled in the art. Of particular interest are a set of normalizations based on clinical-determinants such as time from symptoms, gender, race, or sex, where specific formula are used solely on subjects within a class or continuously combining a clinical-determinants as an input. In other cases, analyte-based biomarkers can be combined into calculated variables which are subsequently presented to a formula.

In addition to the individual parameter values of one subject potentially being normalized, an overall predictive formula for all subjects, or any known class of subjects, may itself be recalibrated or otherwise adjusted based on adjustment for a population's expected prevalence and mean biomarker parameter values, according to the technique outlined in D'Agostino et al., (2001) JAMA 286:180-187, or other similar normalization and recalibration techniques. Such epidemiological adjustment statistics may be captured, confirmed, improved and updated continuously through a registry of past data presented to the model, which may be machine readable or otherwise, or occasionally through the retrospective query of stored samples or reference to historical studies of such parameters and statistics. Additional examples that may be the subject of formula recalibration or other adjustments include statistics used in studies by Pepe, M. S. et al., 2004 on the limitations of odds ratios; Cook, N. R., 2007 relating to ROC curves. Finally, the numeric result of a classifier formula itself may be transformed post-processing by its reference to an actual clinical population and study results and observed endpoints, in order to calibrate to absolute risk and provide confidence intervals for varying numeric results of the classifier or risk formula.

Some determinants may exhibit trends that depends on the patient age (e.g. the population baseline may rise or fall as a function of age). One can use an 'Age dependent normalization or stratification' scheme to adjust for age related differences. Performing age dependent normalization, stratification or distinct mathematical formulas can be used to improve the accuracy of determinants for differentiating between different types of infections. For example, one skilled in the art can generate a function that fits the population mean levels of each determinant as function of age and use it to normalize the determinant of individual subjects levels across different ages. Another example is to stratify subjects according to their age and determine age specific thresholds or index values for each age group independently.

It will be appreciated that if the determinant which is used to diagnose infection type is an RNA which is located on a sex chromosomes, the patient gender may influence the diagnostic accuracy of an RNA based diagnostic signature. Thus, it is proposed that when the RNA determinants EIF1AY and UTY (which are located on the Y chromosome) or the RNA determinant BMX (which is located on the X chromosome) are used, the sex of the subject is taken into account.

In the context of the present invention, the following statistical terms may be used:

"TP" is true positive, means positive test result that accurately reflects the tested-for activity. For example in the context of the present invention a TP, is for example but not limited to, truly classifying a bacterial infection as such.

"TN" is true negative, means negative test result that accurately reflects the tested-for activity. For example in the context of the present invention a TN, is for example but not limited to, truly classifying a viral infection as such.

"FN" is false negative, means a result that appears negative but fails to reveal a situation. For example in the context of the present invention a FN, is for example but not limited to, falsely classifying a bacterial infection as a viral infection.

"FP" is false positive, means test result that is erroneously classified in a positive category. For example in the context of the present invention a FP, is for example but not limited to, falsely classifying a viral infection as a bacterial infection.

"Sensitivity" is calculated by TP/(TP+FN) or the true positive fraction of disease subjects.

"Specificity" is calculated by TN/(TN+FP) or the true negative fraction of non-disease or normal subjects.

"Total accuracy" is calculated by (TN+TP)/(TN+FP+TP+FN).

"Positive predictive value" or "PPV" is calculated by TP/(TP+FP) or the true positive fraction of all positive test results. It is inherently impacted by the prevalence of the disease and pre-test probability of the population intended to be tested.

"Negative predictive value" or "NPV" is calculated by TN/(TN+FN) or the true negative fraction of all negative test results. It also is inherently impacted by the prevalence of the disease and pre-test probability of the population intended to be tested. See, e.g., O'Marcaigh A S, Jacobson R M, "Estimating The Predictive Value Of A Diagnostic Test, How To Prevent Misleading Or Confusing Results," Clin. Ped. 1993, 32(8): 485-491, which discusses specificity, sensitivity, and positive and negative predictive values of a test, e.g., a clinical diagnostic test.

"MCC" (Matthews Correlation coefficient) is calculated as follows: MCC=(TP*TN−FP*FN)/{(TP+FN)*(TP+FP)*(TN+FP)*(TN+FN)}^0.5 where TP, FP, TN, FN are true-positives, false-positives, true-negatives, and false-negatives, respectively. Note that MCC values range between −1 to +1, indicating completely wrong and perfect classification, respectively. An MCC of 0 indicates random classification. MCC has been shown to be a useful for combining sensitivity and specificity into a single metric (Baldi, Brunak et al. 2000). It is also useful for measuring and optimizing classification accuracy in cases of unbalanced class sizes (Baldi, Brunak et al. 2000).

Often, for binary disease state classification approaches using a continuous diagnostic test measurement, the sensitivity and specificity is summarized by a Receiver Operating Characteristics (ROC) curve according to Pepe et al., "Limitations of the Odds Ratio in Gauging the Performance of a Diagnostic, Prognostic, or Screening Marker," Am. J. Epidemiol 2004, 159 (9): 882-890, and summarized by the Area Under the Curve (AUC) or c-statistic, an indicator that allows representation of the sensitivity and specificity of a test, assay, or method over the entire range of test (or assay) cut points with just a single value. See also, e.g., Shultz, "Clinical Interpretation Of Laboratory Procedures," chapter 14 in Teitz, Fundamentals of Clinical Chemistry, Burtis and Ashwood (eds.), 4$^{th}$ edition 1996, W.B. Saunders Company, pages 192-199; and Zweig et al., "ROC Curve Analysis: An Example Showing The Relationships Among Serum Lipid And Apolipoprotein Concentrations In Identifying Subjects With Coronory Artery Disease," Clin. Chem., 1992, 38(8): 1425-1428. An alternative approach using likelihood functions, odds ratios, information theory, predictive values, calibration (including goodness-of-fit), and reclassification measurements is summarized according to Cook, "Use and Misuse of the Receiver Operating Characteristic Curve in Risk Prediction," Circulation 2007, 115: 928-935.

"Accuracy" refers to the degree of conformity of a measured or calculated quantity (a test reported value) to its actual (or true) value. Clinical accuracy relates to the proportion of true outcomes (true positives (TP) or true negatives (TN) versus misclassified outcomes (false positives (FP) or false negatives (FN)), and may be stated as a sensitivity, specificity, positive predictive values (PPV) or negative predictive values (NPV), Matthews correlation coefficient (MCC), or as a likelihood, odds ratio, Receiver Operating Characteristic (ROC) curve, Area Under the Curve (AUC) among other measures.

A "formula," "algorithm," or "model" is any mathematical equation, algorithmic, analytical or programmed process, or statistical technique that takes one or more continuous or categorical inputs (herein called "parameters") and calculates an output value, sometimes referred to as an "index" or "index value". Non-limiting examples of "formulas" include sums, ratios, and regression operators, such as coefficients or exponents, biomarker value transformations and normalizations (including, without limitation, those normalization schemes based on clinical-determinants, such as gender, age, or ethnicity), rules and guidelines, statistical classification models, and neural networks trained on historical populations. Of particular use in combining determinants are linear and non-linear equations and statistical classification analyses to determine the relationship between levels of determinants detected in a subject sample and the subject's probability of having an infection or a certain type of infection. In panel and combination construction, of particular interest are structural and syntactic statistical classification algorithms, and methods of index construction, utilizing pattern recognition features, including established techniques such as cross-correlation, Principal Components Analysis (PCA), factor rotation, Logistic Regression (Log Reg), Linear Discriminant Analysis (LDA), Eigengene Linear Discriminant Analysis (ELDA), Support Vector Machines (SVM), Random Forest (RF), Recursive Partitioning Tree (RPART), as well as other related decision tree classification techniques, Shrunken Centroids (SC), StepAIC, Kth-Nearest Neighbor, Boosting, Decision Trees, Neural Networks, Bayesian Networks, and Hidden Markov Models, among others. Other techniques may be used in survival and time to event hazard analysis, including Cox, Weibull, Kaplan-Meier and Greenwood models well known to those of skill in the art. Many of these techniques are useful either combined with a determinant selection technique, such as forward selection, backwards selection, or stepwise selection, complete enumeration of all potential panels of a given size, genetic algorithms, or they may themselves include biomarker selection methodologies in their own technique. These may be coupled with information criteria, such as Akaike's Information Criterion (AIC) or Bayes Information Criterion (BIC), in order to quantify the tradeoff between additional biomarkers and model improvement, and to aid in minimizing overfit. The resulting predictive models may be validated in other studies, or cross-validated in the study they were originally trained in, using such techniques as Bootstrap, Leave-One-Out (LOO) and 10-Fold cross-validation (10-Fold CV). At various steps, false discovery rates may be estimated by value permutation according to techniques known in the art. A "health economic utility function" is a formula that is derived from a combination of the expected probability of a range of clinical outcomes in an idealized applicable patient population, both before and after the introduction of a diagnostic or therapeutic intervention into the standard of care. It encompasses estimates of the accuracy, effectiveness and performance characteristics of such intervention, and a cost and/or value measurement (a utility) associated with each outcome, which may be derived from actual health system costs of care (services, supplies, devices and drugs, etc.) and/or as an estimated acceptable value per quality adjusted life year (QALY) resulting in each outcome. The sum, across all predicted outcomes, of the product of the predicted population size for an outcome multiplied by the respective outcome's expected utility is the total health economic utility of a given standard of care. The difference between (i) the total health economic utility calculated for the standard of care with the intervention versus (ii) the total health economic utility for the standard of care without the intervention results in an overall measure of the health economic cost or value of the intervention. This may itself be divided amongst the entire patient group being analyzed (or solely amongst the intervention group) to arrive at a cost per unit intervention, and to guide such decisions as market positioning, pricing, and assumptions of health system acceptance. Such health economic utility functions are commonly used to compare the cost-effectiveness of the intervention, but may also be transformed to estimate the acceptable value per QALY the health care system is willing to pay, or the acceptable cost-effective clinical performance characteristics required of a new intervention.

For diagnostic (or prognostic) interventions of the invention, as each outcome (which in a disease classifying diagnostic test may be a TP, FP, TN, or FN) bears a different cost, a health economic utility function may preferentially favor sensitivity over specificity, or PPV over NPV based on the clinical situation and individual outcome costs and value, and thus provides another measure of health economic performance and value which may be different from more direct clinical or analytical performance measures. These different measurements and relative trade-offs generally will converge only in the case of a perfect test, with zero error rate (a.k.a., zero predicted subject outcome misclassifications or FP and FN), which all performance measures will favor over imperfection, but to differing degrees.

"Analytical accuracy" refers to the reproducibility and predictability of the measurement process itself, and may be summarized in such measurements as coefficients of variation (CV), Pearson correlation, and tests of concordance and calibration of the same samples or controls with different times, users, equipment and/or reagents. These and other considerations in evaluating new biomarkers are also summarized in Vasan, 2006.

"Performance" is a term that relates to the overall usefulness and quality of a diagnostic or prognostic test, including, among others, clinical and analytical accuracy, other analytical and process characteristics, such as use characteristics (e.g., stability, ease of use), health economic value, and relative costs of components of the test. Any of these factors may be the source of superior performance and thus usefulness of the test, and may be measured by appropriate "performance metrics," such as AUC and MCC, time to result, shelf life, etc. as relevant.

By "statistically significant", it is meant that the alteration is greater than what might be expected to happen by chance alone (which could be a "false positive"). Statistical significance can be determined by any method known in the art. Commonly used measures of significance include the p-value, which presents the probability of obtaining a result at least as extreme as a given data point, assuming the data point was the result of chance alone. A result is often considered highly significant at a p-value of 0.05 or less.

In the context of the present invention the following abbreviations may be used: Antibiotics (Abx), Adverse Event (AE), Arbitrary Units (A.U.), Complete Blood Count (CBC), Case Report Form (CRF), Chest X-Ray (CXR), Electronic Case Report Form (eCRF), Food and Drug Administration (FDA), Good Clinical Practice (GCP), Gastrointestinal (GI), Gastroenteritis (GE), International Conference on Harmonization (ICH), Infectious Disease (ID), In vitro diagnostics (IVD), Lower Respiratory Tract Infection (LRTI), Myocardial infarction (MI), Polymerase chain reaction (PCR), Per-oss (P.O), Per-rectum (P.R), Standard of Care (SoC), Standard Operating Procedure (SOP), Urinary Tract Infection (UTI), Upper Respiratory Tract Infection (URTI).

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals there between.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non-limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Single and Multiple Exons as Potential Biomarkers

Alternative splicing is a regulated process during gene expression that results in a single gene coding for multiple proteins. In this process, particular exons of a gene may be included within or excluded from the final, processed messenger RNA (mRNA) produced from that gene. Thus, certain exons may be differentially expressed in bacterial or viral patients even though the entire full length gene is not. Indeed, several genes have now been identified for which the expression patterns of specific exons provide stronger differential signal than the full length gene. These exons have the potential to serve as diagnostic biomarkers or to enhance the performance of transcriptomic signatures composed of several full or partial RNA determinants.

Materials and Methods

Figure 1:
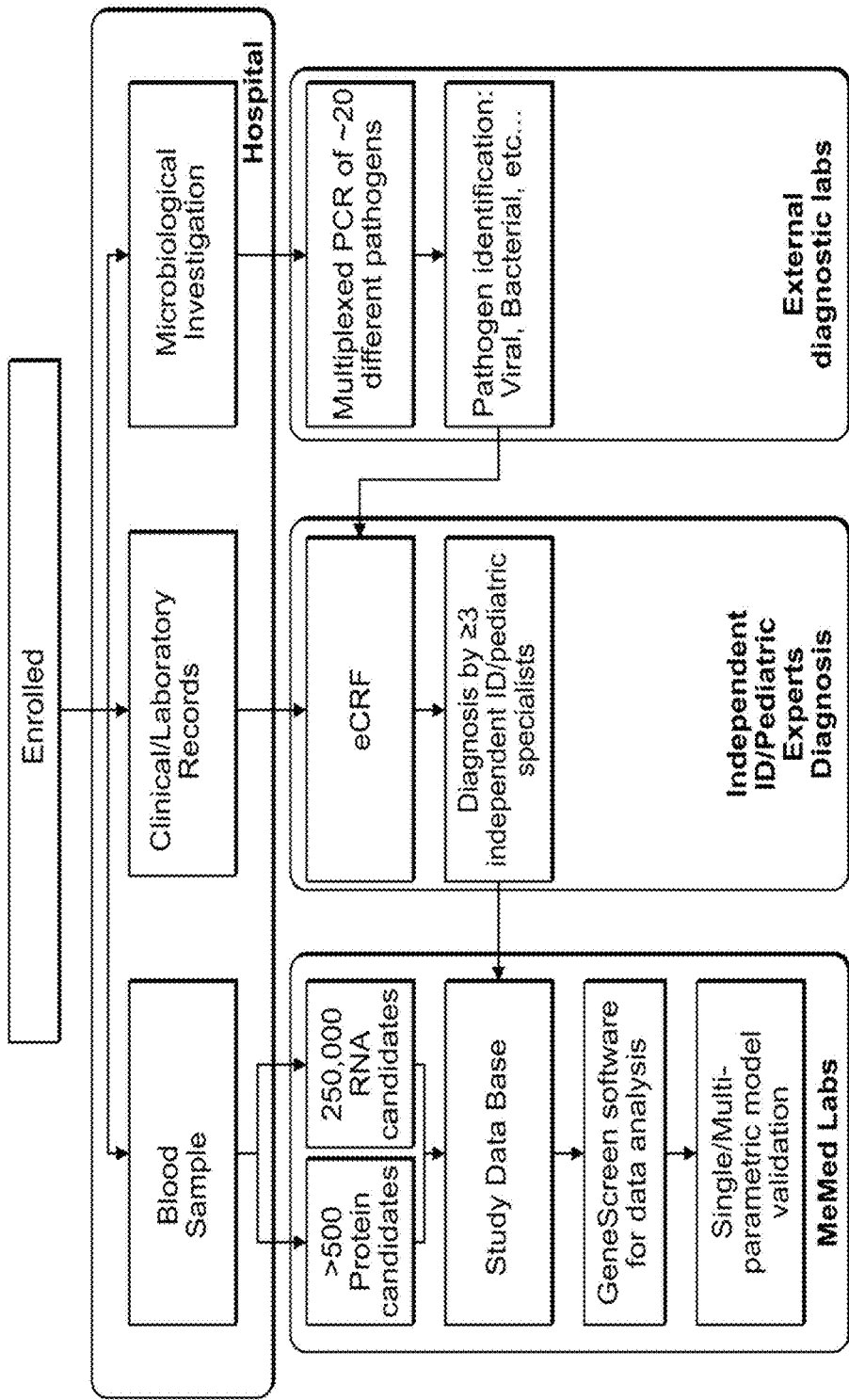

Patient Recruitment:

Patients were prospectively recruited as part of the 'Curiosity' clinical study (NCT01917461; (Oved et al. 2015)). Informed consent was obtained from each participant or legal guardian, as applicable. Inclusion criteria for the infectious disease cohort included: clinical suspicion of an acute infectious disease, peak fever >37.5° C. since symptoms onset, and duration of symptoms ≤12 days. Inclusion criteria for the control group included: clinical impression of a non-infectious disease (e.g. trauma, stroke and myocardial infarction), or healthy subjects. Exclusion criteria included: evidence of any episode of acute infectious disease in the two weeks preceding enrollment; diagnosed congenital immune deficiency; current treatment with immunosuppressive or immunomodulatory therapy; active malignancy, proven or suspected human immunodeficiency virus (HIV)-1, hepatitis B virus (HBV), or hepatitis C virus (HCV) infection. Importantly, in order to enable broad generalization, antibiotic treatment at enrollment did not cause exclusion from the study. An overview of study workflow is depicted in FIG. 1.

Enrollment Process and Data Collection:

For each patient, the following baseline variables were recorded: demographics, physical examination, medical history (e.g. main complaints, underlying diseases, chronically-administered medications, comorbidities, time of symptom onset, and peak temperature), complete blood count (CBC) obtained at enrollment, and chemistry panel (e.g. creatinine, urea, electrolytes, and liver enzymes). A nasal swab was obtained from each patient for further microbiological investigation, and a blood sample was obtained for protein screening and validation. Additional samples were obtained as deemed appropriate by the physician (e.g. urine and stool samples in cases of suspected urinary tract infection [UTI], and gastroenteritis [GI] respectively). Radiological tests were obtained at the discretion of the physician (e.g. chest X-ray for suspected lower respiratory tract infection [LRTI]). Thirty days after enrollment, disease course and response to treatment were recorded. All information was recorded in a custom electronic case report form (eCRF).

Microbiological Investigation:

Patients underwent two multiplex-PCR diagnostic assays from nasal swab samples: (i) Seeplex™ RV15, for detection of parainfluenza virus 1, 2, 3, and 4, coronavirus 229E/NL63, adenovirus A/B/C/D/E, bocavirus 1/2/3/4, influenza virus A and B, metapneumovirus, coronavirus OC43, rhinovirus A/B/C, respiratory syncytial virus A and B, and Enterovirus, and (ii) Seeplex™ PB6 for detection of *Streptococcus pneumoniae, Haemophilus influenzae, Chlamydophila pneumoniae, Legionella pneumophila, Bordetella pertussis*, and *Mycoplasma pneumoniae*. Multiplex-PCR assays were performed by a certified service laboratory. Patients were also tested for additional pathogens according to their suspected clinical syndrome, including: blood culture, urine culture and stool culture for *Shigella* spp., *Campylobacter* spp. and *Salmonella* spp.; serological testing (IgM and/or IgG) for cytomegalovirus (CMV), Epstein-Barr virus (EBV), *Mycoplasma* Pneumonia, and *Coxiella burnetii* (Q-Fever).

Establishing the Reference Standard:

Currently, no single reference standard exists for determining bacterial and viral infections in a wide range of clinical syndromes. Therefore, a rigorous reference standard was created following recommendations of the Standards for Reporting of Diagnostic Accuracy (STARD) (Bossuyt et al. 2003). First, a thorough clinical and microbiological investigation was performed for each patient as described above. Then, all the data collected throughout the disease course was reviewed by a panel of three physicians (the attending pediatrician, an infectious disease expert and a senior attending pediatrician). Each panel member assigned one of the following diagnostic labels to each patient: (i) bacterial; (ii) viral; (iii) no apparent infectious disease or healthy (controls); and (iv) indeterminate. Final diagnosis was determined by consensus agreement of all three panel members. Importantly, the panel members were blinded to the labeling of their peers and to the results of the signature.

Samples, Procedures and RNA Purification:

Nasal swabs and stool samples were stored at 4° C. for up to 72 hours and subsequently transported to a certified service laboratory for multiplex PCR-based assay. Venous blood samples were collected in EDTA contained CBC tube and stored at 4° C. for up to 5 hours on site and subsequently fractionated into plasma and cell pellet. Red cells were lysed using Red Cell Lysis Buffer (RCLB) at room temperature (RT) and total RNA was purified using RNeasy plus Mini Kit (QIAGEN, Cat. 74134) according to manufacturer recommended protocols.

Microarray Experiments

A total of 10 µl of 200 ng/3 µl (66.67 ng/µl) RNA were transferred to microarray chip hybridization. Amplified cRNA was prepared from 200 ng total RNA using the WT cDNA Synthesis and WT cDNA Amplification Kits (900672, Affymetrix). Biotinylated single-stranded cDNA was generated from the amplified cRNA and then fragmented and labeled with the WT Terminal Labeling Kit (Affymetrix), following manufacturer protocol. Samples were hybridized to Human Gene 1.0 ST Arrays (Affymetrix) in which the probes are distributed across the full length of the gene, providing a more complete and accurate picture of overall gene expression. This array interrogates 28,869 well-annotated genes with 764,885 distinct probes. In addition, it contains a subset of probes from Exon 1.0 ST Arrays that focuses on well-annotated content. Arrays were scanned using the Affymetrix GeneChip Scanner 3000 7G. Partek Genomic Suite software was then used to extract raw data, perform mean probe summarization, RMA and quintile normalization and GC content correction (Downey 2006).

Statistical Analysis

Primary analysis was based on area under the receiver operating curve (AUC), Matthews correlation coefficient (MCC), sensitivity, specificity, and total accuracy. These measures are defined as follows:

$$\text{Sensitivity} = \frac{TP}{TP + FN}$$

$$\text{Specificity} = \frac{TN}{TN + FP}$$

$$\text{total accuracy} = \frac{TP + TN}{TP + FN + TN + FP}$$

$$MCC = \frac{TP \times TN - FP \times FN}{\sqrt{(TP - FP)(TP + FN)(TN + FP)(TN + FN)}}$$

P, N, TP, FP, TN, FN are positives, negatives, true-positives, false-positives, true-negatives, and false-negatives, respectively. Unless mentioned otherwise, positives and negatives refer to patients with bacterial and viral infections, respectively.

Results

Patients Characteristics

The studied group of pediatric patients included 7 females (47%) and 8 males (53%) aged 7 months to 16 years. The patients presented with a variety of clinical syndromes affecting different physiological systems (e.g., respiratory, urinal, central nervous system, systemic). Detailed characterization of studied patients is summarized in Table 10C.

TABLE 10C

Detailed description of studied patients. UTI—Urinal tract infection; URTI—Upper respiratory tract infection; WBC—white blood count.

| Patient number | Gender | Age (y) | Etiology | Clinical Syndrome | Maximal temperature (° C.) | Time from symptoms (d) | Hospitalization Duration (d) | WBC (×1000) |
|---|---|---|---|---|---|---|---|---|
| 390 | Male | 6 | Bacterial | Pneumonia | 38 | 3 | 4 | 8.3 |
| 392 | Female | 2 | Bacterial | Acuteotitis media | 38.7 | 2 | 4 | 19.5 |
| 406 | Female | 16 | Bacterial | Pharyngitis | 39 | 6 | 3 | 7.5 |
| 417 | Female | 5 | Bacterial | UTI | 40 | 4 | 3 | 12.2 |
| 418 | Male | 2 | Bacterial | Pneumonia | 38.1 | 4 | 2 | 14.9 |
| 420 | Male | 3 | Bacterial | Pneumonia | 39.5 | 2 | 1 | 27.5 |
| 384 | Male | 3 | Viral | Bronchitis | 39.3 | 1 | 0 | 11.3 |
| 397 | Female | 2 | Viral | Fever Without Source | 38.4 | 4 | 1 | 15.3 |
| 404 | Female | 1 | Viral | Fever Without Source | 38.6 | 1 | 0 | 8.2 |
| 405 | Female | 0.7 | Viral | Bronchiolitis | 39.6 | 2 | 2 | 13.9 |
| 408 | Male | 1.1 | Viral | Fever Without Source | 39.7 | 2 | 1 | 6 |
| 416 | Male | 10.5 | Viral | Meningitis | 38.4 | 5 | 2 | 3.8 |
| 421 | Male | 3 | Viral | URTI | 39.9 | 2 | 0 | 9.4 |
| 422 | Male | 2 | Viral | URTI | 39 | 5 | 0 | 16.7 |
| 423 | Female | 1.8 | Viral | Fever Without Source | 39.5 | 3 | 2 | 9.1 |

RNA Determinants can Distinguish Between Bacterial and Viral Patients

The gene expression profiles of blood leukocytes obtained from the described acute infection patients using the Human Gene 1.0 ST Array (Affymetrix) were studied. The results suggest a differential response of the immune system to bacterial and viral infections. 63 RNA determinants were identified that were differentially expressed in the bacterial and viral patients tested (Table 11; $\log_2$-fold change was calculated compared to bacterial patients baseline The present inventors further calculated for these RNA determinants the measures of accuracy in distinguishing between bacterial and viral patients including AUC, MCC, total accuracy, sensitivity, specificity and Wilcoxon ranksum P-value (Table 11).

TABLE 11

Differentially expressed RNA determinants and their measures of accuracy in differentiating between bacterial or mixed versus viral infected subjects. Changes in expression levels were calculated as log2 (fold change bacterial) − log2 (fold change viral).

| Serial number | DETERMINANT | Bacterial or viral induced | $\log_2$ (fold change bacterial) − $\log_2$ (fold change viral) | AUC | MCC | Total accuracy | Sensitivity | Specificity | ranksum P-value |
|---|---|---|---|---|---|---|---|---|---|
| 1 | AIM2 | Viral | −1.56 | 0.722 | 0.167 | 0.667 | 0.667 | 0.667 | 1.81E−01 |
| 2 | ANKRD22 | Viral | −2.13 | 0.648 | 0.444 | 0.8 | 0.667 | 0.889 | 3.88E−01 |
| 3 | BMX | Viral | −1.53 | 0.667 | 0.444 | 0.733 | 0.667 | 0.778 | 3.28E−01 |
| 4 | C19orf59 | Viral | −1.51 | 0.611 | 0.167 | 0.533 | 0.5 | 0.556 | 5.29E−01 |
| 5 | CCL2 | Viral | −0.95 | 0.87 | 0.764 | 0.867 | 1 | 0.778 | 1.76E−02 |
| 6 | CD177 | Viral | −1.64 | 0.63 | 0.167 | 0.667 | 0.5 | 0.778 | 4.56E−01 |
| 7 | CEACAM1 | Viral | −1.88 | 0.796 | 0.444 | 0.8 | 0.833 | 0.778 | 6.63E−02 |
| 8 | CLEC4D | Viral | −1.48 | 0.685 | 0.444 | 0.733 | 0.667 | 0.778 | 2.72E−01 |
| 9 | CMPK2 | Viral | −2.44 | 0.87 | 0.444 | 0.8 | 0.667 | 0.889 | 1.76E−02 |
| 10 | CXCL10 | Viral | −2.08 | 0.704 | 0.491 | 0.733 | 0.833 | 0.667 | 2.24E−01 |
| 11 | CYBRD1 | Bacterial | 1.35 | 0.852 | 0.444 | 0.8 | 0.833 | 0.778 | 2.56E−02 |
| 12 | CYP1B1 | Bacterial | 1.38 | 0.63 | 0.218 | 0.733 | 0.333 | 1 | 4.56E−01 |
| 13 | DDX60 | Viral | −1.79 | 0.889 | 0.327 | 0.8 | 0.667 | 0.889 | 1.20E−02 |
| 14 | EIF1AY | Viral | −2.14 | 0.611 | −0.492 | 0.8 | 0.667 | 0.889 | 5.29E−01 |
| 15 | EIF2AK2 | Viral | −1.50 | 0.833 | 0.289 | 0.8 | 0.833 | 0.778 | 3.60E−02 |
| 16 | EPSTI1 | Viral | −2.32 | 0.833 | 0.577 | 0.867 | 0.667 | 1 | 3.60E−02 |
| 17 | F13A1 | Bacterial | 1.03 | 0.87 | 0.6 | 0.933 | 0.833 | 1 | 1.76E−02 |
| 18 | FFAR3 | Viral | −1.57 | 0.741 | 0.491 | 0.8 | 1 | 0.667 | 1.81E−01 |
| 19 | FLJ21767 | Bacterial | 0.44 | 0.722 | 0.389 | 0.733 | 0.667 | 0.778 | 2.72E−01 |

TABLE 11-continued

Differentially expressed RNA determinants and their measures of accuracy in differentially between bacterial or mixed versus viral infected subjects. Changes in expression levels were calculated as log2 (fold change bacterial) − log2 (fold change viral).

| Serial number | DETERMINANT | Bacterial or viral induced | Log$_2$ (fold change bacterial) − log$_2$ (fold change viral) | AUC | MCC | Total accuracy | Sensitivity | Specificity | ranksum P-value |
|---|---|---|---|---|---|---|---|---|---|
| 20 | GALM | Viral | −1.46 | 0.944 | 0.6 | 0.933 | 0.833 | 1 | 2.80E−03 |
| 21 | HERC5 | Viral | −2.45 | 0.833 | 0.327 | 0.733 | 0.833 | 0.667 | 3.60E−02 |
| 22 | HLA-DQA1 | Bacterial | 0.40 | 0.611 | 0.389 | 0.6 | 0.833 | 0.444 | 6.07E−01 |
| 23 | IFI27 | Viral | −2.96 | 1 | 0.873 | 0.933 | 1 | 0.889 | 4.00E−04 |
| 24 | IFI44 | Viral | −2.42 | 0.852 | 0.327 | 0.733 | 0.833 | 0.667 | 2.56E−02 |
| 25 | IFI44L | Viral | −3.86 | 0.889 | 0.444 | 0.733 | 0.833 | 0.667 | 1.20E−02 |
| 26 | IFI6 | Viral | −1.80 | 0.815 | 0.327 | 0.733 | 0.833 | 0.667 | 4.96E−02 |
| 27 | IFIT1 | Viral | −2.28 | 0.889 | 0.6 | 0.8 | 0.833 | 0.778 | 1.20E−02 |
| 28 | IFIT2 | Viral | −1.83 | 0.852 | 0.327 | 0.733 | 0.833 | 0.667 | 2.56E−02 |
| 29 | IFIT3 | Viral | −2.26 | 0.796 | 0.444 | 0.8 | 0.667 | 0.889 | 6.63E−02 |
| 30 | IFITM3 | Viral | −1.53 | 0.759 | 0.289 | 0.733 | 0.833 | 0.667 | 1.13E−01 |
| 31 | INCA | Viral | −1.92 | 0.741 | 0.444 | 0.8 | 0.833 | 0.778 | 1.45E−01 |
| 32 | IRF7 | Viral | −1.69 | 0.741 | 0.289 | 0.733 | 0.667 | 0.778 | 1.45E−01 |
| 33 | ISG15 | Viral | −1.22 | 0.907 | 0.6 | 0.867 | 0.833 | 0.889 | 7.59E−03 |
| 34 | JARID1D | Viral | −1.56 | 0.611 | −0.577 | 0.8 | 0.833 | 0.778 | 5.29E−01 |
| 35 | JUP | Viral | −1.47 | 0.796 | 0.218 | 0.733 | 0.667 | 0.778 | 6.63E−02 |
| 36 | LAMP3 | Viral | −2.36 | 0.907 | 0.6 | 0.867 | 0.833 | 0.889 | 7.59E−03 |
| 37 | LOC100132244 | Bacterial | 1.08 | 0.685 | 0.218 | 0.667 | 0.667 | 0.667 | 2.72E−01 |
| 38 | LOC26010 | Viral | −2.23 | 0.87 | 0.444 | 0.867 | 1 | 0.778 | 1.76E−02 |
| 39 | LY6E | Viral | −1.86 | 0.889 | 0.6 | 0.8 | 0.833 | 0.778 | 1.20E−02 |
| 40 | MT2A | Viral | −1.56 | 0.889 | 0.722 | 0.867 | 0.833 | 0.889 | 4.80E−03 |
| 41 | MX1 | Viral | −2.57 | 0.87 | 0.6 | 0.8 | 0.833 | 0.778 | 1.76E−02 |
| 42 | OAS1 | Viral | −2.49 | 0.852 | 0.444 | 0.8 | 0.667 | 0.889 | 2.56E−02 |
| 43 | OAS2 | Viral | −1.89 | 0.907 | 0.444 | 0.867 | 0.667 | 1 | 7.59E−03 |
| 44 | OAS3 | Viral | −2.97 | 0.87 | 0.444 | 0.8 | 0.667 | 0.889 | 1.76E−02 |
| 45 | OASL | Viral | −2.22 | 0.889 | 0.491 | 0.733 | 0.833 | 0.667 | 1.20E−02 |
| 46 | OTOF | Viral | −0.83 | 0.907 | 0.6 | 0.867 | 1 | 0.778 | 7.59E−03 |
| 47 | PHOSPHO1 | Bacterial | 1.01 | 0.722 | 0.327 | 0.733 | 0.833 | 0.667 | 1.81E−01 |
| 48 | PLSCR1 | Viral | −1.68 | 0.704 | 0.289 | 0.733 | 0.5 | 0.889 | 2.24E−01 |
| 49 | PPBP | Bacterial | 1.01 | 0.796 | 0.444 | 0.8 | 0.833 | 0.778 | 6.63E−02 |
| 50 | PSTPIP2 | Viral | −1.61 | 0.611 | 0.327 | 0.733 | 0.667 | 0.778 | 5.29E−01 |
| 51 | RGS1 | Viral | −0.53 | 0.944 | 0.491 | 0.933 | 0.833 | 1 | 2.80E−03 |
| 52 | RSAD2 | Viral | −3.93 | 0.889 | 0.444 | 0.8 | 0.667 | 0.889 | 1.20E−02 |
| 53 | RTP4 | Viral | −1.72 | 0.889 | 0.6 | 0.867 | 0.833 | 0.889 | 1.20E−02 |
| 54 | SERPING1 | Viral | −2.41 | 0.852 | 0.577 | 0.8 | 0.833 | 0.778 | 2.56E−02 |
| 55 | SH3BGRL2 | Bacterial | 1.12 | 0.852 | 0.444 | 0.867 | 1 | 0.778 | 2.56E−02 |
| 56 | SIGLEC1 | Viral | −2.47 | 0.889 | 0.6 | 0.867 | 1 | 0.778 | 1.20E−02 |
| 57 | TMEM176A | Bacterial | 1.17 | 0.667 | 0.218 | 0.733 | 0.333 | 1 | 3.45E−01 |
| 58 | TNFAIP6 | Viral | −1.80 | 0.796 | 0.444 | 0.733 | 0.667 | 0.778 | 6.63E−02 |
| 59 | TREML4 | Viral | −1.64 | 0.833 | 0.6 | 0.8 | 0.833 | 0.778 | 3.60E−02 |
| 60 | USP18 | Viral | −3.12 | 0.926 | 0.6 | 0.867 | 1 | 0.778 | 7.99E−04 |
| 61 | UTY | Viral | −1.86 | 0.611 | −0.492 | 0.867 | 0.833 | 0.889 | 5.29E−01 |
| 62 | XAF1 | Viral | −1.65 | 0.889 | 0.444 | 0.733 | 0.667 | 0.778 | 1.20E−02 |

The exon-level differential expression of the 62 genes described in Table 11 was then calculated and the median log fold change of each individual exon was compared to its full length gene (Table 12, herein below).

TABLE 12

Exon level analysis of 62 genes differentially expressed in bacterial and viral patients. Expression levels data obtained from the 6 bacterial and 9 viral patients described in Table 11. Probest ID is based on Affymetrix chip data. Comparison to full gene was calculated as absolute median log fold change (exon$_i$) − absolute median log fold change (full length gene); "+" and "−" represent higher and lower degree of differential expression of the single exon compared to the full length gene.

| Gene name | Exon # | Genomic location (start) | Genomic location (stop) | Probeset ID (Affymetrix) | Chromosome | Strand | Median log fold change | Comparison to full gene (improvement indicated by "+") |
|---|---|---|---|---|---|---|---|---|
| ISG15 | 1 | 948879 | 948916 | 7896818 | 1 | + | −0.51 | − |
| ISG15 | 2 | 948908 | 948948 | 7896819 | 1 | + | −1.28 | + |

TABLE 12-continued

Exon level analysis of 62 genes differentially expressed in bacterial and viral patients. Expression levels data obtained from the 6 bacterial and 9 viral patients described in Table 11. Probest ID is based on Affymetrix chip data. Comparison to full gene was calculated as absolute median log fold change (exon$_i$) − absolute median log fold change (full length gene); "+" and "−" represent higher and lower degree of differential expression of the single exon compared to the full length gene.

| Gene name | Exon # | Genomic location (start) | Genomic location (stop) | Probeset ID (Affymetrix) | Chromosome | Strand | Median log fold change | Comparison to full gene (improvement indicated by "+") |
|---|---|---|---|---|---|---|---|---|
| ISG15 | 3 | 949444 | 949822 | 7896820 | 1 | + | −2.23 | + |
| ISG15 | 4 | 949859 | 949914 | 7896821 | 1 | + | −1.38 | + |
| IFI44L | 1 | 79086173 | 79086205 | 7902542 | 1 | + | −4.40 | + |
| IFI44L | 2 | 79092813 | 79093150 | 7902543 | 1 | + | −3.42 | − |
| IFI44L | 3 | 79093630 | 79093953 | 7902544 | 1 | + | −4.38 | + |
| IFI44L | 4 | 79094251 | 79094549 | 7902545 | 1 | + | −3.52 | − |
| IFI44L | 5 | 79094640 | 79094666 | 7902546 | 1 | + | −4.39 | + |
| IFI44L | 6 | 79095443 | 79095586 | 7902547 | 1 | + | −3.77 | − |
| IFI44L | 7 | 79101063 | 79101173 | 7902548 | 1 | + | −3.82 | − |
| IFI44L | 8 | 79102723 | 79102849 | 7902549 | 1 | + | −3.37 | − |
| IFI44L | 9 | 79106715 | 79106767 | 7902550 | 1 | + | −3.15 | − |
| IFI44L | 10 | 79107138 | 79107271 | 7902551 | 1 | + | −3.55 | − |
| IFI44L | 11 | 79107469 | 79107559 | 7902552 | 1 | + | −3.54 | − |
| IFI44 | 1 | 79115512 | 79115550 | 7902554 | 1 | + | −1.90 | − |
| IFI44 | 2 | 79115961 | 79116337 | 7902555 | 1 | + | −2.99 | + |
| IFI44 | 3 | 79119928 | 79119955 | 7902556 | 1 | + | −2.12 | − |
| IFI44 | 4 | 79120699 | 79120889 | 7902557 | 1 | + | −2.43 | + |
| IFI44 | 5 | 79121142 | 79121176 | 7902558 | 1 | + | −2.45 | + |
| IFI44 | 6 | 79125081 | 79125168 | 7902559 | 1 | + | −3.07 | + |
| IFI44 | 7 | 79126239 | 79126281 | 7902560 | 1 | + | −2.29 | − |
| IFI44 | 8 | 79128416 | 79128520 | 7902561 | 1 | + | −2.84 | + |
| IFI44 | 9 | 79129461 | 79129597 | 7902562 | 1 | + | −1.60 | − |
| RGS1 | 1 | 1.93E+08 | 1.93E+08 | 7908389 | 1 | + | 0.07 | − |
| RGS1 | 2 | 1.93E+08 | 1.93E+08 | 7908390 | 1 | + | −0.17 | − |
| RGS1 | 3 | 1.93E+08 | 1.93E+08 | 7908391 | 1 | + | −0.40 | − |
| RGS1 | 4 | 1.93E+08 | 1.93E+08 | 7908392 | 1 | + | −0.54 | + |
| RGS1 | 5 | 1.93E+08 | 1.93E+08 | 7908393 | 1 | + | −1.93 | + |
| RGS1 | 6 | 1.93E+08 | 1.93E+08 | 7908394 | 1 | + | −0.22 | − |
| RGS1 | 7 | 1.93E+08 | 1.93E+08 | 7908395 | 1 | + | −0.47 | − |
| RGS1 | 8 | 1.93E+08 | 1.93E+08 | 7908396 | 1 | + | −0.19 | − |
| IFI6 | 1 | 27992621 | 27992865 | 7914128 | 1 | − | −2.08 | + |
| IFI6 | 2 | 27992902 | 27992978 | 7914129 | 1 | − | −1.62 | − |
| IFI6 | 3 | 27994775 | 27994883 | 7914130 | 1 | − | −1.05 | − |
| IFI6 | 4 | 27994995 | 27995045 | 7914131 | 1 | − | −2.27 | + |
| IFI6 | 5 | 27995771 | 27995810 | 7914132 | 1 | − | −2.25 | + |
| IFI6 | 6 | 27995832 | 27995857 | 7914133 | 1 | − | −1.49 | − |
| IFI6 | 7 | 27998687 | 27998711 | 7914134 | 1 | − | −0.33 | − |
| AIM2 | 1 | 1.59E+08 | 1.59E+08 | 7921435 | 1 | − | −0.93 | − |
| AIM2 | 2 | 1.59E+08 | 1.59E+08 | 7921436 | 1 | − | −1.51 | − |
| AIM2 | 3 | 1.59E+08 | 1.59E+08 | 7921437 | 1 | − | −0.82 | − |
| AIM2 | 4 | 1.59E+08 | 1.59E+08 | 7921438 | 1 | − | −2.00 | + |
| AIM2 | 5 | 1.59E+08 | 1.59E+08 | 7921439 | 1 | − | −2.03 | + |
| AIM2 | 6 | 1.59E+08 | 1.59E+08 | 7921440 | 1 | − | −0.87 | − |
| AIM2 | 7 | 1.59E+08 | 1.59E+08 | 7921441 | 1 | − | −1.75 | + |
| IFIT2 | 1 | 91061755 | 91061786 | 7929048 | 10 | + | −0.03 | − |
| IFIT2 | 2 | 91061839 | 91061863 | 7929049 | 10 | + | −1.83 | − |
| IFIT2 | 3 | 91065744 | 91067030 | 7929050 | 10 | + | −1.81 | − |
| IFIT2 | 4 | 91067134 | 91068336 | 7929051 | 10 | + | −2.62 | + |
| IFIT3 | 1 | 91087675 | 91087758 | 7929053 | 10 | + | −0.18 | − |
| IFIT3 | 2 | 91087785 | 91087813 | 7929054 | 10 | + | −2.57 | + |
| IFIT3 | 3 | 91092261 | 91092289 | 7929055 | 10 | + | −2.34 | + |
| IFIT3 | 4 | 91092277 | 91092301 | 7929056 | 10 | + | −3.20 | + |
| IFIT3 | 5 | 91092305 | 91092331 | 7929057 | 10 | + | −2.06 | − |
| IFIT3 | 6 | 91092346 | 91092370 | 7929058 | 10 | + | −1.97 | − |
| IFIT3 | 7 | 91098599 | 91099484 | 7929059 | 10 | + | −2.22 | − |
| IFIT3 | 8 | 91099985 | 91100009 | 7929060 | 10 | + | −2.62 | + |
| IFIT1 | 1 | 91152344 | 91152368 | 7929066 | 10 | + | 0.00 | − |
| IFIT1 | 2 | 91152390 | 91152448 | 7929067 | 10 | + | −1.86 | − |
| IFIT1 | 3 | 91162071 | 91163418 | 7929068 | 10 | + | −3.79 | + |
| IFIT1 | 4 | 91163472 | 91163592 | 7929069 | 10 | + | −3.10 | + |
| ANKRD22 | 1 | 90582163 | 90582243 | 7934899 | 10 | − | −2.79 | + |
| ANKRD22 | 2 | 90582502 | 90582765 | 7934900 | 10 | − | −2.07 | − |
| ANKRD22 | 3 | 90583056 | 90583131 | 7934901 | 10 | − | −2.46 | + |
| ANKRD22 | 4 | 90585796 | 90585838 | 7934902 | 10 | − | −2.12 | − |
| ANKRD22 | 5 | 90588318 | 90588422 | 7934903 | 10 | − | −1.62 | − |
| ANKRD22 | 6 | 90591592 | 90591769 | 7934904 | 10 | − | −1.73 | − |
| ANKRD22 | 7 | 90611365 | 90611523 | 7934905 | 10 | − | −1.95 | − |

TABLE 12-continued

Exon level analysis of 62 genes differentially expressed in bacterial and viral patients. Expression levels data obtained from the 6 bacterial and 9 viral patients described in Table 11. Probest ID is based on Affymetrix chip data. Comparison to full gene was calculated as absolute median log fold change ($exon_i$) – absolute median log fold change (full length gene); "+" and "–" represent higher and lower degree of differential expression of the single exon compared to the full length gene.

| Gene name | Exon # | Genomic location (start) | Genomic location (stop) | Probeset ID (Affymetrix) | Chromosome | Strand | Median log fold change | Comparison to full gene (improvement indicated by "+") |
|---|---|---|---|---|---|---|---|---|
| SERPING1 | 1 | 57365088 | 57365168 | 7940029 | 11 | + | 0.00 | − |
| SERPING1 | 2 | 57365744 | 57365774 | 7940030 | 11 | + | −2.26 | − |
| SERPING1 | 3 | 57367459 | 57367483 | 7940031 | 11 | + | −2.25 | − |
| SERPING1 | 4 | 57367477 | 57367501 | 7940032 | 11 | + | −2.60 | + |
| SERPING1 | 5 | 57367621 | 57367650 | 7940033 | 11 | + | −3.35 | + |
| SERPING1 | 6 | 57367674 | 57367699 | 7940034 | 11 | + | −3.90 | + |
| SERPING1 | 7 | 57367716 | 57367811 | 7940035 | 11 | + | −2.75 | + |
| SERPING1 | 8 | 57369524 | 57369615 | 7940036 | 11 | + | −2.32 | − |
| SERPING1 | 9 | 57373502 | 57373587 | 7940037 | 11 | + | −2.55 | + |
| SERPING1 | 10 | 57373958 | 57373995 | 7940038 | 11 | + | −2.30 | − |
| SERPING1 | 11 | 57379201 | 57379240 | 7940039 | 11 | + | −3.27 | + |
| SERPING1 | 12 | 57381815 | 57382029 | 7940040 | 11 | + | −2.76 | + |
| SERPING1 | 13 | 57382160 | 57382228 | 7940041 | 11 | + | −1.88 | − |
| IFITM3 | 1 | 319739 | 319795 | 7945372 | 11 | − | −1.14 | − |
| IFITM3 | 2 | 319838 | 319864 | 7945373 | 11 | − | −1.51 | − |
| IFITM3 | 3 | 320748 | 320772 | 7945374 | 11 | − | −1.76 | + |
| IFITM3 | 4 | 320786 | 320810 | 7945375 | 11 | − | −2.08 | + |
| IFITM3 | 5 | 320914 | 320947 | 7945376 | 11 | − | −0.10 | − |
| IRF7 | 1 | 612567 | 612591 | 7945463 | 11 | − | −2.12 | + |
| IRF7 | 2 | 612610 | 612707 | 7945464 | 11 | − | −2.27 | + |
| IRF7 | 3 | 613050 | 613078 | 7945465 | 11 | − | −2.19 | + |
| IRF7 | 4 | 613311 | 613595 | 7945466 | 11 | − | −1.22 | − |
| IRF7 | 5 | 613786 | 613835 | 7945467 | 11 | − | −1.15 | − |
| IRF7 | 6 | 613952 | 614022 | 7945468 | 11 | − | −0.46 | − |
| IRF7 | 7 | 614248 | 614370 | 7945469 | 11 | − | −2.09 | + |
| IRF7 | 8 | 614505 | 614530 | 7945470 | 11 | − | −1.31 | − |
| IRF7 | 9 | 614798 | 614918 | 7945471 | 11 | − | −1.82 | + |
| IRF7 | 10 | 615119 | 615168 | 7945472 | 11 | − | −1.56 | − |
| IRF7 | 11 | 615264 | 615344 | 7945473 | 11 | − | 0.04 | − |
| IRF7 | 12 | 615386 | 615627 | 7945474 | 11 | − | −2.01 | + |
| CLEC4D | 1 | 8666154 | 8666233 | 7953750 | 12 | + | −0.72 | − |
| CLEC4D | 2 | 8666280 | 8666317 | 7953751 | 12 | + | −1.40 | − |
| CLEC4D | 3 | 8667843 | 8667869 | 7953752 | 12 | + | −1.88 | + |
| CLEC4D | 4 | 8670776 | 8670839 | 7953753 | 12 | + | −1.73 | + |
| CLEC4D | 5 | 8671621 | 8671751 | 7953754 | 12 | + | −1.44 | − |
| CLEC4D | 6 | 8672832 | 8672856 | 7953755 | 12 | + | −1.43 | − |
| CLEC4D | 7 | 8672851 | 8672926 | 7953756 | 12 | + | −1.97 | + |
| CLEC4D | 8 | 8672913 | 8672937 | 7953757 | 12 | + | −1.79 | + |
| CLEC4D | 9 | 8673723 | 8673850 | 7953758 | 12 | + | −1.37 | − |
| CLEC4D | 10 | 8673931 | 8673955 | 7953759 | 12 | + | −1.24 | − |
| CLEC4D | 11 | 8674672 | 8674696 | 7953760 | 12 | + | −1.38 | − |
| OAS1 | 1 | 1.13E+08 | 1.13E+08 | 7958885 | 12 | + | −2.20 | − |
| OAS1 | 2 | 1.13E+08 | 1.13E+08 | 7958886 | 12 | + | −2.15 | − |
| OAS1 | 3 | 1.13E+08 | 1.13E+08 | 7958887 | 12 | + | −1.75 | − |
| OAS1 | 4 | 1.13E+08 | 1.13E+08 | 7958888 | 12 | + | −1.79 | − |
| OAS1 | 5 | 1.13E+08 | 1.13E+08 | 7958889 | 12 | + | −2.02 | − |
| OAS1 | 6 | 1.13E+08 | 1.13E+08 | 7958890 | 12 | + | −1.77 | − |
| OAS1 | 7 | 1.13E+08 | 1.13E+08 | 7958891 | 12 | + | −1.61 | − |
| OAS1 | 8 | 1.13E+08 | 1.13E+08 | 7958892 | 12 | + | −1.26 | − |
| OAS1 | 9 | 1.13E+08 | 1.13E+08 | 7958893 | 12 | + | −1.17 | − |
| OAS1 | 10 | 1.13E+08 | 1.13E+08 | 7958894 | 12 | + | −2.49 | − |
| OAS3 | 1 | 1.13E+08 | 1.13E+08 | 7958896 | 12 | + | −2.05 | − |
| OAS3 | 2 | 1.13E+08 | 1.13E+08 | 7958897 | 12 | + | −2.48 | − |
| OAS3 | 3 | 1.13E+08 | 1.13E+08 | 7958898 | 12 | + | −3.18 | + |
| OAS3 | 4 | 1.13E+08 | 1.13E+08 | 7958899 | 12 | + | −3.03 | + |
| OAS3 | 5 | 1.13E+08 | 1.13E+08 | 7958900 | 12 | + | −4.10 | + |
| OAS3 | 6 | 1.13E+08 | 1.13E+08 | 7958901 | 12 | + | −2.79 | + |
| OAS3 | 7 | 1.13E+08 | 1.13E+08 | 7958902 | 12 | + | −3.31 | + |
| OAS3 | 8 | 1.13E+08 | 1.13E+08 | 7958903 | 12 | + | −2.56 | − |
| OAS3 | 9 | 1.13E+08 | 1.13E+08 | 7958904 | 12 | + | −3.67 | + |
| OAS3 | 10 | 1.13E+08 | 1.13E+08 | 7958905 | 12 | + | −3.09 | + |
| OAS3 | 11 | 1.13E+08 | 1.13E+08 | 7958906 | 12 | + | −2.76 | − |
| OAS3 | 12 | 1.13E+08 | 1.13E+08 | 7958907 | 12 | + | −3.72 | + |
| OAS3 | 13 | 1.13E+08 | 1.13E+08 | 7958908 | 12 | + | −2.42 | − |
| OAS3 | 14 | 1.13E+08 | 1.13E+08 | 7958909 | 12 | + | −3.01 | + |
| OAS3 | 15 | 1.13E+08 | 1.13E+08 | 7958910 | 12 | + | −3.30 | + |
| OAS3 | 16 | 1.13E+08 | 1.13E+08 | 7958911 | 12 | + | −2.31 | − |

TABLE 12-continued

Exon level analysis of 62 genes differentially expressed in bacterial and viral patients. Expression levels data obtained from the 6 bacterial and 9 viral patients described in Table 11. Probest ID is based on Affymetrix chip data. Comparison to full gene was calculated as absolute median log fold change (exon$_i$) – absolute median log fold change (full length gene); "+" and "–" represent higher and lower degree of differential expression of the single exon compared to the full length gene.

| Gene name | Exon # | Genomic location (start) | Genomic location (stop) | Probeset ID (Affymetrix) | Chromosome | Strand | Median log fold change | Comparison to full gene (improvement indicated by "+") |
|---|---|---|---|---|---|---|---|---|
| OAS3 | 17 | 1.13E+08 | 1.13E+08 | 7958912 | 12 | + | −2.70 | − |
| OAS2 | 1 | 1.13E+08 | 1.13E+08 | 7958914 | 12 | + | −2.00 | + |
| OAS2 | 2 | 1.13E+08 | 1.13E+08 | 7958915 | 12 | + | −1.65 | − |
| OAS2 | 3 | 1.13E+08 | 1.13E+08 | 7958916 | 12 | + | −2.50 | + |
| OAS2 | 4 | 1.13E+08 | 1.13E+08 | 7958917 | 12 | + | −0.72 | − |
| OAS2 | 5 | 1.13E+08 | 1.13E+08 | 7958918 | 12 | + | −2.63 | + |
| OAS2 | 6 | 1.13E+08 | 1.13E+08 | 7958919 | 12 | + | −1.24 | − |
| OAS2 | 7 | 1.13E+08 | 1.13E+08 | 7958920 | 12 | + | −1.26 | − |
| OAS2 | 8 | 1.13E+08 | 1.13E+08 | 7958921 | 12 | + | −1.43 | − |
| OAS2 | 9 | 1.13E+08 | 1.13E+08 | 7958922 | 12 | + | −2.92 | + |
| OAS2 | 10 | 1.13E+08 | 1.13E+08 | 7958923 | 12 | + | −1.69 | − |
| OAS2 | 11 | 1.13E+08 | 1.13E+08 | 7958924 | 12 | + | −1.51 | − |
| OAS2 | 12 | 1.13E+08 | 1.13E+08 | 7958925 | 12 | + | −1.70 | − |
| OAS2 | 13 | 1.13E+08 | 1.13E+08 | 7958926 | 12 | + | −2.20 | + |
| OAS2 | 14 | 1.13E+08 | 1.13E+08 | 7958927 | 12 | + | −1.50 | − |
| OAS2 | 15 | 1.13E+08 | 1.13E+08 | 7958928 | 12 | + | −1.77 | − |
| OAS2 | 16 | 1.13E+08 | 1.13E+08 | 7958929 | 12 | + | −0.77 | − |
| OAS2 | 17 | 1.13E+08 | 1.13E+08 | 7958930 | 12 | + | −2.07 | + |
| OASL | 1 | 1.21E+08 | 1.21E+08 | 7967118 | 12 | − | −2.28 | + |
| OASL | 2 | 1.21E+08 | 1.21E+08 | 7967119 | 12 | − | −3.56 | + |
| OASL | 3 | 1.21E+08 | 1.21E+08 | 7967120 | 12 | − | −2.07 | − |
| OASL | 4 | 1.21E+08 | 1.21E+08 | 7967121 | 12 | − | −2.36 | + |
| OASL | 5 | 1.21E+08 | 1.21E+08 | 7967122 | 12 | − | −2.53 | + |
| OASL | 6 | 1.21E+08 | 1.21E+08 | 7967123 | 12 | − | −2.35 | + |
| OASL | 7 | 1.21E+08 | 1.21E+08 | 7967124 | 12 | − | −1.86 | − |
| OASL | 8 | 1.21E+08 | 1.21E+08 | 7967125 | 12 | − | −0.27 | − |
| OASL | 9 | 1.21E+08 | 1.21E+08 | 7967126 | 12 | − | −0.15 | − |
| EPSTI1 | 1 | 43462266 | 43462452 | 7971298 | 13 | − | −1.52 | − |
| EPSTI1 | 2 | 43463349 | 43463375 | 7971299 | 13 | − | −3.12 | + |
| EPSTI1 | 3 | 43469178 | 43469236 | 7971300 | 13 | − | −2.23 | − |
| EPSTI1 | 4 | 43474446 | 43474471 | 7971301 | 13 | − | −2.17 | − |
| EPSTI1 | 5 | 43491727 | 43491753 | 7971302 | 13 | − | −2.44 | + |
| EPSTI1 | 6 | 43493437 | 43493468 | 7971303 | 13 | − | −3.02 | + |
| EPSTI1 | 7 | 43500509 | 43500534 | 7971304 | 13 | − | −2.45 | + |
| EPSTI1 | 8 | 43528084 | 43528108 | 7971305 | 13 | − | −1.21 | − |
| EPSTI1 | 9 | 43537406 | 43537459 | 7971306 | 13 | − | −2.30 | − |
| EPSTI1 | 10 | 43538213 | 43538240 | 7971307 | 13 | − | −2.02 | − |
| EPSTI1 | 11 | 43543239 | 43543266 | 7971308 | 13 | − | −3.11 | + |
| EPSTI1 | 12 | 43544773 | 43544806 | 7971309 | 13 | − | −2.45 | + |
| EPSTI1 | 13 | 43566128 | 43566296 | 7971310 | 13 | − | −2.75 | + |
| IFI27 | 1 | 94577158 | 94577309 | 7976444 | 14 | + | −0.20 | − |
| IFI27 | 2 | 94577977 | 94578004 | 7976445 | 14 | + | −1.63 | − |
| IFI27 | 3 | 94578063 | 94578119 | 7976446 | 14 | + | −2.46 | − |
| IFI27 | 4 | 94581198 | 94581225 | 7976447 | 14 | + | −4.41 | + |
| IFI27 | 5 | 94582163 | 94582259 | 7976448 | 14 | + | −2.10 | − |
| IFI27 | 6 | 94582782 | 94582840 | 7976449 | 14 | + | −5.12 | + |
| IFI27 | 7 | 94582887 | 94582955 | 7976450 | 14 | + | −4.19 | + |
| MT2A | 1 | 56642511 | 56642544 | 7995784 | 16 | + | −1.87 | + |
| MT2A | 2 | 56642915 | 56642942 | 7995785 | 16 | + | −1.77 | + |
| MT2A | 3 | 56643280 | 56643368 | 7995786 | 16 | + | −1.53 | − |
| XAF1 | 1 | 6658886 | 6658910 | 8004185 | 17 | + | 0.18 | − |
| XAF1 | 2 | 6659261 | 6659340 | 8004186 | 17 | + | −0.18 | − |
| XAF1 | 3 | 6659398 | 6659429 | 8004187 | 17 | + | −1.18 | − |
| XAF1 | 4 | 6661409 | 6661494 | 8004188 | 17 | + | −2.06 | + |
| XAF1 | 5 | 6662981 | 6663029 | 8004189 | 17 | + | −2.07 | + |
| XAF1 | 6 | 6663735 | 6663903 | 8004190 | 17 | + | −1.84 | + |
| XAF1 | 7 | 6665488 | 6665521 | 8004191 | 17 | + | −1.83 | + |
| XAF1 | 8 | 6673962 | 6674302 | 8004192 | 17 | + | −1.48 | − |
| XAF1 | 9 | 6676433 | 6676823 | 8004193 | 17 | + | −1.71 | + |
| XAF1 | 10 | 6678425 | 6678819 | 8004194 | 17 | + | −1.93 | + |
| CCL2 | 1 | 32582306 | 32582330 | 8006434 | 17 | + | 0.14 | − |
| CCL2 | 2 | 32582321 | 32582368 | 8006435 | 17 | + | −0.60 | − |
| CCL2 | 3 | 32582369 | 32582441 | 8006436 | 17 | + | −0.84 | − |
| CCL2 | 4 | 32583269 | 32583358 | 8006437 | 17 | + | −1.39 | + |
| CCL2 | 5 | 32583749 | 32583846 | 8006438 | 17 | + | −1.84 | + |

TABLE 12-continued

Exon level analysis of 62 genes differentially expressed in bacterial and viral patients. Expression levels data obtained from the 6 bacterial and 9 viral patients described in Table 11. Probest ID is based on Affymetrix chip data. Comparison to full gene was calculated as absolute median log fold change (exon$_i$) – absolute median log fold change (full length gene); "+" and "–" represent higher and lower degree of differential expression of the single exon compared to the full length gene.

| Gene name | Exon # | Genomic location (start) | Genomic location (stop) | Probeset ID (Affymetrix) | Chromosome | Strand | Median log fold change | Comparison to full gene (improvement indicated by "+") |
|---|---|---|---|---|---|---|---|---|
| CCL2 | 6 | 32584004 | 32584109 | 8006439 | 17 | + | −0.98 | + |
| JUP | 1 | 39910921 | 39911168 | 8015413 | 17 | − | −0.38 | − |
| JUP | 2 | 39911325 | 39911456 | 8015414 | 17 | − | −1.18 | − |
| JUP | 3 | 39911556 | 39911611 | 8015415 | 17 | − | −0.62 | − |
| JUP | 4 | 39911740 | 39911944 | 8015416 | 17 | − | −1.34 | − |
| JUP | 5 | 39911996 | 39912105 | 8015417 | 17 | − | −0.71 | − |
| JUP | 6 | 39912431 | 39912456 | 8015418 | 17 | − | −2.11 | + |
| JUP | 7 | 39913673 | 39913745 | 8015419 | 17 | − | −1.60 | + |
| JUP | 8 | 39913996 | 39914036 | 8015420 | 17 | − | −1.61 | + |
| JUP | 9 | 39914665 | 39914742 | 8015421 | 17 | − | −1.86 | + |
| JUP | 10 | 39914971 | 39915122 | 8015422 | 17 | − | −0.25 | − |
| JUP | 11 | 39919268 | 39919310 | 8015423 | 17 | − | −1.62 | + |
| JUP | 12 | 39920966 | 39921003 | 8015424 | 17 | − | −0.79 | − |
| JUP | 13 | 39921190 | 39921312 | 8015425 | 17 | − | −0.88 | − |
| JUP | 14 | 39923755 | 39923823 | 8015426 | 17 | − | −1.43 | − |
| JUP | 15 | 39925344 | 39925443 | 8015427 | 17 | − | −2.13 | + |
| JUP | 16 | 39925740 | 39925925 | 8015428 | 17 | − | −1.49 | + |
| JUP | 17 | 39927937 | 39928044 | 8015429 | 17 | − | −1.03 | − |
| JUP | 18 | 39941202 | 39941451 | 8015430 | 17 | − | 0.04 | − |
| JUP | 19 | 39942899 | 39942931 | 8015431 | 17 | − | −0.21 | − |
| PHOSPHO1 | 1 | 47300933 | 47300957 | 8016541 | 17 | − | −0.30 | − |
| PHOSPHO1 | 2 | 47301244 | 47301555 | 8016542 | 17 | − | 1.74 | + |
| PHOSPHO1 | 3 | 47301807 | 47302321 | 8016543 | 17 | − | 1.83 | + |
| PHOSPHO1 | 4 | 47304009 | 47304089 | 8016544 | 17 | − | 0.97 | − |
| PHOSPHO1 | 5 | 47307844 | 47308042 | 8016545 | 17 | − | 0.76 | − |
| PSTPIP2 | 1 | 43564676 | 43565362 | 8023044 | 18 | − | −1.13 | − |
| PSTPIP2 | 2 | 43568676 | 43568705 | 8023045 | 18 | − | −1.55 | − |
| PSTPIP2 | 3 | 43570688 | 43570713 | 8023046 | 18 | − | −1.10 | − |
| PSTPIP2 | 4 | 43571868 | 43571899 | 8023047 | 18 | − | −1.00 | − |
| PSTPIP2 | 5 | 43572085 | 43572168 | 8023048 | 18 | − | −1.43 | − |
| PSTPIP2 | 6 | 43573572 | 43573637 | 8023049 | 18 | − | −1.25 | − |
| PSTPIP2 | 7 | 43577748 | 43577780 | 8023050 | 18 | − | −2.13 | + |
| PSTPIP2 | 8 | 43578761 | 43578786 | 8023051 | 18 | − | −1.25 | − |
| PSTPIP2 | 9 | 43579415 | 43579454 | 8023052 | 18 | − | −1.17 | − |
| PSTPIP2 | 10 | 43585459 | 43585485 | 8023053 | 18 | − | −1.64 | + |
| PSTPIP2 | 11 | 43591209 | 43591241 | 8023054 | 18 | − | −1.16 | − |
| PSTPIP2 | 12 | 43595872 | 43595899 | 8023055 | 18 | − | −2.19 | + |
| PSTPIP2 | 13 | 43604575 | 43604616 | 8023056 | 18 | − | −1.69 | + |
| PSTPIP2 | 14 | 43619939 | 43619996 | 8023057 | 18 | − | −0.95 | − |
| PSTPIP2 | 15 | 43652125 | 43652209 | 8023058 | 18 | − | −1.26 | − |
| C19orf59 | 1 | 7741577 | 7741818 | 8025286 | 19 | + | −0.19 | − |
| C19orf59 | 2 | 7741931 | 7741962 | 8025287 | 19 | + | −0.62 | − |
| C19orf59 | 3 | 7741977 | 7742047 | 8025288 | 19 | + | −0.37 | − |
| C19orf59 | 4 | 7742537 | 7742609 | 8025289 | 19 | + | −1.24 | − |
| C19orf59 | 5 | 7743000 | 7743123 | 8025290 | 19 | + | −0.95 | − |
| C19orf59 | 6 | 7743236 | 7743281 | 8025291 | 19 | + | −1.84 | + |
| C19orf59 | 7 | 7743386 | 7743488 | 8025292 | 19 | + | −0.88 | − |
| C19orf59 | 8 | 7743833 | 7743869 | 8025293 | 19 | + | −1.06 | − |
| C19orf59 | 9 | 7744046 | 7744070 | 8025294 | 19 | + | −2.08 | + |
| C19orf59 | 10 | 7744532 | 7744632 | 8025295 | 19 | + | −2.38 | + |
| FFAR3 | 1 | 35849505 | 35849550 | 8027857 | 19 | + | −1.40 | − |
| FFAR3 | 2 | 35849821 | 35850883 | 8027858 | 19 | + | −1.60 | + |
| FFAR3 | 3 | 35850944 | 35851301 | 8027859 | 19 | + | −1.24 | − |
| FFAR3 | 4 | 35862290 | 35863262 | 8027861 | 19 | + | −1.57 | − |
| CD177 | 1 | 43857842 | 43857866 | 8029281 | 19 | + | −1.30 | − |
| CD177 | 2 | 43857867 | 43857892 | 8029282 | 19 | + | −1.05 | − |
| CD177 | 3 | 43858043 | 43858142 | 8029283 | 19 | + | −1.48 | − |
| CD177 | 4 | 43858362 | 43858510 | 8029284 | 19 | + | −1.53 | − |
| CD177 | 5 | 43864436 | 43864557 | 8029285 | 19 | + | −0.58 | − |
| CD177 | 6 | 43866241 | 43866470 | 8029286 | 19 | + | −1.21 | − |
| CD177 | 7 | 43866648 | 43866672 | 8029287 | 19 | + | −2.66 | + |
| CD177 | 8 | 43866831 | 43866855 | 8029288 | 19 | + | −1.91 | + |
| CEACAM1 | 1 | 43011571 | 43012421 | 8037206 | 19 | − | −3.05 | + |
| CEACAM1 | 2 | 43012867 | 43013056 | 8037207 | 19 | − | −2.82 | + |
| CEACAM1 | 3 | 43013332 | 43013362 | 8037208 | 19 | − | −1.31 | − |
| CEACAM1 | 4 | 43015041 | 43015067 | 8037209 | 19 | − | −1.49 | − |
| CEACAM1 | 5 | 43015731 | 43015780 | 8037210 | 19 | − | −1.50 | − |

TABLE 12-continued

Exon level analysis of 62 genes differentially expressed in bacterial and viral patients. Expression levels data obtained from the 6 bacterial and 9 viral patients described in Table 11. Probest ID is based on Affymetrix chip data. Comparison to full gene was calculated as absolute median log fold change (exon$_i$) − absolute median log fold change (full length gene); "+" and "−" represent higher and lower degree of differential expression of the single exon compared to the full length gene.

| Gene name | Exon # | Genomic location (start) | Genomic location (stop) | Probeset ID (Affymetrix) | Chromosome | Strand | Median log fold change | Comparison to full gene (improvement indicated by "+") |
|---|---|---|---|---|---|---|---|---|
| CEACAM1 | 6 | 43016532 | 43016564 | 8037211 | 19 | − | −1.91 | + |
| CEACAM1 | 7 | 43023038 | 43023074 | 8037212 | 19 | − | −0.60 | − |
| CEACAM1 | 8 | 43023127 | 43023253 | 8037213 | 19 | − | −1.84 | − |
| CEACAM1 | 9 | 43023259 | 43023288 | 8037214 | 19 | − | −2.17 | + |
| CEACAM1 | 10 | 43024843 | 43025132 | 8037215 | 19 | − | −0.88 | − |
| CEACAM1 | 11 | 43025470 | 43025570 | 8037216 | 19 | − | −1.80 | − |
| CEACAM1 | 12 | 43026106 | 43026248 | 8037217 | 19 | − | −1.16 | − |
| CEACAM1 | 13 | 43031489 | 43031518 | 8037218 | 19 | − | −2.14 | + |
| CEACAM1 | 14 | 43032480 | 43032504 | 8037219 | 19 | − | −2.82 | + |
| CEACAM1 | 15 | 43032527 | 43032596 | 8037220 | 19 | − | −1.52 | − |
| CEACAM1 | 16 | 43032579 | 43032603 | 8037221 | 19 | − | −3.09 | + |
| CD177 | 1 | 43882867 | 43882899 | 8037299 | 19 | − | −1.23 | − |
| CD177 | 2 | 43883163 | 43883194 | 8037300 | 19 | − | −1.68 | + |
| RSAD2 | 1 | 7017857 | 7017911 | 8040081 | 2 | + | −0.21 | − |
| RSAD2 | 2 | 7017966 | 7018200 | 8040082 | 2 | + | −4.18 | + |
| RSAD2 | 3 | 7023529 | 7023638 | 8040083 | 2 | + | −4.41 | + |
| RSAD2 | 4 | 7027075 | 7027295 | 8040084 | 2 | + | −4.16 | + |
| RSAD2 | 5 | 7030307 | 7030452 | 8040085 | 2 | + | −4.44 | + |
| RSAD2 | 6 | 7033802 | 7033827 | 8040086 | 2 | + | −5.25 | + |
| RSAD2 | 7 | 7036012 | 7036238 | 8040087 | 2 | + | −3.68 | − |
| RSAD2 | 8 | 7037065 | 7037774 | 8040088 | 2 | + | −5.24 | + |
| RSAD2 | 9 | 7038184 | 7038208 | 8040089 | 2 | + | −4.14 | + |
| GALM | 1 | 38893153 | 38893242 | 8041543 | 2 | + | −0.15 | − |
| GALM | 2 | 38893237 | 38893261 | 8041544 | 2 | + | 0.14 | − |
| GALM | 3 | 38893380 | 38893443 | 8041545 | 2 | + | −0.90 | − |
| GALM | 4 | 38903097 | 38903194 | 8041546 | 2 | + | −2.63 | + |
| GALM | 5 | 38908461 | 38908560 | 8041547 | 2 | + | −1.95 | + |
| GALM | 6 | 38916976 | 38917013 | 8041548 | 2 | + | −2.07 | + |
| GALM | 7 | 38956715 | 38956818 | 8041549 | 2 | + | −1.98 | + |
| GALM | 8 | 38958893 | 38959022 | 8041550 | 2 | + | −2.21 | + |
| GALM | 9 | 38960661 | 38960955 | 8041551 | 2 | + | −1.68 | + |
| GALM | 10 | 38961613 | 38961753 | 8041552 | 2 | + | −1.32 | − |
| TNFAIP6 | 1 | 1.52E+08 | 1.52E+08 | 8045689 | 2 | + | −1.87 | + |
| TNFAIP6 | 2 | 1.52E+08 | 1.52E+08 | 8045690 | 2 | + | −2.31 | + |
| TNFAIP6 | 3 | 1.52E+08 | 1.52E+08 | 8045691 | 2 | + | −1.97 | + |
| TNFAIP6 | 4 | 1.52E+08 | 1.52E+08 | 8045692 | 2 | + | −1.50 | − |
| TNFAIP6 | 5 | 1.52E+08 | 1.52E+08 | 8045693 | 2 | + | −1.14 | − |
| TNFAIP6 | 6 | 1.52E+08 | 1.52E+08 | 8045694 | 2 | + | −1.71 | − |
| CYBRD1 | 1 | 1.72E+08 | 1.72E+08 | 8046334 | 2 | + | 0.37 | − |
| CYBRD1 | 2 | 1.72E+08 | 1.72E+08 | 8046335 | 2 | + | 1.39 | + |
| CYBRD1 | 3 | 1.72E+08 | 1.72E+08 | 8046336 | 2 | + | 1.35 | + |
| CYBRD1 | 4 | 1.72E+08 | 1.72E+08 | 8046337 | 2 | + | 1.50 | + |
| CYBRD1 | 5 | 1.72E+08 | 1.72E+08 | 8046338 | 2 | + | 1.40 | + |
| CYBRD1 | 6 | 1.72E+08 | 1.72E+08 | 8046339 | 2 | + | 1.43 | + |
| CMPK2 | 1 | 6980702 | 6980805 | 8050103 | 2 | − | −3.72 | + |
| CMPK2 | 2 | 6988578 | 6990019 | 8050104 | 2 | − | −3.41 | + |
| CMPK2 | 3 | 6990079 | 6990104 | 8050105 | 2 | − | −2.75 | + |
| CMPK2 | 4 | 6991597 | 6991723 | 8050106 | 2 | − | −3.25 | + |
| CMPK2 | 5 | 7001489 | 7001515 | 8050107 | 2 | − | −2.92 | + |
| CMPK2 | 6 | 7003605 | 7003666 | 8050108 | 2 | − | −3.38 | + |
| CMPK2 | 7 | 7005192 | 7005814 | 8050109 | 2 | − | −0.93 | − |
| CMPK2 | 8 | 7005920 | 7005950 | 8050110 | 2 | − | −0.93 | − |
| OTOF | 1 | 26680446 | 26680947 | 8050943 | 2 | − | −0.29 | − |
| OTOF | 2 | 26682921 | 26683071 | 8050944 | 2 | − | −0.95 | + |
| OTOF | 3 | 26683582 | 26683606 | 8050945 | 2 | − | −0.17 | − |
| OTOF | 4 | 26683733 | 26683757 | 8050946 | 2 | − | −4.65 | + |
| OTOF | 5 | 26684630 | 26684654 | 8050947 | 2 | − | −4.21 | + |
| OTOF | 6 | 26684951 | 26684975 | 8050948 | 2 | − | −3.80 | + |
| OTOF | 7 | 26686357 | 26686381 | 8050949 | 2 | − | −2.12 | + |
| OTOF | 8 | 26686946 | 26686970 | 8050950 | 2 | − | −0.76 | − |
| OTOF | 9 | 26687766 | 26687897 | 8050951 | 2 | − | −0.65 | − |
| OTOF | 10 | 26688686 | 26688710 | 8050952 | 2 | − | −0.88 | + |
| OTOF | 11 | 26688817 | 26688841 | 8050953 | 2 | − | −0.41 | − |
| OTOF | 12 | 26689695 | 26689719 | 8050954 | 2 | − | −0.47 | − |
| OTOF | 13 | 26690036 | 26690060 | 8050955 | 2 | − | −2.40 | + |
| OTOF | 14 | 26690343 | 26690367 | 8050956 | 2 | − | −1.06 | + |
| OTOF | 15 | 26691307 | 26691331 | 8050957 | 2 | − | −0.82 | − |

TABLE 12-continued

Exon level analysis of 62 genes differentially expressed in bacterial and viral patients. Expression levels data obtained from the 6 bacterial and 9 viral patients described in Table 11. Probest ID is based on Affymetrix chip data. Comparison to full gene was calculated as absolute median log fold change (exon$_i$) − absolute median log fold change (full length gene); "+" and "−" represent higher and lower degree of differential expression of the single exon compared to the full length gene.

| Gene name | Exon # | Genomic location (start) | Genomic location (stop) | Probeset ID (Affymetrix) | Chromosome | Strand | Median log fold change | Comparison to full gene (improvement indicated by "+") |
|---|---|---|---|---|---|---|---|---|
| OTOF | 16 | 26693462 | 26693567 | 8050958 | 2 | − | −1.31 | + |
| OTOF | 17 | 26693993 | 26694017 | 8050959 | 2 | − | −2.47 | + |
| OTOF | 18 | 26695414 | 26695438 | 8050960 | 2 | − | −1.73 | + |
| OTOF | 19 | 26695483 | 26695507 | 8050961 | 2 | − | −0.23 | − |
| OTOF | 20 | 26696113 | 26696137 | 8050962 | 2 | − | −0.35 | − |
| OTOF | 21 | 26696320 | 26696344 | 8050963 | 2 | − | −2.79 | + |
| OTOF | 22 | 26696860 | 26696884 | 8050964 | 2 | − | −0.81 | − |
| OTOF | 23 | 26697515 | 26697539 | 8050965 | 2 | − | −1.96 | + |
| OTOF | 24 | 26698294 | 26698318 | 8050966 | 2 | − | −0.45 | − |
| OTOF | 25 | 26698867 | 26698891 | 8050967 | 2 | − | −1.27 | + |
| OTOF | 26 | 26699091 | 26699115 | 8050968 | 2 | − | −1.38 | + |
| OTOF | 27 | 26699768 | 26699792 | 8050969 | 2 | − | −2.23 | + |
| OTOF | 28 | 26700065 | 26700089 | 8050970 | 2 | − | −1.17 | + |
| OTOF | 29 | 26700337 | 26700361 | 8050971 | 2 | − | −1.21 | + |
| OTOF | 30 | 26700557 | 26700615 | 8050972 | 2 | − | −0.13 | − |
| OTOF | 31 | 26700677 | 26700701 | 8050973 | 2 | − | −0.13 | − |
| OTOF | 32 | 26700716 | 26700797 | 8050974 | 2 | − | 0.01 | − |
| OTOF | 33 | 26702204 | 26702228 | 8050975 | 2 | − | −0.11 | − |
| OTOF | 34 | 26702412 | 26702436 | 8050976 | 2 | − | 0.15 | − |
| OTOF | 35 | 26703113 | 26703137 | 8050977 | 2 | − | −0.09 | − |
| OTOF | 36 | 26703715 | 26703739 | 8050978 | 2 | − | −0.02 | − |
| OTOF | 37 | 26705306 | 26705330 | 8050979 | 2 | − | −0.22 | − |
| OTOF | 38 | 26706455 | 26706479 | 8050980 | 2 | − | −0.07 | − |
| OTOF | 39 | 26707473 | 26707497 | 8050981 | 2 | − | 0.32 | − |
| OTOF | 40 | 26712092 | 26712116 | 8050982 | 2 | − | −0.56 | − |
| OTOF | 41 | 26712572 | 26712596 | 8050983 | 2 | − | −0.25 | − |
| OTOF | 42 | 26717886 | 26717910 | 8050984 | 2 | − | 0.53 | − |
| OTOF | 43 | 26724622 | 26724646 | 8050985 | 2 | − | −0.02 | − |
| OTOF | 44 | 26725248 | 26725272 | 8050986 | 2 | − | −0.12 | − |
| OTOF | 45 | 26726664 | 26726713 | 8050987 | 2 | − | −0.01 | − |
| OTOF | 46 | 26739331 | 26739355 | 8050988 | 2 | − | −0.51 | − |
| OTOF | 47 | 26741945 | 26741969 | 8050989 | 2 | − | 0.08 | − |
| OTOF | 48 | 26750711 | 26750788 | 8050990 | 2 | − | 0.13 | − |
| OTOF | 49 | 26760615 | 26760639 | 8050991 | 2 | − | −0.30 | − |
| OTOF | 50 | 26781365 | 26781512 | 8050992 | 2 | − | −0.26 | − |
| EIF2AK2 | 1 | 37334374 | 37334411 | 8051502 | 2 | − | −1.80 | + |
| EIF2AK2 | 2 | 37334452 | 37334488 | 8051503 | 2 | − | −1.76 | + |
| EIF2AK2 | 3 | 37334643 | 37334668 | 8051504 | 2 | − | −2.01 | + |
| EIF2AK2 | 4 | 37336376 | 37336406 | 8051505 | 2 | − | −1.37 | − |
| EIF2AK2 | 5 | 37341890 | 37341929 | 8051506 | 2 | − | −1.25 | − |
| EIF2AK2 | 6 | 37347127 | 37347276 | 8051507 | 2 | − | −1.80 | + |
| EIF2AK2 | 7 | 37349686 | 37349750 | 8051508 | 2 | − | −1.41 | − |
| EIF2AK2 | 8 | 37353461 | 37353518 | 8051509 | 2 | − | −1.74 | + |
| EIF2AK2 | 9 | 37362655 | 37362685 | 8051510 | 2 | − | −1.96 | + |
| EIF2AK2 | 10 | 37364132 | 37364158 | 8051511 | 2 | − | −1.34 | − |
| EIF2AK2 | 11 | 37365413 | 37365490 | 8051512 | 2 | − | −0.80 | − |
| EIF2AK2 | 12 | 37365681 | 37365712 | 8051513 | 2 | − | −0.77 | − |
| EIF2AK2 | 13 | 37366795 | 37366859 | 8051514 | 2 | − | −1.10 | − |
| EIF2AK2 | 14 | 37368754 | 37368825 | 8051515 | 2 | − | −2.11 | + |
| EIF2AK2 | 15 | 37374001 | 37374053 | 8051516 | 2 | − | −0.67 | − |
| EIF2AK2 | 16 | 37374832 | 37374909 | 8051517 | 2 | − | −1.52 | + |
| EIF2AK2 | 17 | 37376018 | 37376125 | 8051518 | 2 | − | −2.13 | + |
| EIF2AK2 | 18 | 37376275 | 37376299 | 8051519 | 2 | − | −0.27 | − |
| CYP1B1 | 1 | 38295325 | 38296536 | 8051584 | 2 | − | 1.13 | − |
| CYP1B1 | 2 | 38297455 | 38297824 | 8051585 | 2 | − | 1.36 | − |
| CYP1B1 | 3 | 38297893 | 38298453 | 8051586 | 2 | − | 0.94 | − |
| CYP1B1 | 4 | 38301504 | 38302295 | 8051587 | 2 | − | 1.40 | + |
| CYP1B1 | 5 | 38302989 | 38303267 | 8051588 | 2 | − | 1.49 | + |
| SIGLEC1 | 1 | 3667953 | 3668359 | 8064717 | 20 | − | −2.45 | − |
| SIGLEC1 | 2 | 3669232 | 3669256 | 8064718 | 20 | − | −2.83 | + |
| SIGLEC1 | 3 | 3669820 | 3669844 | 8064719 | 20 | − | −4.01 | + |
| SIGLEC1 | 4 | 3670322 | 3670346 | 8064720 | 20 | − | −1.08 | − |
| SIGLEC1 | 5 | 3670869 | 3670893 | 8064721 | 20 | − | −2.34 | − |
| SIGLEC1 | 6 | 3672040 | 3672064 | 8064722 | 20 | − | −2.24 | − |
| SIGLEC1 | 7 | 3672564 | 3672588 | 8064723 | 20 | − | −2.29 | − |
| SIGLEC1 | 8 | 3673299 | 3673323 | 8064724 | 20 | − | −3.45 | + |
| SIGLEC1 | 9 | 3673571 | 3673771 | 8064725 | 20 | − | −1.71 | − |

TABLE 12-continued

Exon level analysis of 62 genes differentially expressed in bacterial and viral patients. Expression levels data obtained from the 6 bacterial and 9 viral patients described in Table 11. Probest ID is based on Affymetrix chip data. Comparison to full gene was calculated as absolute median log fold change (exon$_i$) − absolute median log fold change (full length gene); "+" and "−" represent higher and lower degree of differential expression of the single exon compared to the full length gene.

| Gene name | Exon # | Genomic location (start) | Genomic location (stop) | Probeset ID (Affymetrix) | Chromosome | Strand | Median log fold change | Comparison to full gene (improvement indicated by "+") |
|---|---|---|---|---|---|---|---|---|
| SIGLEC1 | 10 | 3674167 | 3674191 | 8064726 | 20 | − | −2.89 | + |
| SIGLEC1 | 11 | 3674948 | 3674972 | 8064727 | 20 | − | −3.17 | + |
| SIGLEC1 | 12 | 3675460 | 3675484 | 8064728 | 20 | − | −2.34 | − |
| SIGLEC1 | 13 | 3677464 | 3677488 | 8064729 | 20 | − | −1.85 | − |
| SIGLEC1 | 14 | 3677732 | 3677935 | 8064730 | 20 | − | −4.07 | + |
| SIGLEC1 | 15 | 3678524 | 3678548 | 8064731 | 20 | − | −3.46 | + |
| SIGLEC1 | 16 | 3679992 | 3680016 | 8064732 | 20 | − | −3.78 | + |
| SIGLEC1 | 17 | 3682105 | 3682129 | 8064733 | 20 | − | −2.78 | + |
| SIGLEC1 | 18 | 3683919 | 3683943 | 8064734 | 20 | − | −4.40 | + |
| SIGLEC1 | 19 | 3684532 | 3684733 | 8064735 | 20 | − | −1.83 | − |
| SIGLEC1 | 20 | 3686400 | 3686424 | 8064736 | 20 | − | −1.99 | − |
| SIGLEC1 | 21 | 3687224 | 3687248 | 8064737 | 20 | − | −0.81 | − |
| SIGLEC1 | 22 | 3687750 | 3687774 | 8064738 | 20 | − | −1.16 | − |
| MX1 | 1 | 42798144 | 42798169 | 8068714 | 21 | + | −0.22 | − |
| MX1 | 2 | 42799159 | 42799188 | 8068715 | 21 | + | −3.38 | + |
| MX1 | 3 | 42799687 | 42799718 | 8068716 | 21 | + | −2.42 | − |
| MX1 | 4 | 42802470 | 42802496 | 8068717 | 21 | + | −3.12 | + |
| MX1 | 5 | 42803998 | 42804067 | 8068718 | 21 | + | −1.91 | − |
| MX1 | 6 | 42807923 | 42807948 | 8068719 | 21 | + | −3.73 | + |
| MX1 | 7 | 42808944 | 42809062 | 8068720 | 21 | + | −2.26 | − |
| MX1 | 8 | 42811658 | 42811715 | 8068721 | 21 | + | −3.45 | + |
| MX1 | 9 | 42812837 | 42812922 | 8068722 | 21 | + | −2.70 | + |
| MX1 | 10 | 42813649 | 42813729 | 8068723 | 21 | + | −2.67 | + |
| MX1 | 11 | 42815734 | 42815760 | 8068724 | 21 | + | −3.01 | + |
| MX1 | 12 | 42817432 | 42817474 | 8068725 | 21 | + | −2.79 | + |
| MX1 | 13 | 42817947 | 42818036 | 8068726 | 21 | + | −3.32 | + |
| MX1 | 14 | 42821077 | 42821222 | 8068727 | 21 | + | −2.86 | + |
| MX1 | 15 | 42823137 | 42823161 | 8068728 | 21 | + | −2.59 | + |
| MX1 | 16 | 42824621 | 42824786 | 8068729 | 21 | + | −2.73 | + |
| MX1 | 17 | 42830499 | 42830810 | 8068730 | 21 | + | −2.90 | + |
| USP18 | 1 | 18632822 | 18632955 | 8071156 | 22 | + | −0.24 | − |
| USP18 | 2 | 18640328 | 18640363 | 8071157 | 22 | + | −2.78 | − |
| USP18 | 3 | 18640431 | 18640587 | 8071158 | 22 | + | −1.79 | − |
| USP18 | 4 | 18650665 | 18650705 | 8071159 | 22 | + | −2.95 | − |
| USP18 | 5 | 18652646 | 18652670 | 8071160 | 22 | + | −4.34 | + |
| USP18 | 6 | 20717915 | 20717951 | 8074607 | 22 | − | −3.27 | + |
| USP18 | 7 | 20718484 | 20718566 | 8074608 | 22 | − | −2.80 | − |
| USP18 | 8 | 20720870 | 20721024 | 8074609 | 22 | − | −2.65 | − |
| USP18 | 9 | 20721861 | 20721932 | 8074610 | 22 | − | −3.25 | + |
| USP18 | 10 | 20724425 | 20724455 | 8074612 | 22 | − | −3.85 | + |
| USP18 | 11 | 20729874 | 20729899 | 8074613 | 22 | − | −4.27 | + |
| USP18 | 12 | 20731508 | 20731532 | 8074614 | 22 | − | −1.94 | − |
| RTP4 | 1 | 1.87E+08 | 1.87E+08 | 8084733 | 3 | + | −0.13 | − |
| RTP4 | 2 | 1.87E+08 | 1.87E+08 | 8084734 | 3 | + | −2.14 | + |
| RTP4 | 3 | 1.87E+08 | 1.87E+08 | 8084735 | 3 | + | −2.39 | + |
| RTP4 | 4 | 1.87E+08 | 1.87E+08 | 8084736 | 3 | + | −2.10 | + |
| PLSCR1 | 1 | 1.46E+08 | 1.46E+08 | 8091328 | 3 | − | −1.47 | − |
| PLSCR1 | 2 | 1.46E+08 | 1.46E+08 | 8091329 | 3 | − | −1.55 | − |
| PLSCR1 | 3 | 1.46E+08 | 1.46E+08 | 8091330 | 3 | − | −1.30 | − |
| PLSCR1 | 4 | 1.46E+08 | 1.46E+08 | 8091331 | 3 | − | −1.79 | + |
| PLSCR1 | 5 | 1.46E+08 | 1.46E+08 | 8091332 | 3 | − | −1.67 | − |
| PLSCR1 | 6 | 1.46E+08 | 1.46E+08 | 8091333 | 3 | − | −1.77 | + |
| PLSCR1 | 7 | 1.46E+08 | 1.46E+08 | 8091334 | 3 | − | −1.33 | − |
| PLSCR1 | 8 | 1.46E+08 | 1.46E+08 | 8091335 | 3 | − | −1.87 | + |
| PLSCR1 | 9 | 1.46E+08 | 1.46E+08 | 8091336 | 3 | − | −1.81 | + |
| PLSCR1 | 10 | 1.46E+08 | 1.46E+08 | 8091337 | 3 | − | −2.06 | + |
| PLSCR1 | 11 | 1.46E+08 | 1.46E+08 | 8091338 | 3 | − | −1.74 | + |
| PLSCR1 | 12 | 1.46E+08 | 1.46E+08 | 8091339 | 3 | − | −0.39 | − |
| LAMP3 | 1 | 1.83E+08 | 1.83E+08 | 8092349 | 3 | − | −3.44 | + |
| LAMP3 | 2 | 1.83E+08 | 1.83E+08 | 8092350 | 3 | − | −2.70 | + |
| LAMP3 | 3 | 1.83E+08 | 1.83E+08 | 8092351 | 3 | − | −2.92 | + |
| LAMP3 | 4 | 1.83E+08 | 1.83E+08 | 8092352 | 3 | − | −1.88 | − |
| LAMP3 | 5 | 1.83E+08 | 1.83E+08 | 8092353 | 3 | − | −2.20 | + |
| LAMP3 | 6 | 1.83E+08 | 1.83E+08 | 8092354 | 3 | − | −1.89 | − |
| LAMP3 | 7 | 1.83E+08 | 1.83E+08 | 8092355 | 3 | − | 0.00 | − |
| HERC5 | 1 | 89378313 | 89378596 | 8096362 | 4 | + | −0.77 | − |
| HERC5 | 2 | 89380522 | 89380546 | 8096363 | 4 | + | −3.69 | + |

TABLE 12-continued

Exon level analysis of 62 genes differentially expressed in bacterial and viral patients. Expression levels data obtained from the 6 bacterial and 9 viral patients described in Table 11. Probest ID is based on Affymetrix chip data. Comparison to full gene was calculated as absolute median log fold change (exon$_i$) − absolute median log fold change (full length gene); "+" and "−" represent higher and lower degree of differential expression of the single exon compared to the full length gene.

| Gene name | Exon # | Genomic location (start) | Genomic location (stop) | Probeset ID (Affymetrix) | Chromosome | Strand | Median log fold change | Comparison to full gene (improvement indicated by "+") |
|---|---|---|---|---|---|---|---|---|
| HERC5 | 3 | 89381291 | 89381315 | 8096364 | 4 | + | −4.45 | + |
| HERC5 | 4 | 89383287 | 89383409 | 8096365 | 4 | + | −2.56 | + |
| HERC5 | 5 | 89384730 | 89384754 | 8096366 | 4 | + | −2.78 | + |
| HERC5 | 6 | 89385011 | 89385035 | 8096367 | 4 | + | −2.88 | + |
| HERC5 | 7 | 89388297 | 89388321 | 8096368 | 4 | + | −2.44 | − |
| HERC5 | 8 | 89389499 | 89389523 | 8096369 | 4 | + | −2.78 | + |
| HERC5 | 9 | 89390333 | 89390357 | 8096370 | 4 | + | −3.67 | + |
| HERC5 | 10 | 89391792 | 89391816 | 8096371 | 4 | + | −3.41 | + |
| HERC5 | 11 | 89393629 | 89393653 | 8096372 | 4 | + | −2.65 | + |
| HERC5 | 12 | 89396992 | 89397179 | 8096373 | 4 | + | −1.61 | − |
| HERC5 | 13 | 89400532 | 89400556 | 8096374 | 4 | + | −3.84 | + |
| HERC5 | 14 | 89407313 | 89407337 | 8096375 | 4 | + | −2.76 | + |
| HERC5 | 15 | 89408245 | 89408269 | 8096376 | 4 | + | −2.24 | − |
| HERC5 | 16 | 89410385 | 89410409 | 8096377 | 4 | + | −2.94 | + |
| HERC5 | 17 | 89414188 | 89414212 | 8096378 | 4 | + | −1.48 | − |
| HERC5 | 18 | 89415354 | 89415378 | 8096379 | 4 | + | −1.92 | − |
| HERC5 | 19 | 89421079 | 89421103 | 8096380 | 4 | + | −3.46 | + |
| HERC5 | 20 | 89422098 | 89422122 | 8096381 | 4 | + | −2.24 | − |
| HERC5 | 21 | 89425413 | 89425437 | 8096382 | 4 | + | −2.54 | + |
| HERC5 | 22 | 89425646 | 89425670 | 8096383 | 4 | + | −3.30 | + |
| HERC5 | 23 | 89426915 | 89427223 | 8096384 | 4 | + | −1.55 | − |
| PPBP | 1 | 74852806 | 74852923 | 8100972 | 4 | − | 1.26 | + |
| PPBP | 2 | 74853017 | 74853072 | 8100973 | 4 | − | 0.76 | − |
| PPBP | 3 | 74853234 | 74853343 | 8100974 | 4 | − | 1.17 | + |
| PPBP | 4 | 74853674 | 74853816 | 8100975 | 4 | − | 0.80 | − |
| PPBP | 5 | 74853827 | 74853893 | 8100976 | 4 | − | 1.21 | + |
| CXCL10 | 1 | 76942595 | 76943052 | 8101127 | 4 | − | −1.77 | − |
| CXCL10 | 2 | 76943521 | 76943583 | 8101128 | 4 | − | −2.47 | + |
| CXCL10 | 3 | 76943848 | 76943942 | 8101129 | 4 | − | −2.90 | + |
| CXCL10 | 4 | 76944524 | 76944637 | 8101130 | 4 | − | −1.26 | − |
| DDX60 | 1 | 1.69E+08 | 1.69E+08 | 8103564 | 4 | − | −1.37 | − |
| DDX60 | 2 | 1.69E+08 | 1.69E+08 | 8103565 | 4 | − | −1.43 | − |
| DDX60 | 3 | 1.69E+08 | 1.69E+08 | 8103566 | 4 | − | −2.26 | + |
| DDX60 | 4 | 1.69E+08 | 1.69E+08 | 8103567 | 4 | − | −2.16 | + |
| DDX60 | 5 | 1.69E+08 | 1.69E+08 | 8103568 | 4 | − | −2.07 | + |
| DDX60 | 6 | 1.69E+08 | 1.69E+08 | 8103569 | 4 | − | −2.18 | + |
| DDX60 | 7 | 1.69E+08 | 1.69E+08 | 8103570 | 4 | − | −1.79 | + |
| DDX60 | 8 | 1.69E+08 | 1.69E+08 | 8103571 | 4 | − | −2.47 | + |
| DDX60 | 9 | 1.69E+08 | 1.69E+08 | 8103572 | 4 | − | −2.28 | + |
| DDX60 | 10 | 1.69E+08 | 1.69E+08 | 8103573 | 4 | − | −2.16 | + |
| DDX60 | 11 | 1.69E+08 | 1.69E+08 | 8103574 | 4 | − | −2.03 | + |
| DDX60 | 12 | 1.69E+08 | 1.69E+08 | 8103575 | 4 | − | −2.21 | + |
| DDX60 | 13 | 1.69E+08 | 1.69E+08 | 8103576 | 4 | − | −2.51 | + |
| DDX60 | 14 | 1.69E+08 | 1.69E+08 | 8103577 | 4 | − | −1.27 | − |
| DDX60 | 15 | 1.69E+08 | 1.69E+08 | 8103578 | 4 | − | −1.75 | − |
| DDX60 | 16 | 1.69E+08 | 1.69E+08 | 8103579 | 4 | − | −1.41 | − |
| DDX60 | 17 | 1.69E+08 | 1.69E+08 | 8103580 | 4 | − | −1.88 | + |
| DDX60 | 18 | 1.69E+08 | 1.69E+08 | 8103581 | 4 | − | −1.99 | + |
| DDX60 | 19 | 1.69E+08 | 1.69E+08 | 8103582 | 4 | − | −1.85 | + |
| DDX60 | 20 | 1.69E+08 | 1.69E+08 | 8103583 | 4 | − | −0.75 | − |
| DDX60 | 21 | 1.69E+08 | 1.69E+08 | 8103584 | 4 | − | −1.37 | − |
| DDX60 | 22 | 1.69E+08 | 1.69E+08 | 8103585 | 4 | − | −1.58 | − |
| DDX60 | 23 | 1.69E+08 | 1.69E+08 | 8103586 | 4 | − | −1.37 | − |
| DDX60 | 24 | 1.69E+08 | 1.69E+08 | 8103587 | 4 | − | −1.79 | + |
| DDX60 | 25 | 1.69E+08 | 1.69E+08 | 8103588 | 4 | − | −1.80 | + |
| DDX60 | 26 | 1.69E+08 | 1.69E+08 | 8103589 | 4 | − | −1.46 | − |
| DDX60 | 27 | 1.69E+08 | 1.69E+08 | 8103590 | 4 | − | −1.38 | − |
| DDX60 | 28 | 1.69E+08 | 1.69E+08 | 8103591 | 4 | − | −1.50 | − |
| DDX60 | 29 | 1.69E+08 | 1.69E+08 | 8103592 | 4 | − | −2.08 | + |
| DDX60 | 30 | 1.69E+08 | 1.69E+08 | 8103593 | 4 | − | −2.73 | + |
| DDX60 | 31 | 1.69E+08 | 1.69E+08 | 8103594 | 4 | − | −2.37 | + |
| DDX60 | 32 | 1.69E+08 | 1.69E+08 | 8103595 | 4 | − | −1.82 | + |
| DDX60 | 33 | 1.69E+08 | 1.69E+08 | 8103596 | 4 | − | −2.17 | + |
| DDX60 | 34 | 1.69E+08 | 1.69E+08 | 8103597 | 4 | − | −0.34 | − |
| DDX60 | 35 | 1.69E+08 | 1.69E+08 | 8103598 | 4 | − | −1.83 | + |
| DDX60 | 36 | 1.69E+08 | 1.69E+08 | 8103599 | 4 | − | −1.14 | − |
| DDX60 | 37 | 1.69E+08 | 1.69E+08 | 8103600 | 4 | − | −1.53 | − |

TABLE 12-continued

Exon level analysis of 62 genes differentially expressed in bacterial and viral patients. Expression levels data obtained from the 6 bacterial and 9 viral patients described in Table 11. Probest ID is based on Affymetrix chip data. Comparison to full gene was calculated as absolute median log fold change (exon$_i$) − absolute median log fold change (full length gene); "+" and "−" represent higher and lower degree of differential expression of the single exon compared to the full length gene.

| Gene name | Exon # | Genomic location (start) | Genomic location (stop) | Probeset ID (Affymetrix) | Chromosome | Strand | Median log fold change | Comparison to full gene (improvement indicated by "+") |
|---|---|---|---|---|---|---|---|---|
| HLA-DQA1 | 1 | 32605263 | 32605291 | 8118557 | 6 | + | 0.01 | − |
| HLA-DQA1 | 2 | 32609096 | 32609271 | 8118558 | 6 | + | 5.68 | + |
| HLA-DQA1 | 3 | 32609791 | 32609815 | 8118559 | 6 | + | 0.11 | − |
| HLA-DQA1 | 4 | 32610514 | 32610538 | 8118560 | 6 | + | 0.28 | − |
| HLA-DQA1 | 5 | 32610776 | 32610970 | 8118561 | 6 | + | 3.59 | + |
| HLA-DQA1 | 6 | 32611066 | 32611328 | 8118562 | 6 | + | −0.14 | − |
| HLA-DQA1 | 7 | 32611368 | 32611428 | 8118563 | 6 | + | 0.44 | + |
| HLA-DQA1 | 8 | 32714096 | 32714153 | 8118569 | 6 | + | −0.21 | − |
| TREML4 | 1 | 41196075 | 41196210 | 8119428 | 6 | + | −0.40 | − |
| TREML4 | 2 | 41196468 | 41196729 | 8119429 | 6 | + | −3.76 | + |
| TREML4 | 3 | 41197268 | 41197299 | 8119430 | 6 | + | −1.17 | − |
| TREML4 | 4 | 41197803 | 41197857 | 8119431 | 6 | + | −0.52 | − |
| TREML4 | 5 | 41204262 | 41204345 | 8119432 | 6 | + | −1.05 | − |
| TREML4 | 6 | 41204804 | 41204828 | 8119433 | 6 | + | −2.05 | + |
| TREML4 | 7 | 41204938 | 41205826 | 8119434 | 6 | + | −3.62 | + |
| SH3BGRL2 | 1 | 80341010 | 80341219 | 8120834 | 6 | + | 0.45 | − |
| SH3BGRL2 | 2 | 80383340 | 80383516 | 8120835 | 6 | + | 1.19 | + |
| SH3BGRL2 | 3 | 80406252 | 80406282 | 8120836 | 6 | + | 1.35 | + |
| SH3BGRL2 | 4 | 80409573 | 80413298 | 8120837 | 6 | + | 1.12 | + |
| F13A1 | 1 | 6145383 | 6145951 | 8123745 | 6 | − | 1.04 | + |
| F13A1 | 2 | 6152088 | 6152180 | 8123746 | 6 | − | 0.69 | − |
| F13A1 | 3 | 6167699 | 6167793 | 8123747 | 6 | − | 1.05 | + |
| F13A1 | 4 | 6175043 | 6175082 | 8123748 | 6 | − | 0.64 | − |
| F13A1 | 5 | 6182262 | 6182345 | 8123749 | 6 | − | 1.02 | − |
| F13A1 | 6 | 6196053 | 6196098 | 8123750 | 6 | − | 0.67 | − |
| F13A1 | 7 | 6197519 | 6197544 | 8123751 | 6 | − | 0.87 | − |
| F13A1 | 8 | 6222266 | 6222354 | 8123752 | 6 | − | 1.08 | + |
| F13A1 | 9 | 6224953 | 6225079 | 8123753 | 6 | − | 0.71 | − |
| F13A1 | 10 | 6248559 | 6248608 | 8123754 | 6 | − | 0.86 | − |
| F13A1 | 11 | 6251086 | 6251162 | 8123755 | 6 | − | 1.21 | + |
| F13A1 | 12 | 6266796 | 6266872 | 8123756 | 6 | − | 1.84 | + |
| F13A1 | 13 | 6305584 | 6305762 | 8123757 | 6 | − | 1.38 | + |
| F13A1 | 14 | 6318841 | 6318885 | 8123758 | 6 | − | 1.01 | − |
| F13A1 | 15 | 6320842 | 6320883 | 8123759 | 6 | − | 0.06 | − |
| TMEM176A | 1 | 1.5E+08 | 1.5E+08 | 8137265 | 7 | + | 0.79 | − |
| TMEM176A | 2 | 1.5E+08 | 1.5E+08 | 8137266 | 7 | + | 1.65 | + |
| TMEM176A | 3 | 1.51E+08 | 1.51E+08 | 8137267 | 7 | + | 1.62 | + |
| TMEM176A | 4 | 1.51E+08 | 1.51E+08 | 8137268 | 7 | + | 1.11 | − |
| TMEM176A | 5 | 1.51E+08 | 1.51E+08 | 8137269 | 7 | + | 1.37 | + |
| TMEM176A | 6 | 1.51E+08 | 1.51E+08 | 8137270 | 7 | + | 0.76 | − |
| LY6E | 1 | 1.44E+08 | 1.44E+08 | 8148573 | 8 | + | −0.88 | − |
| LY6E | 2 | 1.44E+08 | 1.44E+08 | 8148574 | 8 | + | −1.78 | − |
| LY6E | 3 | 1.44E+08 | 1.44E+08 | 8148575 | 8 | + | −1.70 | − |
| LY6E | 4 | 1.44E+08 | 1.44E+08 | 8148576 | 8 | + | −2.35 | + |
| LY6E | 5 | 1.44E+08 | 1.44E+08 | 8148577 | 8 | + | −1.39 | − |
| LY6E | 6 | 1.44E+08 | 1.44E+08 | 8148578 | 8 | + | −1.79 | − |
| LY6E | 7 | 1.44E+08 | 1.44E+08 | 8148579 | 8 | + | −2.79 | + |
| BMX | 1 | 15482386 | 15482545 | 8166158 | X | + | −0.33 | − |
| BMX | 2 | 15518993 | 15519054 | 8166159 | X | + | −0.93 | − |
| BMX | 3 | 15525500 | 15525532 | 8166160 | X | + | −0.03 | − |
| BMX | 4 | 15526500 | 15526609 | 8166161 | X | + | −0.39 | − |
| BMX | 5 | 15527459 | 15527548 | 8166162 | X | + | −1.53 | + |
| BMX | 6 | 15529571 | 15529595 | 8166163 | X | + | −2.36 | + |
| BMX | 7 | 15534268 | 15534330 | 8166164 | X | + | −1.84 | + |
| BMX | 8 | 15536054 | 15536105 | 8166165 | X | + | −1.01 | − |
| BMX | 9 | 15540469 | 15540618 | 8166166 | X | + | −1.61 | + |
| BMX | 10 | 15543463 | 15543488 | 8166167 | X | + | −1.04 | − |
| BMX | 11 | 15544170 | 15544195 | 8166168 | X | + | −0.89 | − |
| BMX | 12 | 15548098 | 15548130 | 8166169 | X | + | −1.82 | + |
| BMX | 13 | 15549471 | 15549510 | 8166170 | X | + | −2.36 | + |
| BMX | 14 | 15552349 | 15552418 | 8166171 | X | + | −2.06 | + |
| BMX | 15 | 15554511 | 15554544 | 8166172 | X | + | −0.04 | − |
| BMX | 16 | 15555355 | 15555380 | 8166173 | X | + | −0.70 | − |
| BMX | 17 | 15560230 | 15560306 | 8166174 | X | + | −1.69 | + |
| BMX | 18 | 15561210 | 15561234 | 8166175 | X | + | −2.39 | + |
| BMX | 19 | 15564985 | 15565044 | 8166176 | X | + | −1.74 | + |
| BMX | 20 | 15567997 | 15568098 | 8166177 | X | + | −1.30 | − |

TABLE 12-continued

Exon level analysis of 62 genes differentially expressed in bacterial and viral patients. Expression levels data obtained from the 6 bacterial and 9 viral patients described in Table 11. Probest ID is based on Affymetrix chip data. Comparison to full gene was calculated as absolute median log fold change (exon$_i$) − absolute median log fold change (full length gene); "+" and "−" represent higher and lower degree of differential expression of the single exon compared to the full length gene.

| Gene name | Exon # | Genomic location (start) | Genomic location (stop) | Probeset ID (Affymetrix) | Chromosome | Strand | Median log fold change | Comparison to full gene (improvement indicated by "+") |
|---|---|---|---|---|---|---|---|---|
| BMX | 21 | 15574229 | 15574539 | 8166178 | X | + | −2.19 | + |
| EIF1AY | 1 | 22737617 | 22737641 | 8176720 | Y | + | 0.01 | − |
| EIF1AY | 2 | 22737673 | 22737697 | 8176721 | Y | + | −1.98 | − |
| EIF1AY | 3 | 22737707 | 22737731 | 8176722 | Y | + | −2.76 | + |
| EIF1AY | 4 | 22741510 | 22741541 | 8176723 | Y | + | −2.50 | + |
| EIF1AY | 5 | 22744499 | 22744566 | 8176724 | Y | + | −3.23 | + |
| EIF1AY | 6 | 22746370 | 22746410 | 8176725 | Y | + | −2.16 | + |
| EIF1AY | 7 | 22749936 | 22749988 | 8176726 | Y | + | −2.23 | + |
| EIF1AY | 8 | 22751413 | 22751442 | 8176727 | Y | + | −1.43 | − |
| EIF1AY | 9 | 22754278 | 22754353 | 8176728 | Y | + | −1.82 | − |
| EIF1AY | 10 | 22754633 | 22754904 | 8176729 | Y | + | 0.02 | − |
| UTY | 1 | 15360263 | 15360287 | 8177138 | Y | − | −0.03 | − |
| UTY | 2 | 15360400 | 15361761 | 8177139 | Y | − | −0.94 | − |
| UTY | 3 | 15362908 | 15362962 | 8177140 | Y | − | −0.83 | − |
| UTY | 4 | 15409468 | 15409492 | 8177141 | Y | − | 0.99 | − |
| UTY | 5 | 15410879 | 15410903 | 8177142 | Y | − | −2.35 | + |
| UTY | 6 | 15414804 | 15414828 | 8177143 | Y | − | −0.67 | − |
| UTY | 7 | 15417280 | 15417304 | 8177144 | Y | − | −0.54 | − |
| UTY | 8 | 15417319 | 15417343 | 8177145 | Y | − | −2.47 | + |
| UTY | 9 | 15417925 | 15417949 | 8177146 | Y | − | −2.36 | + |
| UTY | 10 | 15418069 | 15418093 | 8177147 | Y | − | −1.76 | − |
| UTY | 11 | 15434960 | 15434984 | 8177148 | Y | − | −0.25 | − |
| UTY | 12 | 15435036 | 15435060 | 8177149 | Y | − | 0.09 | − |
| UTY | 13 | 15435459 | 15435617 | 8177150 | Y | − | −0.59 | − |
| UTY | 14 | 15438197 | 15438221 | 8177151 | Y | − | −2.41 | + |
| UTY | 15 | 15447513 | 15447920 | 8177152 | Y | − | −2.51 | + |
| UTY | 16 | 15467108 | 15467132 | 8177153 | Y | − | −2.41 | + |
| UTY | 17 | 15467825 | 15467849 | 8177154 | Y | − | −2.07 | + |
| UTY | 18 | 15469784 | 15469808 | 8177155 | Y | − | −4.08 | + |
| UTY | 19 | 15471663 | 15471814 | 8177156 | Y | − | −2.07 | + |
| UTY | 20 | 15478154 | 15478178 | 8177157 | Y | − | −3.52 | + |
| UTY | 21 | 15481139 | 15481223 | 8177158 | Y | − | −1.92 | + |
| UTY | 22 | 15505739 | 15505763 | 8177159 | Y | − | −3.86 | + |
| UTY | 23 | 15508820 | 15508844 | 8177160 | Y | − | −2.49 | + |
| UTY | 24 | 15526625 | 15526649 | 8177161 | Y | − | −3.29 | + |
| UTY | 25 | 15560898 | 15560922 | 8177162 | Y | − | −2.08 | + |
| UTY | 26 | 15582085 | 15582109 | 8177163 | Y | − | 0.02 | − |
| UTY | 27 | 15590323 | 15591106 | 8177164 | Y | − | 0.59 | − |
| UTY | 28 | 15591140 | 15591164 | 8177165 | Y | − | −1.60 | − |
| UTY | 29 | 15591415 | 15591651 | 8177166 | Y | − | −0.89 | − |
| UTY | 30 | 15591830 | 15591854 | 8177167 | Y | − | −0.97 | − |
| UTY | 31 | 15592002 | 15592483 | 8177168 | Y | − | −0.11 | − |
| HLA-DQA1 | 1 | | | 8178200 | 6 | --- | −0.47 | + |
| HLA-DQA1 | 2 | | | 8178201 | 6 | --- | 0.46 | + |
| HLA-DQA1 | 3 | | | 8178202 | 6 | --- | −0.11 | − |
| HLA-DQA1 | 4 | | | 8178203 | 6 | --- | −0.27 | − |
| HLA-DQA1 | 5 | | | 8178204 | 6 | --- | 0.01 | − |
| HLA-DQA1 | 6 | 32714096 | 32714153 | 8178209 | 6 | + | −0.21 | − |
| HLA-DQA1 | 7 | | | 8179490 | 6 | --- | −0.47 | + |
| HLA-DQA1 | 8 | | | 8179491 | 6 | --- | 0.46 | + |
| HLA-DQA1 | 9 | | | 8179492 | 6 | --- | −0.11 | − |
| HLA-DQA1 | 10 | | | 8179493 | 6 | --- | −0.27 | − |
| HLA-DQA1 | 11 | | | 8179494 | 6 | --- | 0.01 | − |

As can be seen from Tables 11 and 12, the full length OTOF gene was found to be a moderate discriminator between bacterial and viral patients (log 2-fold change of −0.83; Table 3), while a subset of its exons was highly discriminative (log 2-fold change between −2.3 and −3.9; FIG. 2A, Table 12) and could potentially serve as useful biomarkers. Similarly, exons 2 and 7 of TREML4 are much more informative than the full length gene (log 2-fold change of −3.76 and −3.62 compared to −1.64; FIG. 2B, Tables 11 and 12); exon 5 of RGS1 is much more informative than the full length gene (log 2-fold change of −1.93 compared to −0.53; FIG. 2C, Tables 11 and 12).

Example 2

Whole Transcriptome Expression Analysis to Identify Single and Multiple Exons for Discriminating Between Patients with Bacterial and Viral Infections To further identify exons that are differentially expressed in bacterial or viral patients even though the entire full length gene is not, the investors performed full transcriptome analysis on a large cohort of well characterized patients with bacterial and viral infections.

Materials and Methods

Patient Recruitment

Patients were prospectively recruited as part of the 'Curiosity' and the 'Tailored-Treatment' clinical studies (NCT01917461 and NCT02025699). Informed consent was obtained from each participant or legal guardian, as applicable. Inclusion criteria for the infectious disease cohort included: clinical suspicion of an acute infectious disease, peak fever >37.5° C. since symptoms onset, and duration of symptoms ≤12 days. Inclusion criteria for the control group included: clinical impression of a non-infectious disease (e.g. trauma, stroke and myocardial infarction), or healthy subjects. Exclusion criteria included: evidence of any episode of acute infectious disease in the two weeks preceding enrollment; diagnosed congenital immune deficiency; current treatment with immunosuppressive or immunomodulatory therapy; active malignancy, proven or suspected human immunodeficiency virus (HIV)-1, hepatitis B virus (HBV), or hepatitis C virus (HCV) infection. Importantly, in order to enable broad generalization, antibiotic treatment at enrollment did not cause exclusion from the study. An overview of study workflow is depicted in FIG. 1.

Enrollment process and data collection: as in Example 1.
Microbiological investigation: as in Example 1.
Establishing the reference standard: as in Example 1.
Samples, Procedures and RNA Purification:

Venous blood samples were collected in EDTA contained CBC tube and stored at 4° C. for up to 5 hours on site and subsequently fractionated into plasma and cell pellet. Red cells were lysed using EL buffer (QIAGEN, Cat 79217) at room temperature (RT). Leukocytes were lysed in RLT buffer (QIAGEN, Cat 79216) and Homogenized via QIAshredder homogenizer (QIAGEN, Cat 79654). Total RNA was purified from 400 µl lysed Leukocytes using RNeasy™ Micro Kit (QIAGEN, Cat. 74004) according to manufacturer recommended protocols.

Microarray Experiments:

A total of 3 µl of 255 ng/3 µl (85 ng/µl) RNA were transferred and prepare for whole transcriptome expression analysis with GeneChip™ Whole Transcript (WT) Expression Arrays. Amplified ss-cDNA was prepared from 255 ng total RNA using GeneChip™ WT PLUS Reagent Kit (902310, Affymetrix), following manufacturer protocol. Samples were hybridized to GeneChip Human Transcriptome Arrays 2.0 (HTA-Affymetrix) which is the highest resolution microarray for gene expression profiling of all transcript isoforms. HTA display approximately ten probes per exon and four probes per exon-exon splice junction. This array interrogates >245,000 coding transcripts, >40,000 non coding transcripts and >339,000 probe sets covering exon-exon junctions. Arrays were scanned using the Affymetrix GeneChip Scanner 3000 7G.

Statistical analysis: Primary analysis was performed as in example 1.

Results

Patient Characteristics

The studied group of patients included 71 children and 59 adults and was gender balanced (65 females and 65 males). The cohort included 51 patients with bacterial infection and 79 patients with viral infections as determined by the expert panel as described above. Additionally, 13 non-infectious patients were studied (as controls). The patients presented with a variety of clinical syndromes affecting different physiological systems (e.g., respiratory, urinal, central nervous system, systemic).

Single and Multiple Exons can Distinguish Between Bacterial and Viral Patients

The gene expression profiles of blood leukocytes obtained from the described acute infection patients using the GeneChip Human Transcriptome Arrays 2.0 (HTA-Affymetrix) were studied. The inventors identified 140 additional coding and non-coding RNA determinants (in addition to the ones presented in Example 1) for which one or more individual exons presented improved differential expression as compared to their full gene. The present inventors further calculated for these exons the measures of accuracy in distinguishing between bacterial and viral patients including AUC, sensitivity, specificity and t-test P-value (Table 13).

Table 14 describes the expression levels of the whole genes included in Table 13, as well as their measures of accuracy in distinguishing between bacterial and viral patients.

TABLE 13

Exon level analysis of 140 RNA determinants differentially expressed in bacterial and viral patients. Probe set ID is based on GeneChip Human Transcriptome Arrays 2.0 (HTA-Affymetrix) data. Comparison to full gene was calculated as absolute fold change (exon$_i$) - absolute fold change (full length gene); Only exons that presented higher of differential expression of the single exon compared to the full length gene were included.

| Gene Symbol | mRNA Accession | Exon # | Probe Set ID | Chromosome | Strand | Start | Stop | Exon AUC | FC | T-Test | Up in B/V |
|---|---|---|---|---|---|---|---|---|---|---|---|
| PGD | NM_002631 | 2 | PSR01002037.hg.1 | 1 | + | 10459138 | 10459168 | 0.88 | 6.5 | 9.5005E−16 | B |
| PGD | NM_002631 | 5 | PSR01002043.hg.1 | 1 | + | 10459689 | 10459748 | 0.88 | 4.3 | 1.6178E−15 | B |
| PGD | NM_002631 | 7 | PSR01002047.hg.1 | 1 | + | 10460450 | 10460503 | 0.83 | 2.4 | 1.9897E−10 | B |
| PGD | NM_002631 | 8 | PSR01002048.hg.1 | 1 | + | 10460504 | 10460598 | 0.89 | 4.8 | 2.7246E−16 | B |
| PGD | NM_002631 | 9 | PSR01002049.hg.1 | 1 | + | 10460599 | 10460629 | 0.89 | 2.9 | 6.8385E−17 | B |
| PGD | NM_002631 | 10 | PSR01002050.hg.1 | 1 | + | 10463128 | 10463193 | 0.89 | 2.5 | 6.9918E−17 | B |
| PGD | NM_002631 | 11 | PSR01002051.hg.1 | 1 | + | 10464218 | 10464333 | 0.89 | 3.0 | 6.3173E−16 | B |
| PGD | NM_002631 | 16 | PSR01002058.hg.1 | 1 | + | 10475349 | 10475449 | 0.79 | 2.4 | 6.2357E−09 | B |
| PGD | NM_002631 | 17 | PSR01002059.hg.1 | 1 | + | 10477044 | 10477089 | 0.89 | 2.4 | 1.0848E−16 | B |

TABLE 13-continued

Exon level analysis of 140 RNA determinants differentially expressed in bacterial and viral patients. Probe set ID is based on GeneChip Human Transcriptome Arrays 2.0 (HTA-Affymetrix) data. Comparison to full gene was calculated as absolute fold change ($exon_i$) - absolute fold change (full length gene); Only exons that presented higher of differential expression of the single exon compared to the full length gene were included.

| Gene Symbol | mRNA Accession | Exon # | Probe Set ID | Chromosome | Strand | Start | Stop | Exon AUC | FC | T-Test | Up in B/V |
|---|---|---|---|---|---|---|---|---|---|---|---|
| PGD | NM_002631 | 18 | PSR01002061.hg.1 | 1 | + | 10477102 | 10477174 | 0.89 | 2.6 | 2.4165E-16 | B |
| PGD | NM_002631 | 26 | PSR01002072.hg.1 | 1 | + | 10480202 | 10480233 | 0.82 | 2.5 | 2.7608E-11 | B |
| ALPL | NM_000478 | 2 | PSR01004187.hg.1 | 1 | + | 21835951 | 21836010 | 0.89 | 15.2 | 5.3026E-16 | B |
| ALPL | NM_000478 | 4 | PSR01004190.hg.1 | 1 | + | 21880471 | 21880574 | 0.90 | 8.7 | 7.5066E-13 | B |
| ALPL | NM_000478 | 5 | PSR01004191.hg.1 | 1 | + | 21880575 | 21880635 | 0.90 | 7.8 | 4.211E-11 | B |
| ALPL | NM_000478 | 6 | PSR01004192.hg.1 | 1 | + | 21887119 | 21887238 | 0.90 | 6.5 | 1.3328E-11 | B |
| ALPL | NM_000478 | 7 | PSR01004193.hg.1 | 1 | + | 21887590 | 21887630 | 0.90 | 12.9 | 1.5554E-13 | B |
| ALPL | NM_000478 | 8 | PSR01004194.hg.1 | 1 | + | 21887631 | 21887705 | 0.90 | 8.7 | 2.23E-15 | B |
| ALPL | NM_000478 | 9 | PSR01004195.hg.1 | 1 | + | 21889603 | 21889777 | 0.91 | 8.0 | 4.5496E-14 | B |
| ALPL | NM_000478 | 10 | PSR01004196.hg.1 | 1 | + | 21890534 | 21890704 | 0.90 | 7.7 | 4.7535E-12 | B |
| ALPL | NM_000478 | 12 | PSR01004200.hg.1 | 1 | + | 21896798 | 21896867 | 0.89 | 6.7 | 3.828E-13 | B |
| ALPL | NM_000478 | 13 | PSR01004201.hg.1 | 1 | + | 21900158 | 21900292 | 0.89 | 6.4 | 5.7267E-12 | B |
| ALPL | NM_000478 | 15 | PSR01004203.hg.1 | 1 | + | 21902226 | 21902417 | 0.90 | 6.6 | 1.1195E-12 | B |
| ALPL | NM_000478 | 17 | PSR01004205.hg.1 | 1 | + | 21903876 | 21904224 | 0.89 | 9.3 | 1.6746E-14 | B |
| ALPL | NM_000478 | 19 | PSR01004207.hg.1 | 1 | + | 21904506 | 21904817 | 0.87 | 6.6 | 1.0724E-11 | B |
| ZNF684 | NM_152373 | 4 | PSR01008035.hg.1 | 1 | + | 40998815 | 40998853 | 0.84 | -4.9 | 1.1994E-10 | V |
| ZNF684 | NM_152373 | 5 | PSR01008036.hg.1 | 1 | + | 41006258 | 41006384 | 0.84 | -4.8 | 2.8365E-11 | V |
| ZNF684 | NM_152373 | 7 | PSR01008038.hg.1 | 1 | + | 41007287 | 41007783 | 0.84 | -3.5 | 6.0757E-10 | V |
| ZNF684 | NM_152373 | 9 | PSR01008041.hg.1 | 1 | + | 41012234 | 41012380 | 0.84 | -4.9 | 2.1245E-11 | V |
| ZNF684 | NM_152373 | 10 | PSR01008042.hg.1 | 1 | + | 41012381 | 41012437 | 0.85 | -5.1 | 1.2275E-11 | V |
| ZNF684 | NM_152373 | 11 | PSR01008043.hg.1 | 1 | + | 41012438 | 41013457 | 0.85 | -4.6 | 1.9316E-11 | V |
| ZNF684 | NM_152373 | 12 | PSR01008044.hg.1 | 1 | + | 41013458 | 41013838 | 0.84 | -4.1 | 1.0776E-10 | V |
| NEXN | NM_001172309 | 14 | PSR01012590.hg.1 | 1 | + | 78395001 | 78395189 | 0.82 | -4.4 | 1.1145E-10 | V |
| NEXN | NM_001172309 | 17 | PSR01012594.hg.1 | 1 | + | 78398967 | 78399069 | 0.81 | -3.5 | 2.1524E-09 | V |
| NEXN | NM_001172309 | 18 | PSR01012595.hg.1 | 1 | + | 78399070 | 78399164 | 0.83 | -3.4 | 1.0467E-10 | V |
| NEXN | NM_001172309 | 19 | PSR01012596.hg.1 | 1 | + | 78401508 | 78401604 | 0.84 | -4.9 | 1.3688E-11 | V |
| NEXN | NM_001172309 | 20 | PSR01012597.hg.1 | 1 | + | 78401605 | 78401655 | 0.84 | -5.4 | 3.4968E-12 | V |
| NEXN | NM_001172309 | 21 | PSR01012598.hg.1 | 1 | + | 78401656 | 78401729 | 0.84 | -4.4 | 1.3086E-11 | V |
| NEXN | NM_001172309 | 23 | PSR01012600.hg.1 | 1 | + | 78407708 | 78407893 | 0.82 | -5.2 | 4.0086E-11 | V |
| NEXN | NM_001172309 | 24 | PSR01012601.hg.1 | 1 | + | 78408146 | 78408438 | 0.83 | -5.0 | 1.2234E-11 | V |
| NEXN | NM_001172309 | 25 | PSR01012602.hg.1 | 1 | + | 78408439 | 78408503 | 0.81 | -5.0 | 2.9889E-10 | V |
| NEXN | NM_001172309 | 27 | PSR01012606.hg.1 | 1 | + | 78408616 | 78408884 | 0.82 | -5.5 | 1.0437E-10 | V |
| NEXN | NM_001172309 | 28 | PSR01012609.hg.1 | 1 | + | 78408910 | 78409576 | 0.85 | -4.2 | 3.4161E-12 | V |
| MOV10 | NM_001130079 | 9 | PSR01015778.hg.1 | 1 | + | 113217470 | 113217505 | 0.80 | -3.4 | 1.0736E-09 | V |
| MOV10 | NM_001130079 | 11 | PSR01015780.hg.1 | 1 | + | 113217578 | 113217671 | 0.80 | -3.6 | 2.5679E-10 | V |
| MOV10 | NM_001130079 | 13 | PSR01015782.hg.1 | 1 | + | 113229588 | 113229621 | 0.81 | -3.6 | 2.1675E-10 | V |
| MOV10 | NM_001130079 | 15 | PSR01015784.hg.1 | 1 | + | 113230950 | 113231105 | 0.81 | -3.2 | 8.8624E-10 | V |
| MOV10 | NM_001130079 | 17 | PSR01015786.hg.1 | 1 | + | 113231557 | 113231760 | 0.79 | -4.1 | 4.2929E-10 | V |
| MOV10 | NM_001130079 | 18 | PSR01015787.hg.1 | 1 | + | 113232037 | 113232062 | 0.75 | -3.6 | 1.5089E-07 | V |
| MOV10 | NM_001130079 | 19 | PSR01015789.hg.1 | 1 | + | 113232064 | 113232167 | 0.77 | -3.6 | 2.0484E-08 | V |
| MOV10 | NM_001130079 | 20 | PSR01015790.hg.1 | 1 | + | 113232168 | 113232272 | 0.74 | -3.3 | 3.1452E-07 | V |
| MOV10 | NM_001130079 | 22 | PSR01015792.hg.1 | 1 | + | 113234287 | 113234421 | 0.75 | -2.9 | 3.6548E-07 | V |
| MOV10 | NM_001130079 | 25 | PSR01015795.hg.1 | 1 | + | 113236640 | 113236794 | 0.78 | -3.4 | 3.7779E-09 | V |
| MOV10 | NM_001130079 | 26 | PSR01015796.hg.1 | 1 | + | 113237075 | 113237206 | 0.79 | -3.4 | 2.9013E-09 | V |
| MOV10 | NM_001130079 | 28 | PSR01015798.hg.1 | 1 | + | 113237371 | 113237449 | 0.80 | -4.8 | 4.0186E-10 | V |
| MOV10 | NM_001130079 | 29 | PSR01015799.hg.1 | 1 | + | 113237450 | 113237518 | 0.80 | -4.8 | 3.0348E-10 | V |
| MOV10 | NM_001130079 | 30 | PSR01015800.hg.1 | 1 | + | 113238038 | 113238196 | 0.80 | -5.2 | 1.6428E-10 | V |
| MOV10 | NM_001130079 | 31 | PSR01015801.hg.1 | 1 | + | 113238770 | 113238873 | 0.80 | -4.0 | 1.5676E-10 | V |
| MOV10 | NM_001130079 | 33 | PSR01015803.hg.1 | 1 | + | 113239059 | 113239156 | 0.79 | -3.9 | 7.1692E-10 | V |
| MOV10 | NM_001130079 | 35 | PSR01015805.hg.1 | 1 | + | 113239361 | 113239440 | 0.80 | -4.5 | 1.5064E-10 | V |
| MOV10 | NM_001130079 | 36 | PSR01015806.hg.1 | 1 | + | 113239441 | 113239468 | 0.80 | -4.6 | 1.7979E-10 | V |
| MOV10 | NM_001130079 | 38 | PSR01015808.hg.1 | 1 | + | 113240616 | 113240733 | 0.79 | -3.4 | 1.1134E-09 | V |
| MOV10 | NM_001130079 | 39 | PSR01015810.hg.1 | 1 | + | 113240930 | 113240989 | 0.80 | -3.8 | 2.4996E-10 | V |
| MOV10 | NM_001130079 | 43 | PSR01015816.hg.1 | 1 | + | 113241337 | 113241411 | 0.80 | -4.3 | 2.0209E-10 | V |
| MOV10 | NM_001130079 | 46 | PSR01015819.hg.1 | 1 | + | 113241815 | 113242079 | 0.79 | -4.0 | 4.8309E-09 | V |
| MOV10 | NM_001130079 | 47 | PSR01015820.hg.1 | 1 | + | 113242080 | 113242245 | 0.79 | -3.9 | 4.2685E-09 | V |
| MOV10 | NM_001130079 | 49 | PSR01015823.hg.1 | 1 | + | 113242309 | 113242383 | 0.81 | -4.8 | 2.0699E-10 | V |
| MOV10 | NM_001130079 | 50 | PSR01015824.hg.1 | 1 | + | 113242384 | 113242432 | 0.81 | -4.9 | 9.1333E-11 | V |
| MOV10 | NM_001130079 | 52 | PSR01015826.hg.1 | 1 | + | 113242516 | 113242604 | 0.81 | -5.1 | 6.7984E-11 | V |
| MOV10 | NM_001130079 | 53 | PSR01015827.hg.1 | 1 | + | 113242605 | 113242840 | 0.78 | -3.1 | 1.2249E-08 | V |
| MOV10 | NM_001130079 | 54 | PSR01015828.hg.1 | 1 | + | 113242841 | 113242962 | 0.81 | -4.3 | 8.0427E-11 | V |
| MOV10 | NM_001130079 | 56 | PSR01015830.hg.1 | 1 | + | 113243038 | 113243162 | 0.82 | -3.8 | 3.3272E-11 | V |
| MOV10 | NM_001130079 | 58 | PSR01015833.hg.1 | 1 | + | 113243231 | 113243332 | 0.82 | -3.0 | 1.1652E-10 | V |
| RABGAP1L | NM_001035230 | 38 | PSR01023527.hg.1 | 1 | + | 174843609 | 174843644 | 0.94 | -12.8 | 2.4936E-19 | V |
| RABGAP1L | NM_001035230 | 39 | PSR01023528.hg.1 | 1 | + | 174844656 | 174844683 | 0.80 | -3.3 | 3.15E-08 | V |
| RABGAP1L | NM_001035230 | 40 | PSR01023529.hg.1 | 1 | + | 174844684 | 174844851 | 0.76 | -2.0 | 1.1879E-06 | V |
| RABGAP1L | NM_001035230 | 41 | PSR01023530.hg.1 | 1 | + | 174846530 | 174846577 | 0.93 | -17.1 | 7.8753E-20 | V |
| RABGAP1L | NM_001035230 | 42 | PSR01023531.hg.1 | 1 | + | 174846578 | 174846743 | 0.94 | -10.5 | 2.3357E-18 | V |
| RABGAP1L | NM_001035230 | 43 | PSR01023532.hg.1 | 1 | + | 174926594 | 174926686 | 0.90 | -5.0 | 2.5751E-16 | V |

TABLE 13-continued

Exon level analysis of 140 RNA determinants differentially expressed in bacterial and viral patients. Probe set ID is based on GeneChip Human Transcriptome Arrays 2.0 (HTA-Affymetrix) data. Comparison to full gene was calculated as absolute fold change ($exon_i$) - absolute fold change (full length gene); Only exons that presented higher of differential expression of the single exon compared to the full length gene were included.

| Gene Symbol | mRNA Accession | Exon # | Probe Set ID | Chromosome | Strand | Start | Stop | Exon AUC | FC | T-Test | Up in B/V |
|---|---|---|---|---|---|---|---|---|---|---|---|
| RABGAP1L | NM_001035230 | 44 | PSR01023534.hg.1 | 1 | + | 174927028 | 174927310 | 0.92 | −4.9 | 6.3301E−17 | V |
| RABGAP1L | NM_001035230 | 45 | PSR01023539.hg.1 | 1 | + | 174933915 | 174934095 | 0.77 | −1.9 | 5.1453E−09 | V |
| RABGAP1L | NM_001035230 | 46 | PSR01023540.hg.1 | 1 | + | 174934096 | 174934122 | 0.70 | −1.5 | 9.9939E−05 | V |
| RABGAP1L | NM_001035230 | 47 | PSR01023541.hg.1 | 1 | + | 174938414 | 174938524 | 0.86 | −2.9 | 1.043E−12 | V |
| RABGAP1L | NM_001035230 | 48 | PSR01023542.hg.1 | 1 | + | 174945166 | 174945214 | 0.78 | −2.3 | 3.2401E−08 | V |
| RABGAP1L | NM_001035230 | 49 | PSR01023543.hg.1 | 1 | + | 174945215 | 174945319 | 0.84 | −2.7 | 4.5999E−12 | V |
| RABGAP1L | NM_001035230 | 50 | PSR01023544.hg.1 | 1 | + | 174947944 | 174948027 | 0.83 | −2.6 | 2.8296E−11 | V |
| RABGAP1L | NM_001035230 | 51 | PSR01023545.hg.1 | 1 | + | 174951971 | 174952037 | 0.87 | −2.2 | 9.6717E−14 | V |
| RABGAP1L | NM_001035230 | 52 | PSR01023547.hg.1 | 1 | + | 174957778 | 174957881 | 0.85 | −2.7 | 1.0042E−12 | V |
| RABGAP1L | NM_001035230 | 53 | PSR01023548.hg.1 | 1 | + | 174957882 | 174957944 | 0.86 | −2.8 | 2.0742E−13 | V |
| RABGAP1L | NM_001035230 | 54 | PSR01023549.hg.1 | 1 | + | 174957945 | 174957975 | 0.88 | −3.1 | 6.0676E−15 | V |
| RABGAP1L | NM_001035230 | 55 | PSR01023550.hg.1 | 1 | + | 174958986 | 174959478 | 0.84 | −2.8 | 4.573E−12 | V |
| RABGAP1L | NM_001035230 | 56 | PSR01023551.hg.1 | 1 | + | 174959479 | 174959546 | 0.81 | −2.7 | 3.8079E−10 | V |
| RABGAP1L | NM_001035230 | 57 | PSR01023552.hg.1 | 1 | + | 174959547 | 174959622 | 0.82 | −2.5 | 4.186E−10 | V |
| RABGAP1L | NM_001035230 | 58 | PSR01023553.hg.1 | 1 | + | 174959623 | 174959650 | 0.78 | −2.4 | 5.1833E−08 | V |
| RABGAP1L | NM_001035230 | 59 | PSR01023554.hg.1 | 1 | + | 174959651 | 174959730 | 0.81 | −2.4 | 3.3241E−09 | V |
| RABGAP1L | NM_001035230 | 60 | PSR01023555.hg.1 | 1 | + | 174959731 | 174962723 | 0.83 | −2.8 | 1.2983E−11 | V |
| RABGAP1L | NM_001035230 | 61 | PSR01023556.hg.1 | 1 | + | 174962724 | 174963017 | 0.87 | −3.6 | 3.0412E−13 | V |
| RABGAP1L | NM_001035230 | 62 | PSR01023557.hg.1 | 1 | + | 174963018 | 174964438 | 0.86 | −3.0 | 9.6474E−13 | V |
| SRGAP2 | NM_001042758 | 1 | PSR01026804.hg.1 | 1 | + | 206516200 | 206516362 | 0.85 | −3.5 | 1.6724E−11 | V |
| SRGAP2 | NM_001042758 | 2 | PSR01026807.hg.1 | 1 | + | 206557369 | 206557431 | 0.86 | −3.3 | 1.8841E−11 | V |
| SRGAP2 | NM_001042758 | 3 | PSR01026808.hg.1 | 1 | + | 206566046 | 206566212 | 0.88 | −3.5 | 9.5599E−13 | V |
| SRGAP2 | NM_001042758 | 4 | PSR01026809.hg.1 | 1 | + | 206566213 | 206566261 | 0.84 | −3.4 | 2.7328E−11 | V |
| SRGAP2 | NM_001042758 | 5 | PSR01026810.hg.1 | 1 | + | 206566902 | 206567030 | 0.85 | −3.6 | 1.2477E−11 | V |
| SRGAP2 | NM_001042758 | 6 | PSR01026812.hg.1 | 1 | + | 206574783 | 206575004 | 0.87 | −3.7 | 1.0259E−12 | V |
| SRGAP2 | NM_001042758 | 8 | PSR01026814.hg.1 | 1 | + | 206578608 | 206578709 | 0.88 | −3.7 | 1.5194E−12 | V |
| SRGAP2 | NM_001042758 | 9 | PSR01026815.hg.1 | 1 | + | 206579736 | 206579933 | 0.88 | −3.7 | 2.6272E−12 | V |
| SRGAP2 | NM_001042758 | 10 | PSR01026816.hg.1 | 1 | + | 206579934 | 206580621 | 0.84 | −3.3 | 3.0165E−10 | V |
| SRGAP2 | NM_001042758 | 11 | PSR01026817.hg.1 | 1 | + | 206580622 | 206581301 | 0.83 | −3.2 | 1.7314E−10 | V |
| SRGAP2 | NM_001042758 | 12 | PSR01026818.hg.1 | 1 | + | 206581302 | 206581391 | 0.81 | −3.0 | 4.1721E−09 | V |
| SRGAP2 | NM_001042758 | 13 | PSR01026819.hg.1 | 1 | + | 206589249 | 206589333 | 0.87 | −3.8 | 7.1596E−12 | V |
| SRGAP2 | NM_001042758 | 14 | PSR01026820.hg.1 | 1 | + | 206592725 | 206592752 | 0.88 | −5.4 | 5.2589E−13 | V |
| SRGAP2 | NM_001042758 | 15 | PSR01026822.hg.1 | 1 | + | 206603512 | 206603572 | 0.86 | −3.8 | 1.7255E−11 | V |
| SRGAP2 | NM_001042758 | 16 | PSR01026823.hg.1 | 1 | + | 206610315 | 206610392 | 0.88 | −4.2 | 5.0021E−13 | V |
| SRGAP2 | NM_001042758 | 17 | PSR01026824.hg.1 | 1 | + | 206611314 | 206611448 | 0.89 | −4.0 | 5.9185E−13 | V |
| SRGAP2 | NM_001042758 | 18 | PSR01026825.hg.1 | 1 | + | 206613326 | 206613431 | 0.90 | −4.3 | 4.0539E−14 | V |
| SRGAP2 | NM_001042758 | 19 | PSR01026826.hg.1 | 1 | + | 206619421 | 206619645 | 0.88 | −3.8 | 8.2031E−12 | V |
| SRGAP2 | NM_001042758 | 20 | PSR01026827.hg.1 | 1 | + | 206623731 | 206623783 | 0.86 | −3.6 | 4.0345E−11 | V |
| SRGAP2 | NM_001042758 | 21 | PSR01026828.hg.1 | 1 | + | 206623784 | 206623810 | 0.89 | −3.8 | 1.2184E−11 | V |
| SRGAP2 | NM_001042758 | 22 | PSR01026829.hg.1 | 1 | + | 206626546 | 206626690 | 0.87 | −2.6 | 1.0562E−09 | V |
| SRGAP2 | NM_001042758 | 24 | PSR01026831.hg.1 | 1 | + | 206627490 | 206627855 | 0.85 | −3.0 | 2.2555E−09 | V |
| SRGAP2 | NM_001042758 | 25 | PSR01026833.hg.1 | 1 | + | 206627875 | 206628046 | 0.83 | −2.7 | 8.6877E−09 | V |
| SRGAP2 | NM_001042758 | 26 | PSR01026834.hg.1 | 1 | + | 206628224 | 206628370 | 0.89 | −4.2 | 1.9472E−13 | V |
| SRGAP2 | NM_001042758 | 27 | PSR01026835.hg.1 | 1 | + | 206628371 | 206629118 | 0.88 | −4.6 | 1.2052E−12 | V |
| SRGAP2 | NM_001042758 | 28 | PSR01026836.hg.1 | 1 | + | 206629119 | 206629477 | 0.89 | −3.6 | 4.766E−11 | V |
| SRGAP2 | NM_001042758 | 30 | PSR01026839.hg.1 | 1 | + | 206631717 | 206631755 | 0.75 | −2.5 | 4.8212E−07 | V |
| SRGAP2 | NM_001042758 | 33 | PSR01026843.hg.1 | 1 | + | 206634382 | 206635245 | 0.85 | −3.4 | 1.7454E−12 | V |
| SRGAP2 | NM_001042758 | 34 | PSR01026845.hg.1 | 1 | + | 206635248 | 206636191 | 0.82 | −2.5 | 5.9596E−10 | V |
| CR1 | NM_000573 | 2 | PSR01027185.hg.1 | 1 | + | 207669573 | 207669612 | 0.89 | 5.9 | 2.8248E−18 | B |
| CR1 | NM_000573 | 4 | PSR01027187.hg.1 | 1 | + | 207669686 | 207669733 | 0.90 | 5.2 | 2.0042E−17 | B |
| CR1 | NM_000573 | 5 | PSR01027188.hg.1 | 1 | + | 207679249 | 207679428 | 0.89 | 4.5 | 7.8864E−17 | B |
| CR1 | NM_000573 | 6 | PSR01027189.hg.1 | 1 | + | 207680059 | 207680158 | 0.90 | 4.7 | 1.9531E−17 | B |
| CR1 | NM_000573 | 8 | PSR01027191.hg.1 | 1 | + | 207684914 | 207684999 | 0.90 | 4.2 | 2.2329E−17 | B |
| CR1 | NM_000573 | 10 | PSR01027193.hg.1 | 1 | + | 207700098 | 207700274 | 0.90 | 4.3 | 2.8706E−17 | B |
| CR1 | NM_000573 | 19 | PSR01027203.hg.1 | 1 | + | 207718653 | 207718829 | 0.90 | 4.2 | 5.2432E−17 | B |
| CR1 | NM_000573 | 29 | PSR01027213.hg.1 | 1 | + | 207737209 | 207737385 | 0.89 | 4.0 | 1.3019E−16 | B |
| CR1 | NM_000573 | 38 | PSR01027222.hg.1 | 1 | + | 207753585 | 207753761 | 0.88 | 4.8 | 9.1082E−16 | B |
| CR1 | NM_000573 | 39 | PSR01027223.hg.1 | 1 | + | 207753856 | 207753958 | 0.90 | 4.1 | 1.8255E−16 | B |
| CR1 | NM_000573 | 44 | PSR01027228.hg.1 | 1 | + | 207780596 | 207780681 | 0.90 | 4.1 | 3.7891E−17 | B |
| CR1 | NM_000573 | 45 | PSR01027229.hg.1 | 1 | + | 207782635 | 207783033 | 0.89 | 4.8 | 4.8383E−17 | B |
| CR1 | NM_000573 | 46 | PSR01027230.hg.1 | 1 | + | 207785022 | 207785198 | 0.88 | 4.7 | 8.689E−16 | B |
| CR1 | NM_000573 | 49 | PSR01027233.hg.1 | 1 | + | 207789920 | 207790147 | 0.89 | 4.1 | 6.4433E−17 | B |
| CR1 | NM_000573 | 50 | PSR01027234.hg.1 | 1 | + | 207791416 | 207791592 | 0.89 | 4.2 | 4.8923E−16 | B |
| CR1 | NM_000573 | 51 | PSR01027235.hg.1 | 1 | + | 207793225 | 207793410 | 0.90 | 4.4 | 9.7728E−18 | B |
| CR1 | NM_000573 | 54 | PSR01027240.hg.1 | 1 | + | 207812755 | 207813553 | 0.91 | 3.9 | 6.3714E−17 | B |
| CR1 | NM_000573 | 55 | PSR01027241.hg.1 | 1 | + | 207813554 | 207813992 | 0.90 | 5.8 | 3.1487E−18 | B |
| CR1 | NM_000573 | 56 | PSR01027242.hg.1 | 1 | + | 207813993 | 207815110 | 0.90 | 4.7 | 6.1068E−18 | B |
| CR1L | NM_175710 | 5 | PSR01027249.hg.1 | 1 | + | 207842790 | 207842910 | 0.90 | 4.4 | 1.1022E−18 | B |
| CR1L | NM_175710 | 6 | PSR01027250.hg.1 | 1 | + | 207850734 | 207850913 | 0.90 | 3.2 | 4.2921E−17 | B |

TABLE 13-continued

Exon level analysis of 140 RNA determinants differentially expressed in bacterial and viral patients. Probe set ID is based on GeneChip Human Transcriptome Arrays 2.0 (HTA-Affymetrix) data. Comparison to full gene was calculated as absolute fold change (exon$_i$) - absolute fold change (full length gene); Only exons that presented higher of differential expression of the single exon compared to the full length gene were included.

| Gene Symbol | mRNA Accession | Exon # | Probe Set ID | Chromosome | Strand | Start | Stop | Exon AUC | FC | T-Test | Up in B/V |
|---|---|---|---|---|---|---|---|---|---|---|---|
| CR1L | NM_175710 | 7 | PSR01027251.hg.1 | 1 | + | 207851543 | 207851612 | 0.90 | 5.2 | 9.6256E−18 | B |
| CR1L | NM_175710 | 11 | PSR01027255.hg.1 | 1 | + | 207867698 | 207868096 | 0.88 | 2.9 | 4.141E−16 | B |
| CR1L | NM_175710 | 13 | PSR01027257.hg.1 | 1 | + | 207871116 | 207871218 | 0.90 | 2.9 | 7.2171E−18 | B |
| CR1L | NM_175710 | 14 | PSR01027258.hg.1 | 1 | + | 207872534 | 207872619 | 0.89 | 3.4 | 1.0389E−16 | B |
| CR1L | NM_175710 | 15 | PSR01027259.hg.1 | 1 | + | 207874864 | 207874963 | 0.88 | 3.6 | 4.8142E−16 | B |
| CR1L | NM_175710 | 16 | PSR01027261.hg.1 | 1 | + | 207881523 | 207881608 | 0.88 | 3.2 | 3.5723E−16 | B |
| CR1L | NM_175710 | 18 | PSR01027263.hg.1 | 1 | + | 207888657 | 207888742 | 0.90 | 3.4 | 2.3018E−16 | B |
| CR1L | NM_175710 | 22 | PSR01027271.hg.1 | 1 | + | 207911749 | 207911885 | 0.90 | 4.6 | 2.4525E−16 | B |
| — | ENST00000442385 | 3 | PSR01034493.hg.1 | 1 | − | 16543622 | 16543655 | 0.86 | −7.7 | 5.1717E−12 | V |
| — | ENST00000442385 | 4 | PSR01034494.hg.1 | 1 | − | 16543656 | 16543823 | 0.86 | −2.6 | 1.8109E−09 | V |
| PADI2 | NM_007365 | 7 | PSR01034860.hg.1 | 1 | − | 17401351 | 17401444 | 0.86 | 3.7 | 1.502E−13 | B |
| PADI2 | NM_007365 | 12 | PSR01034865.hg.1 | 1 | − | 17405759 | 17405910 | 0.86 | 4.2 | 1.227E−13 | B |
| PADI2 | NM_007365 | 13 | PSR01034866.hg.1 | 1 | − | 17409040 | 17409147 | 0.86 | 5.3 | 4.0981E−14 | B |
| PADI2 | NM_007365 | 16 | PSR01034869.hg.1 | 1 | − | 17410221 | 17410332 | 0.87 | 4.8 | 7.2426E−14 | B |
| PADI2 | NM_007365 | 17 | PSR01034870.hg.1 | 1 | − | 17411094 | 17411197 | 0.88 | 4.0 | 5.4975E−14 | B |
| PADI2 | NM_007365 | 18 | PSR01034871.hg.1 | 1 | − | 17413016 | 17413194 | 0.87 | 3.9 | 1.6657E−13 | B |
| PADI2 | NM_007365 | 19 | PSR01034872.hg.1 | 1 | − | 17418903 | 17419028 | 0.87 | 4.4 | 1.5149E−14 | B |
| PADI2 | NM_007365 | 22 | PSR01034875.hg.1 | 1 | − | 17429482 | 17429554 | 0.88 | 4.7 | 1.02E−14 | B |
| PADI2 | NM_007365 | 23 | PSR01034876.hg.1 | 1 | − | 17431373 | 17431556 | 0.88 | 5.0 | 3.4241E−16 | B |
| MIR1182 | NR_031593 | 1 | PSR01060037.hg.1 | 1 | − | 231154704 | 231154921 | 0.68 | 1.4 | 0.00016719 | B |
| MIR1182 | NR_031593 | 2 | PSR01060039.hg.1 | 1 | − | 231154933 | 231155163 | 0.66 | 1.7 | 0.00039405 | B |
| MIR1182 | NR_031593 | 3 | PSR01060040.hg.1 | 1 | − | 231155164 | 231155412 | 0.64 | 1.4 | 0.00092686 | B |
| MIR1182 | NR_031593 | 4 | PSR01060042.hg.1 | 1 | − | 231155413 | 231155573 | 0.67 | 1.4 | 0.00039511 | B |
| MIR1182 | NR_031593 | 5 | PSR01060043.hg.1 | 1 | − | 231155574 | 231155670 | 0.68 | 1.5 | 0.00018452 | B |
| MIR1182 | NR_031593 | 6 | PSR01060044.hg.1 | 1 | − | 231155671 | 231155872 | 0.68 | 1.4 | 3.0173E−05 | B |
| — | TCONS_00000869-XLOC_000105 | 1 | PSR01062377.hg.1 | 1 | + | 27371709 | 27371806 | 0.83 | −6.5 | 1.956E−08 | V |
| — | TCONS_00000869-XLOC_000105 | 2 | PSR01062378.hg.1 | 1 | + | 27384889 | 27384983 | 0.82 | −5.0 | 3.2735E−08 | V |
| — | TCONS_00000869-XLOC_000105 | 3 | PSR01062379.hg.1 | 1 | + | 27384988 | 27385013 | 0.75 | −2.4 | 5.7721E−07 | V |
| — | TCONS_00000869-XLOC_000105 | 4 | PSR01062380.hg.1 | 1 | + | 27386505 | 27391197 | 0.78 | −1.6 | 2.1366E−06 | V |
| TRIB2 | NM_021643 | 5 | PSR02001049.hg.1 | 2 | + | 12857948 | 12858363 | 0.88 | −6.1 | 5.8576E−15 | V |
| TRIB2 | NM_021643 | 6 | PSR02001050.hg.1 | 2 | + | 12858364 | 12858703 | 0.88 | −6.8 | 7.4647E−16 | V |
| TRIB2 | NM_021643 | 7 | PSR02001051.hg.1 | 2 | + | 12863386 | 12863678 | 0.87 | −5.6 | 6.66E−15 | V |
| TRIB2 | NM_021643 | 9 | PSR02001053.hg.1 | 2 | + | 12880452 | 12881398 | 0.89 | −8.6 | 6.5E−17 | V |
| TRIB2 | NM_021643 | 10 | PSR02001055.hg.1 | 2 | + | 12881399 | 12881530 | 0.89 | −7.3 | 1.1873E−15 | V |
| TRIB2 | NM_021643 | 11 | PSR02001056.hg.1 | 2 | + | 12881531 | 12882858 | 0.87 | −5.7 | 1.0992E−14 | V |
| PLB1 | NM_001170585 | 6 | PSR02002574.hg.1 | 2 | + | 28742572 | 28742630 | 0.77 | 3.7 | 3.5923E−08 | B |
| PLB1 | NM_001170585 | 10 | PSR02002578.hg.1 | 2 | + | 28752595 | 28752646 | 0.76 | 3.4 | 1.8668E−07 | B |
| PLB1 | NM_001170585 | 11 | PSR02002579.hg.1 | 2 | + | 28754975 | 28755061 | 0.78 | 3.1 | 5.9741E−08 | B |
| PLB1 | NM_001170585 | 28 | PSR02002599.hg.1 | 2 | + | 28802494 | 28802574 | 0.76 | 2.9 | 2.1374E−07 | B |
| PLB1 | NM_001170585 | 32 | PSR02002603.hg.1 | 2 | + | 28808628 | 28808709 | 0.76 | 3.5 | 1.5481E−07 | B |
| PLB1 | NM_001170585 | 33 | PSR02002604.hg.1 | 2 | + | 28812317 | 28812421 | 0.82 | 2.8 | 1.5171E−10 | B |
| PLB1 | NM_001170585 | 34 | PSR02002605.hg.1 | 2 | + | 28812542 | 28812637 | 0.81 | 3.7 | 5.5443E−11 | B |
| PLB1 | NM_001170585 | 35 | PSR02002606.hg.1 | 2 | + | 28812872 | 28812943 | 0.81 | 3.9 | 9.6135E−11 | B |
| PLB1 | NM_001170585 | 36 | PSR02002607.hg.1 | 2 | + | 28814000 | 28814025 | 0.82 | 4.2 | 3.2701E−11 | B |
| PLB1 | NM_001170585 | 38 | PSR02002610.hg.1 | 2 | + | 28815528 | 28815586 | 0.81 | 2.8 | 7.1261E−10 | B |
| PLB1 | NM_001170585 | 41 | PSR02002613.hg.1 | 2 | + | 28816839 | 28818924 | 0.78 | 3.0 | 2.0378E−09 | B |
| PLB1 | NM_001170585 | 42 | PSR02002616.hg.1 | 2 | + | 28820872 | 28820915 | 0.83 | 3.2 | 4.2751E−12 | B |
| PLB1 | NM_001170585 | 43 | PSR02002617.hg.1 | 2 | + | 28821519 | 28821627 | 0.84 | 4.3 | 6.08E−12 | B |
| PLB1 | NM_001170585 | 44 | PSR02002618.hg.1 | 2 | + | 28823676 | 28823727 | 0.84 | 5.2 | 5.1E−12 | B |
| PLB1 | NM_001170585 | 45 | PSR02002619.hg.1 | 2 | + | 28824119 | 28824199 | 0.84 | 4.4 | 5.1101E−12 | B |
| PLB1 | NM_001170585 | 46 | PSR02002622.hg.1 | 2 | + | 28824786 | 28824831 | 0.86 | 6.6 | 1.3174E−13 | B |
| PLB1 | NM_001170585 | 47 | PSR02002623.hg.1 | 2 | + | 28825688 | 28825786 | 0.86 | 6.3 | 3.7204E−15 | B |
| PLB1 | NM_001170585 | 48 | PSR02002624.hg.1 | 2 | + | 28826833 | 28826914 | 0.87 | 6.0 | 4.9754E−16 | B |
| PLB1 | NM_001170585 | 49 | PSR02002625.hg.1 | 2 | + | 28827522 | 28827593 | 0.86 | 5.5 | 3.6385E−15 | B |
| PLB1 | NM_001170585 | 50 | PSR02002626.hg.1 | 2 | + | 28827594 | 28827626 | 0.85 | 5.6 | 4.9296E−14 | B |
| PLB1 | NM_001170585 | 51 | PSR02002627.hg.1 | 2 | + | 28828720 | 28828815 | 0.86 | 6.3 | 1.921E−14 | B |
| PLB1 | NM_001170585 | 52 | PSR02002628.hg.1 | 2 | + | 28829363 | 28829434 | 0.85 | 5.0 | 1.4062E−13 | B |
| PLB1 | NM_001170585 | 53 | PSR02002629.hg.1 | 2 | + | 28836898 | 28836963 | 0.85 | 4.9 | 7.7689E−14 | B |
| PLB1 | NM_001170585 | 54 | PSR02002630.hg.1 | 2 | + | 28840594 | 28840654 | 0.86 | 5.7 | 8.5987E−15 | B |
| PLB1 | NM_001170585 | 55 | PSR02002631.hg.1 | 2 | + | 28841208 | 28841266 | 0.85 | 4.6 | 1.378E−14 | B |
| PLB1 | NM_001170585 | 57 | PSR02002633.hg.1 | 2 | + | 28843132 | 28843199 | 0.86 | 5.3 | 3.6159E−14 | B |
| PLB1 | NM_001170585 | 58 | PSR02002634.hg.1 | 2 | + | 28843467 | 28843510 | 0.86 | 4.5 | 2.3377E−14 | B |
| PLB1 | NM_001170585 | 60 | PSR02002636.hg.1 | 2 | + | 28843746 | 28843845 | 0.86 | 5.7 | 6.9026E−15 | B |
| PLB1 | NM_001170585 | 61 | PSR02002637.hg.1 | 2 | + | 28847924 | 28847975 | 0.86 | 4.6 | 1.9714E−14 | B |
| PLB1 | NM_001170585 | 62 | PSR02002638.hg.1 | 2 | + | 28849295 | 28849375 | 0.86 | 5.0 | 9.1463E−14 | B |

TABLE 13-continued

Exon level analysis of 140 RNA determinants differentially expressed in bacterial and viral patients. Probe set ID is based on GeneChip Human Transcriptome Arrays 2.0 (HTA-Affymetrix) data. Comparison to full gene was calculated as absolute fold change ($exon_i$) - absolute fold change (full length gene); Only exons that presented higher of differential expression of the single exon compared to the full length gene were included.

| Gene Symbol | mRNA Accession | Exon # | Probe Set ID | Chromosome | Strand | Start | Stop | Exon AUC | FC | T-Test | Up in B/V |
|---|---|---|---|---|---|---|---|---|---|---|---|
| PLB1 | NM_001170585 | 64 | PSR02002640.hg.1 | 2 | + | 28851430 | 28851495 | 0.86 | 5.1 | 6.1014E−14 | B |
| PLB1 | NM_001170585 | 65 | PSR02002641.hg.1 | 2 | + | 28851961 | 28852052 | 0.84 | 5.5 | 3.3128E−13 | B |
| PLB1 | NM_001170585 | 66 | PSR02002642.hg.1 | 2 | + | 28853453 | 28853531 | 0.84 | 4.5 | 6.4782E−13 | B |
| PLB1 | NM_001170585 | 67 | PSR02002643.hg.1 | 2 | + | 28854903 | 28855007 | 0.85 | 4.2 | 7.9442E−13 | B |
| PLB1 | NM_001170585 | 68 | PSR02002644.hg.1 | 2 | + | 28855811 | 28855906 | 0.84 | 5.8 | 6.1704E−13 | B |
| PLB1 | NM_001170585 | 69 | PSR02002645.hg.1 | 2 | + | 28863793 | 28863867 | 0.83 | 4.5 | 1.9495E−13 | B |
| PLB1 | NM_001170585 | 70 | PSR02002646.hg.1 | 2 | + | 28865724 | 28866018 | 0.83 | 3.3 | 4.081E−14 | B |
| PLB1 | NM_001170585 | 71 | PSR02002647.hg.1 | 2 | + | 28866019 | 28866099 | 0.81 | 3.1 | 3.0782E−12 | B |
| PLB1 | NM_001170585 | 72 | PSR02002648.hg.1 | 2 | + | 28866100 | 28866132 | 0.83 | 5.9 | 3.1805E−12 | B |
| PLB1 | NM_001170585 | 73 | PSR02002650.hg.1 | 2 | + | 28866134 | 28866430 | 0.85 | 4.2 | 1.4831E−13 | B |
| PLB1 | NM_001170585 | 74 | PSR02002651.hg.1 | 2 | + | 28866431 | 28866613 | 0.85 | 3.5 | 4.3908E−15 | B |
| PLB1 | NM_001170585 | 75 | PSR02002652.hg.1 | 2 | + | 28866614 | 28866653 | 0.85 | 4.0 | 1.3406E−14 | B |
| RASGRP3 | NM_001139488 | 8 | PSR02003298.hg.1 | 2 | + | 33701321 | 33701663 | 0.81 | −2.6 | 9.4195E−08 | V |
| RASGRP3 | NM_001139488 | 11 | PSR02003302.hg.1 | 2 | + | 33701732 | 33701774 | 0.85 | −5.3 | 2.7849E−13 | V |
| RASGRP3 | NM_001139488 | 16 | PSR02003307.hg.1 | 2 | + | 33736777 | 33736878 | 0.82 | −3.2 | 1.1375E−10 | V |
| RASGRP3 | NM_001139488 | 17 | PSR02003308.hg.1 | 2 | + | 33736879 | 33736909 | 0.82 | −4.3 | 4.6115E−11 | V |
| RASGRP3 | NM_001139488 | 19 | PSR02003310.hg.1 | 2 | + | 33740077 | 33740273 | 0.83 | −4.3 | 6.4052E−12 | V |
| RASGRP3 | NM_001139488 | 20 | PSR02003311.hg.1 | 2 | + | 33741609 | 33741640 | 0.84 | −4.9 | 1.4818E−12 | V |
| RASGRP3 | NM_001139488 | 21 | PSR02003312.hg.1 | 2 | + | 33741641 | 33741711 | 0.83 | −4.6 | 1.022E−11 | V |
| RASGRP3 | NM_001139488 | 24 | PSR02003316.hg.1 | 2 | + | 33745019 | 33745076 | 0.84 | −4.2 | 1.1934E−11 | V |
| RASGRP3 | NM_001139488 | 25 | PSR02003318.hg.1 | 2 | + | 33745620 | 33745720 | 0.85 | −5.6 | 2.084E−13 | V |
| RASGRP3 | NM_001139488 | 26 | PSR02003320.hg.1 | 2 | + | 33745724 | 33745751 | 0.84 | −5.7 | 9.7785E−13 | V |
| RASGRP3 | NM_001139488 | 27 | PSR02003321.hg.1 | 2 | + | 33747022 | 33747169 | 0.86 | −4.1 | 3.6296E−13 | V |
| RASGRP3 | NM_001139488 | 28 | PSR02003322.hg.1 | 2 | + | 33748946 | 33749119 | 0.85 | −4.0 | 1.8662E−12 | V |
| RASGRP3 | NM_001139488 | 29 | PSR02003324.hg.1 | 2 | + | 33749499 | 33749615 | 0.85 | −4.8 | 3.3278E−13 | V |
| RASGRP3 | NM_001139488 | 30 | PSR02003325.hg.1 | 2 | + | 33752204 | 33752247 | 0.85 | −2.5 | 1.9024E−11 | V |
| RASGRP3 | NM_001139488 | 31 | PSR02003327.hg.1 | 2 | + | 33752270 | 33752479 | 0.86 | −5.0 | 1.0713E−13 | V |
| RASGRP3 | NM_001139488 | 34 | PSR02003330.hg.1 | 2 | + | 33759390 | 33759467 | 0.86 | −4.6 | 1.418E−13 | V |
| RASGRP3 | NM_001139488 | 35 | PSR02003332.hg.1 | 2 | + | 33764164 | 33764277 | 0.85 | −3.0 | 7.8181E−12 | V |
| RASGRP3 | NM_001139488 | 43 | PSR02003340.hg.1 | 2 | + | 33768579 | 33768694 | 0.86 | −3.3 | 1.2266E−12 | V |
| RASGRP3 | NM_001139488 | 44 | PSR02003341.hg.1 | 2 | + | 33774671 | 33774818 | 0.84 | −3.1 | 2.4772E−11 | V |
| RASGRP3 | NM_001139488 | 45 | PSR02003342.hg.1 | 2 | + | 33780598 | 33780634 | 0.86 | −4.9 | 9.4748E−14 | V |
| RASGRP3 | NM_001139488 | 47 | PSR02003344.hg.1 | 2 | + | 33783739 | 33784097 | 0.84 | −2.1 | 1.4931E−10 | V |
| RASGRP3 | NM_001139488 | 48 | PSR02003345.hg.1 | 2 | + | 33787796 | 33787976 | 0.88 | −5.3 | 3.5706E−15 | V |
| RASGRP3 | NM_001139488 | 49 | PSR02003347.hg.1 | 2 | + | 33787981 | 33789658 | 0.87 | −5.0 | 2.5797E−14 | V |
| RASGRP3 | NM_001139488 | 50 | PSR02003349.hg.1 | 2 | + | 33789673 | 33789798 | 0.85 | −3.4 | 7.9972E−12 | V |
| IGKV3D-15 | ENST00000417279 | 3 | PSR02008583.hg.1 | 2 | + | 90153963 | 90154258 | 0.73 | −5.2 | 5.5232E−06 | V |
| IL1RN | NM_173843 | 2 | PSR02011142.hg.1 | 2 | + | 113864791 | 113864962 | 0.78 | −2.8 | 6.1897E−07 | V |
| IL1RN | NM_173843 | 3 | PSR02011143.hg.1 | 2 | + | 113868693 | 113868776 | 0.72 | −5.3 | 4.9597E−06 | V |
| IL1RN | NM_173843 | 4 | PSR02011144.hg.1 | 2 | + | 113870577 | 113870691 | 0.77 | −4.9 | 7.1178E−07 | V |
| IL1RN | NM_173843 | 5 | PSR02011145.hg.1 | 2 | + | 113873082 | 113873267 | 0.57 | −1.6 | 0.00254957 | V |
| IL1RN | NM_173843 | 10 | PSR02011152.hg.1 | 2 | + | 113879025 | 113879195 | 0.75 | −4.0 | 5.8076E−06 | V |
| IL1RN | NM_173843 | 11 | PSR02011154.hg.1 | 2 | + | 113885153 | 113885265 | 0.67 | −1.7 | 0.00280923 | V |
| IL1RN | NM_173843 | 13 | PSR02011156.hg.1 | 2 | + | 113887153 | 113887241 | 0.67 | −1.6 | 0.00545514 | V |
| IL1RN | NM_173843 | 16 | PSR02011159.hg.1 | 2 | + | 113888622 | 113888734 | 0.67 | −1.6 | 0.00305058 | V |
| IL1RN | NM_173843 | 17 | PSR02011160.hg.1 | 2 | + | 113890233 | 113890698 | 0.68 | −1.7 | 0.00111773 | V |
| IL1RN | NM_173843 | 18 | PSR02011161.hg.1 | 2 | + | 113890699 | 113891037 | 0.68 | −1.7 | 0.00274478 | V |
| IL1RN | NM_173843 | 19 | PSR02011162.hg.1 | 2 | + | 113891038 | 113891179 | 0.67 | −1.7 | 0.00172968 | V |
| IL1RN | NM_173843 | 20 | PSR02011163.hg.1 | 2 | + | 113891180 | 113891590 | 0.66 | −2.0 | 0.00229078 | V |
| — | ENST00000436616 | 2 | PSR02015941.hg.1 | 2 | + | 179278750 | 179278840 | 0.89 | −3.4 | 1.2084E−13 | V |
| — | ENST00000436616 | 5 | PSR02015944.hg.1 | 2 | + | 179291093 | 179291232 | 0.88 | −4.0 | 5.4058E−13 | V |
| — | ENST00000436616 | 6 | PSR02015945.hg.1 | 2 | + | 179291233 | 179291388 | 0.88 | −3.3 | 5.2925E−13 | V |
| — | ENST00000436616 | 7 | PSR02015950.hg.1 | 2 | + | 179295422 | 179295496 | 0.91 | −4.6 | 1.0425E−14 | V |
| — | ENST00000436616 | 8 | PSR02015951.hg.1 | 2 | + | 179295497 | 179295551 | 0.91 | −3.9 | 2.3303E−15 | V |
| — | ENST00000436616 | 9 | PSR02015952.hg.1 | 2 | + | 179295552 | 179295616 | 0.88 | −4.3 | 9.7587E−14 | V |
| — | ENST00000436616 | 12 | PSR02015955.hg.1 | 2 | + | 179298109 | 179298202 | 0.92 | −4.8 | 2.7667E−16 | V |
| — | ENST00000436616 | 13 | PSR02015956.hg.1 | 2 | + | 179298203 | 179298242 | 0.92 | −4.1 | 4.4255E−16 | V |
| — | ENST00000436616 | 14 | PSR02015957.hg.1 | 2 | + | 179298243 | 179298394 | 0.92 | −3.8 | 3.2558E−16 | V |
| — | ENST00000436616 | 15 | PSR02015958.hg.1 | 2 | + | 179298395 | 179298716 | 0.90 | −3.8 | 1.2384E−14 | V |
| — | ENST00000436616 | 16 | PSR02015959.hg.1 | 2 | + | 179303594 | 179303866 | 0.91 | −3.8 | 2.6341E−14 | V |
| SPATS2L | NM_001100422 | 14 | PSR02017502.hg.1 | 2 | + | 201194154 | 201194203 | 0.86 | −12.5 | 9.4364E−14 | V |
| SPATS2L | NM_001100422 | 20 | PSR02017508.hg.1 | 2 | + | 201242960 | 201243094 | 0.84 | −20.0 | 6.1343E−11 | V |
| SPATS2L | NM_001100422 | 22 | PSR02017510.hg.1 | 2 | + | 201253946 | 201254006 | 0.87 | −17.3 | 1.769E−15 | V |
| SPATS2L | NM_001100422 | 25 | PSR02017514.hg.1 | 2 | + | 201277034 | 201277065 | 0.87 | −17.4 | 3.2246E−15 | V |
| SPATS2L | NM_001100422 | 26 | PSR02017515.hg.1 | 2 | + | 201277066 | 201277142 | 0.88 | −16.2 | 2.448E−16 | V |
| SPATS2L | NM_001100422 | 27 | PSR02017516.hg.1 | 2 | + | 201281102 | 201281148 | 0.86 | −18.4 | 9.3855E−15 | V |
| SPATS2L | NM_001100422 | 28 | PSR02017518.hg.1 | 2 | + | 201283973 | 201284056 | 0.87 | −12.5 | 5.4564E−15 | V |
| SPATS2L | NM_001100422 | 29 | PSR02017519.hg.1 | 2 | + | 201284057 | 201284120 | 0.85 | −9.4 | 2.2355E−13 | V |

TABLE 13-continued

Exon level analysis of 140 RNA determinants differentially expressed in bacterial and viral patients. Probe set ID is based on GeneChip Human Transcriptome Arrays 2.0 (HTA-Affymetrix) data. Comparison to full gene was calculated as absolute fold change ($exon_i$) - absolute fold change (full length gene); Only exons that presented higher of differential expression of the single exon compared to the full length gene were included.

| Gene Symbol | mRNA Accession | Exon # | Probe Set ID | Chromosome | Strand | Start | Stop | Exon AUC | FC | T-Test | Up in B/V |
|---|---|---|---|---|---|---|---|---|---|---|---|
| SPATS2L | NM_001100422 | 30 | PSR02017521.hg.1 | 2 | + | 201284137 | 201284193 | 0.86 | −17.7 | 3.3166E−14 | V |
| SPATS2L | NM_001100422 | 31 | PSR02017522.hg.1 | 2 | + | 201284194 | 201284219 | 0.87 | −15.1 | 6.7708E−16 | V |
| SPATS2L | NM_001100422 | 32 | PSR02017524.hg.1 | 2 | + | 201303863 | 201303963 | 0.85 | −12.7 | 1.0387E−12 | V |
| SPATS2L | NM_001100422 | 33 | PSR02017525.hg.1 | 2 | + | 201303964 | 201304051 | 0.86 | −15.1 | 1.3056E−13 | V |
| SPATS2L | NM_001100422 | 34 | PSR02017526.hg.1 | 2 | + | 201305372 | 201305447 | 0.87 | −21.5 | 9.1778E−16 | V |
| SPATS2L | NM_001100422 | 35 | PSR02017527.hg.1 | 2 | + | 201305448 | 201305507 | 0.88 | −16.1 | 2.8807E−16 | V |
| SPATS2L | NM_001100422 | 36 | PSR02017528.hg.1 | 2 | + | 201324492 | 201324550 | 0.88 | −15.7 | 2.1012E−16 | V |
| SPATS2L | NM_001100422 | 39 | PSR02017531.hg.1 | 2 | + | 201332013 | 201332101 | 0.87 | −17.5 | 2.6638E−15 | V |
| SPATS2L | NM_001100422 | 41 | PSR02017534.hg.1 | 2 | + | 201334637 | 201334683 | 0.88 | −19.7 | 1.507E−16 | V |
| SPATS2L | NM_001100422 | 42 | PSR02017535.hg.1 | 2 | + | 201334684 | 201334739 | 0.89 | −19.3 | 3.4388E−17 | V |
| SPATS2L | NM_001100422 | 43 | PSR02017536.hg.1 | 2 | + | 201337555 | 201337715 | 0.89 | −16.9 | 5.1761E−17 | V |
| SPATS2L | NM_001100422 | 44 | PSR02017537.hg.1 | 2 | + | 201337716 | 201337770 | 0.87 | −9.3 | 3.8298E−13 | V |
| SPATS2L | NM_001100422 | 45 | PSR02017539.hg.1 | 2 | + | 201342359 | 201342605 | 0.88 | −12.4 | 1.0497E−15 | V |
| SPATS2L | NM_001100422 | 46 | PSR02017540.hg.1 | 2 | + | 201342606 | 201342825 | 0.87 | −11.8 | 1.5752E−14 | V |
| SPATS2L | NM_001100422 | 47 | PSR02017541.hg.1 | 2 | + | 201342826 | 201342869 | 0.86 | −13.6 | 3.3575E−14 | V |
| SPATS2L | NM_001100422 | 48 | PSR02017542.hg.1 | 2 | + | 201342870 | 201342932 | 0.86 | −13.5 | 2.1869E−13 | V |
| SPATS2L | NM_001100422 | 49 | PSR02017543.hg.1 | 2 | + | 201342933 | 201343252 | 0.88 | −18.8 | 1.2402E−15 | V |
| — | ENST00000366140 | 1 | PSR02024945.hg.1 | 2 | − | 6968645 | 6969010 | 0.87 | −4.9 | 1.2791E−13 | V |
| — | ENST00000366140 | 3 | PSR02024947.hg.1 | 2 | − | 6970099 | 6970237 | 0.89 | −14.6 | 8.6183E−19 | V |
| GALNT14 | NM_001253826 | 4 | PSR02027578.hg.1 | 2 | − | 31133663 | 31133925 | 0.84 | 4.0 | 1.3811E−13 | B |
| GALNT14 | NM_001253826 | 5 | PSR02027579.hg.1 | 2 | − | 31135089 | 31135208 | 0.83 | 3.5 | 6.8753E−13 | B |
| GALNT14 | NM_001253826 | 6 | PSR02027580.hg.1 | 2 | − | 31146985 | 31147063 | 0.84 | 4.9 | 6.4209E−13 | B |
| GALNT14 | NM_001253826 | 7 | PSR02027581.hg.1 | 2 | − | 31147064 | 31147129 | 0.83 | 6.2 | 6.546E−13 | B |
| GALNT14 | NM_001253826 | 9 | PSR02027583.hg.1 | 2 | − | 31147606 | 31147650 | 0.85 | 7.9 | 5.2038E−13 | B |
| GALNT14 | NM_001253826 | 10 | PSR02027584.hg.1 | 2 | − | 31147651 | 31147689 | 0.85 | 5.7 | 2.4699E−14 | B |
| GALNT14 | NM_001253826 | 12 | PSR02027586.hg.1 | 2 | − | 31154934 | 31154982 | 0.83 | 2.9 | 8.9534E−13 | B |
| GALNT14 | NM_001253826 | 13 | PSR02027587.hg.1 | 2 | − | 31154983 | 31155032 | 0.81 | 3.3 | 1.4968E−11 | B |
| GALNT14 | NM_001253826 | 14 | PSR02027588.hg.1 | 2 | − | 31155033 | 31155060 | 0.83 | 5.2 | 1.1028E−12 | B |
| GALNT14 | NM_001253826 | 15 | PSR02027589.hg.1 | 2 | − | 31165067 | 31165170 | 0.84 | 6.8 | 2.2731E−13 | B |
| GALNT14 | NM_001253826 | 17 | PSR02027591.hg.1 | 2 | − | 31168649 | 31168707 | 0.84 | 6.3 | 1.0776E−13 | B |
| GALNT14 | NM_001253826 | 21 | PSR02027597.hg.1 | 2 | − | 31178795 | 31178843 | 0.82 | 4.1 | 4.8575E−12 | B |
| GALNT14 | NM_001253826 | 22 | PSR02027598.hg.1 | 2 | − | 31181263 | 31181330 | 0.85 | 7.8 | 3.7301E−14 | B |
| GALNT14 | NM_001253826 | 23 | PSR02027599.hg.1 | 2 | − | 31189070 | 31189137 | 0.84 | 4.3 | 2.0121E−13 | B |
| GALNT14 | NM_001253826 | 24 | PSR02027602.hg.1 | 2 | − | 31189138 | 31189168 | 0.84 | 9.4 | 1.6954E−12 | B |
| GALNT14 | NM_001253826 | 25 | PSR02027603.hg.1 | 2 | − | 31189143 | 31189168 | 0.82 | 8.2 | 9.9959E−12 | B |
| GALNT14 | NM_001253826 | 27 | PSR02027605.hg.1 | 2 | − | 31215704 | 31215873 | 0.84 | 4.8 | 3.6867E−13 | B |
| GALNT14 | NM_001253826 | 31 | PSR02027609.hg.1 | 2 | − | 31337609 | 31337693 | 0.82 | 3.2 | 8.4014E−12 | B |
| GALNT14 | NM_001253826 | 37 | PSR02027616.hg.1 | 2 | − | 31360824 | 31360887 | 0.85 | 4.4 | 1.1479E−13 | B |
| GALNT14 | NM_001253826 | 38 | PSR02027617.hg.1 | 2 | − | 31360888 | 31360921 | 0.85 | 5.8 | 1.1909E−13 | B |
| NLRC4 | NM_001199138 | 6 | PSR02027788.hg.1 | 2 | − | 32474676 | 32476670 | 0.86 | 3.6 | 6.2463E−14 | B |
| NLRC4 | NM_001199138 | 8 | PSR02027790.hg.1 | 2 | − | 32481844 | 32481962 | 0.86 | 3.6 | 2.8689E−13 | B |
| NLRC4 | NM_001199138 | 11 | PSR02027797.hg.1 | 2 | − | 32490690 | 32490801 | 0.86 | 5.0 | 4.4783E−15 | B |
| NLRC4 | NM_001199138 | 13 | PSR02027800.hg.1 | 2 | − | 32490606 | 32490689 | 0.87 | 5.2 | 1.9888E−15 | B |
| PNPT1 | NM_033109 | 9 | PSR02029840.hg.1 | 2 | − | 55863361 | 55863504 | 0.93 | −7.9 | 2.9073E−18 | V |
| PNPT1 | NM_033109 | 11 | PSR02029843.hg.1 | 2 | − | 55867762 | 55867840 | 0.93 | −10.5 | 1.0559E−19 | V |
| PNPT1 | NM_033109 | 14 | PSR02029847.hg.1 | 2 | − | 55871772 | 55871855 | 0.93 | −6.8 | 1.486E−18 | V |
| PNPT1 | NM_033109 | 16 | PSR02029849.hg.1 | 2 | − | 55872484 | 55872567 | 0.92 | −8.4 | 6.2136E−18 | V |
| PNPT1 | NM_033109 | 17 | PSR02029850.hg.1 | 2 | − | 55873394 | 55873457 | 0.93 | −9.4 | 2.1453E−19 | V |
| PNPT1 | NM_033109 | 18 | PSR02029851.hg.1 | 2 | − | 55873550 | 55873621 | 0.92 | −9.9 | 1.0681E−18 | V |
| PNPT1 | NM_033109 | 19 | PSR02029853.hg.1 | 2 | − | 55874482 | 55874517 | 0.93 | −11.6 | 7.6891E−20 | V |
| PNPT1 | NM_033109 | 20 | PSR02029855.hg.1 | 2 | − | 55874536 | 55874588 | 0.93 | −8.2 | 1.4614E−18 | V |
| PNPT1 | NM_033109 | 21 | PSR02029856.hg.1 | 2 | − | 55882035 | 55882088 | 0.93 | −9.8 | 7.7042E−22 | V |
| PNPT1 | NM_033109 | 22 | PSR02029857.hg.1 | 2 | − | 55883266 | 55883355 | 0.91 | −8.1 | 9.042E−18 | V |
| PNPT1 | NM_033109 | 23 | PSR02029858.hg.1 | 2 | − | 55883440 | 55883506 | 0.92 | −8.6 | 3.6016E−18 | V |
| PNPT1 | NM_033109 | 24 | PSR02029859.hg.1 | 2 | − | 55887292 | 55887328 | 0.91 | −10.2 | 1.2624E−18 | V |
| PNPT1 | NM_033109 | 25 | PSR02029860.hg.1 | 2 | − | 55889091 | 55889161 | 0.91 | −7.9 | 4.589E−17 | V |
| PNPT1 | NM_033109 | 26 | PSR02029861.hg.1 | 2 | − | 55894126 | 55894228 | 0.92 | −8.7 | 8.8658E−19 | V |
| PNPT1 | NM_033109 | 27 | PSR02029862.hg.1 | 2 | − | 55894997 | 55895093 | 0.92 | −7.6 | 1.9147E−18 | V |
| PNPT1 | NM_033109 | 29 | PSR02029865.hg.1 | 2 | − | 55899130 | 55899181 | 0.93 | −10.4 | 2.2862E−20 | V |
| PNPT1 | NM_033109 | 30 | PSR02029866.hg.1 | 2 | − | 55900028 | 55900214 | 0.93 | −9.4 | 3.6997E−20 | V |
| PNPT1 | NM_033109 | 31 | PSR02029867.hg.1 | 2 | − | 55906817 | 55906930 | 0.93 | −8.2 | 9.5391E−19 | V |
| PNPT1 | NM_033109 | 34 | PSR02029870.hg.1 | 2 | − | 55907990 | 55908053 | 0.92 | −8.9 | 4.0201E−18 | V |
| PNPT1 | NM_033109 | 35 | PSR02029871.hg.1 | 2 | − | 55910920 | 55910969 | 0.91 | −8.8 | 6.9197E−17 | V |
| PNPT1 | NM_033109 | 37 | PSR02029873.hg.1 | 2 | − | 55913505 | 55913579 | 0.92 | −8.4 | 1.6009E−18 | V |
| IGKC | ENST00000390237 | 5 | PSR02033245.hg.1 | 2 | − | 89156682 | 89156708 | 0.73 | −5.9 | 5.977E−06 | V |
| IGKC | ENST00000390237 | 6 | PSR02033246.hg.1 | 2 | − | 89156709 | 89156873 | 0.73 | −5.1 | 3.3835E−06 | V |
| IGKC | ENST00000390237 | 7 | PSR02033247.hg.1 | 2 | − | 89156874 | 89156991 | 0.73 | −4.4 | 4.8188E−06 | V |
| IGKC | ENST00000390237 | 13 | PSR02033260.hg.1 | 2 | − | 89160080 | 89160117 | 0.73 | −4.6 | 6.8438E−06 | V |
| IGKC | ENST00000390237 | 16 | PSR02033270.hg.1 | 2 | − | 89160733 | 89160767 | 0.72 | −5.2 | 1.7034E−05 | V |

TABLE 13-continued

Exon level analysis of 140 RNA determinants differentially expressed in bacterial and viral patients. Probe set ID is based on GeneChip Human Transcriptome Arrays 2.0 (HTA-Affymetrix) data. Comparison to full gene was calculated as absolute fold change (exon$_i$) - absolute fold change (full length gene); Only exons that presented higher of differential expression of the single exon compared to the full length gene were included.

| Gene Symbol | mRNA Accession | Exon # | Probe Set ID | Chromosome | Strand | Start | Stop | Exon AUC | FC | T-Test | Up in B/V |
|---|---|---|---|---|---|---|---|---|---|---|---|
| IGKC | ENST00000390237 | 22 | PSR02033539.hg.1 | 2 | − | 89384674 | 89384968 | 0.72 | −4.6 | 9.9003E−06 | V |
| IGKC | ENST00000390237 | 28 | PSR02033578.hg.1 | 2 | − | 89442059 | 89442353 | 0.72 | −4.3 | 1.4652E−05 | V |
| IGKC | ENST00000390237 | 31 | PSR02033622.hg.1 | 2 | − | 89545001 | 89545055 | 0.74 | −4.5 | 5.6983E−06 | V |
| IGKC | ENST00000390237 | 32 | PSR02033627.hg.1 | 2 | − | 89567766 | 89568053 | 0.71 | −4.8 | 1.9531E−05 | V |
| IGKC | ENST00000390237 | 35 | PSR02033642.hg.1 | 2 | − | 89619388 | 89619678 | 0.68 | −4.4 | 0.00018253 | V |
| IGKV1-9 | ENST00000493819 | 1 | PSR02033498.hg.1 | 2 | − | 89309479 | 89309774 | 0.72 | −5.0 | 5.427E−06 | V |
| — | ENST00000443397 | 2 | PSR02033656.hg.1 | 2 | − | 90537856 | 90538113 | 0.72 | −5.0 | 9.9942E−06 | V |
| IFIH1 | NM_022168 | 1 | PSR02039138.hg.1 | 2 | − | 163123612 | 163123650 | 0.81 | −6.4 | 1.536E−10 | V |
| IFIH1 | NM_022168 | 2 | PSR02039139.hg.1 | 2 | − | 163123651 | 163123889 | 0.82 | −5.7 | 2.7014E−11 | V |
| IFIH1 | NM_022168 | 3 | PSR02039140.hg.1 | 2 | − | 163123989 | 163124079 | 0.83 | −6.0 | 5.9244E−12 | V |
| IFIH1 | NM_022168 | 4 | PSR02039141.hg.1 | 2 | − | 163124597 | 163124787 | 0.83 | −6.0 | 4.8929E−12 | V |
| IFIH1 | NM_022168 | 5 | PSR02039142.hg.1 | 2 | − | 163128736 | 163128897 | 0.83 | −6.2 | 2.5324E−12 | V |
| IFIH1 | NM_022168 | 6 | PSR02039143.hg.1 | 2 | − | 163130305 | 163130454 | 0.84 | −5.3 | 9.9158E−13 | V |
| IFIH1 | NM_022168 | 7 | PSR02039144.hg.1 | 2 | − | 163133197 | 163133456 | 0.84 | −5.2 | 1.3759E−12 | V |
| IFIH1 | NM_022168 | 9 | PSR02039146.hg.1 | 2 | − | 163134715 | 163134838 | 0.82 | −5.3 | 2.8219E−11 | V |
| IFIH1 | NM_022168 | 10 | PSR02039147.hg.1 | 2 | − | 163136506 | 163136622 | 0.83 | −5.2 | 8.5008E−12 | V |
| PGAP1 | NM_024989 | 4 | PSR02042371.hg.1 | 2 | − | 197702595 | 197703253 | 0.86 | −3.3 | 3.075E−13 | V |
| PGAP1 | NM_024989 | 7 | PSR02042374.hg.1 | 2 | − | 197707445 | 197707549 | 0.87 | −3.8 | 1.535E−13 | V |
| PGAP1 | NM_024989 | 9 | PSR02042376.hg.1 | 2 | − | 197709248 | 197709298 | 0.87 | −3.7 | 1.1337E−12 | V |
| PGAP1 | NM_024989 | 12 | PSR02042379.hg.1 | 2 | − | 197711727 | 197711924 | 0.85 | −3.5 | 9.2781E−12 | V |
| PGAP1 | NM_024989 | 15 | PSR02042382.hg.1 | 2 | − | 197712671 | 197712761 | 0.84 | −3.2 | 1.2843E−11 | V |
| PGAP1 | NM_024989 | 18 | PSR02042385.hg.1 | 2 | − | 197737165 | 197737273 | 0.86 | −3.0 | 2.5042E−11 | V |
| PGAP1 | NM_024989 | 21 | PSR02042388.hg.1 | 2 | − | 197738252 | 197738303 | 0.87 | −4.3 | 2.7607E−13 | V |
| PGAP1 | NM_024989 | 22 | PSR02042389.hg.1 | 2 | − | 197738409 | 197738482 | 0.87 | −4.5 | 1.4754E−13 | V |
| PGAP1 | NM_024989 | 26 | PSR02042393.hg.1 | 2 | − | 197744800 | 197744877 | 0.87 | −4.3 | 2.5946E−13 | V |
| PGAP1 | NM_024989 | 29 | PSR02042398.hg.1 | 2 | − | 197755552 | 197755581 | 0.85 | −3.0 | 1.9059E−11 | V |
| PGAP1 | NM_024989 | 33 | PSR02042403.hg.1 | 2 | − | 197761855 | 197761921 | 0.86 | −3.7 | 1.1116E−12 | V |
| PGAP1 | NM_024989 | 35 | PSR02042405.hg.1 | 2 | − | 197767309 | 197767466 | 0.88 | −5.1 | 3.6707E−14 | V |
| PGAP1 | NM_024989 | 36 | PSR02042406.hg.1 | 2 | − | 197777606 | 197777777 | 0.87 | −3.7 | 5.5485E−13 | V |
| PGAP1 | NM_024989 | 37 | PSR02042407.hg.1 | 2 | − | 197781142 | 197781317 | 0.86 | −3.5 | 4.059E−12 | V |
| PGAP1 | NM_024989 | 40 | PSR02042410.hg.1 | 2 | − | 197791194 | 197791379 | 0.86 | −4.7 | 8.9483E−13 | V |
| — | n407780 | 4 | PSR02048141.hg.1 | 2 | + | 12857692 | 12858075 | 0.87 | −6.0 | 7.0931E−15 | V |
| — | n407780 | 5 | PSR02048142.hg.1 | 2 | + | 12858077 | 12858703 | 0.89 | −7.2 | 3.6568E−16 | V |
| — | n407780 | 6 | PSR02048143.hg.1 | 2 | + | 12863386 | 12863678 | 0.87 | −5.7 | 7.0938E−15 | V |
| — | n407780 | 7 | PSR02048144.hg.1 | 2 | + | 12880452 | 12881616 | 0.89 | −7.8 | 2.0125E−16 | V |
| — | n407780 | 8 | PSR02048145.hg.1 | 2 | + | 12881672 | 12882664 | 0.86 | −6.3 | 3.0298E−14 | V |
| — | n383778 | 2 | PSR02051212.hg.1 | 2 | + | 179278750 | 179278840 | 0.90 | −4.0 | 1.5457E−15 | V |
| — | n383778 | 5 | PSR02051215.hg.1 | 2 | + | 179291093 | 179291232 | 0.88 | −3.8 | 4.9161E−13 | V |
| — | n383778 | 6 | PSR02051216.hg.1 | 2 | + | 179291233 | 179291388 | 0.88 | −2.9 | 5.2194E−12 | V |
| — | n383778 | 7 | PSR02051217.hg.1 | 2 | + | 179295422 | 179295496 | 0.91 | −4.5 | 1.1841E−14 | V |
| — | n383778 | 8 | PSR02051218.hg.1 | 2 | + | 179295497 | 179295551 | 0.89 | −4.0 | 1.4085E−14 | V |
| — | n383778 | 9 | PSR02051219.hg.1 | 2 | + | 179295552 | 179295616 | 0.90 | −4.4 | 1.5794E−14 | V |
| — | n383778 | 12 | PSR02051222.hg.1 | 2 | + | 179298109 | 179298202 | 0.91 | −4.5 | 5.4701E−15 | V |
| — | n383778 | 13 | PSR02051223.hg.1 | 2 | + | 179298203 | 179298242 | 0.92 | −4.1 | 4.4255E−16 | V |
| — | n383778 | 14 | PSR02051224.hg.1 | 2 | + | 179298243 | 179298394 | 0.92 | −4.5 | 9.2793E−17 | V |
| — | n383778 | 15 | PSR02051225.hg.1 | 2 | + | 179298395 | 179298716 | 0.92 | −4.8 | 6.3868E−17 | V |
| — | n383778 | 16 | PSR02051226.hg.1 | 2 | + | 179303594 | 179303866 | 0.91 | −5.5 | 1.765E−16 | V |
| — | n346494 | 9 | PSR02052318.hg.1 | 2 | + | 243064444 | 243064504 | 0.81 | 2.5 | 2.6048E−10 | B |
| — | n346494 | 10 | PSR02052319.hg.1 | 2 | + | 243064505 | 243064606 | 0.80 | 2.4 | 2.539E−10 | B |
| — | n346494 | 11 | PSR02052320.hg.1 | 2 | + | 243064629 | 243064759 | 0.82 | 3.5 | 3.9023E−11 | B |
| — | n346494 | 12 | PSR02052321.hg.1 | 2 | + | 243065559 | 243067562 | 0.82 | 1.9 | 3.3985E−11 | B |
| — | n346494 | 13 | PSR02052322.hg.1 | 2 | + | 243072806 | 243072963 | 0.81 | 2.9 | 9.5467E−11 | B |
| — | n346494 | 14 | PSR02052323.hg.1 | 2 | + | 243072964 | 243073017 | 0.82 | 3.6 | 2.352E−11 | B |
| — | n346494 | 16 | PSR02052325.hg.1 | 2 | + | 243082385 | 243082789 | 0.74 | 2.4 | 6.5111E−07 | B |
| — | n346494 | 17 | PSR02052326.hg.1 | 2 | + | 243101510 | 243101538 | 0.78 | 2.8 | 1.9953E−08 | B |
| — | n346494 | 18 | PSR02052327.hg.1 | 2 | + | 243101539 | 243101569 | 0.79 | 3.0 | 1.8551E−09 | B |
| — | n346494 | 19 | PSR02052328.hg.1 | 2 | + | 243101575 | 243101623 | 0.74 | 4.8 | 6.3798E−07 | B |
| — | n346494 | 20 | PSR02052329.hg.1 | 2 | + | 243102107 | 243102147 | 0.77 | 2.5 | 1.4346E−08 | B |
| — | n346494 | 21 | PSR02052330.hg.1 | 2 | + | 243102158 | 243102469 | 0.80 | 3.1 | 9.6581E−10 | B |
| — | TCONS_00003184-XLOC_001966 | 3 | PSR02052679.hg.1 | 2 | − | 6970099 | 6970237 | 0.89 | −18.7 | 1.5208E−19 | V |
| — | TCONS_00003184-XLOC_001966 | 4 | PSR02052680.hg.1 | 2 | − | 6970238 | 6970833 | 0.88 | −8.2 | 1.7666E−14 | V |
| — | n346551 | 32 | PSR02054270.hg.1 | 2 | − | 89384690 | 89384918 | 0.73 | −5.2 | 8.4466E−06 | V |
| — | n346551 | 45 | PSR02054283.hg.1 | 2 | − | 89442261 | 89442287 | 0.73 | −6.4 | 1.146E−05 | V |
| — | n346551 | 52 | PSR02054290.hg.1 | 2 | − | 89521185 | 89521340 | 0.73 | −5.3 | 4.0058E−06 | V |
| — | n346551 | 53 | PSR02054291.hg.1 | 2 | − | 89521341 | 89521470 | 0.73 | −5.4 | 6.639E−06 | V |
| — | n336681 | 2 | PSR02054304.hg.1 | 2 | − | 89476567 | 89476595 | 0.74 | −4.8 | 4.2174E−06 | V |

TABLE 13-continued

Exon level analysis of 140 RNA determinants differentially
expressed in bacterial and viral patients. Probe set ID is based on GeneChip
Human Transcriptome Arrays 2.0 (HTA-Affymetrix) data. Comparison to full
gene was calculated as absolute fold change ($exon_i$) - absolute fold change (full
length gene); Only exons that presented higher of differential expression of the
single exon compared to the full length gene were included.

| Gene Symbol | mRNA Accession | Exon # | Probe Set ID | Chromosome | Strand | Start | Stop | Exon AUC | FC | T-Test | Up in B/V |
|---|---|---|---|---|---|---|---|---|---|---|---|
| TTC21A | NM_001105513 | 4 | PSR03003865.hg.1 | 3 | + | 39150576 | 39150705 | 0.85 | −3.3 | 1.0596E−09 | V |
| TTC21A | NM_001105513 | 5 | PSR03003866.hg.1 | 3 | + | 39151520 | 39151630 | 0.85 | −2.9 | 2.5036E−09 | V |
| TTC21A | NM_001105513 | 8 | PSR03003869.hg.1 | 3 | + | 39152342 | 39152508 | 0.87 | −3.7 | 2.7462E−10 | V |
| TTC21A | NM_001105513 | 9 | PSR03003871.hg.1 | 3 | + | 39153949 | 39154071 | 0.91 | −4.0 | 3.9878E−12 | V |
| TTC21A | NM_001105513 | 10 | PSR03003872.hg.1 | 3 | + | 39156076 | 39156233 | 0.90 | −4.4 | 1.8636E−11 | V |
| TTC21A | NM_001105513 | 11 | PSR03003873.hg.1 | 3 | + | 39159560 | 39159644 | 0.91 | −7.4 | 8.3563E−15 | V |
| TTC21A | NM_001105513 | 12 | PSR03003875.hg.1 | 3 | + | 39159669 | 39161122 | 0.83 | −1.8 | 3.4726E−07 | V |
| TTC21A | NM_001105513 | 13 | PSR03003879.hg.1 | 3 | + | 39161413 | 39161459 | 0.87 | −4.9 | 6.9522E−12 | V |
| TTC21A | NM_001105513 | 14 | PSR03003880.hg.1 | 3 | + | 39161460 | 39161511 | 0.76 | −1.7 | 3.691E−06 | V |
| TTC21A | NM_001105513 | 15 | PSR03003881.hg.1 | 3 | + | 39162488 | 39162680 | 0.86 | −2.5 | 4.0189E−09 | V |
| TTC21A | NM_001105513 | 16 | PSR03003882.hg.1 | 3 | + | 39166554 | 39166591 | 0.87 | −4.5 | 2.7366E−11 | V |
| TTC21A | NM_001105513 | 17 | PSR03003883.hg.1 | 3 | + | 39166592 | 39166621 | 0.82 | −2.8 | 3.41E−08 | V |
| TTC21A | NM_001105513 | 18 | PSR03003884.hg.1 | 3 | + | 39166622 | 39166651 | 0.86 | −3.0 | 4.5996E−09 | V |
| TTC21A | NM_001105513 | 19 | PSR03003885.hg.1 | 3 | + | 39166823 | 39167023 | 0.89 | −3.3 | 1.1044E−10 | V |
| TTC21A | NM_001105513 | 20 | PSR03003886.hg.1 | 3 | + | 39167752 | 39167881 | 0.90 | −7.5 | 3.9239E−14 | V |
| TTC21A | NM_001105513 | 21 | PSR03003888.hg.1 | 3 | + | 39169825 | 39169979 | 0.83 | −2.3 | 1.1955E−08 | V |
| TTC21A | NM_001105513 | 22 | PSR03003889.hg.1 | 3 | + | 39170208 | 39170301 | 0.78 | −1.7 | 7.2392E−07 | V |
| TTC21A | NM_001105513 | 23 | PSR03003890.hg.1 | 3 | + | 39170302 | 39170423 | 0.70 | −1.7 | 1.6188E−05 | V |
| TTC21A | NM_001105513 | 25 | PSR03003893.hg.1 | 3 | + | 39170583 | 39170801 | 0.88 | −3.0 | 3.9851E−10 | V |
| TTC21A | NM_001105513 | 26 | PSR03003894.hg.1 | 3 | + | 39171570 | 39171642 | 0.81 | −1.6 | 1.609E−06 | V |
| TTC21A | NM_001105513 | 27 | PSR03003896.hg.1 | 3 | + | 39171739 | 39171849 | 0.79 | −1.6 | 4.4276E−07 | V |
| TTC21A | NM_001105513 | 29 | PSR03003898.hg.1 | 3 | + | 39172192 | 39172330 | 0.82 | −2.3 | 1.9991E−08 | V |
| TTC21A | NM_001105513 | 31 | PSR03003900.hg.1 | 3 | + | 39172483 | 39172586 | 0.83 | −2.2 | 6.4466E−09 | V |
| TTC21A | NM_001105513 | 32 | PSR03003901.hg.1 | 3 | + | 39173012 | 39173137 | 0.77 | −2.1 | 3.6226E−07 | V |
| TTC21A | NM_001105513 | 33 | PSR03003902.hg.1 | 3 | + | 39174212 | 39174465 | 0.70 | −1.6 | 3.1457E−05 | V |
| TTC21A | NM_001105513 | 34 | PSR03003903.hg.1 | 3 | + | 39174466 | 39174542 | 0.81 | −2.3 | 8.6537E−08 | V |
| TTC21A | NM_001105513 | 35 | PSR03003904.hg.1 | 3 | + | 39174543 | 39174648 | 0.86 | −2.5 | 1.8615E−08 | V |
| TTC21A | NM_001105513 | 36 | PSR03003905.hg.1 | 3 | + | 39174649 | 39174731 | 0.89 | −4.9 | 1.3316E−12 | V |
| TTC21A | NM_001105513 | 37 | PSR03003906.hg.1 | 3 | + | 39175709 | 39175819 | 0.76 | −1.9 | 1.7434E−06 | V |
| TTC21A | NM_001105513 | 40 | PSR03003909.hg.1 | 3 | + | 39176584 | 39176665 | 0.89 | −3.5 | 6.4133E−11 | V |
| TTC21A | NM_001105513 | 42 | PSR03003911.hg.1 | 3 | + | 39177848 | 39177998 | 0.83 | −1.9 | 5.0354E−08 | V |
| TTC21A | NM_001105513 | 44 | PSR03003913.hg.1 | 3 | + | 39178390 | 39178518 | 0.71 | −1.6 | 2.2997E−05 | V |
| TTC21A | NM_001105513 | 45 | PSR03003914.hg.1 | 3 | + | 39178519 | 39178551 | 0.79 | −2.4 | 9.7449E−08 | V |
| TTC21A | NM_001105513 | 48 | PSR03003917.hg.1 | 3 | + | 39178977 | 39179201 | 0.87 | −2.0 | 1.3879E−08 | V |
| TTC21A | NM_001105513 | 50 | PSR03003920.hg.1 | 3 | + | 39179758 | 39179878 | 0.89 | −3.7 | 6.0733E−11 | V |
| TTC21A | NM_001105513 | 51 | PSR03003921.hg.1 | 3 | + | 39180047 | 39180114 | 0.86 | −3.5 | 3.0554E−11 | V |
| TREX1 | NM_016381 | 4 | PSR03005647.hg.1 | 3 | + | 48491443 | 48491576 | 0.73 | −1.3 | 1.8002E−05 | V |
| TREX1 | NM_016381 | 7 | PSR03005650.hg.1 | 3 | + | 48495700 | 48495757 | 0.66 | −1.2 | 0.00163645 | V |
| TREX1 | NM_016381 | 17 | PSR03005660.hg.1 | 3 | + | 48502108 | 48502198 | 0.67 | −1.2 | 9.4496E−05 | V |
| TREX1 | NM_016381 | 23 | PSR03005666.hg.1 | 3 | + | 48506445 | 48506482 | 0.76 | −1.3 | 3.932E−07 | V |
| TREX1 | NM_016381 | 30 | PSR03005678.hg.1 | 3 | + | 48507669 | 48507708 | 0.71 | −1.4 | 0.00010235 | V |
| TREX1 | NM_016381 | 32 | PSR03005680.hg.1 | 3 | + | 48507890 | 48508028 | 0.77 | −1.4 | 5.9042E−07 | V |
| TREX1 | NM_016381 | 33 | PSR03005682.hg.1 | 3 | + | 48508041 | 48508066 | 0.87 | −2.6 | 9.0734E−12 | V |
| TREX1 | NM_016381 | 34 | PSR03005683.hg.1 | 3 | + | 48508067 | 48508138 | 0.88 | −4.4 | 1.2281E−13 | V |
| TREX1 | NM_016381 | 36 | PSR03005685.hg.1 | 3 | + | 48508177 | 48508463 | 0.89 | −6.0 | 3.542E−16 | V |
| TREX1 | NM_016381 | 37 | PSR03005686.hg.1 | 3 | + | 48508464 | 48508832 | 0.91 | −6.7 | 3.2874E−18 | V |
| TREX1 | NM_016381 | 38 | PSR03005687.hg.1 | 3 | + | 48508833 | 48509000 | 0.89 | −5.6 | 3.6161E−16 | V |
| TREX1 | NM_016381 | 39 | PSR03005688.hg.1 | 3 | + | 48509001 | 48509041 | 0.76 | −1.5 | 1.4796E−07 | V |
| PARP14 | NM_017554 | 5 | PSR03011433.hg.1 | 3 | + | 122405606 | 122405926 | 0.70 | −2.9 | 8.0272E−05 | V |
| PARP14 | NM_017554 | 12 | PSR03011440.hg.1 | 3 | + | 122418170 | 122418236 | 0.72 | −3.6 | 7.0637E−06 | V |
| PARP14 | NM_017554 | 18 | PSR03011446.hg.1 | 3 | + | 122422589 | 122422825 | 0.75 | −2.8 | 6.662E−08 | V |
| PARP14 | NM_017554 | 19 | PSR03011447.hg.1 | 3 | + | 122423374 | 122423595 | 0.78 | −2.9 | 1.1594E−08 | V |
| PARP14 | NM_017554 | 20 | PSR03011448.hg.1 | 3 | + | 122427037 | 122427115 | 0.77 | −2.9 | 2.145E−08 | V |
| PARP14 | NM_017554 | 21 | PSR03011449.hg.1 | 3 | + | 122432271 | 122432416 | 0.79 | −2.8 | 3.5622E−09 | V |
| PARP14 | NM_017554 | 23 | PSR03011453.hg.1 | 3 | + | 122433109 | 122433276 | 0.77 | −2.8 | 1.2013E−08 | V |
| PARP14 | NM_017554 | 24 | PSR03011454.hg.1 | 3 | + | 122436918 | 122437124 | 0.78 | −2.9 | 4.5548E−09 | V |
| PARP14 | NM_017554 | 25 | PSR03011455.hg.1 | 3 | + | 122437206 | 122437230 | 0.78 | −3.4 | 8.2098E−09 | V |
| PARP14 | NM_017554 | 27 | PSR03011457.hg.1 | 3 | + | 122439102 | 122439235 | 0.79 | −2.8 | 1.2941E−09 | V |
| PARP14 | NM_017554 | 28 | PSR03011458.hg.1 | 3 | + | 122439236 | 122439674 | 0.77 | −4.6 | 1.7165E−08 | V |
| PARP14 | NM_017554 | 30 | PSR03011460.hg.1 | 3 | + | 122439774 | 122439815 | 0.79 | −4.7 | 3.4452E−09 | V |
| PARP14 | NM_017554 | 31 | PSR03011461.hg.1 | 3 | + | 122439816 | 122440500 | 0.80 | −4.8 | 7.7177E−10 | V |
| PARP14 | NM_017554 | 32 | PSR03011462.hg.1 | 3 | + | 122440501 | 122441494 | 0.76 | −3.9 | 2.8659E−07 | V |
| PARP14 | NM_017554 | 33 | PSR03011463.hg.1 | 3 | + | 122446659 | 122446833 | 0.79 | −3.1 | 1.6532E−09 | V |
| PARP14 | NM_017554 | 35 | PSR03011465.hg.1 | 3 | + | 122447444 | 122449686 | 0.78 | −3.1 | 8.7136E−09 | V |
| HESX1 | NM_003865 | 2 | PSR03027097.hg.1 | 3 | − | 57232009 | 57232166 | 0.82 | −5.6 | 2.3572E−09 | V |
| HESX1 | NM_003865 | 3 | PSR03027098.hg.1 | 3 | − | 57232167 | 57232224 | 0.87 | −3.8 | 7.9268E−11 | V |
| HESX1 | NM_003865 | 4 | PSR03027099.hg.1 | 3 | − | 57232225 | 57232323 | 0.84 | −6.7 | 2.6785E−10 | V |
| HESX1 | NM_003865 | 5 | PSR03027100.hg.1 | 3 | − | 57232419 | 57232520 | 0.83 | −7.4 | 3.7958E−10 | V |
| HESX1 | NM_003865 | 6 | PSR03027101.hg.1 | 3 | − | 57232781 | 57232980 | 0.81 | −3.7 | 1.3329E−08 | V |

TABLE 13-continued

Exon level analysis of 140 RNA determinants differentially expressed in bacterial and viral patients. Probe set ID is based on GeneChip Human Transcriptome Arrays 2.0 (HTA-Affymetrix) data. Comparison to full gene was calculated as absolute fold change ($exon_i$) - absolute fold change (full length gene); Only exons that presented higher of differential expression of the single exon compared to the full length gene were included.

| Gene Symbol | mRNA Accession | Exon # | Probe Set ID | Chromosome | Strand | Start | Stop | Exon AUC | FC | T-Test | Up in B/V |
|---|---|---|---|---|---|---|---|---|---|---|---|
| HESX1 | NM_003865 | 7 | PSR03027102.hg.1 | 3 | − | 57233790 | 57233966 | 0.87 | −4.0 | 1.7772E−09 | V |
| ZDHHC19 | NM_001039617 | 1 | PSR03038115.hg.1 | 3 | − | 195924325 | 195924596 | 0.81 | 4.9 | 4.3393E−11 | B |
| ZDHHC19 | NM_001039617 | 2 | PSR03038116.hg.1 | 3 | − | 195925147 | 195925264 | 0.80 | 2.4 | 9.0709E−10 | B |
| ZDHHC19 | NM_001039617 | 3 | PSR03038117.hg.1 | 3 | − | 195925265 | 195925322 | 0.82 | 6.6 | 2.0843E−12 | B |
| ZDHHC19 | NM_001039617 | 4 | PSR03038118.hg.1 | 3 | − | 195925323 | 195925461 | 0.76 | 1.8 | 4.6282E−08 | B |
| ZDHHC19 | NM_001039617 | 5 | PSR03038119.hg.1 | 3 | − | 195925660 | 195925740 | 0.83 | 10.6 | 1.8756E−12 | B |
| ZDHHC19 | NM_001039617 | 8 | PSR03038123.hg.1 | 3 | − | 195926394 | 195926523 | 0.80 | 2.0 | 3.1082E−09 | B |
| ZDHHC19 | NM_001039617 | 9 | PSR03038124.hg.1 | 3 | − | 195934269 | 195934374 | 0.83 | 12.0 | 1.8022E−12 | B |
| ZDHHC19 | NM_001039617 | 14 | PSR03038130.hg.1 | 3 | − | 195937487 | 195937530 | 0.77 | 1.9 | 1.3848E−09 | B |
| FAM200B | NM_001145191 | 2 | PSR04002242.hg.1 | 4 | + | 15683380 | 15683407 | 0.74 | 1.4 | 1.4431E−06 | B |
| FAM200B | NM_001145191 | 9 | PSR04002256.hg.1 | 4 | + | 15686509 | 15686582 | 0.69 | 1.4 | 0.00037617 | B |
| FAM200B | NM_001145191 | 10 | PSR04002257.hg.1 | 4 | + | 15687859 | 15688019 | 0.75 | 1.5 | 6.5633E−07 | B |
| FAM200B | NM_001145191 | 11 | PSR04002258.hg.1 | 4 | + | 15688020 | 15688085 | 0.72 | 1.4 | 1.5914E−05 | B |
| FAM200B | NM_001145191 | 12 | PSR04002259.hg.1 | 4 | + | 15688086 | 15688191 | 0.80 | 1.7 | 9.0057E−10 | B |
| FAM200B | NM_001145191 | 13 | PSR04002260.hg.1 | 4 | + | 15688192 | 15688229 | 0.74 | 5.0 | 5.2171E−06 | B |
| FAM200B | NM_001145191 | 14 | PSR04002261.hg.1 | 4 | + | 15688230 | 15688554 | 0.76 | 1.5 | 8.5806E−08 | B |
| FAM200B | NM_001145191 | 15 | PSR04002262.hg.1 | 4 | + | 15688555 | 15688600 | 0.68 | 1.4 | 0.00036696 | B |
| FAM200B | NM_001145191 | 16 | PSR04002264.hg.1 | 4 | + | 15688624 | 15688673 | 0.74 | 1.6 | 4.9592E−06 | B |
| FAM200B | NM_001145191 | 17 | PSR04002265.hg.1 | 4 | + | 15688674 | 15688764 | 0.74 | 1.6 | 4.4213E−06 | B |
| FAM200B | NM_001145191 | 18 | PSR04002268.hg.1 | 4 | + | 15688772 | 15688928 | 0.82 | 1.6 | 4.8849E−10 | B |
| FAM200B | NM_001145191 | 19 | PSR04002270.hg.1 | 4 | + | 15688936 | 15689083 | 0.79 | 1.6 | 7.0192E−09 | B |
| FAM200B | NM_001145191 | 20 | PSR04002272.hg.1 | 4 | + | 15689086 | 15690173 | 0.82 | 1.7 | 5.3235E−10 | B |
| FAM200B | NM_001145191 | 21 | PSR04002273.hg.1 | 4 | + | 15690174 | 15690236 | 0.76 | 1.6 | 1.959E−06 | B |
| FAM200B | NM_001145191 | 22 | PSR04002275.hg.1 | 4 | + | 15690243 | 15690317 | 0.76 | 1.7 | 4.322E−07 | B |
| FAM200B | NM_001145191 | 23 | PSR04002276.hg.1 | 4 | + | 15690318 | 15690574 | 0.73 | 1.6 | 1.0523E−05 | B |
| NSUN7 | NM_024677 | 4 | PSR04003604.hg.1 | 4 | + | 40752620 | 40753008 | 0.85 | 5.0 | 3.284E−13 | B |
| NSUN7 | NM_024677 | 5 | PSR04003605.hg.1 | 4 | + | 40762451 | 40762509 | 0.86 | 4.0 | 2.2321E−13 | B |
| NSUN7 | NM_024677 | 6 | PSR04003606.hg.1 | 4 | + | 40763188 | 40763318 | 0.86 | 4.4 | 9.3928E−14 | B |
| NSUN7 | NM_024677 | 9 | PSR04003609.hg.1 | 4 | + | 40776282 | 40776434 | 0.85 | 4.8 | 3.4931E−13 | B |
| NSUN7 | NM_024677 | 10 | PSR04003610.hg.1 | 4 | + | 40776784 | 40776967 | 0.85 | 4.7 | 4.4978E−13 | B |
| NSUN7 | NM_024677 | 12 | PSR04003612.hg.1 | 4 | + | 40778066 | 40778091 | 0.86 | 3.8 | 1.0934E−13 | B |
| NSUN7 | NM_024677 | 14 | PSR04003614.hg.1 | 4 | + | 40778206 | 40778276 | 0.84 | 4.4 | 3.4843E−13 | B |
| NSUN7 | NM_024677 | 16 | PSR04003616.hg.1 | 4 | + | 40792619 | 40792762 | 0.85 | 4.9 | 3.6907E−13 | B |
| NSUN7 | NM_024677 | 17 | PSR04003617.hg.1 | 4 | + | 40796392 | 40796493 | 0.84 | 4.7 | 3.3483E−12 | B |
| NSUN7 | NM_024677 | 18 | PSR04003618.hg.1 | 4 | + | 40800804 | 40800890 | 0.84 | 3.8 | 7.8202E−13 | B |
| NSUN7 | NM_024677 | 19 | PSR04003619.hg.1 | 4 | + | 40800891 | 40800921 | 0.82 | 3.7 | 2.0428E−11 | B |
| NSUN7 | NM_024677 | 20 | PSR04003620.hg.1 | 4 | + | 40809078 | 40809201 | 0.86 | 4.1 | 3.1383E−13 | B |
| NSUN7 | NM_024677 | 21 | PSR04003622.hg.1 | 4 | + | 40810324 | 40810520 | 0.85 | 4.3 | 4.8497E−13 | B |
| NSUN7 | NM_024677 | 22 | PSR04003623.hg.1 | 4 | + | 40810521 | 40810560 | 0.85 | 5.1 | 4.3052E−13 | B |
| NSUN7 | NM_024677 | 23 | PSR04003624.hg.1 | 4 | + | 40810561 | 40811743 | 0.85 | 4.4 | 1.9857E−13 | B |
| STAP1 | NM_012108 | 3 | PSR04004945.hg.1 | 4 | + | 68436802 | 68436873 | 0.84 | 7.2 | 8.3664E−13 | V |
| STAP1 | NM_012108 | 4 | PSR04004946.hg.1 | 4 | + | 68441103 | 68441216 | 0.85 | 7.7 | 4.6116E−14 | V |
| STAP1 | NM_012108 | 6 | PSR04004948.hg.1 | 4 | + | 68447023 | 68447189 | 0.85 | 8.0 | 6.3543E−14 | V |
| STAP1 | NM_012108 | 7 | PSR04004949.hg.1 | 4 | + | 68449292 | 68449420 | 0.86 | 7.2 | 2.5638E−14 | V |
| STAP1 | NM_012108 | 8 | PSR04004950.hg.1 | 4 | + | 68456602 | 68456671 | 0.85 | 6.8 | 2.7014E−13 | V |
| STAP1 | NM_012108 | 9 | PSR04004951.hg.1 | 4 | + | 68458978 | 68459074 | 0.86 | 8.0 | 1.0425E−14 | V |
| STAP1 | NM_012108 | 10 | PSR04004952.hg.1 | 4 | + | 68472014 | 68472107 | 0.86 | 6.8 | 1.3884E−14 | V |
| ANXA3 | NM_005139 | 3 | PSR04006272.hg.1 | 4 | + | 79472924 | 79472980 | 0.80 | 3.4 | 1.6071E−09 | B |
| ANXA3 | NM_005139 | 4 | PSR04006273.hg.1 | 4 | + | 79472981 | 79473013 | 0.80 | 5.9 | 1.6593E−09 | B |
| ANXA3 | NM_005139 | 8 | PSR04006277.hg.1 | 4 | + | 79475590 | 79475642 | 0.81 | 2.7 | 2.3661E−08 | B |
| ANXA3 | NM_005139 | 10 | PSR04006279.hg.1 | 4 | + | 79494334 | 79494421 | 0.80 | 3.6 | 7.0543E−09 | B |
| ANXA3 | NM_005139 | 11 | PSR04006280.hg.1 | 4 | + | 79500181 | 79500275 | 0.81 | 3.7 | 4.0885E−09 | B |
| ANXA3 | NM_005139 | 12 | PSR04006281.hg.1 | 4 | + | 79503331 | 79503444 | 0.80 | 3.6 | 7.1844E−09 | B |
| ANXA3 | NM_005139 | 13 | PSR04006283.hg.1 | 4 | + | 79503446 | 79503575 | 0.73 | 2.7 | 5.2557E−06 | B |
| ANXA3 | NM_005139 | 14 | PSR04006284.hg.1 | 4 | + | 79507414 | 79507504 | 0.80 | 3.0 | 2.4624E−08 | B |
| ANXA3 | NM_005139 | 15 | PSR04006285.hg.1 | 4 | + | 79512698 | 79512757 | 0.81 | 3.1 | 1.8836E−08 | B |
| ANXA3 | NM_005139 | 16 | PSR04006287.hg.1 | 4 | + | 79516535 | 79516591 | 0.81 | 3.0 | 2.9878E−08 | B |
| ANXA3 | NM_005139 | 18 | PSR04006289.hg.1 | 4 | + | 79518227 | 79518472 | 0.74 | 3.1 | 6.0489E−07 | B |
| ANXA3 | NM_005139 | 20 | PSR04006291.hg.1 | 4 | + | 79522664 | 79522722 | 0.79 | 2.7 | 6.4003E−08 | B |
| ANXA3 | NM_005139 | 22 | PSR04006293.hg.1 | 4 | + | 79525431 | 79525553 | 0.79 | 3.0 | 3.7313E−08 | B |
| ANXA3 | NM_005139 | 23 | PSR04006294.hg.1 | 4 | + | 79531210 | 79531517 | 0.79 | 3.0 | 7.934E−08 | B |
| HERC6 | NM_001165136 | 11 | PSR04006999.hg.1 | 4 | + | 89314640 | 89314734 | 0.92 | −13.0 | 6.6641E−21 | V |
| HERC6 | NM_001165136 | 13 | PSR04007001.hg.1 | 4 | + | 89318003 | 89318139 | 0.92 | −13.4 | 8.5055E−22 | V |
| HERC6 | NM_001165136 | 15 | PSR04007004.hg.1 | 4 | + | 89319294 | 89319361 | 0.93 | −13.4 | 3.3613E−22 | V |
| HERC6 | NM_001165136 | 21 | PSR04007010.hg.1 | 4 | + | 89334229 | 89334417 | 0.92 | −12.2 | 1.2415E−21 | V |
| HERC6 | NM_001165136 | 22 | PSR04007012.hg.1 | 4 | + | 89338577 | 89338731 | 0.92 | −11.3 | 7.8756E−21 | V |
| HERC6 | NM_001165136 | 23 | PSR04007014.hg.1 | 4 | + | 89345013 | 89345125 | 0.92 | −11.4 | 3.7799E−21 | V |
| HERC6 | NM_001165136 | 24 | PSR04007015.hg.1 | 4 | + | 89345747 | 89345854 | 0.92 | −14.6 | 6.5951E−22 | V |
| HERC6 | NM_001165136 | 27 | PSR04007018.hg.1 | 4 | + | 89352314 | 89352457 | 0.93 | −15.3 | 6.9856E−23 | V |

TABLE 13-continued

Exon level analysis of 140 RNA determinants differentially expressed in bacterial and viral patients. Probe set ID is based on GeneChip Human Transcriptome Arrays 2.0 (HTA-Affymetrix) data. Comparison to full gene was calculated as absolute fold change (exon$_i$) - absolute fold change (full length gene); Only exons that presented higher of differential expression of the single exon compared to the full length gene were included.

| Gene Symbol | mRNA Accession | Exon # | Probe Set ID | Chromosome | Strand | Start | Stop | Exon AUC | FC | T-Test | Up in B/V |
|---|---|---|---|---|---|---|---|---|---|---|---|
| HERC6 | NM_001165136 | 28 | PSR04007019.hg.1 | 4 | + | 89356877 | 89357043 | 0.93 | −11.9 | 7.577E−22 | V |
| HERC6 | NM_001165136 | 29 | PSR04007020.hg.1 | 4 | + | 89358057 | 89358123 | 0.92 | −14.9 | 2.9143E−22 | V |
| HERC6 | NM_001165136 | 30 | PSR04007021.hg.1 | 4 | + | 89358863 | 89358933 | 0.93 | −14.4 | 1.0775E−22 | V |
| HERC6 | NM_001165136 | 31 | PSR04007023.hg.1 | 4 | + | 89361026 | 89361209 | 0.93 | −14.9 | 1.3804E−22 | V |
| HERC6 | NM_001165136 | 34 | PSR04007026.hg.1 | 4 | + | 89363386 | 89364248 | 0.93 | −13.9 | 6.2757E−22 | V |
| SULT1B1 | NM_014465 | 2 | PSR04017258.hg.1 | 4 | − | 70592699 | 70592918 | 0.88 | 3.7 | 8.8038E−16 | B |
| SULT1B1 | NM_014465 | 3 | PSR04017259.hg.1 | 4 | − | 70596219 | 70596399 | 0.88 | 3.8 | 5.8187E−16 | B |
| SULT1B1 | NM_014465 | 5 | PSR04017261.hg.1 | 4 | − | 70599856 | 70599890 | 0.88 | 3.7 | 6.4959E−16 | B |
| SULT1B1 | NM_014465 | 6 | PSR04017262.hg.1 | 4 | − | 70599891 | 70599982 | 0.89 | 4.2 | 2.1248E−16 | B |
| SULT1B1 | NM_014465 | 7 | PSR04017263.hg.1 | 4 | − | 70615439 | 70615536 | 0.88 | 3.7 | 6.1258E−16 | B |
| IGJ | NM_144646 | 4 | PSR04017312.hg.1 | 4 | − | 71522046 | 71522079 | 0.72 | −4.8 | 9.2352E−06 | V |
| PPM1K | NM_152542 | 1 | PSR04019196.hg.1 | 4 | − | 89181532 | 89183022 | 0.90 | −5.3 | 4.2542E−18 | V |
| PPM1K | NM_152542 | 2 | PSR04019198.hg.1 | 4 | − | 89183043 | 89183314 | 0.90 | −4.9 | 1.3097E−17 | V |
| PPM1K | NM_152542 | 3 | PSR04019199.hg.1 | 4 | − | 89183315 | 89183427 | 0.90 | −6.1 | 2.7221E−18 | V |
| PPM1K | NM_152542 | 4 | PSR04019201.hg.1 | 4 | − | 89183431 | 89183728 | 0.91 | −6.6 | 2.8559E−19 | V |
| PPM1K | NM_152542 | 5 | PSR04019202.hg.1 | 4 | − | 89183729 | 89183878 | 0.91 | −5.7 | 1.7424E−18 | V |
| PPM1K | NM_152542 | 6 | PSR04019203.hg.1 | 4 | − | 89186153 | 89186287 | 0.91 | −6.2 | 1.12E−19 | V |
| PPM1K | NM_152542 | 7 | PSR04019204.hg.1 | 4 | − | 89189342 | 89189486 | 0.92 | −6.2 | 1.4773E−19 | V |
| PPM1K | NM_152542 | 8 | PSR04019208.hg.1 | 4 | − | 89189914 | 89190058 | 0.90 | −4.2 | 1.0987E−17 | V |
| PPM1K | NM_152542 | 13 | PSR04019213.hg.1 | 4 | − | 89196461 | 89198294 | 0.89 | −4.3 | 7.0246E−16 | V |
| PPM1K | NM_152542 | 14 | PSR04019214.hg.1 | 4 | − | 89198295 | 89198395 | 0.90 | −5.3 | 1.0185E−18 | V |
| PPM1K | NM_152542 | 16 | PSR04019216.hg.1 | 4 | − | 89199296 | 89199344 | 0.91 | −6.1 | 1.1914E−18 | V |
| PPM1K | NM_152542 | 19 | PSR04019219.hg.1 | 4 | − | 89199719 | 89199794 | 0.90 | −5.2 | 1.1405E−16 | V |
| PPM1K | NM_152542 | 22 | PSR04019222.hg.1 | 4 | − | 89205558 | 89205713 | 0.90 | −4.2 | 1.2705E−17 | V |
| PPM1K | NM_152542 | 23 | PSR04019226.hg.1 | 4 | − | 89205748 | 89205783 | 0.90 | −6.8 | 1.0476E−18 | V |
| HPGD | NM_000860 | 2 | PSR04024158.hg.1 | 4 | − | 175411380 | 175412254 | 0.82 | 4.1 | 4.9707E−11 | B |
| HPGD | NM_000860 | 3 | PSR04024159.hg.1 | 4 | − | 175412255 | 175412608 | 0.81 | 6.1 | 5.8836E−10 | B |
| HPGD | NM_000860 | 4 | PSR04024160.hg.1 | 4 | − | 175412609 | 175412721 | 0.80 | 5.8 | 7.2441E−10 | B |
| HPGD | NM_000860 | 5 | PSR04024161.hg.1 | 4 | − | 175412722 | 175412905 | 0.81 | 5.7 | 7.387E−10 | B |
| HPGD | NM_000860 | 6 | PSR04024162.hg.1 | 4 | − | 175412906 | 175412935 | 0.79 | 5.0 | 6.2478E−09 | B |
| HPGD | NM_000860 | 7 | PSR04024164.hg.1 | 4 | − | 175412945 | 175413020 | 0.81 | 7.3 | 1.5417E−10 | B |
| HPGD | NM_000860 | 8 | PSR04024165.hg.1 | 4 | − | 175413021 | 175413083 | 0.81 | 6.7 | 3.6599E−10 | B |
| HPGD | NM_000860 | 9 | PSR04024166.hg.1 | 4 | − | 175413084 | 175413245 | 0.81 | 7.2 | 2.8059E−10 | B |
| HPGD | NM_000860 | 10 | PSR04024169.hg.1 | 4 | − | 175414310 | 175414465 | 0.82 | 7.4 | 3.5508E−11 | B |
| HPGD | NM_000860 | 13 | PSR04024172.hg.1 | 4 | − | 175416699 | 175416775 | 0.82 | 6.8 | 8.2983E−11 | B |
| HPGD | NM_000860 | 16 | PSR04024175.hg.1 | 4 | − | 175429847 | 175429943 | 0.82 | 7.9 | 2.931E−11 | B |
| HPGD | NM_000860 | 17 | PSR04024176.hg.1 | 4 | − | 175439122 | 175439228 | 0.82 | 7.3 | 6.3258E−11 | B |
| HPGD | NM_000860 | 18 | PSR04024177.hg.1 | 4 | − | 175443095 | 175443218 | 0.83 | 7.7 | 1.586E−11 | B |
| ANKRD34B | NM_001004441 | 1 | PSR05020972.hg.1 | 5 | − | 79853364 | 79853503 | 0.78 | 2.7 | 1.3589E−09 | B |
| ANKRD34B | NM_001004441 | 2 | PSR05020974.hg.1 | 5 | − | 79853366 | 79853614 | 0.78 | 2.6 | 1.7156E−08 | B |
| ANKRD34B | NM_001004441 | 3 | PSR05020975.hg.1 | 5 | − | 79853615 | 79854293 | 0.79 | 3.5 | 3.0718E−10 | B |
| ANKRD34B | NM_001004441 | 4 | PSR05020976.hg.1 | 5 | − | 79854294 | 79855787 | 0.79 | 4.0 | 1.4868E−10 | B |
| ANKRD34B | NM_001004441 | 5 | PSR05020977.hg.1 | 5 | − | 79855788 | 79855838 | 0.82 | 3.1 | 1.3467E−11 | B |
| ANKRD34B | NM_001004441 | 6 | PSR05020979.hg.1 | 5 | − | 79859554 | 79859634 | 0.83 | 5.3 | 2.7585E−12 | B |
| ANKRD34B | NM_001004441 | 7 | PSR05020980.hg.1 | 5 | − | 79860203 | 79860288 | 0.78 | 2.4 | 5.5908E−09 | B |
| ANKRD34B | NM_001004441 | 8 | PSR05020981.hg.1 | 5 | − | 79862508 | 79862590 | 0.82 | 3.5 | 5.6152E−12 | B |
| ANKRD34B | NM_001004441 | 9 | PSR05020982.hg.1 | 5 | − | 79864779 | 79864896 | 0.83 | 2.8 | 1.0174E−11 | B |
| MAPK14 | NM_001315 | 5 | PSR06005613.hg.1 | 6 | + | 35995935 | 35995967 | 0.85 | 5.3 | 2.4267E−13 | B |
| MAPK14 | NM_001315 | 6 | PSR06005615.hg.1 | 6 | + | 35995976 | 35996050 | 0.86 | 4.1 | 1.0282E−13 | B |
| MAPK14 | NM_001315 | 9 | PSR06005618.hg.1 | 6 | + | 36027066 | 36027124 | 0.88 | 2.9 | 1.2271E−14 | B |
| MAPK14 | NM_001315 | 10 | PSR06005619.hg.1 | 6 | + | 36040650 | 36040761 | 0.88 | 3.1 | 7.8599E−15 | B |
| MAPK14 | NM_001315 | 12 | PSR06005621.hg.1 | 6 | + | 36041468 | 36041497 | 0.89 | 2.7 | 4.9099E−15 | B |
| MAPK14 | NM_001315 | 13 | PSR06005622.hg.1 | 6 | + | 36041826 | 36041873 | 0.88 | 2.9 | 5.3718E−15 | B |
| MAPK14 | NM_001315 | 15 | PSR06005625.hg.1 | 6 | + | 36043642 | 36043739 | 0.87 | 2.8 | 1.2881E−14 | B |
| MAPK14 | NM_001315 | 17 | PSR06005628.hg.1 | 6 | + | 36044386 | 36044665 | 0.77 | 2.9 | 8.2414E−08 | B |
| MAPK14 | NM_001315 | 18 | PSR06005629.hg.1 | 6 | + | 36063764 | 36063843 | 0.87 | 2.6 | 2.045E−14 | B |
| MAPK14 | NM_001315 | 20 | PSR06005631.hg.1 | 6 | + | 36067965 | 36068044 | 0.85 | 2.9 | 1.8242E−13 | B |
| MAPK14 | NM_001315 | 27 | PSR06005639.hg.1 | 6 | + | 36076448 | 36078531 | 0.86 | 3.1 | 6.2792E−14 | B |
| MAPK14 | NM_001315 | 28 | PSR06005641.hg.1 | 6 | + | 36078533 | 36079013 | 0.82 | 2.8 | 1.5631E−12 | B |
| FTSJD2 | NM_015050 | 12 | PSR06006001.hg.1 | 6 | + | 37421016 | 37421088 | 0.81 | −3.3 | 6.0397E−11 | V |
| FTSJD2 | NM_015050 | 13 | PSR06006002.hg.1 | 6 | + | 37426388 | 37426465 | 0.81 | −3.3 | 1.2995E−10 | V |
| FTSJD2 | NM_015050 | 20 | PSR06006011.hg.1 | 6 | + | 37429849 | 37429878 | 0.81 | −3.4 | 1.4947E−11 | V |
| FTSJD2 | NM_015050 | 22 | PSR06006013.hg.1 | 6 | + | 37430647 | 37430784 | 0.83 | −3.3 | 2.2569E−11 | V |
| FTSJD2 | NM_015050 | 23 | PSR06006014.hg.1 | 6 | + | 37438797 | 37438853 | 0.83 | −3.5 | 3.6318E−12 | V |
| FTSJD2 | NM_015050 | 24 | PSR06006015.hg.1 | 6 | + | 37439623 | 37439680 | 0.84 | −3.4 | 1.9697E−12 | V |
| FTSJD2 | NM_015050 | 25 | PSR06006016.hg.1 | 6 | + | 37440195 | 37440263 | 0.84 | −3.3 | 3.6012E−12 | V |
| FTSJD2 | NM_015050 | 26 | PSR06006017.hg.1 | 6 | + | 37441246 | 37441343 | 0.85 | −3.6 | 6.7767E−14 | V |
| FTSJD2 | NM_015050 | 27 | PSR06006018.hg.1 | 6 | + | 37441344 | 37441377 | 0.85 | −4.7 | 3.6163E−13 | V |
| FTSJD2 | NM_015050 | 28 | PSR06006019.hg.1 | 6 | + | 37442300 | 37442422 | 0.85 | −3.5 | 3.411E−13 | V |

TABLE 13-continued

Exon level analysis of 140 RNA determinants differentially expressed in bacterial and viral patients. Probe set ID is based on GeneChip Human Transcriptome Arrays 2.0 (HTA-Affymetrix) data. Comparison to full gene was calculated as absolute fold change (exon$_i$) - absolute fold change (full length gene); Only exons that presented higher of differential expression of the single exon compared to the full length gene were included.

| Gene Symbol | mRNA Accession | Exon # | Probe Set ID | Chromosome | Strand | Start | Stop | Exon AUC | FC | T-Test | Up in B/V |
|---|---|---|---|---|---|---|---|---|---|---|---|
| FTSJD2 | NM_015050 | 29 | PSR06006022.hg.1 | 6 | + | 37443121 | 37443188 | 0.87 | -4.1 | 5.4483E-15 | V |
| FTSJD2 | NM_015050 | 31 | PSR06006024.hg.1 | 6 | + | 37443902 | 37443970 | 0.88 | -4.5 | 1.6449E-16 | V |
| FTSJD2 | NM_015050 | 32 | PSR06006025.hg.1 | 6 | + | 37445368 | 37445415 | 0.87 | -3.7 | 2.2043E-15 | V |
| FTSJD2 | NM_015050 | 33 | PSR06006026.hg.1 | 6 | + | 37446185 | 37446297 | 0.89 | -5.4 | 2.2274E-17 | V |
| FTSJD2 | NM_015050 | 34 | PSR06006027.hg.1 | 6 | + | 37446923 | 37446971 | 0.88 | -4.2 | 1.383E-16 | V |
| FTSJD2 | NM_015050 | 35 | PSR06006028.hg.1 | 6 | + | 37446972 | 37447002 | 0.88 | -4.4 | 6.2651E-16 | V |
| FTSJD2 | NM_015050 | 36 | PSR06006029.hg.1 | 6 | + | 37447003 | 37447031 | 0.89 | -5.2 | 1.2648E-16 | V |
| FTSJD2 | NM_015050 | 38 | PSR06006032.hg.1 | 6 | + | 37448168 | 37448855 | 0.87 | -3.6 | 1.4963E-14 | V |
| FTSJD2 | NM_015050 | 39 | PSR06006033.hg.1 | 6 | + | 37448856 | 37448922 | 0.88 | -3.4 | 1.7934E-14 | V |
| CD2AP | NM_012120 | 3 | PSR06007687.hg.1 | 6 | + | 47471016 | 47471176 | 0.88 | -4.1 | 5.3692E-17 | V |
| CD2AP | NM_012120 | 4 | PSR06007688.hg.1 | 6 | + | 47501338 | 47501420 | 0.91 | -4.3 | 1.0544E-18 | V |
| CD2AP | NM_012120 | 5 | PSR06007689.hg.1 | 6 | + | 47501421 | 47501491 | 0.89 | -4.7 | 2.8941E-18 | V |
| CD2AP | NM_012120 | 6 | PSR06007690.hg.1 | 6 | + | 47512342 | 47512442 | 0.88 | -4.0 | 5.1992E-17 | V |
| CD2AP | NM_012120 | 8 | PSR06007692.hg.1 | 6 | + | 47522382 | 47522502 | 0.89 | -3.5 | 1.2219E-16 | V |
| CD2AP | NM_012120 | 9 | PSR06007693.hg.1 | 6 | + | 47541800 | 47541987 | 0.89 | -4.3 | 7.3083E-17 | V |
| CD2AP | NM_012120 | 10 | PSR06007695.hg.1 | 6 | + | 47544260 | 47544338 | 0.90 | -4.4 | 1.1843E-17 | V |
| CD2AP | NM_012120 | 11 | PSR06007696.hg.1 | 6 | + | 47544745 | 47544839 | 0.90 | -4.6 | 1.1004E-17 | V |
| CD2AP | NM_012120 | 12 | PSR06007698.hg.1 | 6 | + | 47547130 | 47547225 | 0.90 | -4.9 | 3.06E-18 | V |
| CD2AP | NM_012120 | 15 | PSR06007701.hg.1 | 6 | + | 47549739 | 47549801 | 0.88 | -3.8 | 3.8413E-15 | V |
| CD2AP | NM_012120 | 17 | PSR06007703.hg.1 | 6 | + | 47563597 | 47563762 | 0.88 | -3.8 | 2.1794E-16 | V |
| CD2AP | NM_012120 | 18 | PSR06007704.hg.1 | 6 | + | 47567037 | 47567179 | 0.90 | -4.2 | 2.3459E-17 | V |
| CD2AP | NM_012120 | 19 | PSR06007705.hg.1 | 6 | + | 47573901 | 47574013 | 0.89 | -4.5 | 1.807E-17 | V |
| CD2AP | NM_012120 | 21 | PSR06007707.hg.1 | 6 | + | 47575663 | 47575764 | 0.89 | -3.7 | 2.8729E-17 | V |
| CD2AP | NM_012120 | 22 | PSR06007708.hg.1 | 6 | + | 47576859 | 47577040 | 0.88 | -3.7 | 3.3225E-16 | V |
| CD2AP | NM_012120 | 24 | PSR06007710.hg.1 | 6 | + | 47580209 | 47580272 | 0.89 | -3.7 | 3.7296E-17 | V |
| CD2AP | NM_012120 | 25 | PSR06007711.hg.1 | 6 | + | 47591922 | 47592011 | 0.88 | -4.2 | 2.7781E-16 | V |
| CD2AP | NM_012120 | 26 | PSR06007712.hg.1 | 6 | + | 47592012 | 47594996 | 0.88 | -4.7 | 1.3452E-16 | V |
| NCOA7 | NM_001122842 | 3 | PSR06011211.hg.1 | 6 | + | 126107283 | 126107359 | 0.52 | 1.2 | 0.24716264 | B |
| NCOA7 | NM_001122842 | 10 | PSR06011219.hg.1 | 6 | + | 126136437 | 126136550 | 0.60 | 1.2 | 0.03902208 | B |
| NCOA7 | NM_001122842 | 14 | PSR06011223.hg.1 | 6 | + | 126196035 | 126196114 | 0.64 | 1.2 | 0.00915867 | B |
| NCOA7 | NM_001122842 | 15 | PSR06011224.hg.1 | 6 | + | 126199409 | 126199516 | 0.65 | 1.2 | 0.00580473 | B |
| NCOA7 | NM_001122842 | 16 | PSR06011225.hg.1 | 6 | + | 126202236 | 126202349 | 0.62 | 1.3 | 0.00991852 | B |
| NCOA7 | NM_001122842 | 17 | PSR06011226.hg.1 | 6 | + | 126203572 | 126203697 | 0.65 | 1.2 | 0.03273458 | B |
| NCOA7 | NM_001122842 | 19 | PSR06011228.hg.1 | 6 | + | 126206305 | 126206489 | 0.65 | 1.3 | 0.00216239 | B |
| NCOA7 | NM_001122842 | 21 | PSR06011230.hg.1 | 6 | + | 126210085 | 126210117 | 0.61 | 1.2 | 0.01607899 | B |
| NCOA7 | NM_001122842 | 23 | PSR06011233.hg.1 | 6 | + | 126211801 | 126211956 | 0.60 | 1.2 | 0.04274364 | B |
| NCOA7 | NM_001122842 | 27 | PSR06011238.hg.1 | 6 | + | 126240370 | 126240450 | 0.75 | -1.6 | 5.1504E-07 | V |
| NCOA7 | NM_001122842 | 28 | PSR06011239.hg.1 | 6 | + | 126240451 | 126240577 | 0.82 | -9.9 | 1.8631E-11 | V |
| NCOA7 | NM_001122842 | 29 | PSR06011240.hg.1 | 6 | + | 126242089 | 126242214 | 0.80 | -4.4 | 2.1954E-09 | V |
| NCOA7 | NM_001122842 | 30 | PSR06011241.hg.1 | 6 | + | 126243828 | 126243980 | 0.81 | -5.3 | 5.0566E-10 | V |
| NCOA7 | NM_001122842 | 31 | PSR06011242.hg.1 | 6 | + | 126248809 | 126248904 | 0.81 | -5.1 | 6.6849E-10 | V |
| NCOA7 | NM_001122842 | 32 | PSR06011244.hg.1 | 6 | + | 126249329 | 126249393 | 0.81 | -4.2 | 5.6339E-09 | V |
| NCOA7 | NM_001122842 | 33 | PSR06011245.hg.1 | 6 | + | 126249782 | 126249982 | 0.81 | -5.0 | 2.8245E-10 | V |
| NCOA7 | NM_001122842 | 34 | PSR06011246.hg.1 | 6 | + | 126249983 | 126250173 | 0.77 | -4.1 | 6.879E-08 | V |
| NCOA7 | NM_001122842 | 35 | PSR06011247.hg.1 | 6 | + | 126250174 | 126252257 | 0.81 | -4.8 | 1.502E-09 | V |
| NCOA7 | NM_001122842 | 36 | PSR06011249.hg.1 | 6 | + | 126252267 | 126253176 | 0.72 | -1.6 | 0.00010919 | V |
| ARG1 | NM_000045 | 2 | PSR06011580.hg.1 | 6 | + | 131894417 | 131894417 | 0.78 | 6.6 | 2.5199E-08 | B |
| ARG1 | NM_000045 | 6 | PSR06011585.hg.1 | 6 | + | 131900251 | 131900341 | 0.78 | 6.6 | 1.8906E-08 | B |
| ARG1 | NM_000045 | 15 | PSR06011599.hg.1 | 6 | + | 131904200 | 131904245 | 0.76 | 6.5 | 1.4303E-07 | B |
| ARG1 | NM_000045 | 17 | PSR06011602.hg.1 | 6 | + | 131904499 | 131904538 | 0.77 | 6.6 | 3.5483E-08 | B |
| VNN1 | NM_004666 | 7 | PSR06026573.hg.1 | 6 | − | 133013362 | 133013723 | 0.84 | 10.1 | 3.8946E-12 | B |
| LRRN3 | NM_001099658 | 4 | PSR07011047.hg.1 | 7 | + | 110731183 | 110731560 | 0.73 | -3.0 | 8.2054E-06 | V |
| LRRN3 | NM_001099658 | 8 | PSR07011051.hg.1 | 7 | + | 110762471 | 110762828 | 0.73 | -4.9 | 6.2734E-06 | V |
| LRRN3 | NM_001099658 | 9 | PSR07011052.hg.1 | 7 | + | 110762829 | 110763649 | 0.72 | -3.7 | 2.4734E-05 | V |
| LRRN3 | NM_001099658 | 10 | PSR07011053.hg.1 | 7 | + | 110763650 | 110764955 | 0.72 | -3.7 | 2.9163E-05 | V |
| LRRN3 | NM_001099658 | 12 | PSR07011055.hg.1 | 7 | + | 110764989 | 110765462 | 0.71 | -2.7 | 2.4696E-05 | V |
| MGAM | NM_004668 | 7 | PSR07013939.hg.1 | 7 | + | 141704190 | 141704288 | 0.85 | 5.7 | 1.7948E-13 | B |
| MGAM | NM_004668 | 10 | PSR07013942.hg.1 | 7 | + | 141718999 | 141719040 | 0.88 | 5.3 | 2.3988E-15 | B |
| MGAM | NM_004668 | 11 | PSR07013943.hg.1 | 7 | + | 141719041 | 141719100 | 0.90 | 5.5 | 1.7669E-16 | B |
| MGAM | NM_004668 | 14 | PSR07013948.hg.1 | 7 | + | 141722068 | 141722239 | 0.90 | 4.4 | 1.3435E-15 | B |
| MGAM | NM_004668 | 15 | PSR07013949.hg.1 | 7 | + | 141724850 | 141724949 | 0.89 | 4.3 | 1.2111E-15 | B |
| MGAM | NM_004668 | 17 | PSR07013951.hg.1 | 7 | + | 141727410 | 141727535 | 0.89 | 4.4 | 1.1612E-15 | B |
| MGAM | NM_004668 | 19 | PSR07013953.hg.1 | 7 | + | 141730162 | 141730293 | 0.89 | 4.5 | 3.0873E-15 | B |
| MGAM | NM_004668 | 20 | PSR07013954.hg.1 | 7 | + | 141730441 | 141730557 | 0.90 | 4.6 | 5.7434E-15 | B |
| MGAM | NM_004668 | 23 | PSR07013958.hg.1 | 7 | + | 141734062 | 141734179 | 0.89 | 4.6 | 1.4405E-14 | B |
| MGAM | NM_004668 | 27 | PSR07013963.hg.1 | 7 | + | 141738346 | 141738415 | 0.89 | 6.4 | 8.0368E-16 | B |
| MGAM | NM_004668 | 36 | PSR07013972.hg.1 | 7 | + | 141754554 | 141754708 | 0.89 | 4.3 | 5.8469E-14 | B |
| MGAM | NM_004668 | 37 | PSR07013973.hg.1 | 7 | + | 141755358 | 141755526 | 0.89 | 4.4 | 3.2428E-14 | B |
| MGAM | NM_004668 | 40 | PSR07013976.hg.1 | 7 | + | 141758003 | 141758128 | 0.88 | 4.7 | 1.2166E-13 | B |

TABLE 13-continued

Exon level analysis of 140 RNA determinants differentially
expressed in bacterial and viral patients. Probe set ID is based on GeneChip
Human Transcriptome Arrays 2.0 (HTA-Affymetrix) data. Comparison to full
gene was calculated as absolute fold change (exon$_i$) - absolute fold change (full
length gene); Only exons that presented higher of differential expression of the
single exon compared to the full length gene were included.

| Gene Symbol | mRNA Accession | Exon # | Probe Set ID | Chromosome | Strand | Start | Stop | Exon AUC | FC | T-Test | Up in B/V |
|---|---|---|---|---|---|---|---|---|---|---|---|
| MGAM | NM_004668 | 41 | PSR07013977.hg.1 | 7 | + | 141759272 | 141759400 | 0.88 | 4.7 | 9.7156E-14 | B |
| MGAM | NM_004668 | 42 | PSR07013978.hg.1 | 7 | + | 141759656 | 141759766 | 0.88 | 4.9 | 1.4552E-14 | B |
| MGAM | NM_004668 | 45 | PSR07013981.hg.1 | 7 | + | 141763299 | 141763386 | 0.88 | 4.8 | 1.0056E-13 | B |
| MGAM | NM_004668 | 46 | PSR07013982.hg.1 | 7 | + | 141764184 | 141764322 | 0.88 | 5.7 | 3.1126E-15 | B |
| MGAM | NM_004668 | 48 | PSR07013984.hg.1 | 7 | + | 141765388 | 141765422 | 0.86 | 4.7 | 1.7566E-10 | B |
| MGAM | NM_004668 | 51 | PSR07013987.hg.1 | 7 | + | 141767141 | 141767225 | 0.88 | 4.4 | 8.3147E-13 | B |
| MGAM | NM_004668 | 55 | PSR07013992.hg.1 | 7 | + | 141776003 | 141776052 | 0.86 | 4.5 | 1.4561E-07 | B |
| MGAM | NM_004668 | 60 | PSR07013997.hg.1 | 7 | + | 141780591 | 141780745 | 0.88 | 4.3 | 9.9671E-12 | B |
| MGAM | NM_004668 | 64 | PSR07014001.hg.1 | 7 | + | 141784319 | 141784444 | 0.87 | 4.7 | 4.5665E-12 | B |
| MGAM | NM_004668 | 65 | PSR07014002.hg.1 | 7 | + | 141785633 | 141785761 | 0.88 | 4.8 | 1.2921E-12 | B |
| MGAM | NM_004668 | 66 | PSR07014003.hg.1 | 7 | + | 141786018 | 141786128 | 0.87 | 4.9 | 2.3365E-12 | B |
| MGAM | NM_004668 | 70 | PSR07014007.hg.1 | 7 | + | 141792321 | 141792408 | 0.87 | 4.8 | 1.3447E-12 | B |
| MGAM | NM_004668 | 71 | PSR07014008.hg.1 | 7 | + | 141793212 | 141793350 | 0.85 | 5.8 | 4.637E-12 | B |
| MGAM | NM_004668 | 72 | PSR07014009.hg.1 | 7 | + | 141794164 | 141794297 | 0.86 | 4.6 | 1.2094E-11 | B |
| MGAM | NM_004668 | 73 | PSR07014010.hg.1 | 7 | + | 141794420 | 141794454 | 0.86 | 4.4 | 1.1802E-11 | B |
| MGAM | NM_004668 | 83 | PSR07014020.hg.1 | 7 | + | 141802430 | 141802479 | 0.89 | 4.8 | 8.5362E-15 | B |
| MGAM | NM_004668 | 85 | PSR07014022.hg.1 | 7 | + | 141805614 | 141805879 | 0.89 | 4.7 | 5.9353E-15 | B |
| PARP12 | NM_022750 | 3 | PSR07029693.hg.1 | 7 | − | 139724334 | 139724380 | 0.88 | −8.4 | 5.4101E-16 | V |
| PARP12 | NM_022750 | 5 | PSR07029696.hg.1 | 7 | − | 139724468 | 139724678 | 0.91 | −6.7 | 1.123E-19 | V |
| PARP12 | NM_022750 | 8 | PSR07029702.hg.1 | 7 | − | 139727076 | 139727118 | 0.90 | −9.3 | 1.1132E-18 | V |
| PARP12 | NM_022750 | 11 | PSR07029705.hg.1 | 7 | − | 139728413 | 139728488 | 0.89 | −7.4 | 3.2439E-18 | V |
| PARP12 | NM_022750 | 14 | PSR07029708.hg.1 | 7 | − | 139734035 | 139734131 | 0.91 | −6.7 | 4.3237E-20 | V |
| PARP12 | NM_022750 | 16 | PSR07029710.hg.1 | 7 | − | 139737515 | 139737656 | 0.90 | −6.5 | 4.5318E-19 | V |
| PARP12 | NM_022750 | 18 | PSR07029712.hg.1 | 7 | − | 139741444 | 139741528 | 0.90 | −6.8 | 1.8471E-19 | V |
| PARP12 | NM_022750 | 28 | PSR07029722.hg.1 | 7 | − | 139762322 | 139762351 | 0.89 | −11.8 | 6.038E-18 | V |
| AKAP2 | NM_001004065 | 27 | PSR09006138.hg.1 | 9 | + | 112898430 | 112898614 | 0.71 | −1.3 | 3.0117E-05 | V |
| AKAP2 | NM_001004065 | 28 | PSR09006139.hg.1 | 9 | + | 112898615 | 112900450 | 0.64 | −1.3 | 0.00887188 | V |
| AKAP2 | NM_001004065 | 29 | PSR09006140.hg.1 | 9 | + | 112900451 | 112900706 | 0.69 | −1.5 | 0.00042177 | V |
| AKAP2 | NM_001004065 | 30 | PSR09006141.hg.1 | 9 | + | 112900707 | 112900819 | 0.73 | −1.5 | 8.6858E-06 | V |
| AKAP2 | NM_001004065 | 31 | PSR09006142.hg.1 | 9 | + | 112910808 | 112910983 | 0.90 | −2.4 | 3.1842E-16 | V |
| AKAP2 | NM_001004065 | 32 | PSR09006143.hg.1 | 9 | + | 112918599 | 112918777 | 0.89 | −5.0 | 5.6277E-16 | V |
| AKAP2 | NM_001004065 | 33 | PSR09006144.hg.1 | 9 | + | 112924374 | 112924412 | 0.79 | −1.5 | 1.0117E-08 | V |
| AKAP2 | NM_001004065 | 34 | PSR09006146.hg.1 | 9 | + | 112930687 | 112930777 | 0.88 | −5.4 | 1.3290E-16 | V |
| AKAP2 | NM_001004065 | 35 | PSR09006147.hg.1 | 9 | + | 112930778 | 112930913 | 0.89 | −6.1 | 3.0385E-16 | V |
| AKAP2 | NM_001004065 | 36 | PSR09006148.hg.1 | 9 | + | 112930914 | 112931091 | 0.89 | −5.5 | 8.7866E-17 | V |
| AKAP2 | NM_001004065 | 37 | PSR09006149.hg.1 | 9 | + | 112931092 | 112931169 | 0.88 | −5.4 | 6.37E-16 | V |
| AKAP2 | NM_001004065 | 38 | PSR09006150.hg.1 | 9 | + | 112931170 | 112932189 | 0.87 | −6.5 | 3.3113E-15 | V |
| AKAP2 | NM_001004065 | 39 | PSR09006151.hg.1 | 9 | + | 112932190 | 112934791 | 0.87 | −5.7 | 9.7401E-15 | V |
| C9orf91 | NM_153045 | 7 | PSR09006672.hg.1 | 9 | + | 117386630 | 117386735 | 0.78 | −2.7 | 1.5813E-08 | V |
| C9orf91 | NM_153045 | 8 | PSR09006674.hg.1 | 9 | + | 117389179 | 117389286 | 0.78 | −2.3 | 1.3511E-07 | V |
| C9orf91 | NM_153045 | 9 | PSR09006675.hg.1 | 9 | + | 117390381 | 117390505 | 0.77 | −2.4 | 3.3283E-08 | V |
| C9orf91 | NM_153045 | 10 | PSR09006677.hg.1 | 9 | + | 117396048 | 117396158 | 0.80 | −2.2 | 1.2676E-08 | V |
| C9orf91 | NM_153045 | 11 | PSR09006678.hg.1 | 9 | + | 117399270 | 117399350 | 0.80 | −3.4 | 5.7162E-10 | V |
| C9orf91 | NM_153045 | 12 | PSR09006679.hg.1 | 9 | + | 117400824 | 117401006 | 0.84 | −3.4 | 1.9964E-11 | V |
| C9orf91 | NM_153045 | 13 | PSR09006680.hg.1 | 9 | + | 117405414 | 117405546 | 0.85 | −3.3 | 2.8005E-12 | V |
| C9orf91 | NM_153045 | 14 | PSR09006681.hg.1 | 9 | + | 117405547 | 117405679 | 0.87 | −3.4 | 1.4493E-13 | V |
| C9orf91 | NM_153045 | 15 | PSR09006682.hg.1 | 9 | + | 117405680 | 117406335 | 0.88 | −4.0 | 9.8118E-15 | V |
| C9orf91 | NM_153045 | 16 | PSR09006684.hg.1 | 9 | + | 117406347 | 117406441 | 0.88 | −4.9 | 1.4549E-15 | V |
| C9orf91 | NM_153045 | 17 | PSR09006685.hg.1 | 9 | + | 117406442 | 117406984 | 0.88 | −4.7 | 9.724E-16 | V |
| C9orf91 | NM_153045 | 18 | PSR09006686.hg.1 | 9 | + | 117406985 | 117408702 | 0.85 | −3.1 | 3.3102E-12 | V |
| GSN | NM_198252 | 3 | PSR09006917.hg.1 | 9 | + | 123971574 | 123971675 | 0.83 | −3.5 | 2.4396E-10 | V |
| GSN | NM_198252 | 4 | PSR09006918.hg.1 | 9 | + | 123972514 | 123972607 | 0.90 | −4.2 | 4.2569E-14 | V |
| GSN | NM_198252 | 5 | PSR09006919.hg.1 | 9 | + | 123973062 | 123973145 | 0.90 | −14.6 | 7.9808E-15 | V |
| GSN | NM_198252 | 6 | PSR09006920.hg.1 | 9 | + | 123993443 | 123993581 | 0.88 | −5.7 | 1.0536E-12 | V |
| GSN | NM_198252 | 8 | PSR09006922.hg.1 | 9 | + | 124027432 | 124027464 | 0.83 | −5.8 | 4.0913E-11 | V |
| GSN | NM_198252 | 9 | PSR09006923.hg.1 | 9 | + | 124027465 | 124027575 | 0.85 | −3.6 | 2.5032E-10 | V |
| GSN | NM_198252 | 10 | PSR09006924.hg.1 | 9 | + | 124027939 | 124028032 | 0.86 | −6.9 | 1.0381E-12 | V |
| GSN | NM_198252 | 13 | PSR09006929.hg.1 | 9 | + | 124030456 | 124030497 | 0.69 | 1.2 | 0.00015075 | B |
| GSN | NM_198252 | 14 | PSR09006931.hg.1 | 9 | + | 124043750 | 124043788 | 0.68 | 1.7 | 0.00061361 | B |
| GSN | NM_198252 | 15 | PSR09006932.hg.1 | 9 | + | 124043789 | 124043840 | 0.73 | 1.8 | 8.2884E-06 | B |
| GSN | NM_198252 | 16 | PSR09006933.hg.1 | 9 | + | 124044153 | 124044231 | 0.59 | −1.4 | 0.0181671 | V |
| GSN | NM_198252 | 20 | PSR09006937.hg.1 | 9 | + | 124048870 | 124049039 | 0.56 | −1.2 | 0.07541154 | V |
| GSN | NM_198252 | 21 | PSR09006938.hg.1 | 9 | + | 124060044 | 124060120 | 0.63 | −1.6 | 0.00276838 | V |
| GSN | NM_198252 | 24 | PSR09006943.hg.1 | 9 | + | 124062343 | 124062404 | 0.63 | −1.6 | 0.00231671 | V |
| GSN | NM_198252 | 26 | PSR09006947.hg.1 | 9 | + | 124064249 | 124064325 | 0.80 | 1.6 | 3.0202E-09 | B |
| GSN | NM_198252 | 27 | PSR09006948.hg.1 | 9 | + | 124064326 | 124064373 | 0.82 | 3.0 | 5.8521E-11 | B |
| GSN | NM_198252 | 28 | PSR09006949.hg.1 | 9 | + | 124064374 | 124064426 | 0.81 | 2.5 | 4.9501E-10 | B |
| GSN | NM_198252 | 29 | PSR09006951.hg.1 | 9 | + | 124065189 | 124065255 | 0.79 | 1.8 | 3.2962E-09 | B |
| GSN | NM_198252 | 30 | PSR09006952.hg.1 | 9 | + | 124065256 | 124065333 | 0.81 | 2.6 | 2.9138E-10 | B |

TABLE 13-continued

Exon level analysis of 140 RNA determinants differentially expressed in bacterial and viral patients. Probe set ID is based on GeneChip Human Transcriptome Arrays 2.0 (HTA-Affymetrix) data. Comparison to full gene was calculated as absolute fold change (exon$_i$) - absolute fold change (full length gene); Only exons that presented higher of differential expression of the single exon compared to the full length gene were included.

| Gene Symbol | mRNA Accession | Exon # | Probe Set ID | Chromosome | Strand | Start | Stop | Exon AUC | FC | T-Test | Up in B/V |
|---|---|---|---|---|---|---|---|---|---|---|---|
| GSN | NM_198252 | 32 | PSR09006955.hg.1 | 9 | + | 124072962 | 124073123 | 0.82 | 2.3 | 6.5416E-10 | B |
| GSN | NM_198252 | 35 | PSR09006958.hg.1 | 9 | + | 124074617 | 124074753 | 0.82 | 2.1 | 1.9325E-10 | B |
| GSN | NM_198252 | 37 | PSR09006964.hg.1 | 9 | + | 124076212 | 124076301 | 0.82 | 2.1 | 1.7478E-10 | B |
| GSN | NM_198252 | 38 | PSR09006965.hg.1 | 9 | + | 124079364 | 124079390 | 0.81 | 2.5 | 5.009E-10 | B |
| GSN | NM_198252 | 39 | PSR09006966.hg.1 | 9 | + | 124079391 | 124079496 | 0.83 | 2.2 | 7.9359E-11 | B |
| GSN | NM_198252 | 41 | PSR09006968.hg.1 | 9 | + | 124080684 | 124080772 | 0.82 | 2.0 | 7.7519E-10 | B |
| GSN | NM_198252 | 42 | PSR09006969.hg.1 | 9 | + | 124080943 | 124081011 | 0.80 | 1.7 | 7.3422E-09 | B |
| GSN | NM_198252 | 43 | PSR09006970.hg.1 | 9 | + | 124081012 | 124081158 | 0.81 | 1.9 | 2.0522E-09 | B |
| GSN | NM_198252 | 44 | PSR09006971.hg.1 | 9 | + | 124083546 | 124083589 | 0.82 | 2.4 | 4.2672E-10 | B |
| GSN | NM_198252 | 45 | PSR09006972.hg.1 | 9 | + | 124083590 | 124083679 | 0.83 | 2.3 | 2.1104E-10 | B |
| GSN | NM_198252 | 46 | PSR09006973.hg.1 | 9 | + | 124086832 | 124086922 | 0.82 | 2.2 | 3.047E-10 | B |
| GSN | NM_198252 | 47 | PSR09006974.hg.1 | 9 | + | 124088790 | 124088859 | 0.82 | 2.0 | 5.2408E-10 | B |
| GSN | NM_198252 | 51 | PSR09006978.hg.1 | 9 | + | 124089586 | 124089760 | 0.81 | 1.7 | 2.1236E-09 | B |
| GSN | NM_198252 | 53 | PSR09006980.hg.1 | 9 | + | 124091169 | 124091293 | 0.78 | 1.8 | 1.0631E-08 | B |
| GSN | NM_198252 | 55 | PSR09006982.hg.1 | 9 | + | 124091516 | 124091593 | 0.80 | 2.2 | 1.1259E-09 | B |
| GSN | NM_198252 | 56 | PSR09006984.hg.1 | 9 | + | 124093666 | 124093726 | 0.78 | 1.8 | 4.8938E-08 | B |
| GSN | NM_198252 | 58 | PSR09006986.hg.1 | 9 | + | 124094712 | 124094867 | 0.81 | 1.8 | 1.0001E-09 | B |
| GSN | NM_198252 | 59 | PSR09006987.hg.1 | 9 | + | 124094868 | 124094934 | 0.80 | 1.5 | 1.1725E-08 | B |
| GSN | NM_198252 | 61 | PSR09006990.hg.1 | 9 | + | 124095017 | 124095080 | 0.74 | 1.7 | 5.0244E-06 | B |
| CNTNAP3 | NM_033655 | 1 | PSR09014552.hg.1 | 9 | − | 39072764 | 39073670 | 0.75 | 3.9 | 2.6134E-07 | B |
| CNTNAP3 | NM_033655 | 3 | PSR09014554.hg.1 | 9 | − | 39073734 | 39074008 | 0.74 | 3.3 | 1.4666E-06 | B |
| CNTNAP3 | NM_033655 | 5 | PSR09014556.hg.1 | 9 | − | 39078382 | 39078453 | 0.74 | 2.7 | 9.8482E-07 | B |
| CNTNAP3 | NM_033655 | 9 | PSR09014561.hg.1 | 9 | − | 39085733 | 39085820 | 0.71 | 3.3 | 1.512E-05 | B |
| CNTNAP3 | NM_033655 | 10 | PSR09014562.hg.1 | 9 | − | 39085821 | 39086045 | 0.76 | 4.1 | 2.3549E-07 | B |
| CNTNAP3 | NM_033655 | 11 | PSR09014563.hg.1 | 9 | − | 39086046 | 39086145 | 0.75 | 3.8 | 3.6816E-07 | B |
| CNTNAP3 | NM_033655 | 12 | PSR09014564.hg.1 | 9 | − | 39086146 | 39086712 | 0.74 | 3.9 | 1.0082E-06 | B |
| CNTNAP3 | NM_033655 | 13 | PSR09014565.hg.1 | 9 | − | 39086713 | 39086846 | 0.74 | 3.7 | 1.2788E-06 | B |
| CNTNAP3 | NM_033655 | 14 | PSR09014566.hg.1 | 9 | − | 39088420 | 39088470 | 0.74 | 3.2 | 1.1066E-06 | B |
| CNTNAP3 | NM_033655 | 15 | PSR09014568.hg.1 | 9 | − | 39088473 | 39088644 | 0.74 | 4.7 | 1.179E-06 | B |
| CNTNAP3 | NM_033655 | 17 | PSR09014570.hg.1 | 9 | − | 39099908 | 39100147 | 0.74 | 3.7 | 1.2554E-06 | B |
| CNTNAP3 | NM_033655 | 18 | PSR09014572.hg.1 | 9 | − | 39102494 | 39102672 | 0.74 | 3.3 | 1.391E-06 | B |
| CNTNAP3 | NM_033655 | 20 | PSR09014577.hg.1 | 9 | − | 39103741 | 39103905 | 0.76 | 4.8 | 2.6485E-07 | B |
| CNTNAP3 | NM_033655 | 22 | PSR09014580.hg.1 | 9 | − | 39109157 | 39109284 | 0.75 | 3.4 | 1.0941E-06 | B |
| CNTNAP3 | NM_033655 | 23 | PSR09014583.hg.1 | 9 | − | 39117924 | 39118099 | 0.77 | 3.1 | 1.7724E-07 | B |
| CNTNAP3 | NM_033655 | 24 | PSR09014584.hg.1 | 9 | − | 39118100 | 39118256 | 0.75 | 3.8 | 4.5818E-07 | B |
| CNTNAP3 | NM_033655 | 30 | PSR09014592.hg.1 | 9 | − | 39149803 | 39149974 | 0.75 | 2.7 | 8.0496E-07 | B |
| CNTNAP3 | NM_033655 | 31 | PSR09014593.hg.1 | 9 | − | 39165930 | 39166073 | 0.76 | 3.5 | 1.2957E-07 | B |
| CNTNAP3 | NM_033655 | 32 | PSR09014594.hg.1 | 9 | − | 39171366 | 39171627 | 0.73 | 5.1 | 1.4932E-06 | B |
| CNTNAP3 | NM_033655 | 33 | PSR09014595.hg.1 | 9 | − | 39172783 | 39174537 | 0.72 | 2.7 | 8.9931E-06 | B |
| CNTNAP3 | NM_033655 | 34 | PSR09014596.hg.1 | 9 | − | 39175946 | 39176089 | 0.75 | 5.2 | 2.4124E-07 | B |
| CNTNAP3 | NM_033655 | 35 | PSR09014597.hg.1 | 9 | − | 39177315 | 39177499 | 0.74 | 4.5 | 9.347E-07 | B |
| CNTNAP3 | NM_033655 | 36 | PSR09014598.hg.1 | 9 | − | 39178154 | 39178357 | 0.75 | 4.7 | 1.8635E-07 | B |
| CNTNAP3 | NM_033655 | 37 | PSR09014599.hg.1 | 9 | − | 39193125 | 39193272 | 0.74 | 3.5 | 3.6586E-07 | B |
| CNTNAP3 | NM_033655 | 38 | PSR09014600.hg.1 | 9 | − | 39238990 | 39239171 | 0.76 | 4.3 | 8.9651E-08 | B |
| — | uc004abr.1 | 2 | PSR09014641.hg.1 | 9 | − | 40501666 | 40501809 | 0.75 | 4.9 | 2.3991E-07 | B |
| — | uc004abr.1 | 3 | PSR09014642.hg.1 | 9 | − | 40503019 | 40503203 | 0.76 | 3.4 | 1.2987E-07 | B |
| — | uc004abr.1 | 4 | PSR09014643.hg.1 | 9 | − | 40503853 | 40504056 | 0.75 | 4.4 | 1.9875E-07 | B |
| — | uc004abr.1 | 5 | PSR09014644.hg.1 | 9 | − | 40518834 | 40518981 | 0.76 | 3.7 | 1.3087E-07 | B |
| — | uc004abr.1 | 6 | PSR09014645.hg.1 | 9 | − | 40582251 | 40582444 | 0.77 | 4.5 | 5.0951E-08 | B |
| — | ENST00000438517 | 2 | PSR09014869.hg.1 | 9 | − | 47297431 | 47299314 | 0.75 | 3.2 | 8.3071E-07 | B |
| — | ENST00000438517 | 3 | PSR09014870.hg.1 | 9 | − | 47299315 | 47299651 | 0.74 | 3.1 | 2.1328E-06 | B |
| — | ENST00000438517 | 10 | PSR09014880.hg.1 | 9 | − | 47310649 | 47311408 | 0.75 | 2.3 | 4.0146E-06 | B |
| — | ENST00000438517 | 11 | PSR09014881.hg.1 | 9 | − | 47311409 | 47311496 | 0.73 | 3.0 | 4.1707E-06 | B |
| — | ENST00000438517 | 12 | PSR09014882.hg.1 | 9 | − | 47311497 | 47311721 | 0.76 | 2.3 | 1.8503E-06 | B |
| — | ENST00000438517 | 13 | PSR09014883.hg.1 | 9 | − | 47311722 | 47311820 | 0.74 | 2.6 | 1.8885E-06 | B |
| — | ENST00000438517 | 16 | PSR09014887.hg.1 | 9 | − | 47312395 | 47312525 | 0.74 | 3.6 | 1.0643E-06 | B |
| — | ENST00000438517 | 17 | PSR09014889.hg.1 | 9 | − | 47314098 | 47314148 | 0.74 | 3.2 | 1.1066E-06 | B |
| — | ENST00000438517 | 18 | PSR09014890.hg.1 | 9 | − | 47314149 | 47314222 | 0.75 | 4.9 | 6.8196E-07 | B |
| — | ENST00000438517 | 19 | PSR09014891.hg.1 | 9 | − | 47314223 | 47314322 | 0.73 | 4.5 | 1.8248E-06 | B |
| CDK5RAP2 | NM_001011649 | 1 | PSR09019152.hg.1 | 9 | − | 123151154 | 123151472 | 0.82 | 3.0 | 4.0205E-12 | B |
| CDK5RAP2 | NM_001011649 | 2 | PSR09019157.hg.1 | 9 | − | 123151479 | 123151570 | 0.85 | 4.2 | 2.7546E-14 | B |
| CDK5RAP2 | NM_001011649 | 3 | PSR09019158.hg.1 | 9 | − | 123152019 | 123152065 | 0.85 | 5.6 | 5.7005E-14 | B |
| CDK5RAP2 | NM_001011649 | 4 | PSR09019159.hg.1 | 9 | − | 123152066 | 123152555 | 0.69 | 1.4 | 3.8573E-06 | B |
| CDK5RAP2 | NM_001011649 | 5 | PSR09019162.hg.1 | 9 | − | 123156812 | 123156872 | 0.84 | 5.1 | 1.4876E-13 | B |
| CDK5RAP2 | NM_001011649 | 6 | PSR09019163.hg.1 | 9 | − | 123156873 | 123156916 | 0.83 | 4.5 | 6.723E-12 | B |
| CDK5RAP2 | NM_001011649 | 7 | PSR09019164.hg.1 | 9 | − | 123163020 | 123163163 | 0.85 | 5.4 | 8.6531E-14 | B |
| CDK5RAP2 | NM_001011649 | 8 | PSR09019165.hg.1 | 9 | − | 123163164 | 123163297 | 0.79 | 1.6 | 1.962E-08 | B |
| CDK5RAP2 | NM_001011649 | 9 | PSR09019166.hg.1 | 9 | − | 123165084 | 123165349 | 0.85 | 6.9 | 1.4675E-14 | B |
| CDK5RAP2 | NM_001011649 | 10 | PSR09019167.hg.1 | 9 | − | 123165350 | 123165520 | 0.87 | 4.9 | 1.0514E-16 | B |

TABLE 13-continued

Exon level analysis of 140 RNA determinants differentially
expressed in bacterial and viral patients. Probe set ID is based on GeneChip
Human Transcriptome Arrays 2.0 (HTA-Affymetrix) data. Comparison to full
gene was calculated as absolute fold change (exon$_i$) - absolute fold change (full
length gene); Only exons that presented higher of differential expression of the
single exon compared to the full length gene were included.

| Gene Symbol | mRNA Accession | Exon # | Probe Set ID | Chromosome | Strand | Start | Stop | Exon AUC | FC | T-Test | Up in B/V |
|---|---|---|---|---|---|---|---|---|---|---|---|
| CDK5RAP2 | NM_001011649 | 11 | PSR09019168.hg.1 | 9 | − | 123165521 | 123165593 | 0.87 | 8.8 | 2.4065E−15 | B |
| CDK5RAP2 | NM_001011649 | 12 | PSR09019169.hg.1 | 9 | − | 123165594 | 123165730 | 0.86 | 8.0 | 1.4226E−14 | B |
| CDK5RAP2 | NM_001011649 | 13 | PSR09019170.hg.1 | 9 | − | 123165731 | 123165773 | 0.61 | 1.1 | 0.03879782 | B |
| CDK5RAP2 | NM_001011649 | 14 | PSR09019171.hg.1 | 9 | − | 123165774 | 123165940 | 0.56 | 1.2 | 0.13139395 | B |
| CDK5RAP2 | NM_001011649 | 15 | PSR09019172.hg.1 | 9 | − | 123166314 | 123166391 | 0.54 | 1.1 | 0.42933718 | B |
| CDK5RAP2 | NM_001011649 | 16 | PSR09019174.hg.1 | 9 | − | 123168425 | 123169289 | 0.63 | 1.1 | 0.07188673 | B |
| CDK5RAP2 | NM_001011649 | 18 | PSR09019177.hg.1 | 9 | − | 123169527 | 123170624 | 0.55 | 1.1 | 0.39642231 | B |
| CDK5RAP2 | NM_001011649 | 19 | PSR09019178.hg.1 | 9 | − | 123170625 | 123170746 | 0.53 | 1.1 | 0.36854206 | B |
| CDK5RAP2 | NM_001011649 | 20 | PSR09019179.hg.1 | 9 | − | 123171405 | 123171594 | 0.57 | 1.1 | 0.17704375 | B |
| CDK5RAP2 | NM_001011649 | 21 | PSR09019180.hg.1 | 9 | − | 123173636 | 123173752 | 0.63 | 1.3 | 0.00796222 | B |
| CDK5RAP2 | NM_001011649 | 22 | PSR09019181.hg.1 | 9 | − | 123177318 | 123177437 | 0.54 | 1.1 | 0.32522625 | B |
| CDK5RAP2 | NM_001011649 | 23 | PSR09019182.hg.1 | 9 | − | 123182066 | 123182238 | 0.58 | 1.2 | 0.09259396 | B |
| CDK5RAP2 | NM_001011649 | 24 | PSR09019183.hg.1 | 9 | − | 123184971 | 123185019 | 0.58 | 1.2 | 0.11923627 | B |
| CDK5RAP2 | NM_001011649 | 25 | PSR09019184.hg.1 | 9 | − | 123199573 | 123199805 | 0.55 | 1.2 | 0.24114559 | B |
| CDK5RAP2 | NM_001011649 | 26 | PSR09019185.hg.1 | 9 | − | 123201677 | 123201795 | 0.52 | 1.1 | 0.45587939 | B |
| CDK5RAP2 | NM_001011649 | 27 | PSR09019186.hg.1 | 9 | − | 123201796 | 123202067 | 0.55 | 1.1 | 0.2387649 | B |
| CDK5RAP2 | NM_001011649 | 28 | PSR09019187.hg.1 | 9 | − | 123202068 | 123202250 | 0.53 | 1.1 | 0.39723802 | B |
| CDK5RAP2 | NM_001011649 | 30 | PSR09019189.hg.1 | 9 | − | 123205898 | 123206020 | 0.53 | 1.1 | 0.41258989 | B |
| CDK5RAP2 | NM_001011649 | 31 | PSR09019190.hg.1 | 9 | − | 123210173 | 123210350 | 0.59 | −1.1 | 0.03849942 | V |
| CDK5RAP2 | NM_001011649 | 33 | PSR09019192.hg.1 | 9 | − | 123215734 | 123216151 | 0.58 | −1.1 | 0.22240671 | V |
| CDK5RAP2 | NM_001011649 | 35 | PSR09019194.hg.1 | 9 | − | 123220801 | 123220900 | 0.58 | −1.1 | 0.13643044 | V |
| CDK5RAP2 | NM_001011649 | 36 | PSR09019198.hg.1 | 9 | − | 123222862 | 123222945 | 0.57 | −1.1 | 0.20709193 | V |
| CDK5RAP2 | NM_001011649 | 39 | PSR09019201.hg.1 | 9 | − | 123232389 | 123232495 | 0.67 | −1.2 | 0.00305452 | V |
| CDK5RAP2 | NM_001011649 | 40 | PSR09019203.hg.1 | 9 | − | 123234026 | 123234156 | 0.62 | −1.1 | 0.06849622 | V |
| CDK5RAP2 | NM_001011649 | 41 | PSR09019205.hg.1 | 9 | − | 123239633 | 123239728 | 0.73 | −1.4 | 4.4522E−05 | V |
| CDK5RAP2 | NM_001011649 | 42 | PSR09019206.hg.1 | 9 | − | 123249572 | 123249715 | 0.74 | −1.4 | 2.7979E−05 | V |
| CDK5RAP2 | NM_001011649 | 43 | PSR09019207.hg.1 | 9 | − | 123253585 | 123253755 | 0.76 | −1.5 | 4.4977E−07 | V |
| CDK5RAP2 | NM_001011649 | 46 | PSR09019210.hg.1 | 9 | − | 123280705 | 123280877 | 0.75 | −1.4 | 2.3202E−06 | V |
| CDK5RAP2 | NM_001011649 | 47 | PSR09019211.hg.1 | 9 | − | 123280878 | 123280923 | 0.76 | −1.5 | 2.2661E−06 | V |
| CDK5RAP2 | NM_001011649 | 48 | PSR09019212.hg.1 | 9 | − | 123287264 | 123287356 | 0.75 | −1.5 | 1.5374E−06 | V |
| CDK5RAP2 | NM_001011649 | 49 | PSR09019214.hg.1 | 9 | − | 123290104 | 123290199 | 0.71 | −1.4 | 2.1483E−05 | V |
| CDK5RAP2 | NM_001011649 | 50 | PSR09019216.hg.1 | 9 | − | 123291022 | 123291051 | 0.59 | −1.2 | 0.15730285 | V |
| CDK5RAP2 | NM_001011649 | 51 | PSR09019219.hg.1 | 9 | − | 123292256 | 123292418 | 0.70 | −1.4 | 0.00011244 | V |
| CDK5RAP2 | NM_001011649 | 53 | PSR09019221.hg.1 | 9 | − | 123298650 | 123298715 | 0.69 | −1.3 | 0.00069026 | V |
| CDK5RAP2 | NM_001011649 | 54 | PSR09019222.hg.1 | 9 | − | 123298716 | 123298804 | 0.66 | −1.2 | 0.00204243 | V |
| CDK5RAP2 | NM_001011649 | 55 | PSR09019225.hg.1 | 9 | − | 123301319 | 123301398 | 0.70 | −1.3 | 5.9356E−05 | V |
| CDK5RAP2 | NM_001011649 | 56 | PSR09019226.hg.1 | 9 | − | 123301399 | 123301442 | 0.61 | −1.1 | 0.02661205 | V |
| CDK5RAP2 | NM_001011649 | 57 | PSR09019227.hg.1 | 9 | − | 123307992 | 123308068 | 0.66 | −1.2 | 0.00265048 | V |
| CDK5RAP2 | NM_001011649 | 58 | PSR09019228.hg.1 | 9 | − | 123313070 | 123313180 | 0.73 | −1.3 | 1.8007E−05 | V |
| CDK5RAP2 | NM_001011649 | 59 | PSR09019229.hg.1 | 9 | − | 123330599 | 123330666 | 0.76 | −1.5 | 2.0431E−06 | V |
| CDK5RAP2 | NM_001011649 | 60 | PSR09019230.hg.1 | 9 | − | 123334025 | 123334251 | 0.59 | −1.1 | 0.09370754 | V |
| CDK5RAP2 | NM_001011649 | 61 | PSR09019232.hg.1 | 9 | − | 123334255 | 123334319 | 0.74 | −1.6 | 1.0812E−05 | V |
| CDK5RAP2 | NM_001011649 | 62 | PSR09019233.hg.1 | 9 | − | 123342198 | 123342283 | 0.67 | −1.2 | 0.00262695 | V |
| SDCCAG3 | NM_001039707 | 1 | PSR09022138.hg.1 | 9 | − | 139296377 | 139296402 | 0.82 | −5.9 | 3.1239E−11 | V |
| SDCCAG3 | NM_001039707 | 2 | PSR09022139.hg.1 | 9 | − | 139296403 | 139296931 | 0.69 | −1.2 | 0.00058769 | V |
| SDCCAG3 | NM_001039707 | 3 | PSR09022140.hg.1 | 9 | − | 139296932 | 139297095 | 0.66 | −1.2 | 0.00440647 | V |
| SDCCAG3 | NM_001039707 | 4 | PSR09022143.hg.1 | 9 | − | 139297134 | 139297339 | 0.65 | −1.2 | 0.02027377 | V |
| SDCCAG3 | NM_001039707 | 6 | PSR09022145.hg.1 | 9 | − | 139298507 | 139298560 | 0.64 | −1.2 | 0.01857021 | V |
| SDCCAG3 | NM_001039707 | 8 | PSR09022148.hg.1 | 9 | − | 139299083 | 139299145 | 0.63 | −1.2 | 0.03134151 | V |
| SDCCAG3 | NM_001039707 | 9 | PSR09022149.hg.1 | 9 | − | 139299146 | 139299232 | 0.64 | −1.2 | 0.0140932 | V |
| SDCCAG3 | NM_001039707 | 10 | PSR09022150.hg.1 | 9 | − | 139299543 | 139299569 | 0.68 | −1.3 | 0.00052316 | V |
| SDCCAG3 | NM_001039707 | 11 | PSR09022151.hg.1 | 9 | − | 139299570 | 139299654 | 0.64 | −1.2 | 0.00839152 | V |
| SDCCAG3 | NM_001039707 | 12 | PSR09022152.hg.1 | 9 | − | 139299655 | 139299800 | 0.66 | −1.4 | 0.00224861 | V |
| SDCCAG3 | NM_001039707 | 14 | PSR09022154.hg.1 | 9 | − | 139301398 | 139301468 | 0.66 | −1.4 | 0.00331751 | V |
| SDCCAG3 | NM_001039707 | 16 | PSR09022156.hg.1 | 9 | − | 139301597 | 139301637 | 0.60 | −1.2 | 0.13146198 | V |
| SDCCAG3 | NM_001039707 | 17 | PSR09022158.hg.1 | 9 | − | 139301661 | 139302013 | 0.65 | −1.2 | 0.00871798 | V |
| SDCCAG3 | NM_001039707 | 18 | PSR09022159.hg.1 | 9 | − | 139302278 | 139302326 | 0.68 | −1.3 | 0.00118109 | V |
| SDCCAG3 | NM_001039707 | 19 | PSR09022160.hg.1 | 9 | − | 139302327 | 139302390 | 0.67 | −1.2 | 0.00639845 | V |
| SDCCAG3 | NM_001039707 | 20 | PSR09022161.hg.1 | 9 | − | 139302391 | 139302418 | 0.63 | −1.4 | 0.02046578 | V |
| TMEM255A | NM_001104544 | 1 | PSR0X017751.hg.1 | X | − | 119392506 | 119394110 | 0.84 | −7.3 | 5.7202E−11 | V |
| TMEM255A | NM_001104544 | 2 | PSR0X017753.hg.1 | X | − | 119394112 | 119394883 | 0.73 | −2.1 | 3.3308E−06 | V |
| TMEM255A | NM_001104544 | 3 | PSR0X017754.hg.1 | X | − | 119402099 | 119402217 | 0.80 | −3.6 | 5.4743E−09 | V |
| TMEM255A | NM_001104544 | 4 | PSR0X017756.hg.1 | X | − | 119410740 | 119410902 | 0.81 | −5.1 | 8.9723E−10 | V |
| TMEM255A | NM_001104544 | 5 | PSR0X017757.hg.1 | X | − | 119418982 | 119419070 | 0.86 | −5.3 | 8.2262E−11 | V |
| TMEM255A | NM_001104544 | 8 | PSR0X017760.hg.1 | X | − | 119421009 | 119421077 | 0.86 | −10.0 | 2.9633E−12 | V |
| TMEM255A | NM_001104544 | 9 | PSR0X017761.hg.1 | X | − | 119425106 | 119425195 | 0.85 | −9.2 | 4.7791E−12 | V |
| TMEM255A | NM_001104544 | 10 | PSR0X017762.hg.1 | X | − | 119427844 | 119427906 | 0.83 | −5.4 | 1.5875E−10 | V |
| IFIT5 | NM_012420 | 5 | PSR10007050.hg.1 | 10 | + | 91177575 | 91178571 | 0.87 | −5.2 | 9.4053E−16 | V |
| CD44 | NM_001001391 | 2 | PSR11004261.hg.1 | 11 | + | 35160735 | 35160832 | 0.89 | 3.4 | 1.7759E−15 | B |

TABLE 13-continued

Exon level analysis of 140 RNA determinants differentially expressed in bacterial and viral patients. Probe set ID is based on GeneChip Human Transcriptome Arrays 2.0 (HTA-Affymetrix) data. Comparison to full gene was calculated as absolute fold change (exon$_i$) - absolute fold change (full length gene); Only exons that presented higher of differential expression of the single exon compared to the full length gene were included.

| Gene Symbol | mRNA Accession | Exon # | Probe Set ID | Chromosome | Strand | Start | Stop | Exon AUC | FC | T-Test | Up in B/V |
|---|---|---|---|---|---|---|---|---|---|---|---|
| CD44 | NM_001001391 | 3 | PSR11004264.hg.1 | 11 | + | 35160851 | 35160917 | 0.90 | 2.6 | 2.5319E-16 | B |
| CD44 | NM_001001391 | 5 | PSR11004266.hg.1 | 11 | + | 35198288 | 35198684 | 0.72 | 2.1 | 3.0621E-06 | B |
| CD44 | NM_001001391 | 10 | PSR11004271.hg.1 | 11 | + | 35219668 | 35219793 | 0.82 | 2.3 | 2.398E-11 | B |
| CD44 | NM_001001391 | 11 | PSR11004272.hg.1 | 11 | + | 35222629 | 35222742 | 0.72 | 2.1 | 2.3244E-06 | B |
| CD44 | NM_001001391 | 13 | PSR11004275.hg.1 | 11 | + | 35226059 | 35226187 | 0.77 | 2.3 | 1.1505E-08 | B |
| CD44 | NM_001001391 | 14 | PSR11004276.hg.1 | 11 | + | 35227659 | 35227790 | 0.81 | 2.4 | 6.9696E-11 | B |
| CD44 | NM_001001391 | 15 | PSR11004277.hg.1 | 11 | + | 35229652 | 35229753 | 0.86 | 3.4 | 1.4192E-13 | B |
| CD44 | NM_001001391 | 16 | PSR11004279.hg.1 | 11 | + | 35231512 | 35231601 | 0.88 | 4.2 | 7.4465E-16 | B |
| CD44 | NM_001001391 | 17 | PSR11004280.hg.1 | 11 | + | 35232793 | 35232996 | 0.91 | 5.1 | 1.7027E-19 | B |
| CD44 | NM_001001391 | 18 | PSR11004281.hg.1 | 11 | + | 35236399 | 35236461 | 0.90 | 2.6 | 1.0032E-15 | B |
| CD44 | NM_001001391 | 19 | PSR11004282.hg.1 | 11 | + | 35240863 | 35240934 | 0.88 | 2.2 | 5.3074E-15 | B |
| CD44 | NM_001001391 | 23 | PSR11004286.hg.1 | 11 | + | 35250676 | 35250880 | 0.89 | 2.1 | 6.6641E-14 | B |
| CD44 | NM_001001391 | 24 | PSR11004287.hg.1 | 11 | + | 35250881 | 35250916 | 0.88 | 2.3 | 4.6463E-14 | B |
| CD44 | NM_001001391 | 27 | PSR11004290.hg.1 | 11 | + | 35251214 | 35251568 | 0.89 | 3.1 | 1.0103E-15 | B |
| CD44 | NM_001001391 | 28 | PSR11004292.hg.1 | 11 | + | 35251575 | 35253949 | 0.91 | 3.0 | 6.6431E-18 | B |
| DGAT2 | NM_001253891 | 5 | PSR11010371.hg.1 | 11 | + | 75495663 | 75495791 | 0.88 | 6.1 | 1.3699E-15 | B |
| DGAT2 | NM_001253891 | 6 | PSR11010372.hg.1 | 11 | + | 75501233 | 75501340 | 0.89 | 5.1 | 2.7812E-15 | B |
| DGAT2 | NM_001253891 | 7 | PSR11010373.hg.1 | 11 | + | 75501706 | 75501776 | 0.89 | 4.8 | 7.3407E-15 | B |
| DGAT2 | NM_001253891 | 8 | PSR11010374.hg.1 | 11 | + | 75507373 | 75507577 | 0.89 | 5.4 | 1.1685E-15 | B |
| DGAT2 | NM_001253891 | 9 | PSR11010375.hg.1 | 11 | + | 75508203 | 75508377 | 0.89 | 5.0 | 2.9352E-15 | B |
| DGAT2 | NM_001253891 | 10 | PSR11010376.hg.1 | 11 | + | 75509272 | 75509474 | 0.89 | 5.3 | 8.0242E-15 | B |
| DGAT2 | NM_001253891 | 11 | PSR11010377.hg.1 | 11 | + | 75511399 | 75511678 | 0.88 | 4.9 | 1.7155E-14 | B |
| TMEM123 | NM_052932 | 1 | PSR11026596.hg.1 | 11 | − | 102267068 | 102269397 | 0.93 | −4.4 | 1.8799E-22 | V |
| TMEM123 | NM_052932 | 3 | PSR11026599.hg.1 | 11 | − | 102269555 | 102269586 | 0.92 | −3.4 | 9.5705E-22 | V |
| TMEM123 | NM_052932 | 4 | PSR11026600.hg.1 | 11 | − | 102269587 | 102269622 | 0.90 | −4.4 | 5.6393E-19 | V |
| TMEM123 | NM_052932 | 8 | PSR11026605.hg.1 | 11 | − | 102321933 | 102321962 | 0.88 | −5.9 | 6.7605E-15 | V |
| TMEM123 | NM_052932 | 9 | PSR11026606.hg.1 | 11 | − | 102322925 | 102323097 | 0.88 | −4.0 | 9.409E-14 | V |
| TMEM123 | NM_052932 | 10 | PSR11026607.hg.1 | 11 | − | 102323255 | 102323452 | 0.90 | −4.0 | 1.909E-18 | V |
| MMP8 | NM_002424 | 3 | PSR11026652.hg.1 | 11 | − | 102583861 | 102584057 | 0.74 | 4.5 | 2.0614E-06 | B |
| MMP8 | NM_002424 | 4 | PSR11026653.hg.1 | 11 | − | 102584058 | 102584188 | 0.71 | 4.9 | 1.2179E-05 | B |
| MMP8 | NM_002424 | 5 | PSR11026654.hg.1 | 11 | − | 102584485 | 102584525 | 0.71 | 4.4 | 1.2407E-05 | B |
| MMP8 | NM_002424 | 7 | PSR11026657.hg.1 | 11 | − | 102585287 | 102585440 | 0.74 | 4.2 | 3.5133E-06 | B |
| MMP8 | NM_002424 | 8 | PSR11026658.hg.1 | 11 | − | 102586035 | 102586168 | 0.73 | 4.4 | 3.5E-06 | B |
| MMP8 | NM_002424 | 9 | PSR11026659.hg.1 | 11 | − | 102587033 | 102587150 | 0.72 | 4.3 | 8.6279E-06 | B |
| MMP8 | NM_002424 | 10 | PSR11026660.hg.1 | 11 | − | 102589145 | 102589306 | 0.71 | 4.2 | 1.3526E-05 | B |
| MMP8 | NM_002424 | 11 | PSR11026661.hg.1 | 11 | − | 102592132 | 102592257 | 0.70 | 4.3 | 3.7954E-05 | B |
| MMP8 | NM_002424 | 12 | PSR11026662.hg.1 | 11 | − | 102592345 | 102592493 | 0.70 | 4.1 | 3.9521E-05 | B |
| MMP8 | NM_002424 | 13 | PSR11026663.hg.1 | 11 | − | 102593160 | 102593404 | 0.70 | 4.4 | 2.5512E-05 | B |
| MMP8 | NM_002424 | 16 | PSR11026668.hg.1 | 11 | − | 102595517 | 102595568 | 0.70 | 4.9 | 3.2641E-05 | B |
| — | n333961 | 1 | PSR11030576.hg.1 | 11 | + | 57373517 | 57373686 | 0.76 | −7.2 | 7.5193E-08 | V |
| — | n333961 | 3 | PSR11030578.hg.1 | 11 | + | 57379191 | 57379409 | 0.76 | −6.5 | 1.5918E-07 | V |
| — | n333961 | 4 | PSR11030579.hg.1 | 11 | + | 57381802 | 57381926 | 0.75 | −6.0 | 1.9341E-07 | V |
| LTA4H | NM_000895 | 8 | PSR12024252.hg.1 | 12 | − | 96405073 | 96405530 | 0.86 | 4.7 | 5.9277E-14 | B |
| LTA4H | NM_000895 | 9 | PSR12024253.hg.1 | 12 | − | 96405531 | 96405643 | 0.86 | 5.0 | 2.1462E-14 | B |
| LTA4H | NM_000895 | 17 | PSR12024262.hg.1 | 12 | − | 96412541 | 96412681 | 0.92 | 4.7 | 5.945E-21 | B |
| LTA4H | NM_000895 | 18 | PSR12024263.hg.1 | 12 | − | 96412946 | 96413018 | 0.93 | 4.9 | 3.3613E-21 | B |
| LTA4H | NM_000895 | 19 | PSR12024264.hg.1 | 12 | − | 96414863 | 96414915 | 0.92 | 4.9 | 2.177E-19 | B |
| LTA4H | NM_000895 | 21 | PSR12024266.hg.1 | 12 | − | 96418257 | 96418325 | 0.91 | 5.1 | 7.2191E-19 | B |
| LTA4H | NM_000895 | 22 | PSR12024267.hg.1 | 12 | − | 96421222 | 96421281 | 0.92 | 5.9 | 5.4396E-21 | B |
| LTA4H | NM_000895 | 23 | PSR12024268.hg.1 | 12 | − | 96421282 | 96421342 | 0.92 | 4.5 | 9.6436E-20 | B |
| LTA4H | NM_000895 | 25 | PSR12024270.hg.1 | 12 | − | 96429139 | 96429345 | 0.92 | 5.5 | 1.4381E-18 | B |
| — | ENST00000552784 | 1 | PSR12026010.hg.1 | 12 | − | 113345433 | 113345562 | 0.83 | −2.5 | 5.7652E-09 | V |
| — | ENST00000552784 | 2 | PSR12026011.hg.1 | 12 | − | 113346392 | 113346483 | 0.88 | −7.2 | 1.5975E-15 | V |
| TDRD9 | NM_153046 | 5 | PSR14008773.hg.1 | 14 | + | 104422001 | 104422107 | 0.83 | 3.6 | 5.8172E-13 | B |
| TDRD9 | NM_153046 | 6 | PSR14008774.hg.1 | 14 | + | 104429416 | 104429513 | 0.83 | 5.5 | 2.9935E-13 | B |
| TDRD9 | NM_153046 | 7 | PSR14008775.hg.1 | 14 | + | 104431670 | 104431818 | 0.83 | 3.4 | 1.4464E-12 | B |
| TDRD9 | NM_153046 | 9 | PSR14008777.hg.1 | 14 | + | 104433046 | 104433165 | 0.83 | 5.1 | 5.2424E-13 | B |
| TDRD9 | NM_153046 | 10 | PSR14008779.hg.1 | 14 | + | 104436878 | 104436943 | 0.80 | 4.6 | 2.3339E-11 | B |
| TDRD9 | NM_153046 | 11 | PSR14008781.hg.1 | 14 | + | 104441726 | 104441890 | 0.83 | 4.9 | 4.5043E-13 | B |
| TDRD9 | NM_153046 | 12 | PSR14008782.hg.1 | 14 | + | 104452554 | 104452657 | 0.81 | 3.9 | 3.5429E-11 | B |
| TDRD9 | NM_153046 | 14 | PSR14008784.hg.1 | 14 | + | 104460669 | 104460723 | 0.83 | 4.7 | 6.3867E-13 | B |
| TDRD9 | NM_153046 | 15 | PSR14008785.hg.1 | 14 | + | 104460856 | 104460940 | 0.84 | 3.8 | 3.1313E-13 | B |
| TDRD9 | NM_153046 | 16 | PSR14008786.hg.1 | 14 | + | 104462087 | 104462144 | 0.82 | 4.7 | 3.2055E-12 | B |
| TDRD9 | NM_153046 | 17 | PSR14008787.hg.1 | 14 | + | 104464961 | 104465065 | 0.82 | 4.2 | 2.7611E-12 | B |
| TDRD9 | NM_153046 | 18 | PSR14008788.hg.1 | 14 | + | 104470575 | 104470672 | 0.83 | 5.3 | 9.6219E-13 | B |
| TDRD9 | NM_153046 | 20 | PSR14008790.hg.1 | 14 | + | 104471611 | 104471742 | 0.82 | 3.9 | 2.4894E-12 | B |
| TDRD9 | NM_153046 | 22 | PSR14008792.hg.1 | 14 | + | 104472983 | 104473046 | 0.83 | 4.3 | 1.904E-12 | B |
| TDRD9 | NM_153046 | 23 | PSR14008793.hg.1 | 14 | + | 104473119 | 104473182 | 0.83 | 4.2 | 8.2485E-13 | B |
| TDRD9 | NM_153046 | 25 | PSR14008797.hg.1 | 14 | + | 104474750 | 104474803 | 0.82 | 4.6 | 1.1401E-11 | B |

TABLE 13-continued

Exon level analysis of 140 RNA determinants differentially
expressed in bacterial and viral patients. Probe set ID is based on GeneChip
Human Transcriptome Arrays 2.0 (HTA-Affymetrix) data. Comparison to full
gene was calculated as absolute fold change (exon$_i$) - absolute fold change (full
length gene); Only exons that presented higher of differential expression of the
single exon compared to the full length gene were included.

| Gene Symbol | mRNA Accession | Exon # | Probe Set ID | Chromosome | Strand | Start | Stop | Exon AUC | FC | T-Test | Up in B/V |
|---|---|---|---|---|---|---|---|---|---|---|---|
| TDRD9 | NM_153046 | 26 | PSR14008798.hg.1 | 14 | + | 104481062 | 104481178 | 0.80 | 4.9 | 8.2472E−11 | B |
| TDRD9 | NM_153046 | 29 | PSR14008801.hg.1 | 14 | + | 104488494 | 104488667 | 0.80 | 3.4 | 5.1223E−11 | B |
| TDRD9 | NM_153046 | 30 | PSR14008802.hg.1 | 14 | + | 104490906 | 104491017 | 0.80 | 3.6 | 5.5997E−11 | B |
| TDRD9 | NM_153046 | 35 | PSR14008807.hg.1 | 14 | + | 104498354 | 104498388 | 0.78 | 3.3 | 4.6122E−10 | B |
| TDRD9 | NM_153046 | 36 | PSR14008809.hg.1 | 14 | + | 104498390 | 104498424 | 0.81 | 4.2 | 1.0571E−11 | B |
| TDRD9 | NM_153046 | 37 | PSR14008810.hg.1 | 14 | + | 104500297 | 104500406 | 0.82 | 3.4 | 1.3199E−11 | B |
| TDRD9 | NM_153046 | 38 | PSR14008811.hg.1 | 14 | + | 104501297 | 104501393 | 0.81 | 3.8 | 3.1008E−11 | B |
| PYGL | NM_001163940 | 2 | PSR14012787.hg.1 | 14 | − | 51371939 | 51372274 | 0.90 | 3.9 | 4.2908E−17 | B |
| PYGL | NM_001163940 | 6 | PSR14012792.hg.1 | 14 | − | 51376744 | 51376820 | 0.91 | 4.1 | 1.0791E−17 | B |
| PYGL | NM_001163940 | 7 | PSR14012793.hg.1 | 14 | − | 51378448 | 51378589 | 0.91 | 4.1 | 1.6426E−17 | B |
| PYGL | NM_001163940 | 8 | PSR14012794.hg.1 | 14 | − | 51378696 | 51378754 | 0.91 | 4.4 | 3.788E−18 | B |
| PYGL | NM_001163940 | 9 | PSR14012795.hg.1 | 14 | − | 51378874 | 51379021 | 0.91 | 4.0 | 1.2264E−18 | B |
| PYGL | NM_001163940 | 10 | PSR14012796.hg.1 | 14 | − | 51379747 | 51379848 | 0.91 | 4.9 | 2.0913E−18 | B |
| PYGL | NM_001163940 | 11 | PSR14012797.hg.1 | 14 | − | 51381419 | 51381533 | 0.91 | 4.6 | 6.8285E−18 | B |
| PYGL | NM_001163940 | 12 | PSR14012798.hg.1 | 14 | − | 51382054 | 51382217 | 0.91 | 3.7 | 6.768E−18 | B |
| PYGL | NM_001163940 | 13 | PSR14012799.hg.1 | 14 | − | 51382543 | 51382689 | 0.92 | 4.8 | 2.0299E−19 | B |
| PYGL | NM_001163940 | 14 | PSR14012801.hg.1 | 14 | − | 51383360 | 51383452 | 0.92 | 4.1 | 3.9483E−19 | B |
| PYGL | NM_001163940 | 15 | PSR14012802.hg.1 | 14 | − | 51383680 | 51383823 | 0.90 | 3.9 | 9.3898E−18 | B |
| PYGL | NM_001163940 | 17 | PSR14012804.hg.1 | 14 | − | 51387674 | 51387785 | 0.91 | 3.9 | 5.2491E−18 | B |
| PYGL | NM_001163940 | 18 | PSR14012805.hg.1 | 14 | − | 51389969 | 51390686 | 0.87 | 4.3 | 7.8489E−15 | B |
| PYGL | NM_001163940 | 23 | PSR14012810.hg.1 | 14 | − | 51410879 | 51411174 | 0.92 | 4.4 | 2.2109E−20 | B |
| — | n334829 | 3 | PSR14023700.hg.1 | 14 | + | 94581198 | 94581226 | 0.89 | −84.3 | 7.6064E−19 | V |
| ATP10A | NM_024490 | 3 | PSR15009782.hg.1 | 15 | − | 25925268 | 25925455 | 0.87 | −3.2 | 2.2386E−14 | V |
| ATP10A | NM_024490 | 4 | PSR15009783.hg.1 | 15 | − | 25925957 | 25926061 | 0.90 | −5.6 | 7.7913E−18 | V |
| ATP10A | NM_024490 | 6 | PSR15009785.hg.1 | 15 | − | 25928433 | 25928633 | 0.91 | −2.8 | 1.8097E−18 | V |
| ATP10A | NM_024490 | 7 | PSR15009786.hg.1 | 15 | − | 25932850 | 25932975 | 0.89 | −5.3 | 2.5207E−16 | V |
| ATP10A | NM_024490 | 8 | PSR15009787.hg.1 | 15 | − | 25936862 | 25936938 | 0.89 | −3.0 | 1.252E−16 | V |
| ATP10A | NM_024490 | 10 | PSR15009789.hg.1 | 15 | − | 25947063 | 25947247 | 0.89 | −3.1 | 7.2739E−17 | V |
| ATP10A | NM_024490 | 11 | PSR15009790.hg.1 | 15 | − | 25953123 | 25953249 | 0.89 | −2.7 | 1.6179E−17 | V |
| ATP10A | NM_024490 | 16 | PSR15009795.hg.1 | 15 | − | 25966804 | 25967056 | 0.90 | −4.6 | 2.6253E−17 | V |
| ATP10A | NM_024490 | 17 | PSR15009796.hg.1 | 15 | − | 25969038 | 25969168 | 0.89 | −3.8 | 5.0759E−17 | V |
| ATP10A | NM_024490 | 19 | PSR15009798.hg.1 | 15 | − | 25972307 | 25972413 | 0.89 | −2.9 | 3.4037E−17 | V |
| ATP10A | NM_024490 | 20 | PSR15009799.hg.1 | 15 | − | 25981203 | 25981288 | 0.88 | −3.7 | 1.6893E−16 | V |
| ATP10A | NM_024490 | 22 | PSR15009802.hg.1 | 15 | − | 26086636 | 26086727 | 0.82 | −2.6 | 6.1697E−10 | V |
| — | n332456 | 1 | PSR15020176.hg.1 | 15 | + | 67457682 | 67457722 | 0.88 | −4.3 | 1.0539E−14 | V |
| MT1A | NM_005946 | 2 | PSR16006469.hg.1 | 16 | + | 56673176 | 56673241 | 0.86 | −6.8 | 3.2295E−14 | V |
| MT1M | NM_176870 | 3 | PSR16006478.hg.1 | 16 | + | 56667252 | 56667317 | 0.86 | −8.7 | 9.4249E−14 | V |
| MT1M | NM_176870 | 5 | PSR16006480.hg.1 | 16 | + | 56667808 | 56667893 | 0.70 | −1.3 | 8.6035E−05 | V |
| MT1E | NM_175617 | 3 | PSR16006487.hg.1 | 16 | + | 56659718 | 56659791 | 0.77 | −1.9 | 8.231E−07 | V |
| MT1E | NM_175617 | 4 | PSR16006488.hg.1 | 16 | + | 56660378 | 56660443 | 0.85 | −8.2 | 6.729E−14 | V |
| MT1E | NM_175617 | 6 | PSR16006490.hg.1 | 16 | + | 56660792 | 56660936 | 0.86 | −3.5 | 1.1131E−12 | V |
| MT1E | NM_175617 | 7 | PSR16006491.hg.1 | 16 | + | 56660937 | 56661023 | 0.78 | −2.0 | 1.6529E−06 | V |
| MT1Jp | NR_036677 | 3 | PSR16006496.hg.1 | 16 | + | 56670351 | 56670416 | 0.85 | −8.1 | 7.6664E−14 | V |
| MT1Jp | NR_036677 | 4 | PSR16006497.hg.1 | 16 | + | 56670764 | 56670998 | 0.85 | −4.0 | 1.0414E−13 | V |
| MT1DP | NR_003658 | 3 | PSR16006500.hg.1 | 16 | + | 56678023 | 56678088 | 0.86 | −6.7 | 7.8254E−14 | V |
| MT1DP | NR_003658 | 4 | PSR16006501.hg.1 | 16 | + | 56678622 | 56678724 | 0.86 | −3.1 | 9.3538E−15 | V |
| MT1B | NM_005947 | 2 | PSR16006508.hg.1 | 16 | + | 56685844 | 56685893 | 0.81 | −3.6 | 8.909E−11 | V |
| MT1B | NM_005947 | 3 | PSR16006509.hg.1 | 16 | + | 56686483 | 56686548 | 0.85 | −6.6 | 3.0417E−13 | V |
| MT1F | NM_005949 | 2 | PSR16006515.hg.1 | 16 | + | 56692587 | 56692652 | 0.85 | −6.4 | 1.3108E−13 | V |
| MT1H | NM_005951 | 2 | PSR16006523.hg.1 | 16 | + | 56703775 | 56703824 | 0.81 | −3.0 | 1.4789E−10 | V |
| MT1H | NM_005951 | 3 | PSR16006524.hg.1 | 16 | + | 56704418 | 56704483 | 0.86 | −7.5 | 6.0509E−14 | V |
| MT1H | NM_005951 | 4 | PSR16006525.hg.1 | 16 | + | 56704810 | 56704929 | 0.85 | −2.4 | 6.1236E−12 | V |
| MT1Ip | NR_003669 | 4 | PSR16006534.hg.1 | 16 | + | 56710983 | 56711026 | 0.84 | −8.7 | 8.2449E−13 | V |
| MT1Ip | NR_003669 | 6 | PSR16006536.hg.1 | 16 | + | 56711564 | 56711653 | 0.80 | −1.9 | 3.318E−09 | V |
| MT1X | NM_005952 | 2 | PSR16006542.hg.1 | 16 | + | 56716397 | 56716480 | 0.81 | −2.4 | 4.1221E−08 | V |
| MT1X | NM_005952 | 3 | PSR16006543.hg.1 | 16 | + | 56717077 | 56717142 | 0.87 | −6.7 | 1.2182E−14 | V |
| MT1X | NM_005952 | 5 | PSR16006545.hg.1 | 16 | + | 56717870 | 56718015 | 0.84 | −2.5 | 9.6554E−10 | V |
| MT1X | NM_005952 | 6 | PSR16006548.hg.1 | 16 | + | 56718022 | 56718108 | 0.79 | −2.0 | 3.8103E−07 | V |
| HP | NM_001126102 | 6 | PSR16008650.hg.1 | 16 | + | 72091291 | 72091365 | 0.83 | 9.4 | 7.6384E−12 | B |
| HP | NM_001126102 | 7 | PSR16008651.hg.1 | 16 | + | 72092153 | 72092254 | 0.83 | 10.2 | 4.0684E−12 | B |
| HP | NM_001126102 | 8 | PSR16008652.hg.1 | 16 | + | 72093013 | 72093087 | 0.83 | 10.2 | 2.5189E−12 | B |
| HPR | NM_020995 | 1 | PSR16008662.hg.1 | 16 | + | 72097125 | 72097154 | 0.83 | 3.1 | 9.3355E−12 | B |
| HPR | NM_020995 | 3 | PSR16008666.hg.1 | 16 | + | 72107791 | 72107876 | 0.81 | 2.6 | 2.2269E−10 | B |
| HPR | NM_020995 | 4 | PSR16008667.hg.1 | 16 | + | 72108183 | 72108284 | 0.84 | 3.3 | 6.5904E−11 | B |
| HPR | NM_020995 | 5 | PSR16008668.hg.1 | 16 | + | 72109044 | 72109118 | 0.83 | 9.4 | 7.6384E−12 | B |
| MT1G | NM_005950 | 2 | PSR16015818.hg.1 | 16 | − | 56701224 | 56701289 | 0.86 | −7.1 | 7.5336E−14 | V |
| — | n382996 | 3 | PSR16019885.hg.1 | 16 | + | 56670351 | 56670416 | 0.85 | −8.5 | 4.86E−14 | V |
| — | n382996 | 4 | PSR16019886.hg.1 | 16 | + | 56670764 | 56670998 | 0.85 | −2.6 | 1.1644E−11 | V |

TABLE 13-continued

Exon level analysis of 140 RNA determinants differentially expressed in bacterial and viral patients. Probe set ID is based on GeneChip Human Transcriptome Arrays 2.0 (HTA-Affymetrix) data. Comparison to full gene was calculated as absolute fold change (exon$_i$) - absolute fold change (full length gene); Only exons that presented higher of differential expression of the single exon compared to the full length gene were included.

| Gene Symbol | mRNA Accession | Exon # | Probe Set ID | Chromosome | Strand | Start | Stop | Exon AUC | FC | T-Test | Up in B/V |
|---|---|---|---|---|---|---|---|---|---|---|---|
| — | TCONS_00024856-XLOC_011736 | 5 | PSR16019891.hg.1 | 16 | + | 56678023 | 56678088 | 0.85 | −6.8 | 7.1072E−14 | V |
| — | TCONS_00024856-XLOC_011736 | 6 | PSR16019892.hg.1 | 16 | + | 56678622 | 56678852 | 0.82 | −1.3 | 4.7908E−09 | V |
| — | n406211 | 4 | PSR16019896.hg.1 | 16 | + | 56710967 | 56711026 | 0.85 | −9.9 | 7.1097E−13 | V |
| — | n406211 | 6 | PSR16019898.hg.1 | 16 | + | 56711564 | 56711628 | 0.83 | −3.9 | 4.1742E−12 | V |
| FBXO39 | NM_153230 | 3 | PSR17000955.hg.1 | 17 | + | 6683108 | 6684210 | 0.81 | −6.9 | 7.6586E−11 | V |
| FBXO39 | NM_153230 | 4 | PSR17000956.hg.1 | 17 | + | 6690099 | 6690275 | 0.78 | −2.3 | 3.7218E−08 | V |
| FBXO39 | NM_153230 | 5 | PSR17000957.hg.1 | 17 | + | 6690619 | 6690853 | 0.80 | −2.9 | 5.2588E−09 | V |
| CCL8 | NM_005623 | 3 | PSR17004889.hg.1 | 17 | + | 32647288 | 32647405 | 0.84 | −14.4 | 7.5638E−10 | V |
| CCL8 | NM_005623 | 4 | PSR17004890.hg.1 | 17 | + | 32647821 | 32647992 | 0.78 | −4.1 | 1.3114E−06 | V |
| CCL8 | NM_005623 | 5 | PSR17004891.hg.1 | 17 | + | 32647993 | 32648420 | 0.70 | −2.3 | 0.00012612 | V |
| CA4 | NM_000717 | 4 | PSR17009587.hg.1 | 17 | + | 58233921 | 58234076 | 0.87 | 4.3 | 7.1666E−15 | B |
| CA4 | NM_000717 | 5 | PSR17009588.hg.1 | 17 | + | 58234788 | 58234933 | 0.86 | 4.9 | 4.2638E−14 | B |
| CA4 | NM_000717 | 6 | PSR17009589.hg.1 | 17 | + | 58235051 | 58235149 | 0.87 | 3.9 | 1.5776E−14 | B |
| CA4 | NM_000717 | 7 | PSR17009590.hg.1 | 17 | + | 58235422 | 58235488 | 0.86 | 3.8 | 8.2936E−14 | B |
| CA4 | NM_000717 | 8 | PSR17009591.hg.1 | 17 | + | 58235644 | 58235807 | 0.86 | 3.3 | 1.0219E−13 | B |
| CA4 | NM_000717 | 10 | PSR17009594.hg.1 | 17 | + | 58236836 | 58236901 | 0.86 | 3.4 | 9.7931E−14 | B |
| GAS7 | NM_201433 | 1 | PSR17015199.hg.1 | 17 | − | 9813926 | 9817166 | 0.93 | 5.1 | 1.7657E−22 | B |
| GAS7 | NM_201433 | 8 | PSR17015207.hg.1 | 17 | − | 9820520 | 9820658 | 0.91 | 5.2 | 7.3911E−20 | B |
| GAS7 | NM_201433 | 9 | PSR17015208.hg.1 | 17 | − | 9821318 | 9821416 | 0.91 | 5.1 | 2.5424E−20 | B |
| GAS7 | NM_201433 | 10 | PSR17015209.hg.1 | 17 | − | 9822943 | 9823022 | 0.91 | 5.5 | 1.2604E−20 | B |
| GAS7 | NM_201433 | 11 | PSR17015210.hg.1 | 17 | − | 9828793 | 9828916 | 0.91 | 4.9 | 9.9913E−21 | B |
| GAS7 | NM_201433 | 12 | PSR17015211.hg.1 | 17 | − | 9829958 | 9830086 | 0.91 | 4.9 | 3.7906E−20 | B |
| GAS7 | NM_201433 | 14 | PSR17015213.hg.1 | 17 | − | 9843443 | 9843517 | 0.91 | 4.9 | 1.7485E−19 | B |
| GAS7 | NM_201433 | 16 | PSR17015215.hg.1 | 17 | − | 9850211 | 9850300 | 0.91 | 6.1 | 7.0065E−20 | B |
| GAS7 | NM_201433 | 21 | PSR17015220.hg.1 | 17 | − | 9885121 | 9885201 | 0.91 | 6.0 | 1.0764E−20 | B |
| GAS7 | NM_201433 | 22 | PSR17015221.hg.1 | 17 | − | 9923094 | 9923214 | 0.91 | 5.9 | 3.1874E−21 | B |
| GAS7 | NM_201433 | 26 | PSR17015226.hg.1 | 17 | − | 9939751 | 9939878 | 0.92 | 5.4 | 5.739E−22 | B |
| KRT19 | NM_002276 | 1 | PSR17019927.hg.1 | 17 | − | 39679872 | 39679965 | 0.52 | 1.0 | 0.90751055 | B |
| KRT19 | NM_002276 | 2 | PSR17019928.hg.1 | 17 | − | 39679966 | 39680249 | 0.59 | 1.1 | 0.08916123 | B |
| KRT19 | NM_002276 | 3 | PSR17019929.hg.1 | 17 | − | 39680250 | 39680394 | 0.55 | 1.0 | 0.25980658 | B |
| KRT19 | NM_002276 | 4 | PSR17019931.hg.1 | 17 | − | 39680400 | 39680520 | 0.56 | 1.0 | 0.1401154 | B |
| KRT19 | NM_002276 | 5 | PSR17019932.hg.1 | 17 | − | 39680631 | 39680744 | 0.52 | −1.0 | 0.80602688 | V |
| KRT19 | NM_002276 | 6 | PSR17019933.hg.1 | 17 | − | 39680745 | 39680770 | 0.57 | −1.1 | 0.10448473 | V |
| KRT19 | NM_002276 | 7 | PSR17019935.hg.1 | 17 | − | 39680793 | 39680899 | 0.55 | 1.0 | 0.50250233 | B |
| KRT19 | NM_002276 | 8 | PSR17019936.hg.1 | 17 | − | 39681095 | 39681229 | 0.50 | −1.0 | 0.94950467 | V |
| KRT19 | NM_002276 | 9 | PSR17019939.hg.1 | 17 | − | 39681252 | 39681442 | 0.59 | 1.1 | 0.10031113 | B |
| KRT19 | NM_002276 | 10 | PSR17019940.hg.1 | 17 | − | 39681443 | 39681473 | 0.87 | −6.5 | 3.7632E−14 | V |
| KRT19 | NM_002276 | 11 | PSR17019941.hg.1 | 17 | − | 39681474 | 39681525 | 0.51 | 1.0 | 0.70057602 | B |
| KRT19 | NM_002276 | 12 | PSR17019942.hg.1 | 17 | − | 39681526 | 39681924 | 0.61 | 1.1 | 0.0378847 | B |
| KRT19 | NM_002276 | 13 | PSR17019943.hg.1 | 17 | − | 39684080 | 39684172 | 0.66 | 1.1 | 0.00242979 | B |
| KRT19 | NM_002276 | 14 | PSR17019944.hg.1 | 17 | − | 39684173 | 39684543 | 0.56 | 1.0 | 0.23413563 | B |
| KRT19 | NM_002276 | 15 | PSR17019949.hg.1 | 17 | − | 39684561 | 39684641 | 0.48 | −1.0 | 0.6028224 | V |
| DHX58 | NM_024119 | 1 | PSR17020283.hg.1 | 17 | − | 40253453 | 40253964 | 0.89 | −10.6 | 3.5797E−17 | V |
| DHX58 | NM_024119 | 2 | PSR17020284.hg.1 | 17 | − | 40254234 | 40254330 | 0.88 | −8.3 | 9.9473E−16 | V |
| DHX58 | NM_024119 | 8 | PSR17020290.hg.1 | 17 | − | 40259622 | 40259710 | 0.87 | −7.8 | 6.8179E−15 | V |
| DHX58 | NM_024119 | 10 | PSR17020292.hg.1 | 17 | − | 40260000 | 40260126 | 0.87 | −7.7 | 2.049E−15 | V |
| DHX58 | NM_024119 | 11 | PSR17020293.hg.1 | 17 | − | 40261288 | 40261404 | 0.87 | −7.7 | 4.0795E−14 | V |
| DHX58 | NM_024119 | 13 | PSR17020295.hg.1 | 17 | − | 40262834 | 40262905 | 0.86 | −8.2 | 1.3325E−14 | V |
| DHX58 | NM_024119 | 14 | PSR17020298.hg.1 | 17 | − | 40263314 | 40263399 | 0.87 | −6.5 | 2.3204E−13 | V |
| DHX58 | NM_024119 | 15 | PSR17020299.hg.1 | 17 | − | 40263400 | 40263515 | 0.87 | −10.9 | 5.2884E−15 | V |
| DHX58 | NM_024119 | 16 | PSR17020301.hg.1 | 17 | − | 40263764 | 40263911 | 0.86 | −8.8 | 9.2666E−15 | V |
| LGALS3BP | NM_005567 | 1 | PSR17026201.hg.1 | 17 | − | 76967338 | 76967412 | 0.85 | −6.2 | 7.5502E−13 | V |
| LGALS3BP | NM_005567 | 2 | PSR17026202.hg.1 | 17 | − | 76967413 | 76968786 | 0.84 | −8.3 | 1.4992E−12 | V |
| LGALS3BP | NM_005567 | 3 | PSR17026203.hg.1 | 17 | − | 76969052 | 76969207 | 0.79 | −5.7 | 4.1609E−09 | V |
| LGALS3BP | NM_005567 | 5 | PSR17026205.hg.1 | 17 | − | 76970770 | 76970844 | 0.77 | −3.1 | 1.7225E−07 | V |
| LGALS3BP | NM_005567 | 7 | PSR17026208.hg.1 | 17 | − | 76972047 | 76972145 | 0.76 | −3.0 | 5.2204E−07 | V |
| — | n407998 | 3 | PSR17030719.hg.1 | 17 | − | 66536026 | 66536107 | 0.84 | 4.4 | 4.3541E−13 | B |
| — | n407998 | 5 | PSR17030721.hg.1 | 17 | − | 66538126 | 66538306 | 0.84 | 3.7 | 2.8353E−13 | B |
| — | n407998 | 6 | PSR17030722.hg.1 | 17 | − | 66538835 | 66538950 | 0.84 | 4.2 | 2.3816E−13 | B |
| — | n407998 | 7 | PSR17030723.hg.1 | 17 | − | 66539770 | 66539858 | 0.84 | 4.9 | 5.4634E−13 | B |
| IMPA2 | NM_014214 | 4 | PSR18000628.hg.1 | 18 | + | 11999061 | 11999186 | 0.93 | 5.7 | 1.0535E−22 | B |
| IMPA2 | NM_014214 | 6 | PSR18000630.hg.1 | 18 | + | 12009882 | 12009886 | 0.93 | 6.0 | 5.0676E−23 | B |
| IMPA2 | NM_014214 | 7 | PSR18000631.hg.1 | 18 | + | 12012169 | 12012214 | 0.93 | 5.9 | 1.1127E−22 | B |
| IMPA2 | NM_014214 | 8 | PSR18000632.hg.1 | 18 | + | 12014264 | 12014372 | 0.93 | 4.4 | 6.7358E−22 | B |
| IMPA2 | NM_014214 | 10 | PSR18000635.hg.1 | 18 | + | 12028042 | 12028150 | 0.92 | 5.3 | 6.1216E−22 | B |
| IMPA2 | NM_014214 | 11 | PSR18000636.hg.1 | 18 | + | 12028841 | 12028992 | 0.93 | 5.4 | 2.6008E−22 | B |
| IMPA2 | NM_014214 | 12 | PSR18000637.hg.1 | 18 | + | 12030342 | 12030876 | 0.93 | 4.5 | 9.7139E−23 | B |

TABLE 13-continued

Exon level analysis of 140 RNA determinants differentially expressed in bacterial and viral patients. Probe set ID is based on GeneChip Human Transcriptome Arrays 2.0 (HTA-Affymetrix) data. Comparison to full gene was calculated as absolute fold change (exon$_i$) − absolute fold change (full length gene); Only exons that presented higher of differential expression of the single exon compared to the full length gene were included.

| Gene Symbol | mRNA Accession | Exon # | Probe Set ID | Chromosome | Strand | Start | Stop | Exon AUC | FC | T-Test | Up in B/V |
|---|---|---|---|---|---|---|---|---|---|---|---|
| ZCCHC2 | NM_017742 | 12 | PSR18002544.hg.1 | 18 | + | 60232235 | 60232329 | 0.87 | −5.2 | 8.6497E−16 | V |
| ZCCHC2 | NM_017742 | 14 | PSR18002546.hg.1 | 18 | + | 60241290 | 60242783 | 0.89 | −5.3 | 1.746E−17 | V |
| ZCCHC2 | NM_017742 | 15 | PSR18002547.hg.1 | 18 | + | 60243745 | 60243885 | 0.88 | −5.5 | 6.1802E−17 | V |
| RFX2 | NM_000635 | 2 | PSR19014912.hg.1 | 19 | − | 5993538 | 5994961 | 0.84 | 2.7 | 7.3386E−13 | B |
| RFX2 | NM_000635 | 3 | PSR19014913.hg.1 | 19 | − | 5995612 | 5995654 | 0.84 | 2.9 | 6.9403E−13 | B |
| RFX2 | NM_000635 | 7 | PSR19014917.hg.1 | 19 | − | 6004212 | 6004309 | 0.86 | 4.8 | 3.218E−13 | B |
| RFX2 | NM_000635 | 9 | PSR19014919.hg.1 | 19 | − | 6007701 | 6007813 | 0.85 | 2.8 | 1.3112E−12 | B |
| RFX2 | NM_000635 | 12 | PSR19014922.hg.1 | 19 | − | 6012997 | 6013116 | 0.85 | 3.2 | 3.7879E−12 | B |
| RFX2 | NM_000635 | 13 | PSR19014923.hg.1 | 19 | − | 6016101 | 6016282 | 0.86 | 3.6 | 4.4035E−13 | B |
| RFX2 | NM_000635 | 14 | PSR19014924.hg.1 | 19 | − | 6026174 | 6026248 | 0.86 | 4.3 | 1.7565E−13 | B |
| RFX2 | NM_000635 | 16 | PSR19014926.hg.1 | 19 | − | 6042055 | 6042134 | 0.85 | 3.7 | 7.253E−13 | B |
| RFX2 | NM_000635 | 19 | PSR19014929.hg.1 | 19 | − | 6110404 | 6110545 | 0.86 | 3.2 | 8.7471E−13 | B |
| RIN2 | NM_001242581 | 7 | PSR20001702.hg.1 | 20 | + | 19915743 | 19915768 | 0.80 | −5.0 | 1.6264E−09 | V |
| RIN2 | NM_001242581 | 8 | PSR20001703.hg.1 | 20 | + | 19915769 | 19915843 | 0.83 | −5.1 | 1.2202E−10 | V |
| RIN2 | NM_001242581 | 9 | PSR20001704.hg.1 | 20 | + | 19916083 | 19916194 | 0.85 | −8.4 | 3.7392E−12 | V |
| RIN2 | NM_001242581 | 10 | PSR20001705.hg.1 | 20 | + | 19916195 | 19916251 | 0.85 | −7.4 | 5.562E−12 | V |
| RIN2 | NM_001242581 | 11 | PSR20001706.hg.1 | 20 | + | 19937259 | 19937451 | 0.84 | −6.4 | 2.5575E−11 | V |
| RIN2 | NM_001242581 | 12 | PSR20001707.hg.1 | 20 | + | 19941344 | 19941455 | 0.83 | −5.5 | 7.5487E−11 | V |
| RIN2 | NM_001242581 | 13 | PSR20001708.hg.1 | 20 | + | 19945596 | 19945668 | 0.84 | −6.1 | 5.8253E−11 | V |
| RIN2 | NM_001242581 | 14 | PSR20001709.hg.1 | 20 | + | 19951482 | 19951573 | 0.83 | −6.1 | 3.8412E−11 | V |
| RIN2 | NM_001242581 | 15 | PSR20001710.hg.1 | 20 | + | 19955298 | 19956431 | 0.78 | −3.3 | 4.7416E−08 | V |
| RIN2 | NM_001242581 | 16 | PSR20001711.hg.1 | 20 | + | 19970650 | 19970955 | 0.79 | −3.9 | 4.0266E−09 | V |
| RIN2 | NM_001242581 | 17 | PSR20001712.hg.1 | 20 | + | 19972812 | 19972943 | 0.80 | −4.9 | 4.0647E−09 | V |
| RIN2 | NM_001242581 | 18 | PSR20001713.hg.1 | 20 | + | 19977323 | 19977486 | 0.80 | −4.5 | 3.405E−09 | V |
| RIN2 | NM_001242581 | 19 | PSR20001714.hg.1 | 20 | + | 19981257 | 19981992 | 0.81 | −4.0 | 5.4803E−10 | V |
| RIN2 | NM_001242581 | 20 | PSR20001715.hg.1 | 20 | + | 19981993 | 19983101 | 0.78 | −3.6 | 2.1067E−08 | V |
| MMP9 | NM_004994 | 1 | PSR20005242.hg.1 | 20 | + | 44637561 | 44637703 | 0.82 | 5.0 | 1.0668E−10 | B |
| MMP9 | NM_004994 | 2 | PSR20005243.hg.1 | 20 | + | 44638505 | 44638737 | 0.83 | 6.3 | 5.0438E−11 | B |
| MMP9 | NM_004994 | 3 | PSR20005244.hg.1 | 20 | + | 44639122 | 44639270 | 0.82 | 6.9 | 7.265E−11 | B |
| MMP9 | NM_004994 | 4 | PSR20005245.hg.1 | 20 | + | 44639561 | 44639689 | 0.82 | 5.3 | 1.8284E−10 | B |
| MMP9 | NM_004994 | 5 | PSR20005246.hg.1 | 20 | + | 44639782 | 44639955 | 0.81 | 5.9 | 2.7334E−11 | B |
| MMP9 | NM_004994 | 6 | PSR20005247.hg.1 | 20 | + | 44640213 | 44640386 | 0.81 | 5.8 | 9.9521E−10 | B |
| MMP9 | NM_004994 | 9 | PSR20005250.hg.1 | 20 | + | 44640856 | 44640909 | 0.80 | 5.5 | 9.9389E−10 | B |
| MMP9 | NM_004994 | 13 | PSR20005254.hg.1 | 20 | + | 44641994 | 44642173 | 0.82 | 6.1 | 1.6625E−10 | B |
| MMP9 | NM_004994 | 17 | PSR20005258.hg.1 | 20 | + | 44643010 | 44643113 | 0.80 | 5.1 | 4.2473E−09 | B |
| MMP9 | NM_004994 | 18 | PSR20005259.hg.1 | 20 | + | 44644889 | 44645199 | 0.82 | 5.9 | 2.0473E−10 | B |
| ATP9A | NM_006045 | 2 | PSR20013015.hg.1 | 20 | − | 50213314 | 50217401 | 0.82 | 2.7 | 2.836E−09 | B |
| ATP9A | NM_006045 | 4 | PSR20013017.hg.1 | 20 | − | 50217749 | 50217886 | 0.84 | 3.0 | 1.284E−09 | B |
| ATP9A | NM_006045 | 5 | PSR20013018.hg.1 | 20 | − | 50221356 | 50221559 | 0.85 | 2.9 | 1.2811E−09 | B |
| ATP9A | NM_006045 | 6 | PSR20013019.hg.1 | 20 | − | 50224066 | 50224123 | 0.80 | 2.8 | 2.8842E−09 | B |
| ATP9A | NM_006045 | 7 | PSR20013020.hg.1 | 20 | − | 50225057 | 50225165 | 0.83 | 4.6 | 2.6655E−12 | B |
| ATP9A | NM_006045 | 8 | PSR20013021.hg.1 | 20 | − | 50226640 | 50226704 | 0.83 | 2.9 | 2.9165E−09 | B |
| ATP9A | NM_006045 | 9 | PSR20013022.hg.1 | 20 | − | 50230216 | 50230371 | 0.78 | 2.4 | 1.333E−07 | B |
| ATP9A | NM_006045 | 13 | PSR20013027.hg.1 | 20 | − | 50238613 | 50238711 | 0.81 | 3.0 | 5.8264E−09 | B |
| ATP9A | NM_006045 | 16 | PSR20013030.hg.1 | 20 | − | 50245519 | 50245611 | 0.82 | 2.5 | 2.4173E−10 | B |
| ATP9A | NM_006045 | 19 | PSR20013033.hg.1 | 20 | − | 50286536 | 50286648 | 0.81 | 4.3 | 3.1452E−10 | B |
| ATP9A | NM_006045 | 20 | PSR20013034.hg.1 | 20 | − | 50287654 | 50287796 | 0.85 | 5.9 | 1.8766E−12 | B |
| ATP9A | NM_006045 | 21 | PSR20013035.hg.1 | 20 | − | 50290692 | 50290852 | 0.84 | 5.9 | 1.1781E−12 | B |
| ATP9A | NM_006045 | 23 | PSR20013037.hg.1 | 20 | − | 50292701 | 50292747 | 0.85 | 7.7 | 2.5936E−13 | B |
| ATP9A | NM_006045 | 25 | PSR20013039.hg.1 | 20 | − | 50307278 | 50307358 | 0.85 | 6.7 | 3.7333E−13 | B |
| ATP9A | NM_006045 | 27 | PSR20013041.hg.1 | 20 | − | 50312632 | 50312683 | 0.85 | 5.9 | 2.9512E−11 | B |
| ATP9A | NM_006045 | 28 | PSR20013042.hg.1 | 20 | − | 50313963 | 50314021 | 0.85 | 7.1 | 1.1391E−12 | B |
| ATP9A | NM_006045 | 29 | PSR20013044.hg.1 | 20 | − | 50329505 | 50329613 | 0.86 | 4.2 | 5.0017E−11 | B |
| ATP9A | NM_006045 | 30 | PSR20013045.hg.1 | 20 | − | 50342358 | 50342471 | 0.86 | 6.4 | 9.8383E−13 | B |
| ZBP1 | NM_001160418 | 2 | PSR20013369.hg.1 | 20 | − | 56179111 | 56179319 | 0.81 | −4.7 | 7.8548E−11 | V |
| ZBP1 | NM_001160418 | 3 | PSR20013370.hg.1 | 20 | − | 56179320 | 56179432 | 0.82 | −4.2 | 2.1893E−11 | V |
| ZBP1 | NM_001160418 | 4 | PSR20013371.hg.1 | 20 | − | 56179433 | 56179459 | 0.81 | −5.2 | 2.7665E−10 | V |
| ZBP1 | NM_001160418 | 5 | PSR20013372.hg.1 | 20 | − | 56179460 | 56179802 | 0.81 | −4.1 | 3.4792E−10 | V |
| ZBP1 | NM_001160418 | 6 | PSR20013375.hg.1 | 20 | − | 56182117 | 56182356 | 0.77 | −3.3 | 2.8367E−08 | V |
| ZBP1 | NM_001160418 | 8 | PSR20013377.hg.1 | 20 | − | 56185322 | 56185423 | 0.80 | −4.7 | 5.6516E−10 | V |
| ZBP1 | NM_001160418 | 10 | PSR20013379.hg.1 | 20 | − | 56186783 | 56186986 | 0.80 | −3.4 | 1.1184E−09 | V |
| ZBP1 | NM_001160418 | 12 | PSR20013382.hg.1 | 20 | − | 56188219 | 56188383 | 0.81 | −3.9 | 1.1763E−10 | V |
| ZBP1 | NM_001160418 | 13 | PSR20013384.hg.1 | 20 | − | 56189943 | 56190081 | 0.82 | −3.9 | 3.5171E−11 | V |
| ZBP1 | NM_001160418 | 14 | PSR20013385.hg.1 | 20 | − | 56190082 | 56190116 | 0.80 | −4.1 | 1.9176E−09 | V |
| ZBP1 | NM_001160418 | 15 | PSR20013386.hg.1 | 20 | − | 56190568 | 56190636 | 0.80 | −4.8 | 5.9479E−10 | V |
| ZBP1 | NM_001160418 | 17 | PSR20013388.hg.1 | 20 | − | 56191300 | 56191524 | 0.80 | −5.1 | 4.3141E−10 | V |
| ZBP1 | NM_001160418 | 19 | PSR20013390.hg.1 | 20 | − | 56195275 | 56195317 | 0.78 | −3.4 | 4.1181E−08 | V |
| — | n339591 | 4 | PSR20014695.hg.1 | 20 | + | 19915743 | 19915843 | 0.84 | −5.1 | 6.2518E−11 | V |
| — | n339591 | 5 | PSR20014696.hg.1 | 20 | + | 19937259 | 19937451 | 0.85 | −6.1 | 1.0377E−11 | V |

TABLE 13-continued

Exon level analysis of 140 RNA determinants differentially expressed in bacterial and viral patients. Probe set ID is based on GeneChip Human Transcriptome Arrays 2.0 (HTA-Affymetrix) data. Comparison to full gene was calculated as absolute fold change ($exon_i$) - absolute fold change (full length gene); Only exons that presented higher of differential expression of the single exon compared to the full length gene were included.

| Gene Symbol | mRNA Accession | Exon # | Probe Set ID | Chromosome | Strand | Start | Stop | Exon AUC | FC | T-Test | Up in B/V |
|---|---|---|---|---|---|---|---|---|---|---|---|
| — | n339591 | 6 | PSR20014697.hg.1 | 20 | + | 19941344 | 19941455 | 0.84 | −5.4 | 4.4976E−11 | V |
| — | n339591 | 7 | PSR20014698.hg.1 | 20 | + | 19945596 | 19945668 | 0.84 | −6.3 | 4.4186E−11 | V |
| — | n339591 | 8 | PSR20014699.hg.1 | 20 | + | 19951482 | 19951573 | 0.84 | −6.2 | 2.7182E−11 | V |
| — | n339591 | 10 | PSR20014701.hg.1 | 20 | + | 19970650 | 19970955 | 0.79 | −3.9 | 4.3268E−09 | V |
| — | n339591 | 11 | PSR20014702.hg.1 | 20 | + | 19972812 | 19972943 | 0.80 | −5.0 | 1.3098E−09 | V |
| — | n339591 | 12 | PSR20014703.hg.1 | 20 | + | 19977323 | 19977486 | 0.81 | −4.7 | 6.5257E−10 | V |
| — | n339591 | 13 | PSR20014704.hg.1 | 20 | + | 19981257 | 19981449 | 0.81 | −5.0 | 1.5053E−09 | V |
| — | TCONS_00028139-XLOC_013499 | 2 | PSR20014845.hg.1 | 20 | + | 24911983 | 24912191 | 0.79 | 5.1 | 7.6867E−10 | B |
| MIR650 | NR_030755 | 20 | PSR22001552.hg.1 | 22 | + | 22676832 | 22676909 | 0.74 | −3.5 | 5.8793E−06 | V |
| MIR650 | NR_030755 | 21 | PSR22001553.hg.1 | 22 | + | 22677019 | 22677203 | 0.72 | −4.6 | 1.7537E−05 | V |
| MIR650 | NR_030755 | 22 | PSR22001554.hg.1 | 22 | + | 22677204 | 22677324 | 0.72 | −5.3 | 1.2213E−05 | V |
| MIR650 | NR_030755 | 26 | PSR22001564.hg.1 | 22 | + | 22682051 | 22682144 | 0.72 | −4.0 | 6.7913E−06 | V |
| MIR650 | NR_030755 | 27 | PSR22001565.hg.1 | 22 | + | 22682145 | 22682172 | 0.68 | −3.3 | 0.00037604 | V |
| MIR650 | NR_030755 | 28 | PSR22001572.hg.1 | 22 | + | 22712115 | 22712144 | 0.71 | −2.9 | 8.5728E−05 | V |
| MIR650 | NR_030755 | 30 | PSR22001574.hg.1 | 22 | + | 22712304 | 22712606 | 0.69 | −3.7 | 0.00013314 | V |
| MIR650 | NR_030755 | 32 | PSR22001589.hg.1 | 22 | + | 22730563 | 22730870 | 0.70 | −2.9 | 0.00014734 | V |
| MIR650 | NR_030755 | 34 | PSR22001593.hg.1 | 22 | + | 22735225 | 22735294 | 0.71 | −3.2 | 0.000101 | V |
| MIR650 | NR_030755 | 35 | PSR22001595.hg.1 | 22 | + | 22735410 | 22735598 | 0.69 | −4.2 | 0.00021656 | V |
| MIR650 | NR_030755 | 36 | PSR22001596.hg.1 | 22 | + | 22735599 | 22735709 | 0.71 | −4.8 | 1.5904E−05 | V |
| MIR650 | NR_030755 | 37 | PSR22001619.hg.1 | 22 | + | 22764131 | 22764194 | 0.72 | −3.5 | 1.6297E−05 | V |
| MIR650 | NR_030755 | 38 | PSR22001620.hg.1 | 22 | + | 22764305 | 22764466 | 0.71 | −5.1 | 1.0272E−05 | V |
| MIR650 | NR_030755 | 39 | PSR22001622.hg.1 | 22 | + | 22764472 | 22764597 | 0.72 | −4.8 | 6.5116E−06 | V |
| MIR650 | NR_030755 | 42 | PSR22001642.hg.1 | 22 | + | 22786693 | 22786733 | 0.72 | −4.0 | 8.956E−06 | V |
| MIR650 | NR_030755 | 43 | PSR22001643.hg.1 | 22 | + | 22786734 | 22786786 | 0.72 | −5.0 | 1.3266E−05 | V |
| MIR650 | NR_030755 | 45 | PSR22001770.hg.1 | 22 | + | 23040406 | 23040481 | 0.68 | −3.7 | 0.00034489 | V |
| MIR650 | NR_030755 | 46 | PSR22001773.hg.1 | 22 | + | 23040599 | 23040750 | 0.69 | −3.8 | 0.00030197 | V |
| MIR650 | NR_030755 | 47 | PSR22001775.hg.1 | 22 | + | 23040763 | 23040892 | 0.70 | −4.0 | 0.00011229 | V |
| MIR650 | NR_030755 | 50 | PSR22001789.hg.1 | 22 | + | 23054877 | 23054949 | 0.68 | −3.2 | 0.00093823 | V |
| MIR650 | NR_030755 | 51 | PSR22001792.hg.1 | 22 | + | 23055385 | 23055677 | 0.68 | −3.5 | 0.00070466 | V |
| MIR650 | NR_030755 | 52 | PSR22001812.hg.1 | 22 | + | 23063132 | 23063193 | 0.70 | −4.2 | 0.00015357 | V |
| MIR650 | NR_030755 | 53 | PSR22001813.hg.1 | 22 | + | 23063340 | 23063630 | 0.69 | −4.1 | 0.0003853 | V |
| MIR650 | NR_030755 | 54 | PSR22001863.hg.1 | 22 | + | 23101208 | 23101275 | 0.69 | −3.8 | 0.00016431 | V |
| MIR650 | NR_030755 | 55 | PSR22001865.hg.1 | 22 | + | 23101393 | 23101686 | 0.70 | −4.1 | 0.00012115 | V |
| MIR650 | NR_030755 | 56 | PSR22001912.hg.1 | 22 | + | 23134984 | 23135067 | 0.70 | −4.3 | 5.6797E−05 | V |
| MIR650 | NR_030755 | 57 | PSR22001914.hg.1 | 22 | + | 23135192 | 23135489 | 0.70 | −4.6 | 0.00011571 | V |
| MIR650 | NR_030755 | 59 | PSR22001944.hg.1 | 22 | + | 23154478 | 23154774 | 0.71 | −3.1 | 0.00056063 | V |
| MIR650 | NR_030755 | 61 | PSR22001974.hg.1 | 22 | + | 23165285 | 23165360 | 0.71 | −4.2 | 4.7765E−05 | V |
| MIR650 | NR_030755 | 62 | PSR22001977.hg.1 | 22 | + | 23165487 | 23165715 | 0.71 | −4.1 | 3.4888E−05 | V |
| MIR650 | NR_030755 | 63 | PSR22001978.hg.1 | 22 | + | 23165716 | 23165755 | 0.72 | −3.6 | 1.1246E−05 | V |
| MIR650 | NR_030755 | 69 | PSR22002085.hg.1 | 22 | + | 23235965 | 23235998 | 0.69 | −4.6 | 0.00015309 | V |
| MIR650 | NR_030755 | 71 | PSR22002089.hg.1 | 22 | + | 23237555 | 23237984 | 0.71 | −3.9 | 3.8835E−05 | V |
| MIR650 | NR_030755 | 73 | PSR22002103.hg.1 | 22 | + | 23241805 | 23241835 | 0.70 | −3.5 | 9.1149E−05 | V |
| MIR650 | NR_030755 | 74 | PSR22002109.hg.1 | 22 | + | 23243156 | 23243489 | 0.73 | −3.6 | 1.2025E−05 | V |
| MIR650 | NR_030755 | 75 | PSR22002113.hg.1 | 22 | + | 23243497 | 23243610 | 0.73 | −4.5 | 4.3285E−06 | V |
| MIR650 | NR_030755 | 77 | PSR22002127.hg.1 | 22 | + | 23247172 | 23247205 | 0.70 | −2.8 | 7.7069E−05 | V |
| MIR650 | NR_030755 | 79 | PSR22002131.hg.1 | 22 | + | 23248512 | 23248845 | 0.73 | −3.0 | 8.1816E−06 | V |
| MIR650 | NR_030755 | 80 | PSR22002135.hg.1 | 22 | + | 23248853 | 23248930 | 0.73 | −3.6 | 6.8535E−06 | V |
| MIR650 | NR_030755 | 81 | PSR22002136.hg.1 | 22 | + | 23248931 | 23248963 | 0.73 | −3.7 | 1.9484E−05 | V |
| KREMEN1 | NM_001039570 | 2 | PSR22003491.hg.1 | 22 | + | 29490246 | 29490408 | 0.88 | 6.1 | 2.5421E−15 | B |
| KREMEN1 | NM_001039570 | 3 | PSR22003492.hg.1 | 22 | + | 29494850 | 29494941 | 0.90 | 6.4 | 1.0897E−16 | B |
| KREMEN1 | NM_001039570 | 4 | PSR22003493.hg.1 | 22 | + | 29517345 | 29517428 | 0.90 | 6.4 | 4.1116E−15 | B |
| KREMEN1 | NM_001039570 | 5 | PSR22003494.hg.1 | 22 | + | 29517429 | 29517469 | 0.89 | 7.3 | 1.7131E−15 | B |
| KREMEN1 | NM_001039570 | 7 | PSR22003496.hg.1 | 22 | + | 29521251 | 29521404 | 0.89 | 6.9 | 2.9456E−16 | B |
| KREMEN1 | NM_001039570 | 8 | PSR22003497.hg.1 | 22 | + | 29533330 | 29533489 | 0.89 | 6.2 | 2.5089E−17 | B |
| KREMEN1 | NM_001039570 | 9 | PSR22003498.hg.1 | 22 | + | 29533490 | 29533662 | 0.89 | 6.7 | 1.6066E−16 | B |
| KREMEN1 | NM_001039570 | 10 | PSR22003500.hg.1 | 22 | + | 29534631 | 29534759 | 0.90 | 7.2 | 9.0725E−19 | B |
| KREMEN1 | NM_001039570 | 12 | PSR22003503.hg.1 | 22 | + | 29536270 | 29536354 | 0.90 | 7.8 | 2.6266E−16 | B |
| KREMEN1 | NM_001039570 | 13 | PSR22003504.hg.1 | 22 | + | 29537932 | 29538017 | 0.90 | 7.8 | 1.0495E−16 | B |
| KREMEN1 | NM_001039570 | 14 | PSR22003505.hg.1 | 22 | + | 29538018 | 29538088 | 0.90 | 8.5 | 2.0383E−17 | B |
| KREMEN1 | NM_001039570 | 15 | PSR22003507.hg.1 | 22 | + | 29538101 | 29539731 | 0.90 | 7.7 | 2.0622E−16 | B |
| KREMEN1 | NM_001039570 | 16 | PSR22003508.hg.1 | 22 | + | 29539732 | 29542801 | 0.89 | 6.5 | 2.0632E−17 | B |
| TSPO | NM_000714 | 5 | PSR22006944.hg.1 | 22 | + | 43555216 | 43555426 | 0.89 | 3.1 | 9.7416E−18 | B |
| TSPO | NM_000714 | 7 | PSR22006946.hg.1 | 22 | + | 43557058 | 43557196 | 0.90 | 4.9 | 1.7294E−19 | B |
| TSPO | NM_000714 | 8 | PSR22006947.hg.1 | 22 | + | 43558809 | 43559216 | 0.91 | 2.9 | 1.6793E−19 | B |
| TSPO | NM_000714 | 9 | PSR22006948.hg.1 | 22 | + | 43559217 | 43559247 | 0.88 | 4.2 | 9.4038E−16 | B |
| PRR5 | NM_181333 | 2 | PSR22007158.hg.1 | 22 | + | 45064593 | 45064685 | 0.71 | 1.2 | 3.6612E−05 | B |
| PRR5 | NM_181333 | 4 | PSR22007160.hg.1 | 22 | + | 45072861 | 45072936 | 0.65 | −1.1 | 0.00416537 | V |
| PRR5 | NM_181333 | 11 | PSR22007176.hg.1 | 22 | + | 45110471 | 45110551 | 0.80 | −1.7 | 1.6112E−07 | V |

TABLE 13-continued

Exon level analysis of 140 RNA determinants differentially
expressed in bacterial and viral patients. Probe set ID is based on GeneChip
Human Transcriptome Arrays 2.0 (HTA-Affymetrix) data. Comparison to full
gene was calculated as absolute fold change (exon$_i$) - absolute fold change (full
length gene); Only exons that presented higher of differential expression of the
single exon compared to the full length gene were included.

| Gene Symbol | mRNA Accession | Exon # | Probe Set ID | Chromosome | Strand | Start | Stop | Exon AUC | FC | T-Test | Up in B/V |
|---|---|---|---|---|---|---|---|---|---|---|---|
| PRR5 | NM_181333 | 12 | PSR22007179.hg.1 | 22 | + | 45121141 | 45121172 | 0.83 | −4.9 | 1.0452E−10 | V |
| PRR5 | NM_181333 | 13 | PSR22007181.hg.1 | 22 | + | 45122457 | 45122514 | 0.85 | −4.6 | 4.5865E−11 | V |
| PRR5 | NM_181333 | 14 | PSR22007182.hg.1 | 22 | + | 45125194 | 45125288 | 0.70 | −1.4 | 2.7554E−05 | V |
| PRR5 | NM_181333 | 15 | PSR22007183.hg.1 | 22 | + | 45126490 | 45126683 | 0.66 | −1.3 | 0.00019082 | V |
| PRR5 | NM_181333 | 16 | PSR22007184.hg.1 | 22 | + | 45126684 | 45126763 | 0.65 | −1.1 | 0.00929537 | V |
| PRR5 | NM_181333 | 17 | PSR22007185.hg.1 | 22 | + | 45126764 | 45126812 | 0.82 | −1.8 | 1.1862E−07 | V |
| PRR5 | NM_181333 | 18 | PSR22007186.hg.1 | 22 | + | 45126813 | 45126884 | 0.61 | −1.1 | 0.04462985 | V |
| PRR5 | NM_181333 | 19 | PSR22007187.hg.1 | 22 | + | 45126885 | 45127558 | 0.76 | −1.5 | 6.5545E−06 | V |
| PRR5 | NM_181333 | 20 | PSR22007188.hg.1 | 22 | + | 45127559 | 45127609 | 0.79 | −1.2 | 1.4285E−08 | V |
| PRR5 | NM_181333 | 21 | PSR22007190.hg.1 | 22 | + | 45127615 | 45127701 | 0.86 | −3.4 | 8.2605E−11 | V |
| PRR5 | NM_181333 | 22 | PSR22007191.hg.1 | 22 | + | 45128131 | 45128197 | 0.86 | −2.2 | 1.5205E−10 | V |
| PRR5 | NM_181333 | 23 | PSR22007192.hg.1 | 22 | + | 45128198 | 45128271 | 0.72 | −1.2 | 0.00010856 | V |
| PRR5 | NM_181333 | 25 | PSR22007194.hg.1 | 22 | + | 45130907 | 45131042 | 0.85 | −2.6 | 7.5374E−10 | V |
| PRR5 | NM_181333 | 26 | PSR22007196.hg.1 | 22 | + | 45132667 | 45132754 | 0.84 | −2.1 | 1.0639E−08 | V |
| PRR5 | NM_181333 | 28 | PSR22007198.hg.1 | 22 | + | 45132790 | 45133095 | 0.80 | −1.4 | 1.2387E−06 | V |
| PRR5 | NM_181333 | 29 | PSR22007199.hg.1 | 22 | + | 45133096 | 45133321 | 0.85 | −3.0 | 4.4347E−10 | V |
| PRR5 | NM_181333 | 30 | PSR22007200.hg.1 | 22 | + | 45133322 | 45133512 | 0.84 | −1.9 | 4.3811E−09 | V |
| PRR5 | NM_181333 | 32 | PSR22007210.hg.1 | 22 | + | 45148438 | 45148507 | 0.72 | −1.1 | 2.5123E−05 | V |
| PRR5 | NM_181333 | 33 | PSR22007211.hg.1 | 22 | + | 45148454 | 45148507 | 0.70 | −1.2 | 0.0005654 | V |
| PRR5 | NM_181333 | 34 | PSR22007212.hg.1 | 22 | + | 45148466 | 45148507 | 0.69 | −1.1 | 0.00016043 | V |
| PRR5 | NM_181333 | 45 | PSR22007223.hg.1 | 22 | + | 45204187 | 45204318 | 0.61 | −1.1 | 0.02548305 | V |
| PRR5 | NM_181333 | 47 | PSR22007225.hg.1 | 22 | + | 45204552 | 45204612 | 0.70 | −1.2 | 0.00013354 | V |
| PRR5 | NM_181333 | 48 | PSR22007226.hg.1 | 22 | + | 45204613 | 45204689 | 0.73 | −1.1 | 2.1935E−05 | V |
| PRR5 | NM_181333 | 49 | PSR22007227.hg.1 | 22 | + | 45204886 | 45204978 | 0.59 | −1.1 | 0.12619041 | V |
| PRR5 | NM_181333 | 50 | PSR22007228.hg.1 | 22 | + | 45204979 | 45205681 | 0.67 | 1.1 | 0.00131627 | B |
| PRR5 | NM_181333 | 53 | PSR22007232.hg.1 | 22 | + | 45218251 | 45218349 | 0.62 | −1.1 | 0.01180009 | V |
| PRR5 | NM_181333 | 54 | PSR22007233.hg.1 | 22 | + | 45221363 | 45221431 | 0.65 | −1.1 | 0.00286712 | V |
| PRR5 | NM_181333 | 61 | PSR22007243.hg.1 | 22 | + | 45255611 | 45255658 | 0.70 | 1.1 | 0.00010977 | B |
| PRR5 | NM_181333 | 67 | PSR22007250.hg.1 | 22 | + | 45258552 | 45258586 | 0.60 | −1.1 | 0.03126075 | V |
| PRR5 | NM_181333 | 68 | PSR22007251.hg.1 | 22 | + | 45258587 | 45258616 | 0.59 | 1.1 | 0.10933159 | B |
| PRR5 | NM_181333 | 69 | PSR22007252.hg.1 | 22 | + | 45258617 | 45258664 | 0.61 | 1.1 | 0.04609827 | B |
| USP41 | ENST00000454608 | 2 | PSR22009517.hg.1 | 22 | − | 20717915 | 20717964 | 0.92 | −58.8 | 2.7183E−21 | V |
| USP41 | ENST00000454608 | 3 | PSR22009518.hg.1 | 22 | − | 20718476 | 20718607 | 0.92 | −68.8 | 9.3227E−22 | V |
| USP41 | ENST00000454608 | 4 | PSR22009519.hg.1 | 22 | − | 20720857 | 20721024 | 0.92 | −43.5 | 2.4258E−20 | V |
| USP41 | ENST00000454608 | 5 | PSR22009520.hg.1 | 22 | − | 20721838 | 20721933 | 0.91 | −16.1 | 1.5508E−17 | V |
| USP41 | ENST00000454608 | 6 | PSR22009521.hg.1 | 22 | − | 20723719 | 20723865 | 0.91 | −14.7 | 4.0106E−17 | V |
| USP41 | ENST00000454608 | 7 | PSR22009522.hg.1 | 22 | − | 20724410 | 20724489 | 0.92 | −28.9 | 9.237E−20 | V |
| USP41 | ENST00000454608 | 10 | PSR22009527.hg.1 | 22 | − | 20731445 | 20731541 | 0.90 | −16.4 | 6.8498E−17 | V |
| — | n384079 | 6 | PSR22016114.hg.1 | 22 | + | 18847156 | 18847476 | 0.62 | 1.1 | 0.04755901 | B |
| — | n384079 | 7 | PSR22016115.hg.1 | 22 | + | 18847477 | 18848963 | 0.62 | −1.1 | 0.03900109 | V |
| — | n384079 | 10 | PSR22016118.hg.1 | 22 | + | 18851305 | 18851914 | 0.90 | −13.4 | 6.5733E−16 | V |
| — | n386315 | 3 | PSR22016504.hg.1 | 22 | + | 22657589 | 22657662 | 0.70 | −1.6 | 0.00034851 | V |
| — | n386315 | 4 | PSR22016505.hg.1 | 22 | + | 22658308 | 22658420 | 0.64 | −1.4 | 0.00283381 | V |
| — | n386315 | 5 | PSR22016506.hg.1 | 22 | + | 22658425 | 22658479 | 0.68 | −1.6 | 0.00043744 | V |
| — | n386315 | 6 | PSR22016507.hg.1 | 22 | + | 22661155 | 22661268 | 0.67 | −1.6 | 0.00079357 | V |
| — | n386315 | 7 | PSR22016508.hg.1 | 22 | + | 22661269 | 22661386 | 0.67 | −1.4 | 0.00086729 | V |
| — | n386315 | 8 | PSR22016509.hg.1 | 22 | + | 22661471 | 22661610 | 0.66 | −1.7 | 0.00099046 | V |
| — | n386315 | 10 | PSR22016512.hg.1 | 22 | + | 22661898 | 22661958 | 0.68 | −1.4 | 0.00082402 | V |
| — | n386315 | 13 | PSR22016515.hg.1 | 22 | + | 22663093 | 22663184 | 0.67 | −1.5 | 0.00059708 | V |
| — | n386315 | 15 | PSR22016517.hg.1 | 22 | + | 22664101 | 22664248 | 0.71 | −1.4 | 9.9601E−05 | V |
| — | n386315 | 16 | PSR22016518.hg.1 | 22 | + | 22664591 | 22664766 | 0.70 | −1.4 | 0.00033934 | V |
| — | n386315 | 17 | PSR22016519.hg.1 | 22 | + | 22673254 | 22673606 | 0.63 | −1.4 | 0.01471703 | V |
| — | n386315 | 20 | PSR22016522.hg.1 | 22 | + | 22677019 | 22677324 | 0.72 | −5.3 | 1.1788E−05 | V |
| — | n332472 | 3 | PSR22017809.hg.1 | 22 | − | 23248513 | 23248828 | 0.73 | −4.9 | 1.4978E−06 | V |
| — | n346241 | 5 | PSR22017831.hg.1 | 22 | − | 23264978 | 23265153 | 0.75 | −5.0 | 1.2267E−06 | V |

TABLE 14

Differentially expressed RNA determinants (coding and non-coding) and their measures of accuracy in differentiating between bacterial ("B") versus viral ("V") infected subjects

| Gene Symbol | mRNA Accession | AUC | Sensitivity | Specificity | Fold Change (linear) (Bacterial vs. Viral) | ANOVA p-value (Bacterial vs. Viral) | Up in B/V |
|---|---|---|---|---|---|---|---|
| ZNF684 | NM_152373 | 0.84 | 0.77 | 0.86 | −2.9 | 1.05E−09 | V |
| ZDHHC19 | NM_001039617 | 0.82 | 0.75 | 0.80 | 1.7 | 2.21E−12 | B |
| ZCCHC2 | NM_017742 | 0.87 | 0.80 | 0.76 | −5.18 | 6.66E−16 | V |
| ZBP1 | NM_001160418 | 0.80 | 0.77 | 0.71 | −3.25 | 7.7E−10 | V |
| VNN1 | NM_004666 | 0.84 | 0.73 | 0.81 | 8.7 | 3.45E−12 | B |
| USP41 | ENST00000454608 | 0.91 | 0.92 | 0.82 | −13.84 | 3.33E−16 | V |
| TTC21A | NM_001105513 | 0.89 | 0.88 | 0.80 | −1.53 | 9.96E−09 | V |
| TSPO | NM_000714 | 0.90 | 0.86 | 0.82 | 1.76 | <10−17 | B |
| TRIB2 | NM_021643 | 0.88 | 0.77 | 0.91 | −5.06 | 2.78E−15 | V |
| TREX1 | NM_016381 | 0.91 | 0.88 | 0.84 | −1.21 | <10−17 | V |
| TMEM255A | NM_001104544 | 0.82 | 0.82 | 0.72 | −1.93 | 2.92E−09 | V |
| TMEM123 | NM_052932 | 0.92 | 0.84 | 0.86 | −3.21 | <10−17 | V |
| TDRD9 | NM_153046 | 0.82 | 0.77 | 0.84 | 3.25 | 1.95E−12 | B |
| SULT1B1 | NM_014465 | 0.88 | 0.77 | 0.86 | 3.65 | 3.33E−16 | B |
| STAP1 | NM_012108 | 0.85 | 0.86 | 0.79 | −6.54 | 7.46E−14 | V |
| SRGAP2 | NM_001042758 | 0.88 | 0.78 | 0.85 | −2.41 | 6.08E−12 | V |
| SPATS2L | NM_001100422 | 0.87 | 0.84 | 0.75 | −6.94 | 1.78E−13 | V |
| SLPI | NM_003064 | 0.81 | 0.73 | 0.82 | 8.19 | 4.89E−11 | B |
| SDCCAG3 | NM_001039707 | 0.68 | 0.59 | 0.75 | −1.16 | 0.000961 | V |
| RIN2 | NM_001242581 | 0.82 | 0.80 | 0.73 | −3 | 4.65E−10 | V |
| RFX2 | NM_000635 | 0.86 | 0.80 | 0.86 | 2.55 | 3.13E−14 | B |
| RASGRP3 | NM_001139488 | 0.86 | 0.80 | 0.79 | −2.05 | 3.13E−11 | V |
| RABGAP1L | NM_001035230 | 0.85 | 0.77 | 0.87 | −1.36 | 2.39E−11 | V |
| PYGL | NM_001163940 | 0.91 | 0.88 | 0.84 | 3.57 | <10−17 | B |
| PRR5 | NM_181333 | 0.88 | 0.75 | 0.87 | −1.08 | 1.44E−12 | V |
| PPM1K | NM_152542 | 0.91 | 0.84 | 0.87 | −4.03 | <10−17 | V |
| PNPT1 | NM_033109 | 0.93 | 0.90 | 0.90 | −6.81 | <10−17 | V |
| PLB1 | NM_001170585 | 0.85 | 0.82 | 0.82 | 2.61 | 1.66E−12 | B |
| PI3 | NM_002638 | 0.80 | 0.67 | 0.82 | 16.12 | 9.9E−11 | B |
| PGD | NM_002631 | 0.89 | 0.88 | 0.82 | 2.37 | 2.22E−16 | B |
| PGAP1 | NM_024989 | 0.88 | 0.77 | 0.84 | −2.89 | 6.21E−12 | V |
| PARP14 | NM_017554 | 0.78 | 0.77 | 0.66 | −2.75 | 1.19E−08 | V |
| PARP12 | NM_022750 | 0.89 | 0.78 | 0.89 | −6.42 | <10−17 | V |
| PADI2 | NM_007365 | 0.87 | 0.88 | 0.71 | 3.54 | 5.71E−14 | B |
| NSUN7 | NM_024677 | 0.86 | 0.77 | 0.87 | 3.62 | 1.67E−13 | B |
| NLRC4 | NM_001199138 | 0.87 | 0.77 | 0.89 | 3.54 | 1.39E−14 | B |
| NEXN | NM_001172309 | 0.77 | 0.73 | 0.70 | −1.6 | 4.16E−08 | V |
| NCOA7 | NM_001122842 | 0.62 | 0.53 | 0.76 | −1.13 | 0.084484 | V |
| MT1X | NM_005952 | 0.85 | 0.84 | 0.81 | −1.93 | 5.82E−10 | V |
| MT1M | NM_176870 | 0.84 | 0.75 | 0.79 | −1.33 | 1.16E−11 | V |
| MT1JP | NR_036677 | 0.84 | 0.82 | 0.75 | −1.98 | 3.93E−12 | V |
| MT1IP | NR_003669 | 0.76 | 0.77 | 0.76 | −1.23 | 6.35E−07 | V |
| MT1H | NM_005951 | 0.85 | 0.86 | 0.75 | −2.37 | 4.13E−12 | V |
| MT1G | NM_005950 | 0.82 | 0.77 | 0.80 | −1.98 | 2.1E−10 | V |
| MT1F | NM_005949 | 0.82 | 0.84 | 0.71 | −3.22 | 8.19E−11 | V |
| MT1E | NM_175617 | 0.83 | 0.80 | 0.77 | −1.63 | 1.99E−10 | V |
| MT1DP | NR_003658 | 0.83 | 0.82 | 0.77 | −1.45 | 4.35E−12 | V |
| MT1B | NM_005947 | 0.79 | 0.84 | 0.72 | −1.7 | 8.61E−10 | V |
| MT1A | NM_005946 | 0.83 | 0.86 | 0.77 | −1.69 | 2.22E−12 | V |
| MOV10 | NM_001130079 | 0.80 | 0.61 | 0.84 | −2.77 | 1.83E−09 | V |
| MMP9 | NM_004994 | 0.81 | 0.75 | 0.77 | 4.94 | 5.78E−10 | B |
| MMP8 | NM_002424 | 0.72 | 0.69 | 0.71 | 4.08 | 0.000012 | B |
| MIR650 | NR_030755 | 0.71 | 0.75 | 0.62 | −2.75 | 0.000039 | V |
| MIR1182 | NR_031593 | 0.68 | 0.65 | 0.70 | 1.18 | 0.000057 | B |
| MGAM | NM_004668 | 0.89 | 0.86 | 0.84 | 4.25 | 4.8E−14 | B |
| MAPK14 | NM_001315 | 0.88 | 0.77 | 0.82 | 2.6 | 1.89E−15 | B |
| LTA4H | NM_000895 | 0.93 | 0.86 | 0.92 | 4.25 | <10−17 | B |
| LRRN3 | NM_001099658 | 0.73 | 0.73 | 0.67 | −2.53 | 0.000011 | V |
| LGALS3BP | NM_005567 | 0.79 | 0.75 | 0.72 | −2.76 | 1.88E−08 | V |
| KRT19 | NM_002276 | 0.51 | 0.63 | 0.51 | 1 | 0.686226 | B |
| KREMEN1 | NM_001039570 | 0.89 | 0.80 | 0.89 | 5.9 | 1.11E−16 | B |
| IMPA2 | NM_014214 | 0.93 | 0.88 | 0.85 | 3.58 | <10−17 | B |
| IL1RN | NM_173843 | 0.67 | 0.75 | 0.60 | −1.55 | 0.000095 | V |
| IGKV3D-15 | ENST00000417279 | 0.73 | 0.73 | 0.72 | −3.18 | 0.00002 | V |
| IGKV2D-28 | ENST00000453166 | 0.73 | 0.77 | 0.66 | −6.14 | 0.000005 | V |
| IGKV2-28 | ENST00000482769 | 0.73 | 0.73 | 0.68 | −7.47 | 0.000008 | V |
| IGKV1D-33 | ENST00000390265 | 0.72 | 0.69 | 0.76 | −6.09 | 0.000023 | V |
| IGKV1-9 | ENST00000493819 | 0.72 | 0.73 | 0.68 | −4.98 | 0.000014 | V |
| IGKC | ENST00000390237 | 0.72 | 0.71 | 0.73 | −4.18 | 0.000009 | V |
| IGJ | NM_144646 | 0.72 | 0.71 | 0.71 | −4.74 | 0.00001 | V |
| IFIT5 | NM_012420 | 0.84 | 0.77 | 0.82 | −5.14 | 2.18E−13 | V |

TABLE 14-continued

Differentially expressed RNA determinants (coding and non-coding) and their measures of accuracy in differentiating between bacterial ("B") versus viral ("V") infected subjects

| Gene Symbol | mRNA Accession | AUC | Sensitivity | Specificity | Fold Change (linear) (Bacterial vs. Viral) | ANOVA p-value (Bacterial vs. Viral) | Up in B/V |
|---|---|---|---|---|---|---|---|
| IFIH1 | NM_022168 | 0.82 | 0.80 | 0.71 | −5.17 | 1.18E−11 | V |
| HPR | NM_020995 | 0.84 | 0.77 | 0.82 | 2.38 | 1.68E−11 | B |
| HPGD | NM_000860 | 0.82 | 0.65 | 0.89 | 3.86 | 4.36E−11 | B |
| HP | NM_001126102 | 0.83 | 0.75 | 0.80 | 9.16 | 3.01E−12 | B |
| HESX1 | NM_003865 | 0.86 | 0.82 | 0.80 | −2.25 | 5.8E−09 | V |
| HERC6 | NM_001165136 | 0.92 | 0.88 | 0.84 | −11.16 | <10-17 | V |
| GSN | NM_198252 | 0.70 | 0.78 | 0.57 | 1.23 | 0.000294 | B |
| GAS7 | NM_201433 | 0.91 | 0.82 | 0.87 | 4.54 | <10-17 | B |
| GALNT14 | NM_001253826 | 0.84 | 0.77 | 0.85 | 2.65 | 1.94E−13 | B |
| FTSJD2 | NM_015050 | 0.85 | 0.78 | 0.81 | −3.14 | 4.23E−13 | V |
| FBXO39 | NM_153230 | 0.80 | 0.75 | 0.77 | −2.03 | 1.34E−08 | V |
| FAM200B | NM_001145191 | 0.78 | 0.71 | 0.73 | 1.42 | 2.56E−08 | B |
| DHX58 | NM_024119 | 0.87 | 0.84 | 0.81 | −6.51 | 4.79E−14 | V |
| DGAT2 | NM_001253891 | 0.89 | 0.88 | 0.80 | 4.64 | 7.77E−16 | B |
| CR1L | NM_175710 | 0.90 | 0.86 | 0.81 | 2.68 | <10-17 | B |
| CR1 | NM_000573 | 0.90 | 0.88 | 0.81 | 3.91 | <10-17 | B |
| CNTNAP3 | NM_033655 | 0.75 | 0.73 | 0.66 | 2.6 | 5.62E−07 | B |
| CDK5RAP2 | NM_001011649 | 0.55 | 0.61 | 0.56 | 1.06 | 0.277074 | B |
| CD44 | NM_001001391 | 0.90 | 0.84 | 0.82 | 2.05 | 7.77E−16 | B |
| CD2AP | NM_012120 | 0.89 | 0.82 | 0.79 | −3.46 | <10-17 | V |
| CD177P1 | ENST00000378007 | 0.77 | 0.71 | 0.76 | 14.08 | 1.98E−07 | B |
| CCL8 | NM_005623 | 0.83 | 0.80 | 0.73 | −1.45 | 0.000005 | V |
| CA4 | NM_000717 | 0.86 | 0.71 | 0.89 | 3.05 | 1.54E−13 | B |
| C9orf91 | NM_153045 | 0.84 | 0.71 | 0.89 | −1.93 | 4.69E−11 | V |
| ATP9A | NM_006045 | 0.84 | 0.84 | 0.79 | 2.33 | 3.92E−10 | B |
| ATP10A | NM_024490 | 0.90 | 0.84 | 0.85 | −2.42 | <10-17 | V |
| ARG1 | NM_000045 | 0.78 | 0.67 | 0.77 | 6.41 | 2.25E−08 | B |
| ANXA3 | NM_005139 | 0.80 | 0.78 | 0.73 | 2.64 | 1.03E−08 | B |
| ANKRD34B | NM_001004441 | 0.82 | 0.80 | 0.70 | 2.28 | 3.47E−11 | B |
| ALPL | NM_000478 | 0.90 | 0.86 | 0.85 | 6.32 | 6.33E−13 | B |
| AKAP2 | NM_001004065 | 0.87 | 0.86 | 0.77 | −1.24 | 7.77E−16 | V |
| — | ENST00000442385 | 0.84 | 0.84 | 0.77 | −2.05 | 1.72E−09 | V |
| — | TCONS_00000869-XLOC_000105 | 0.84 | 0.80 | 0.70 | −1.5 | 9.01E−08 | V |
| — | ENST00000436616 | 0.92 | 0.88 | 0.89 | −2.51 | 9.95E−14 | V |
| — | ENST00000366140 | 0.87 | 0.80 | 0.91 | −3.2 | 2.34E−12 | V |
| — | ENST00000443397 | 0.71 | 0.65 | 0.75 | −2.47 | 0.000045 | V |
| — | n332762 | 0.87 | 0.80 | 0.80 | −35.99 | 2.22E−16 | V |
| — | n407780 | 0.88 | 0.80 | 0.85 | −4.41 | 6.55E−15 | V |
| — | n335962 | 0.73 | 0.75 | 0.68 | −6.93 | 0.000006 | V |
| — | n334260 | 0.70 | 0.73 | 0.66 | −9.02 | 0.000036 | V |
| — | n336675 | 0.73 | 0.71 | 0.73 | −6.86 | 0.000004 | V |
| — | n383778 | 0.92 | 0.90 | 0.86 | −2.67 | 3.91E−14 | V |
| — | n346494 | 0.80 | 0.77 | 0.68 | 1.87 | 9.16E−11 | B |
| — | TCONS_00003184-XLOC_001966 | 0.88 | 0.82 | 0.89 | −8.05 | 5.22E−15 | V |
| — | n332362 | 0.88 | 0.86 | 0.82 | −9.82 | 1.15E−11 | V |
| — | n346551 | 0.72 | 0.71 | 0.72 | −5.1 | 0.000007 | V |
| — | n336205 | 0.72 | 0.67 | 0.73 | −5.46 | 0.000017 | V |
| — | n336681 | 0.72 | 0.69 | 0.70 | −3.25 | 0.00003 | V |
| — | uc003hrl.1 | 0.89 | 0.90 | 0.79 | −3.5 | 2.22E−16 | V |
| — | n407800 | 0.82 | 0.67 | 0.85 | 8.21 | 2.48E−11 | B |
| — | uc004abr.1 | 0.76 | 0.75 | 0.63 | 3.26 | 1.7E−07 | B |
| — | ENST00000438517 | 0.75 | 0.67 | 0.72 | 2.16 | 0.000001 | B |
| — | n333961 | 0.76 | 0.61 | 0.82 | −5.67 | 1.11E−07 | V |
| — | ENST00000552784 | 0.87 | 0.78 | 0.82 | −2.31 | 3.22E−12 | V |
| — | n332510 | 0.88 | 0.80 | 0.86 | −10.97 | <10-17 | V |
| — | n334829 | 0.89 | 0.86 | 0.79 | −79.45 | <10-17 | V |
| — | n332456 | 0.89 | 0.84 | 0.89 | −3.73 | 3.11E−15 | V |
| — | n382996 | 0.83 | 0.80 | 0.77 | −1.74 | 8.34E−12 | V |
| — | TCONS_00024856-XLOC_011736 | 0.82 | 0.82 | 0.76 | −1.3 | 5.65E−11 | V |
| — | n406211 | 0.76 | 0.80 | 0.71 | −1.26 | 1.81E−07 | V |
| — | n407998 | 0.84 | 0.73 | 0.81 | 3.21 | 3.11E−13 | B |
| — | TCONS_12_00013127-XLOC_12_007062 | 0.76 | 0.67 | 0.81 | 15.56 | 2.88E−07 | B |
| — | n339591 | 0.82 | 0.75 | 0.77 | −3.5 | 4.95E−10 | V |
| — | TCONS_00028139-XLOC_013499 | 0.77 | 0.69 | 0.75 | 2.1 | 6.96E−08 | B |
| — | n333319 | 0.91 | 0.84 | 0.84 | −15.47 | <10-17 | V |
| — | n384079 | 0.70 | 0.59 | 0.77 | −1.08 | 0.0002 | V |

TABLE 14-continued

Differentially expressed RNA determinants (coding and non-coding) and their measures of accuracy in differentiating between bacterial ("B") versus viral ("V") infected subjects

| Gene Symbol | mRNA Accession | AUC | Sensitivity | Specificity | Fold Change (linear) (Bacterial vs. Viral) | ANOVA p-value (Bacterial vs. Viral) | Up in B/V |
|---|---|---|---|---|---|---|---|
| — | n386315 | 0.69 | 0.82 | 0.56 | −1.36 | 0.000431 | V |
| — | n332472 | 0.74 | 0.67 | 0.72 | −3.15 | 0.000034 | V |
| — | n346241 | 0.73 | 0.75 | 0.68 | −1.81 | 0.000077 | V |

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES

Arias, C. A., and B. E. Murray. 2009. "Antibiotic-Resistant Bugs in the 21st Century—a Clinical Super-Challenge." The New England Journal of Medicine 360 (5): 439-43. doi:10.1056/NEJMp0804651.

Bogaert, D, R De Groot, and P W M Hermans. 2004. "Streptococcus Pneumoniae Colonisation: The Key to Pneumococcal Disease." The Lancet Infectious Diseases 4 (3): 144-54. doi:10.1016/S1473-3099(04)00938-7.

Bossuyt, Patrick M, Johannes B Reitsma, David E Bruns, Constantine A Gatsonis, Paul P Glasziou, Les M Irwig, David Moher, Drummond Rennie, Henrica C. W De Vet, and Jeroen G Lijmer. 2003. "The STARD Statement for Reporting Studies of Diagnostic Accuracy: Explanation and Elaboration." Annals of Internal Medicine 138 (1): W1-12.

Cadieux, G., and R. Tamblyn, et al. 2007. "Predictors of Inappropriate Antibiotic Prescribing among Primary Care Physicians." CMAJ: Canadian Medical Association Journal=Journal De l'Association Medicale Canadienne 177 (8): 877-83.

"CDC—About Antimicrobial Resistance." 2013. Accessed January 17. http://www(dot)cdc(dot)gov/drugresistance/about(dot)html.

"CDC—Get Smart: Fast Facts About Antibiotic Resistance." 2011. http://www(dot)cdc(dot)gov/getsmart/antibiotic-use/fast-facts(dot)html.

Accessed Jan. 17, 2013. http://www(dot)cdc(dot)gov/getsmart/antibiotic-use/fast-facts(dot)html.

Cohen, Asi, Louis Bont, Dan Engelhard, Edward Moore, David Fernández, Racheli Kreisberg-Greenblatt, Kfir Oved, Eran Eden, and John P. Hays. 2015. "A Multifaceted 'Omics' Approach for Addressing the Challenge of Antimicrobial Resistance." Future Microbiology 10 (3): 365-76. doi:10.2217/fmb.14.127.

Davey, P., and E. Brown, et al. 2006. "Systematic Review of Antimicrobial Drug Prescribing in Hospitals." Emerging Infectious Diseases 12 (2): 211-16.

Del Mar, C. 1992. "Managing Sore Throat: A Literature Review. I. Making the Diagnosis." The Medical Journal of Australia 156 (8): 572-75.

Downey, Tom. 2006. "Analysis of a Multifactor Microarray Study Using Partek Genomics Solution." Methods in Enzymology 411: 256-70. doi:10.1016/50076-6879(06)11013-7.

Engel, Madelon F, F P Paling, A I M Hoepelman, V van der Meer, and J J Oosterheert. 2012. "Evaluating the Evidence for the Implementation of C-Reactive Protein Measurement in Adult Patients with Suspected Lower Respiratory Tract Infection in Primary Care: A Systematic Review." Family Practice 29 (4): 383-93. doi:10.1093/fampra/cmr119.

"European Surveillance of Antimicrobial Consumption Network (ESAC-Net)." 2014. Accessed February 26. http://www(dot)ecdc(dot)europa(dot)eu/en/activities/surveillance/ESAC-Net/Pages/index(dot)aspx.

Falk, Gavin, and Tom Fahey. 2009. "C-Reactive Protein and Community-Acquired Pneumonia in Ambulatory Care: Systematic Review of Diagnostic Accuracy Studies." Family Practice 26 (1): 10-21. doi:10.1093/fampra/cmn095.

Houck, P. M., and D. W. Bratzler, et al. 2002. "Pneumonia Treatment Process and Quality." Archives of Internal Medicine 162 (7): 843-44.

Jung, C. L., M. A. Lee, and W. S. Chung. 2010. "Clinical Evaluation of the Multiplex PCR Assay for the Detection of Bacterial Pathogens in Respiratory Specimens from Patients with Pneumonia." Korean Journal of Clinical Microbiology 13 (1): 40. doi:10.5145/KJCM.2010.13.1.40.

Kim, K. H., J. H. Shin, and S. Y. Kim. 2009. "The Clinical Significance of Nasopharyngeal Carriages in Immunocompromised Children as Assessed." The Korean Journal of Hematology 44 (4): 220. doi:10.5045/kjh.2009.44.4.220.

Limper, M., M. D. de Kruif, A. J. Duits, D. P. M. Brandjes, and E. C. M. van Gorp. 2010. "The Diagnostic Role of Procalcitonin and Other Biomarkers in Discriminating Infectious from Non-Infectious Fever." Journal of Infection 60 (6): 409-16. doi:10.1016/j.jinf.2010.03.016.

Linder, J A, and R S Stafford. 2001. "Antibiotic Treatment of Adults with Sore Throat by Community Primary Care Physicians: A National Survey, 1989-1999." JAMA: The Journal of the American Medical Association 286 (10): 1181-86.

Little, P. 2005. "Delayed Prescribing of Antibiotics for Upper Respiratory Tract Infection." *BMJ (Clinical Research Ed.)* 331 (7512): 301-2.

Little, P. S., and I. Williamson. 1994. "Are Antibiotics Appropriate for Sore Throats? Costs Outweigh the Benefits." *BMJ (Clinical Research Ed.)* 309 (6960): 1010-11.

Oved, Kfir, Asi Cohen, Olga Boico, Roy Navon, Tom Friedman, Liat Etshtein, Or Kriger, et al. 2015. "A Novel Host-Proteome Signature for Distinguishing between Acute Bacterial and Viral Infections." *PLoS ONE* 10 (3): e0120012. doi:10.1371/journal.pone.0120012.

Pulcini, C., and E. Cua, et al. 2007. "Antibiotic Misuse: A Prospective Clinical Audit in a French University Hospital." *European Journal of Clinical Microbiology & Infectious Diseases: Official Publication of the European Society of Clinical Microbiology* 26 (4): 277-80.

Quenot, Jean-Pierre, Charles-Edouard Luyt, Nicolas Roche, Martin Chalumeau, Pierre-Emmanuel Charles, Yann-Eric Claessens, Sigismond Lasocki, et al. 2013. "Role of Biomarkers in the Management of Antibiotic Therapy: An Expert Panel Review II: Clinical Use of Biomarkers for Initiation or Discontinuation of Antibiotic Therapy." *Annals of Intensive Care* 3 (July): 21. doi:10.1186/2110-5820-3-21.

Ramilo, Octavio, Windy Allman, Wendy Chung, Asuncion Mejias, Monica Ardura, Casey Glaser, Knut M Wittkowski, et al. 2007. "Gene Expression Patterns in Blood Leukocytes Discriminate Patients with Acute Infections." *Blood* 109 (5): 2066-77. doi:10.1182/blood-2006-02-002477.

Rhedin, Samuel, Ann Lindstrand, Maria Rotzén-Östlund, Thomas Tolfvenstam, Lars Öhrmalm, Malin Ryd Rinder, Benita Zweygberg-Wirgart, et al. 2014. "Clinical Utility of PCR for Common Viruses in Acute Respiratory Illness." *Pediatrics*, February, peds.2013-3042. doi:10.1542/peds.2013-3042.

Scott, J. G., and D. Cohen. 2001. "Antibiotic Use in Acute Respiratory Infections and the Ways Patients Pressure Physicians for a Prescription." *The Journal of Family Practice* 50 (10): 853-58.

Shin, J. H., H. Y. Han, and S. Y. Kim. 2009. "Detection of Nasopharyngeal Carriages in Children by Multiplex Reverse Transcriptase-Polymerase Chain Reaction." *Korean Journal of Pediatrics* 52 (12): 1358. doi:10.3345/kjp.2009.52.12.1358.

Spiro, D. M., and K. Y. Tay, et al. 2006. "Wait-and-See Prescription for the Treatment of Acute Otitis Media: A Randomized Controlled Trial." *JAMA: The Journal of the American Medical Association* 296 (10): 1235-41.

Spuesens, Emiel B. M., Pieter L. A. Fraaij, Eline G. Visser, Theo Hoogenboezem, Wim C. J. Hop, Léon N. A. van Adrichem, Frank Weber, et al. 2013. "Carriage of *Mycoplasma Pneumoniae* in the Upper Respiratory Tract of Symptomatic and Asymptomatic Children: An Observational Study." *PLoS Med* 10 (5): e1001444. doi:10.1371/journal.pmed.1001444.

Tang, Benjamin M P, Guy D Eslick, Jonathan C Craig, and Anthony S McLean. 2007. "Accuracy of Procalcitonin for Sepsis Diagnosis in Critically Ill Patients: Systematic Review and Meta-Analysis." *The Lancet Infectious Diseases* 7 (3): 210-17. doi:10.1016/S1473-3099(07)70052-X.

"Threat Report 2013 | Antimicrobial Resistance | CDC." 2013. Accessed November 10. http://www(dot)cdc(dot)gov/drugresistance/threat-report-2013/.

Tian, Qiang, Serguei B. Stepaniants, Mao Mao, Lee Weng, Megan C. Feetham, Michelle J. Doyle, Eugene C. Yi, et al. 2004. "Integrated Genomic and Proteomic Analyses of Gene Expression in Mammalian Cells." *Molecular & Cellular Proteomics: MCP* 3 (10): 960-69. doi:10.1074/mcp.M400055-MCP200.

Uyeki, Timothy M, Ramakrishna Prasad, Charles Vukotich, Samuel Stebbins, Charles R Rinaldo, Yu-Hui Ferng, Stephen S Morse, et al. 2009. "Low Sensitivity of Rapid Diagnostic Test for Influenza." *Clinical Infectious Diseases: An Official Publication of the Infectious Diseases Society of America* 48 (9): e89-92. doi:10.1086/597828.

van der Meer, Victor, Arie Knuistingh Neven, Peterhans J van den Broek, and Willem J J Assendelft. 2005. "Diagnostic Value of C Reactive Protein in Infections of the Lower Respiratory Tract: Systematic Review." *BMJ (Clinical Research Ed.)* 331 (7507): 26. doi:10.1136/bmj.38483.478183.EB.

"WHO | Antimicrobial Resistance." 2013. Accessed December 5. http://www(dot)who(dot)int/mediacentre/factsheets/fs194/en/index(dot)html.

"WHO Europe-Data and Statistics." 2014. Accessed February 24. http://www(dot)euro(dot)who(dot)int/en/health-topic s/disease-prevention/antimicrobial-resistance/data-and-statistics.

What is claimed is:

1. A kit comprising at least two oligonucleotides, wherein a first of said at least two oligonucleotides specifically hybridizes to human IFI27 RNA expressed from a IFI27 genomic position on the +strand of chromosome 14 selected from one of (i) start location 94581198 to stop location 94581225, (ii) start location 94582782 to stop location 94582840, and (iii) start location 94582887 to stop location 94582955, and a second of said at least two oligonucleotides specifically hybridizes to human JUP RNA expressed from a JUP genomic position on the-strand of chromosome 17 selected from one of (i) start location 39912431 to stop location 39912456, (ii) start location 39913673 to stop location 39913745, (iii) start location 39913996 to stop location 39914036, (iv) start location 39914665 to stop location 39914742, (v) start location 39919268 to stop location 39919310, (vi) start location 39925344 to stop location 39925443, and (vii) start location 39925740 to stop location 39925925, wherein said at least two oligonucleotides are attached to a detectable moiety or are attached to a solid support of an array, wherein said kit comprises oligonucleotides that hybridize to no more than 40 non-identical RNAs.

2. The kit of claim 1, wherein said at least two oligonucleotides are attached to a detectable moiety.

3. The kit of claim 1, wherein said kit comprises oligonucleotides that hybridize to no more than 10 RNAs.

4. The kit of claim 1, wherein said kit comprises oligonucleotides that hybridize to no more than 3 RNAs.

5. The kit of claim 1, wherein the first of said at least two oligonucleotides specifically hybridizes to said IFI27 RNA comprising sequence expressed from said genomic position (ii) start location 94582782 to stop location 94582840 or said (iii) start location 94582887 to stop location 94582955.

6. The kit of claim 1, further comprising oligonucleotides that specifically hybridize to one or more human RNA selected from the group consisting of IFIT1, IFI44L, CD44, OASL, Ly6E, FAM89A, OTOF, RSAD2, MX1, KREMEN1, GAS7, USP18, HERC5, HESX1, CEACAM, ZDHHC 19, RGS1 and IFI4.

* * * * *